US009611315B2

(12) United States Patent
Lu et al.

(10) Patent No.: US 9,611,315 B2
(45) Date of Patent: *Apr. 4, 2017

(54) ANTIBODIES FOR ONCOGENIC STRAINS OF HPV AND METHODS OF THEIR USE

(71) Applicant: Arbor Vita Corporation, Fremont, CA (US)

(72) Inventors: Peter S. Lu, Sunnyvale, CA (US); Jonathan David Garman, San Jose, CA (US); Michael P. Belmares, San Jose, CA (US); Chamorro Somoza Diaz-Sarmiento, Mountain View, CA (US); Johannes Schweizer, Mountain View, CA (US)

(73) Assignee: Arbor Vita Corporation, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/310,138

(22) Filed: Jun. 20, 2014

(65) Prior Publication Data
US 2015/0093742 A1 Apr. 2, 2015

Related U.S. Application Data

(63) Continuation of application No. 13/364,954, filed on Feb. 2, 2012, now abandoned, which is a continuation of application No. 12/660,613, filed on Mar. 1, 2010, now abandoned, which is a continuation of application No. 12/156,013, filed on May 28, 2008, now abandoned, which is a continuation of application No. 11/021,949, filed on Dec. 23, 2004, now Pat. No. 7,399,467.

(60) Provisional application No. 60/532,373, filed on Dec. 23, 2003.

(51) Int. Cl.
*C07K 16/08* (2006.01)
*G01N 33/569* (2006.01)
*G01N 33/574* (2006.01)

(52) U.S. Cl.
CPC ..... *C07K 16/084* (2013.01); *G01N 33/56983* (2013.01); *G01N 33/5748* (2013.01); *G01N 33/57411* (2013.01); *C07K 2317/33* (2013.01); *C07K 2317/34* (2013.01); *C07K 2317/92* (2013.01); *G01N 2333/025* (2013.01)

(58) Field of Classification Search
CPC ...... A61K 39/12; A61K 39/395; A61K 39/42; C07K 14/005; C07K 16/084; C07K 16/30; C12Q 1/708; G01N 33/56983
See application file for complete search history.

(56) References Cited

U.S. PATENT DOCUMENTS

| | | | |
|---|---|---|---|
| 3,817,837 A | 11/1972 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,777,239 A | 10/1988 | Schoolnik | |
| 5,204,061 A | 4/1993 | Covington et al. | |
| 5,371,015 A | 12/1994 | Sanford et al. | |
| 5,415,995 A | 5/1995 | Schoolnik | |
| 5,486,453 A * | 1/1996 | Dillner ................ | C07K 14/005 435/5 |
| 5,571,680 A | 11/1996 | Chen | |
| 5,610,077 A | 3/1997 | Davis et al. | |
| 5,629,161 A | 5/1997 | Muller et al. | |
| 5,643,752 A | 7/1997 | Hawkins et al. | |
| 5,648,459 A | 7/1997 | Cole | |
| 5,665,535 A | 9/1997 | Orth | |
| 5,747,274 A | 5/1998 | Jackowski et al. | |
| 5,753,233 A | 5/1998 | Bleul | |
| 5,876,723 A | 3/1999 | Cole | |
| 5,932,412 A | 8/1999 | Dillner et al. | |
| 5,955,260 A | 9/1999 | Komly et al. | |
| 6,242,266 B1 | 6/2001 | Schleifer et al. | |
| 6,322,794 B1 | 11/2001 | Bleul | |
| 6,344,314 B2 | 2/2002 | Cole | |
| 6,346,416 B1 | 2/2002 | Dean et al. | |

(Continued)

FOREIGN PATENT DOCUMENTS

CA 2457424 A1 2/2003
EP 0235187 B1 * 9/1987
(Continued)

OTHER PUBLICATIONS

Bowie JU, et. al. Science. Mar. 16, 1990;247(4948):1306-10.*
(Continued)

*Primary Examiner* — Rachel B Gill
(74) *Attorney, Agent, or Firm* — Wilson Sonsini Goodrich & Rosati

(57) ABSTRACT

The subject invention provides antibodies, including polyclonal and monoclonal antibodies, that bind to E6 proteins from at least three oncogenic strains of HPV. In general, the antibodies bind to amino acids motifs that are conserved between the E6 proteins of different HPV strains, particularly HPV strains 16 and 18. The subject antibodies may be used to detect HPV E6 protein in a sample, and, accordingly, the antibodies find use in a variety of diagnostic applications, including methods of diagnosing cancer. Kits for performing the subject methods and containing the subject antibodies are also provided.

31 Claims, 4 Drawing Sheets

(56) References Cited

U.S. PATENT DOCUMENTS

| | | | |
|---|---|---|---|
| 6,352,842 | B1 | 3/2002 | Short et al. |
| 6,372,483 | B2 | 4/2002 | Schleifer et al. |
| 6,391,539 | B1 | 5/2002 | Orth |
| 6,410,249 | B1 | 6/2002 | Ngai |
| 6,440,696 | B1 | 8/2002 | Band et al. |
| 6,492,143 | B1 | 12/2002 | Reed |
| 6,610,473 | B1 | 8/2003 | Butz et al. |
| 6,610,511 | B1 | 8/2003 | Carlson |
| 7,312,041 | B2 * | 12/2007 | Lu et al. .......... 435/7.1 |
| 7,399,467 | B2 * | 7/2008 | Lu et al. .......... 424/130.1 |
| 7,972,774 | B2 * | 7/2011 | Lu et al. .......... 435/5 |
| 8,048,676 | B2 * | 11/2011 | Lu et al. .......... 435/5 |
| 2003/0105285 | A1 | 6/2003 | Ngai |
| 2003/0143679 | A1 | 7/2003 | Vosshall |
| 2004/0018487 | A1 | 1/2004 | Lu et al. |
| 2004/0106551 | A1 * | 6/2004 | Khleif et al. .......... 514/12 |
| 2004/0229298 | A1 * | 11/2004 | Lu et al. .......... 435/7.23 |
| 2005/0037337 | A1 | 2/2005 | Ertl et al. |
| 2005/0112552 | A1 | 5/2005 | Herrero et al. |
| 2005/0118139 | A1 | 6/2005 | Huang et al. |
| 2005/0142541 | A1 | 6/2005 | Lu et al. |
| 2005/0255460 | A1 | 11/2005 | Lu et al. |
| 2007/0128699 | A1 | 6/2007 | Lu et al. |
| 2007/0196339 | A1 | 8/2007 | Cid-Arregui et al. |
| 2008/0124702 | A1 | 5/2008 | Lu et al. |
| 2009/0047660 | A1 | 2/2009 | Lu et al. |
| 2010/0209904 | A1 | 8/2010 | Lu et al. |
| 2012/0052484 | A1 | 3/2012 | Lu et al. |
| 2012/0164629 | A1 | 6/2012 | Lu et al. |
| 2013/0017572 | A1 | 1/2013 | Lu et al. |

FOREIGN PATENT DOCUMENTS

| | | |
|---|---|---|
| EP | 0523391 A1 * | 1/1993 |
| JP | 2002-360271 A | 12/2002 |
| WO | WO 90/11092 A1 | 10/1990 |
| WO | WO 94/00153 A1 | 1/1994 |
| WO | WO 96/02555 A1 | 2/1996 |
| WO | WO 96/33739 A1 | 10/1996 |
| WO | WO 97/24447 A1 | 7/1997 |
| WO | WO 97/31115 A2 | 8/1997 |
| WO | WO 97/31115 A3 | 10/1997 |
| WO | WO 97/48370 A2 | 12/1997 |
| WO | WO 97/48370 A3 | 3/1998 |
| WO | WO 98/34640 A2 | 8/1998 |
| WO | WO 98/34640 A3 | 11/1998 |
| WO | WO 99/52549 A1 | 10/1999 |
| WO | WO 00/09159 A1 | 2/2000 |
| WO | WO 00/62800 A2 | 10/2000 |
| WO | WO 00/62800 A3 | 1/2001 |
| WO | WO 2004/022006 A2 | 3/2004 |
| WO | WO 2004/022006 A3 | 7/2004 |

OTHER PUBLICATIONS

Stanley M. Vaccine. Mar. 30, 2006;24 Suppl 1:S16-22.*
Combita AL, et. al. J Virol. Jul. 2002;76(13):6480-6.*
Togtema M, et. al. PLoS One. 2012;7(11):e50730. Epub Nov. 30, 2012.*
Kennedy et. al. NCBI GenBank Deposit No. AAA46939.1, Deposited Apr. 18, 1994.*
Burd EM. Clin Microbiol Rev. Jan. 2003;16(1):1-17.*
Farmer AD. Early transforming protein E6 [Human papillomavirus]. GenBank Acc. No. AAA91658.1. Dep. Nov. 30, 1995.*
Saldanha J. Overview of antibody humanization. Updated Feb. 1, 2001. http://people.cryst.bbk.ac.uk/~ubcg07s/Overview.html.*
U.S. Appl. No. 09/710,059, filed Nov. 10, 2000, Lu et al.
U.S. Appl. No. 09/688,017, filed Oct. 13, 2000, Lu et al.
U.S. Appl. No. 09/724,553, filed Nov. 28, 2000, Lu et al.
U.S. Appl. No. 10/630,590, filed Jul. 29, 2003, Lu et al.
U.S. Appl. No. 10/938,249, filed Sep. 10, 2004, Lu et al.
Ausubel, et al. Current Protocols in Molecular Biology, vol. 1, Wiley & Sons, 1995.
Ausubel, et al. Short Protocols in Molecular Biology, Wiley & Sons, 1999.
Baithun, et al. Squamous change in bladder cancer and its relevance to understanding clonal evolution in development of bladder cancer. Cancer Surv. 1998;31:17-27.
Banchereau, et al. Dendritic cells and the control of immunity. Nature. Mar. 19, 1998;392(6673):245-52.
Banks, et al. Identification of human papillomavirus type 18 E6 polypeptide in cells derived from human cervical carcinomas. J. Gen. Virol., 68:1351-1359, 1987.
Belluscio et al., Mice deficient in Golf are anosmic, Neuron, 20: 69-81, 1988.
Bird, et al. Single-chain antigen-binding proteins. Science. Oct. 21, 1988;242(4877):423-6.
Buck, L.B. The molecular architecture of odor and pheromone sensing in mammals. Cell, 100:611-618, 2000.
Cason, et al. Transmission of cervical cancer-associated human papilloma viruses from mother to child. Intervirology. 1998;41(4-5):213-8.
De Villiers, et al. Two newly identified human papillomavirus types (HPV 40 and 57) isolated from mucosal lesions. Virology. Jul. 1989;171(1):248-53.
Deml, et al. Multiple effects of codon usage optimization on expression and immunogenicity of DNA candidate vaccines encoding the human immunodeficiency virus type 1 Gag protein. J Virol. Nov. 2001;75(22):10991-1001.
Doyle, et al. Crystal structures of a complexed and peptide-free membrane protein-binding domain: molecular basis of peptide recognition by PDZ. Cell. Jun. 28, 1996;85(7):1067-76.
Dryer, et al. Odorant receptors: a plethora of g-protein-coupled receptors. TiPS, 20;413-417, 1999.
European search report dated Jan. 17, 2006 for Application No. 3752248.9.
European search report dated Jan. 19, 2009 for Application No. 8018445.0.
European search report dated Jan. 3, 2008 for Application No. 4815434.8.
European search report dated Nov. 19, 2007 for Application No. 4815434.8.
Firestein, S. How the olfactory system makes sense of scents. Nature, 413:211-218, 2001.
Forslund, et al. Human papillomavirus type 70 genome cloned from overlapping PCR products: complete nucleotide sequence and genomic organization. J Clin Microbiol. Apr. 1996;34(4):802-9.
Fuchs, et al. The human olfactory subgenome: from sequence to structure and evolution. Hum. Genet., 108:1-13, 2001.
Gardiol, et al. Mutational Analysis of the Discs Large Tumour Suppressor Identifies Domains Responsible for Human Papillomavirus Type 18 E6-Mediated Degradation. Journal of General Virology, 2002; 83: 283-289.
Gardiol, et al. Oncogenic human papillomavirus e6 proteins target the discs large tumour suppressor for proteasome-mediated degradation, 1999, Oncogene, 18:5487-96.
GenPept AAH15560, "DLG1 protein [Homo sapiens].," Jan. 2005.
Giovane, et al. Targetting of the n-terminal domain of the human papillomavirus type 16 e6 oncoprotein with monomeric ScFvs blocks the e6-mediated degradation of cellular p53. Journal of Molecular Recognition, 12:141-152, 1999.
Glaunsinger, et al.Interactions of the PDZ-protein MAGI-1 with adenovirus E4-ORF1 and high-risk papillomavirus E6 oncoproteins. 2000, Oncogene, 19:5270-80.
Guiot et al. Immunological detection of E6 region protein from human papillomavirus types 16 and 18 in premalignant cervical lesions. Cancer Cells. 1989; 7:193-196.
Harlow, et al. Antibodies: A Laboratory Manual Cold Spring Harbor Laboratory, Cold Spring Harbor, N.Y. 1989.
Harlow, et al. Antibodies: A Laboratory Manual, First edition. Cold Spring Harbor Laboratory, Cold Spring Harbor, N.Y. 1988.
Harlow, et al. Using Antibodies: A Laboratory Manual. Cold Spring Harbor Laboratory, Cold Spring Harbor, N.Y. 1999.
Haynes, et al. Particle-mediated nucleic acid immunization. J Biotechnol. Jan. 26, 1996;44(1-3):37-42.

(56) References Cited

OTHER PUBLICATIONS

Heaulme et al. Characterization of the binding of [3H]SR 95531, a GABAA antagonist, to rat brain membranes. J Neurochem. Jun. 1987;48(6):1677-86.
Hiraiwa, et al. Binding of Viral Oncogenic Proteins and PDZ Domains of Cellular Proteins: A Focus on the Novel Functions of the Human Papilloma Virus E6 Protein. Tanpakushitsu Kakusan Koso (Protein, nucleic acid and enzyme), 1998; 43(3): 237-243 (in Japanese with English abstract).
Holzinger, et al. Viral RNA Patterns and High Viral Load Reliably Define Oropharynx Carcinomas with Active HPV16 Involvement. Cancer Res. Oct. 1, 2012;72(19):4993-5003. doi: 10.1158/0008-5472.CAN-11-3934. Epub Sep. 18, 2012.
Hood, et al. Immunology, 2nd edition, 1984.
Hunkapiller, et al. The growing immunoglobulin gene superfamily. Nature. Sep. 4-10, 1986;323(6083):15-6.
Huston, et al. Protein engineering of antibody binding sites: recovery of specific activity in an anti-digoxin single-chain Fv analogue produced in Escherichia coli. Proc Natl Acad Sci U S A. Aug. 1988;85(16):5879-83.
International search report and written opinion dated Jul. 30, 2010 for PCT/US2010/033309.
International search report dated Mar. 18, 2005 for PCT Application No. US04/43356.
International search report dated May 4, 2004 for PCT Application No. PCTUS03/28508.
Ivic , et al. Intracellular trafficking of a tagged and functional mammalian olfactory receptor. J Neurobiol., 50:56-68, 2002.
Kawashima, et al. Characterization of a new type of human papillomavirus found in a lesion of Bowen's disease of the skin. J Virol. Feb. 1986;57(2):688-92.
Kehmeier, et al. Cellular steady-state levels of "high risk" but not "low risk" human papillomavirus (HPV) E6 proteins are increased by inhibition of proteasome-dependent degradation independent of their p53- and E6AP-binding capabilities. Virology. 2002; 299(1):72-87.
Kirii, et al. Nucleotide sequence and phylogenetic classification of human papillomavirus type 67. Virus Genes. 1998;17(2):117-21.
Kiyono, et al. Binding of high-risk human papillomavirus e6 oncoproteins to the human homologue of the Drosophila discs large tumor suppressor protein. Proc. Natl. Acad. Sci., 94:11612-6, 1997.
Lanzavecchia, et al. The use of hybrid hybridomas to target human cytotoxic T lymphocytes. Eur J Immunol. Jan. 1987;17(1):105-11.
Lee, et al. Binding of human virus oncoproteins to hdlg/sap97, a mammalian homolog of the Drosophila discs large tumor suppressor protein. Proc. Natl. Acad. Sci., 94:6670-5, 1997.
Lee, et al. Multi-PDZ domain protein MUPP1 is a cellular target for both adenovirus E4-ORF1 and high-risk papillomavirus type 18 E6 oncoproteins. J Virol. Oct. 2000;74(20):9680-93.
Liang, et al. Biomarkers of HPV in Head and Neck Squamous Cell Carcinoma. Cancer Res. Oct. 1, 2012;72(19):5004-5013. Epub Sep. 18, 2012.
Lin, et al. A DNA vaccine encoding a codon-optimized human papillomavirus type 16 E6 gene enhances CTL response and anti-tumor activity. J Biomed Sci. Jul. 2006;13(4):481-8. Epub Apr. 29, 2006.
Liu, et al. Human papillomavirus DNA is present in a subset of unselected breast cancers. J Hum Virol. Nov.-Dec. 2001;4(6):329-34.
Lu, et al. Endoplasmic reticulum retention, degradation, and aggregation of olfactory g-protein coupled receptors. Traffic, 4: 416-533, 2003.
Mahvi, et al. DNA cancer vaccines: a gene gun approach. Immunol Cell Biol. Oct. 1997;75(5):456-60.
Malnic, et al. Combinational receptor codes for odors. Cell, 96:713-723, 1999.
Mao, et al. How does human papillomavirus contribute to head and neck cancer development? J Natl Cancer Inst. Jul. 7, 2004;96(13):978-80.
Masson, et al. Preferential nuclear localization of the human papillomavirus type 16 E6 oncoprotein in cervical carcinoma cells. J Gen Virol. Aug. 2003;84(Pt 8):2099-104.
Mathur, et al. Human Papillomavirus (Hpv)-E6/E7 and Epidermal Growth Facter Receptor (Egf-R) Protein Levels in Cervical Cancer and Cervical Intraepithelial Neoplasia (CIN). American Journal of Re. Immun. 2001; 46(4):280-287.
Matlashewski et al. The expression of human papillomavirus type 18 E6 protein in bacteria and the production of anti-E6 antibodies. J Gen Virol. Sep. 1986;67 (Pt 9):1909-16.
McCarthy, et al. Definition of an HPV18/45 cross-reactive human T-cell epitope after DNA immunisation of HLA-A2/KB transgenic mice. Int J Cancer. May 15, 2006;118(10):2514-21.
Mendez, E. Biomarkers of HPV Infection in Oropharyngeal Carcinomas: Can We Find Simplicity in the Puzzle of Complexity? Cancer Res. Oct. 1, 2012;72(19):4896-8. doi: 10.1158/0008-5472.CAN-12-3285. Epub Sep. 18, 2012.
Meschede, et al. Antibodies against early proteins of human papillomaviruses as diagnostic markers for invasive cervical cancer. J. Clin. Microbiol., 36:475-80, 1998.
Michel. Towards immunotherapy for chronic hepatitis B virus infections. Vaccine. Dec. 19, 2002;20 Suppl 4:A83-8.
Mombairts, et al. Molecular biology of odorant receptors in vertebrates. Annu. Rev. Neurosci, 22:487-509, 1999.
Mosmann, et al. TH1 and TH2 cells: different patterns of lymphokine secretion lead to different functional properties. Annu Rev Immunol. 1989;7:145-73.
Munger, et al. The role of human papillomaviruses in human cancers. Front. Biosci., 7:d641-9, 2002.
Munoz, et al. Epidemiologic classification of human papillomavirus types associated with cervical cancer. N Engl J Med. Feb. 6, 2003;348(6):518-27.
Nakagawa, et al. Human scribble (Vartul) is targeted for ubiquitin-mediated degradation by the high-risk papillomavirus E6 proteins and the E6AP ubiquitin-protein ligase. Mol Cell Biol. Nov. 2000;20(21):8244-53.
Nakamura, et al. Codon usage tabulated from the international DNA sequence databases. Nucleic Acids Res. Jan. 1, 1996;24(1):214-5.
Narum, et al. Codon optimization of gene fragments encoding Plasmodium falciparum merzoite proteins enhances DNA vaccine protein expression and immunogenicity in mice. Infect Immun. Dec. 2001;69(12):7250-3.
NCBI Printout. GenPept AAB91995, putative membrane-associated guanylate kinase 1 (Mus musculus) (Dec. 1997).
Office action dated Jan. 8, 2013 for U.S. Appl. No. 13/212,991.
Office action dated May 13, 2013 for U.S. Appl. No. 12/919,684.
Office action dated Jan. 26, 2010 for U.S. Appl. No. 11/650,455.
Office action dated Jan. 9, 2009 for U.S. Appl. No. 11/881,724.
Office action dated Nov. 20, 2008 for U.S. Appl. No. 11/650,455.
Office action dated Nov. 5, 2009 for U.S. Appl. No. 11/881,724.
Office action dated Dec. 1, 2010 for U.S. Appl. No. 11/881,724.
Office action dated Feb. 16, 2005 for U.S. Appl. No. 10/630,590.
Office action dated Apr. 6, 2007 for U.S. Appl. No. 10/630,590.
Office action dated Apr. 8, 2008 for U.S. Appl. No. 11/650,455.
Office action dated May 18, 2010 for U.S. Appl. No. 11/881,724.
Office action dated May 23, 2008 for U.S. Appl. No. 11/881,724.
Office action dated Jul. 20, 2010 for U.S. Appl. No. 11/650,455.
Office Action dated Jul. 6, 2006 for U.S. Appl. No. 11/053,076.
Office action dated Aug. 10, 2005 for U.S. Appl. No. 10/630,590.
Office action dated Aug. 24, 2007 for U.S. Appl. No. 11/650,455.
Park, et al. HPV-16-related proteins as the serologic markers in cervical neoplasia. Gynecol Oncol. 1998; 69(1):47-55.
Pim, et al. HPV-18 E6*1 protein modulates the e6-directed degradation of p53 by binding to full-length hpv-18 e6. Oncogene, 18:7403-8, 1999.
Raming, et al. Cloning and expression of odorant receptors. Nature, 361: 353-356, 1993.
Ronnet, et al. G proteins and olfactory signal transduction. Annu. Rev. Physiol., 64:189-222, 2002.
Rosales, et al. Antibodies against human papillomavirus (HPV) type 16 and 18 E2, E6 and E7 proteins in sera: Correlation with presence of papillomavirus DNA. J. Medical Virology. 2001; 65:736-744.

(56) References Cited

OTHER PUBLICATIONS

Rubaie, et al. Epidermodysplasia verruciformis with neurological manifestations. Int J Dermatol. Oct. 1998;37(10):766-71.
Sato, et al. Immunostimulatory DNA sequences necessary for effective intradermal gene immunization. Science. Jul. 19, 1996;273(5273):352-4.
Schneider, et al. Nat. Biotech. 1998, 17:170-5.
Sklar, et al. The odorant-sensitive adenylate cyclase of olfactory receptor cells, differential stimulation by distinct classes of odorants. J. Biol. Chem, 261:15538-15543, 1986.
Smith, et al. Human papillomavirus prevalence and types in newborns and parents: concordance and modes of transmission. Sex Transm Dis. Jan. 2004;31(1):57-62.
Snijders, et al. Analysis of p53 status in tonsillar carcinomas associated with human papillomavirus. J Gen Virol. Oct. 1994; 75 ( Pt 10):2769-75.
Thomas, et al. HPV E6 and MAGUK protein interactions: determination of the molecular basis for specific protein recognition and degradation. Oncogene. 2001; 20(39):5431-9.
Thomas, et al. Oncogenic human papillomavirus E6 proteins target the MAGI-2 and MAGI-3 proteins for degradation. Oncogene. Aug. 1, 2002;21(33):5088-96.
Timmerman, et al. Dendritic cell vaccines for cancer immunotherapy. Annu Rev Med. 1999;50:507-29.
Tosi, et al. Use of antibodies against a synthetic peptide of the E6 protein of human papillomavirus (HPV) type 16 for the diagnosis of genital HPV lesions. Cytopathology. 1993;4(1):3-15.
Touhara, et al., Functional identification and reconstitution of an odorant receptor in single olfactory neurons. Proc. Natl. Acad. Sci., 96: 4040-4045, 1999.
Trenfield, et al. Southern blot analysis of skin biopsies for human papillomavirus DNA: renal allograft recipients in south-eastern Queensland. Australas J Dermatol. 1993;34(2):71-8.
Trujillo, et al. Characterization of human papillomavirus type 57b: transforming activity and comparative sequence analysis as probes for biological determinants associated with high-risk oncogenic viruses. Virus Genes. 1996;12(2):165-78.
Verma, et al. Gene therapy—promises, problems and prospects. Nature. Sep. 18, 1997;389(6648):239-42.
Weber, et al. Human papillomavirus infection in Netherton's syndrome. Br J Dermatol. May 2001;144(5):1044-9.
Wlazlo, et al. Generation and characterization of monoclonal antibodies against the E6 and E7 oncoproteins of HPV. Hybridoma. Aug. 2001;20(4):257-63.
Wu, et al. Association of human papillomavirus with nasal neoplasia. Lancet. Feb. 27, 1993;341(8844):522-4.
Xu, et al. Clinical observation on vertical transmission of human papillomavirus. Chin Med Sci J. Mar. 1998;13(1):29-31.
Yu, et al. HPV33 DNA in pregmalignant and malignant breast lesions in Chinese and Japanese populations. Anticancer Res. Nov.-Dec. 1999;19(6B):5057-61.
Zhao et al. Functional expression of a mammalian odorant receptor. Science, 279: 237-242, 1998.
Zhou, et al. Papillomavirus capsid protein expression level depends on the match between codon usage and tRNA availability. J Virol. Jun. 1999;73(6):4972-82.
Zitvogel, et al. Eradication of established murine tumors using a novel cell-free vaccine: dendritic cell-derived exosomes. Nat Med. May 1998;4(5):594-600.
Zozulya, et al. The human olfactory receptor repertoire. Genome Biology, 2:0018.1-0018.12, 2001.

* cited by examiner

FIG. 1

```
HPV58    -------MFQDAEEKPRTLHDLCQALETSVHEIELKCVECKKTLQRSEVYDFVFADLRIV  53
HPV33    -------MFQDTEEKPRTLHDLCQALETTIHNIELQCVECKKPLQRSEVYDFAFADLTVV  53
HPV52    -------MFEDPATRPRTLHELCEVLEESVHEIRLQCVQCKKELQRREVYKFLFTDLRIV  53
HPV31    -------MFKNPAERPRKLHELSSALEIPYDELRLNCVYCKGQLTETEVLDFAFTDLTIV  53
HPV16    MHQKRTAMFQDPQERPRKLPQLCTELQTTIHDIILECVYCKQQLLRREVYDFAFRDLCIV  60
HPV18    -----MARFEDPTRRPYKLPDLCTELNTSLQDIEITCVYCKTVLELTEVFEFAFKDLFVV  55
HPV45    -----MARFDDPKQRPYKLPDLCTELNTSLQDVSIACVYCKATLERTEVYQFAFKDLCIV  55
          : : :   * .: .   :* .* :*.  *:  . .:: :  ** **   *    ** .* * ** :*

HPV58    YRDGNPFAVCKVCLRLLSKISEYRHYNYSLYGDTLEQTLKKCLNEILIRCIICQRPLCPQ 113
HPV33    YREGNPFGICKLCLRFLSKISEYRHYNYSVYGNTLEQTVKKPLNEILIRCIICQRPLCPQ 113
HPV52    YRDNNPYGVCIMCLRFLSKISEYRHYQYSLYGKTLEERVKKPLSETTIRCIICQTPLCPE 113
HPV31    YRDDTPHGVCTKCLRFYSKVSEFRWYRYSVYGTTLEKLTNKGICDLLIRCITCQRPLCPE 113
HPV16    YRDGNPYAVCDKCLKFYSKISEYRHYCYSLYGTTLEQQYNKPLCDLLIRCINCQKPLCPE 120
HPV18    YRDSIPHAACHKCIDFYSRIRELRHYSDSVYGDTLEKLTNTGLYNLLIRCLRCQKPLNPA 115
HPV45    YRDCIAYAACHKCIDFYSRIRELRYYSNSVYGETLEKITNTELYNLLIRCLRCQKPLNPA 115
         **:   ... *  *:  : *::  * *  * *:** ***:  :. .  : :: ***: ** ** *

HPV58    EKKRHVDLNKRFHNISGRWTGRCAVCWRPRRR-------QTQV 149
HPV33    EKKRHVDLNKRFHNISGRWAGRCAACWRSRRR-------ETAL 149
HPV52    EKERHVNANKRFHNIMGRWTGRCSECWRPRP--------VTQV 148
HPV31    EKQRHLDKKKRFHNIGGRWTGRCIACWRRPRT-------ETQV 149
HPV16    EKQRHLDKKQRFHNIRGRWTGRCMSCCRSSRTR-----RETQL 158
HPV18    EKLRHLNEKRRFHNIAGHYRGQCHSCCNRARQERLQRRRETQV 158
HPV45    EKRRHLKDKRRFHSIAGQYRGQCNTCCDQARQERLRRRRETQV 158
         **  **:. ::***.*  *::  *:*   *         : * :
```

FIG. 2

SEQUENCE LISTING

<160> NUMBER OF SEQ ID NOS: 366

<210> SEQ ID NO 1
<211> LENGTH: 25
<212> TYPE: PRT
<213> ORGANISM: Human papillomavirus

<400> SEQUENCE: 1

Phe Gln Asp Pro Gln Glu Arg Pro Arg Lys Leu Pro Gln Leu Cys Thr
1               5                   10                  15

Glu Leu Gln Thr Thr Ile His Asp Ile
            20                  25

<210> SEQ ID NO 2
<211> LENGTH: 25
<212> TYPE: PRT
<213> ORGANISM: Human papillomavirus

<400> SEQUENCE: 2

Phe Glu Asp Pro Thr Arg Arg Pro Tyr Lys Leu Pro Asp Leu Cys Thr
1               5                   10                  15

Glu Leu Asn Thr Ser Leu Gln Asp Ile
            20                  25

<210> SEQ ID NO 3
<211> LENGTH: 23
<212> TYPE: PRT
<213> ORGANISM: Human papillomavirus

<400> SEQUENCE: 3

Leu Leu Ile Arg Cys Ile Asn Cys Gln Lys Pro Leu Cys Pro Glu Glu
1               5                   10                  15

Lys Gln Arg His Leu Asp Lys
            20

<210> SEQ ID NO 4
<211> LENGTH: 23
<212> TYPE: PRT
<213> ORGANISM: Human papillomavirus

<400> SEQUENCE: 4

Leu Leu Ile Arg Cys Leu Arg Cys Gln Lys Pro Leu Asn Pro Ala Glu
1               5                   10                  15

Lys Leu Arg His Leu Asn Glu
            20

<210> SEQ ID NO 5
<211> LENGTH: 24
<212> TYPE: PRT
<213> ORGANISM: Human papillomavirus

<400> SEQUENCE: 5

Arg His Leu Asp Lys Lys Gln Arg Phe His Asn Ile Arg Gly Arg Trp
1               5                   10                  15

Thr Gly Arg Cys Met Ser Cys Cys
            20

<210> SEQ ID NO 6
<211> LENGTH: 24
<212> TYPE: PRT
<213> ORGANISM: Human papillomavirus

<400> SEQUENCE: 6

-continued

Arg His Leu Asn Glu Lys Arg Arg Phe His Asn Ile Ala Gly His Tyr
1               5                   10                  15

Arg Gly Gln Cys His Ser Cys Cys
            20

<210> SEQ ID NO 7
<211> LENGTH: 12
<212> TYPE: PRT
<213> ORGANISM: Human papillomavirus

<400> SEQUENCE: 7

Arg Pro Arg Lys Leu Pro Gln Leu Cys Thr Glu Leu
1               5                   10

<210> SEQ ID NO 8
<211> LENGTH: 12
<212> TYPE: PRT
<213> ORGANISM: Human papillomavirus

<400> SEQUENCE: 8

Arg Pro Tyr Lys Leu Pro Asp Leu Cys Thr Glu Leu
1               5                   10

<210> SEQ ID NO 9
<211> LENGTH: 12
<212> TYPE: PRT
<213> ORGANISM: Human papillomavirus

<400> SEQUENCE: 9

Leu Leu Ile Arg Cys Ile Asn Cys Gln Lys Pro Leu
1               5                   10

<210> SEQ ID NO 10
<211> LENGTH: 12
<212> TYPE: PRT
<213> ORGANISM: Human papillomavirus

<400> SEQUENCE: 10

Leu Leu Ile Arg Cys Leu Arg Cys Gln Lys Pro Leu
1               5                   10

<210> SEQ ID NO 11
<211> LENGTH: 12
<212> TYPE: PRT
<213> ORGANISM: Human papillomavirus

<400> SEQUENCE: 11

Arg His Leu Asp Lys Lys Gln Arg Phe His Asn Ile
1               5                   10

<210> SEQ ID NO 12
<211> LENGTH: 12
<212> TYPE: PRT
<213> ORGANISM: Human papillomavirus

<400> SEQUENCE: 12

Arg His Leu Asn Glu Lys Arg Arg Phe His Asn Ile
1               5                   10

<210> SEQ ID NO 13
<211> LENGTH: 158
<212> TYPE: PRT
<213> ORGANISM: Human papillomavirus

```
<400> SEQUENCE: 13

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Glu Thr Gln Leu
145                 150                 155

<210> SEQ ID NO 14
<211> LENGTH: 149
<212> TYPE: PRT
<213> ORGANISM: Human papillomavirus

<400> SEQUENCE: 14

Met Phe Gln Asp Pro Ala Glu Arg Pro Tyr Lys Leu His Asp Leu Cys
1               5                   10                  15

Asn Glu Val Glu Glu Ser Ile His Glu Ile Cys Leu Asn Cys Val Tyr
                20                  25                  30

Cys Lys Gln Glu Leu Gln Arg Ser Glu Val Tyr Asp Phe Ala Cys Tyr
            35                  40                  45

Asp Leu Cys Ile Val Tyr Arg Glu Gly Gln Pro Tyr Gly Val Cys Met
    50                  55                  60

Lys Cys Leu Lys Phe Tyr Ser Lys Ile Ser Glu Tyr Arg Trp Tyr Arg
65                  70                  75                  80

Tyr Ser Val Tyr Gly Glu Thr Leu Glu Lys Gln Cys Asn Lys Gln Leu
                85                  90                  95

Cys His Leu Leu Ile Arg Cys Ile Thr Cys Gln Lys Pro Leu Cys Pro
            100                 105                 110

Val Glu Lys Gln Arg His Leu Glu Glu Lys Arg Phe His Asn Ile
        115                 120                 125

Gly Gly Arg Trp Thr Gly Arg Cys Met Ser Cys Trp Lys Pro Thr Arg
    130                 135                 140

Arg Glu Thr Glu Val
145

<210> SEQ ID NO 15
<211> LENGTH: 149
<212> TYPE: PRT
<213> ORGANISM: Human papillomavirus

<400> SEQUENCE: 15

Met Phe Gln Asp Ala Glu Glu Lys Pro Arg Thr Leu His Asp Leu Cys
```

```
            1               5                  10                 15
         Gln Ala Leu Glu Thr Ser Val His Glu Ile Glu Leu Lys Cys Val Glu
                        20                  25                 30

Cys Lys Lys Thr Leu Gln Arg Ser Glu Val Tyr Asp Phe Val Phe Ala
                        35                  40                 45

Asp Leu Arg Ile Val Tyr Arg Asp Gly Asn Pro Phe Ala Val Cys Lys
                   50                  55                 60

Val Cys Leu Arg Leu Leu Ser Lys Ile Ser Glu Tyr Arg His Tyr Asn
          65                  70                  75                 80

Tyr Ser Leu Tyr Gly Asp Thr Leu Glu Gln Thr Leu Lys Lys Cys Leu
                             85                  90                 95

Asn Glu Ile Leu Ile Arg Cys Ile Ile Cys Gln Arg Pro Leu Cys Pro
                        100                 105                110

Gln Glu Lys Lys Arg His Val Asp Leu Asn Lys Arg Phe His Asn Ile
                        115                 120                125

Ser Gly Arg Trp Thr Gly Arg Cys Ala Val Cys Trp Arg Pro Arg Arg
                   130                 135                140

Arg Gln Thr Gln Val
         145

<210> SEQ ID NO 16
         <211> LENGTH: 149
         <212> TYPE: PRT
         <213> ORGANISM: Human papillomavirus

<400> SEQUENCE: 16

Met Phe Gln Asp Thr Glu Glu Lys Pro Arg Thr Leu His Asp Leu Cys
          1               5                  10                 15

Gln Ala Leu Glu Thr Thr Ile His Asn Ile Glu Leu Gln Cys Val Glu
                        20                  25                 30

Cys Lys Lys Pro Leu Gln Arg Ser Glu Val Tyr Asp Phe Ala Phe Ala
                        35                  40                 45

Asp Leu Thr Val Val Tyr Arg Glu Gly Asn Pro Phe Gly Ile Cys Lys
                   50                  55                 60

Leu Cys Leu Arg Phe Leu Ser Lys Ile Ser Glu Tyr Arg His Tyr Asn
          65                  70                  75                 80

Tyr Ser Val Tyr Gly Asn Thr Leu Glu Gln Thr Val Lys Lys Pro Leu
                             85                  90                 95

Asn Glu Ile Leu Ile Arg Cys Ile Ile Cys Gln Arg Pro Leu Cys Pro
                        100                 105                110

Gln Glu Lys Lys Arg His Val Asp Leu Asn Lys Arg Phe His Asn Ile
                        115                 120                125

Ser Gly Arg Trp Ala Gly Arg Cys Ala Ala Cys Trp Arg Ser Arg Arg
                   130                 135                140

Arg Glu Thr Ala Leu
         145

<210> SEQ ID NO 17
         <211> LENGTH: 148
         <212> TYPE: PRT
         <213> ORGANISM: Human papillomavirus

<400> SEQUENCE: 17

Met Phe Glu Asp Pro Ala Thr Arg Pro Arg Thr Leu His Glu Leu Cys
          1               5                  10                 15

Glu Val Leu Glu Glu Ser Val His Glu Ile Arg Leu Gln Cys Val Gln
```

```
                20                  25                  30
Cys Lys Lys Glu Leu Gln Arg Arg Glu Val Tyr Lys Phe Leu Phe Thr
             35                  40                  45

Asp Leu Arg Ile Val Tyr Arg Asp Asn Asn Pro Tyr Gly Val Cys Ile
         50                  55                  60

Met Cys Leu Arg Phe Leu Ser Lys Ile Ser Glu Tyr Arg His Tyr Gln
 65                  70                  75                  80

Tyr Ser Leu Tyr Gly Lys Thr Leu Glu Glu Arg Val Lys Lys Pro Leu
                 85                  90                  95

Ser Glu Ile Thr Ile Arg Cys Ile Ile Cys Gln Thr Pro Leu Cys Pro
                100                 105                 110

Glu Glu Lys Glu Arg His Val Asn Ala Asn Lys Arg Phe His Asn Ile
            115                 120                 125

Met Gly Arg Trp Thr Gly Arg Cys Ser Glu Cys Trp Arg Pro Arg Pro
        130                 135                 140

Val Thr Gln Val
145

<210> SEQ ID NO 18
<211> LENGTH: 149
<212> TYPE: PRT
<213> ORGANISM: Human papillomavirus

<400> SEQUENCE: 18

Met Phe Lys Asn Pro Ala Glu Arg Pro Arg Lys Leu His Glu Leu Ser
  1               5                  10                  15

Ser Ala Leu Glu Ile Pro Tyr Asp Glu Leu Arg Leu Asn Cys Val Tyr
                 20                  25                  30

Cys Lys Gly Gln Leu Thr Glu Thr Glu Val Leu Asp Phe Ala Phe Thr
             35                  40                  45

Asp Leu Thr Ile Val Tyr Arg Asp Asp Thr Pro His Gly Val Cys Thr
         50                  55                  60

Lys Cys Leu Arg Phe Tyr Ser Lys Val Ser Glu Phe Arg Trp Tyr Arg
 65                  70                  75                  80

Tyr Ser Val Tyr Gly Thr Thr Leu Glu Lys Leu Thr Asn Lys Gly Ile
                 85                  90                  95

Cys Asp Leu Leu Ile Arg Cys Ile Thr Cys Gln Arg Pro Leu Cys Pro
                100                 105                 110

Glu Glu Lys Gln Arg His Leu Asp Lys Lys Arg Phe His Asn Ile
            115                 120                 125

Gly Gly Arg Trp Thr Gly Arg Cys Ile Ala Cys Trp Arg Arg Pro Arg
        130                 135                 140

Thr Glu Thr Gln Val
145

<210> SEQ ID NO 19
<211> LENGTH: 148
<212> TYPE: PRT
<213> ORGANISM: Human papillomavirus

<400> SEQUENCE: 19

Met Leu Phe Pro Asn Ser Glu Glu Arg Pro Tyr Lys Leu Gln Ala Leu
  1               5                  10                  15

Cys Asp Glu Val Asn Ile Ser Ile His Asp Ile Asn Leu Asp Cys Val
                 20                  25                  30

Phe Cys Gln Arg Gly Leu Tyr Arg Ser Glu Val Tyr Asp Phe Ala Phe
```

```
               35                  40                  45
Ser Asp Leu Cys Ile Val Tyr Arg Lys Asp Lys Pro Tyr Gly Val Cys
 50                  55                  60
Gln Pro Cys Leu Lys Phe Tyr Ser Lys Ile Arg Glu Tyr Arg Arg Tyr
 65                  70                  75                  80
Arg Gln Ser Val Tyr Gly Thr Thr Leu Glu Asn Leu Thr Asn Lys Gln
                     85                  90                  95
Leu Cys Asn Ile Leu Ile Arg Cys Gly Lys Cys Gln Lys Pro Leu Cys
                100                 105                 110
Pro Leu Glu Lys Gln Lys His Val Asp Glu Lys Lys Arg Phe His Gln
                115                 120                 125
Ile Ala Glu Gln Trp Thr Gly Arg Cys Thr Arg Cys Trp Arg Pro Ser
130                 135                 140
Ala Thr Val Val
145

<210> SEQ ID NO 20
<211> LENGTH: 153
<212> TYPE: PRT
<213> ORGANISM: Human papillomavirus

<400> SEQUENCE: 20

Met Ala Phe Lys Phe Glu Asn Thr Gly Glu Arg Pro Arg Thr Val His
 1               5                  10                  15
His Leu Cys Glu Val Gln Glu Thr Ser Leu Leu Glu Leu Gln Leu Gln
                20                  25                  30
Cys Val Tyr Cys Lys Lys Glu Leu Ser Ser Ser Glu Val Tyr Asn Phe
                35                  40                  45
Ala Cys Lys Asp Leu Arg Leu Val Tyr Arg Glu Asp Ser Pro Tyr Ala
 50                  55                  60
Val Cys Asn Phe Cys Leu Leu Phe Tyr Ser Lys Val Arg Lys Ile Arg
 65                  70                  75                  80
His Tyr Asn Tyr Ser Leu Tyr Gly Ala Ser Leu Val Ala Leu Thr Lys
                85                  90                  95
Lys Glu Leu Phe Asp Leu Leu Ile Arg Cys Tyr Arg Cys Gln Gln Pro
                100                 105                 110
Leu Thr Pro Glu Glu Lys Gln Leu His Cys Gly Tyr Lys Lys Arg Phe
                115                 120                 125
His Arg Ile Ser Arg Thr Trp Thr Gly Leu Cys Leu Gln Cys Trp Arg
130                 135                 140
His Thr Thr Ser Thr Glu Thr Ala Val
145                 150

<210> SEQ ID NO 21
<211> LENGTH: 154
<212> TYPE: PRT
<213> ORGANISM: Human papillomavirus

<400> SEQUENCE: 21

Met Asp Arg Gln Leu Phe Glu Asn Thr Glu Glu Arg Pro Arg Thr Leu
 1               5                  10                  15
His Gln Leu Cys Glu Val Val Asn Lys Pro Leu Leu Glu Leu Gln Leu
                20                  25                  30
Gly Cys Val Phe Cys Lys Lys Ala Leu Thr Ala Ser Glu Val Tyr Asn
                35                  40                  45
Phe Ala Tyr Thr Asp Leu Arg Val Val Tyr Arg Asp Gly Tyr Pro Tyr
```

```
                    50                  55                  60
Gly Val Cys Lys Phe Cys Leu Leu Phe Tyr Ser Lys Val Arg Lys Leu
 65                  70                  75                  80

Arg Tyr Tyr Asn Cys Ser Val Tyr Gly Ala Ser Leu Glu Ala Leu Thr
                     85                  90                  95

Lys Lys Lys Leu Ser Asp Leu Ser Ile Arg Cys Tyr Arg Cys Gln His
                100                 105                 110

Pro Leu Thr Pro Glu Glu Lys Gln Leu His Cys Asp Tyr Lys Lys Arg
            115                 120                 125

Phe His Lys Ile Ser His Met Trp Thr Gly Ser Cys Leu Thr Cys Trp
            130                 135                 140

Arg His Thr Thr Ala Thr Glu Ser Ala Val
145                 150

<210> SEQ ID NO 22
<211> LENGTH: 155
<212> TYPE: PRT
<213> ORGANISM: Human papillomavirus

<400> SEQUENCE: 22

Met Glu Pro Gln Phe Asn Asn Pro Gln Glu Arg Pro Arg Ser Leu His
  1               5                  10                  15

His Leu Ser Glu Val Leu Glu Ile Pro Leu Ile Asp Leu Arg Leu Ser
             20                  25                  30

Cys Val Tyr Cys Lys Lys Glu Leu Thr Arg Ala Glu Val Tyr Asn Phe
         35                  40                  45

Ala Cys Thr Glu Leu Lys Leu Val Tyr Arg Asp Asp Phe Pro Tyr Ala
     50                  55                  60

Val Cys Arg Val Cys Leu Leu Phe Tyr Ser Lys Val Arg Lys Tyr Arg
 65                  70                  75                  80

Tyr Tyr Asp Tyr Ser Val Tyr Gly Ala Thr Leu Glu Ser Ile Thr Lys
                     85                  90                  95

Lys Gln Leu Cys Asp Leu Leu Ile Arg Cys Tyr Arg Cys Gln Ser Pro
                100                 105                 110

Leu Thr Pro Glu Glu Lys Gln Leu His Cys Asp Arg Lys Arg Arg Phe
            115                 120                 125

His Leu Ile Ala His Gly Trp Thr Gly Ser Cys Leu Gly Cys Trp Arg
            130                 135                 140

Gln Thr Ser Arg Glu Pro Arg Glu Ser Thr Val
145                 150                 155

<210> SEQ ID NO 23
<211> LENGTH: 155
<212> TYPE: PRT
<213> ORGANISM: Human papillomavirus

<400> SEQUENCE: 23

Met Asp Ser Ile Phe Ser Asn Thr Gln Glu Arg Pro Arg Ser Leu His
  1               5                  10                  15

His Leu Ser Glu Val Leu Gln Ile Pro Leu Leu Asp Leu Arg Leu Ser
             20                  25                  30

Cys Val Tyr Cys Lys Lys Glu Leu Thr Ser Leu Glu Leu Tyr Arg Phe
         35                  40                  45

Ala Cys Ile Glu Leu Lys Leu Val Tyr Arg Asn Asn Trp Pro Tyr Ala
     50                  55                  60

Val Cys Arg Val Cys Leu Leu Phe Tyr Ser Lys Val Arg Lys Tyr Arg
```

```
                65                  70                  75                  80

Tyr Tyr Lys Tyr Ser Val Tyr Gly Ala Thr Leu Glu Ser Ile Thr Lys
                85                  90                  95

Lys Gln Leu Ser Asp Leu Ser Ile Arg Cys Tyr Arg Cys Gln Cys Pro
            100                 105                 110

Leu Thr Pro Glu Glu Lys Gln Leu His Cys Glu His Lys Arg Arg Phe
        115                 120                 125

His Tyr Ile Ala Tyr Ala Trp Thr Gly Ser Cys Leu Gln Cys Trp Arg
    130                 135                 140

His Thr Ser Arg Gln Ala Thr Glu Ser Thr Val
145                 150                 155

<210> SEQ ID NO 24
<211> LENGTH: 151
<212> TYPE: PRT
<213> ORGANISM: Human papillomavirus

<400> SEQUENCE: 24

Met Phe Glu Asp Lys Arg Glu Arg Pro Arg Thr Leu His Glu Leu Cys
1               5                   10                  15

Glu Ala Leu Asn Val Ser Met His Asn Ile Gln Val Val Cys Val Tyr
            20                  25                  30

Cys Lys Lys Glu Leu Cys Arg Ala Asp Val Tyr Asn Val Ala Phe Thr
        35                  40                  45

Glu Ile Lys Ile Val Tyr Arg Asp Asn Asn Pro Tyr Ala Val Cys Lys
    50                  55                  60

Gln Cys Leu Leu Phe Tyr Ser Lys Ile Arg Glu Tyr Arg Arg Tyr Ser
65                  70                  75                  80

Arg Ser Val Tyr Gly Thr Thr Leu Glu Ala Ile Thr Lys Lys Ser Leu
                85                  90                  95

Tyr Asp Leu Ser Ile Arg Cys His Arg Cys Gln Arg Pro Leu Gly Pro
            100                 105                 110

Glu Glu Lys Gln Lys Leu Val Asp Glu Lys Arg Phe His Glu Ile
        115                 120                 125

Ala Gly Arg Trp Thr Gly Gln Cys Ala Asn Cys Trp Gln Arg Thr Arg
    130                 135                 140

Gln Arg Asn Glu Thr Gln Val
145                 150

<210> SEQ ID NO 25
<211> LENGTH: 151
<212> TYPE: PRT
<213> ORGANISM: Human papillomavirus

<400> SEQUENCE: 25

Met Phe Glu Asp Ile Arg Glu Arg Pro Arg Thr Leu His Glu Leu Cys
1               5                   10                  15

Glu Ala Cys Asn Thr Ser Met His Asn Ile Gln Val Leu Cys Val Tyr
            20                  25                  30

Cys Lys Lys Glu Leu Cys Arg Ala Asp Val Tyr Asn Val Ala Phe Thr
        35                  40                  45

Glu Leu Arg Ile Val Tyr Arg Asp Asn Thr Pro Tyr Ala Ala Cys Lys
    50                  55                  60

Lys Cys Leu Met Phe Tyr Ser Arg Ile Arg Glu Tyr Arg Arg Tyr Ser
65                  70                  75                  80

Arg Ser Val Tyr Gly Ala Thr Leu Glu Ala Ile Thr Asn Lys Ser Leu
```

```
            85                  90                  95

Tyr Glu Leu Leu Ile Arg Cys His Arg Cys Gln Arg Pro Leu Gly Pro
            100                 105                 110

Glu Glu Lys Gln Lys Val Val Asp Asp Lys Arg Phe His Glu Ile
        115                 120                 125

Ala Gly Arg Trp Thr Gly Gln Cys Ala Asn Cys Arg Lys Pro Pro Arg
    130                 135                 140

Gln Arg Ser Glu Thr Gln Val
145                 150

<210> SEQ ID NO 26
<211> LENGTH: 151
<212> TYPE: PRT
<213> ORGANISM: Human papillomavirus

<400> SEQUENCE: 26

Met Phe Gln Asp Pro Arg Glu Arg Pro Arg Thr Ile His Glu Leu Cys
1               5                   10                  15

Glu Ala Leu Asn Thr Pro Leu Gln Ser Leu Gln Val Gln Cys Val Tyr
            20                  25                  30

Cys Lys Lys Thr Leu Glu Trp Ala Asp Val Tyr Asn Phe Ala Ile Cys
        35                  40                  45

Asp Leu Arg Ile Val Tyr Arg Asn Asp Ser Ala Tyr Gly Ala Cys Lys
    50                  55                  60

Lys Cys Ile Ile Phe Tyr Ser Lys Ile Ile Glu Tyr Arg Arg Tyr Thr
65                  70                  75                  80

Ser Ser Val Tyr Gly Ala Thr Leu Glu Ala Arg Pro Lys Arg Ser Leu
                85                  90                  95

Cys Asn Leu Leu Ile Arg Cys His Arg Cys Gln Ile Pro Leu Gly Pro
            100                 105                 110

Glu Glu Lys Gln Arg Ile Val Asp Glu Lys Arg Arg Phe His Glu Ile
        115                 120                 125

Ala Gly Tyr Trp Lys Gly Leu Cys Thr Asn Cys Trp Arg Pro Arg Arg
    130                 135                 140

Glu Ala Thr Glu Thr Gln Val
145                 150

<210> SEQ ID NO 27
<211> LENGTH: 150
<212> TYPE: PRT
<213> ORGANISM: Human papillomavirus

<400> SEQUENCE: 27

Met Phe Glu Asp Pro Arg Glu Arg Pro Arg Thr Leu His Glu Leu Cys
1               5                   10                  15

Glu Ser Leu Asn Thr Thr Leu Gln Asn Leu Gln Val Gln Cys Val Tyr
            20                  25                  30

Cys Lys Glu Thr Leu Gln Trp Ala Asp Val Tyr Asn Phe Ala Ile Cys
        35                  40                  45

Asp Leu Arg Val Val Tyr Arg Asp Arg Ser Pro Tyr Ala Ala Cys Lys
    50                  55                  60

Arg Cys Val Ile Phe Tyr Ser Lys Ile Thr Glu Tyr Arg Arg Tyr Thr
65                  70                  75                  80

Cys Ser Val Tyr Gly Ala Thr Leu Glu Ala Leu Thr Lys Lys Ser Leu
                85                  90                  95

Cys Asn Leu Leu Ile Arg Cys His Arg Cys Gln Met Pro Leu Gly Pro
```

```
                    100                 105                 110
Glu Glu Lys Gln Arg Ile Val Asp Glu Lys Arg Arg Phe His Glu Ile
            115                 120                 125

Ala Gly Gln Trp Lys Gly Leu Cys Thr Asn Cys Trp Arg Pro Arg Arg
        130                 135                 140

Gln Thr Glu Thr Gln Val
145                 150

<210> SEQ ID NO 28
<211> LENGTH: 158
<212> TYPE: PRT
<213> ORGANISM: Human papillomavirus

<400> SEQUENCE: 28

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Glu Thr Gln Val
145                 150                 155

<210> SEQ ID NO 29
<211> LENGTH: 158
<212> TYPE: PRT
<213> ORGANISM: Human papillomavirus

<400> SEQUENCE: 29

Met Ala Arg Phe Asp Asp Pro Lys Gln Arg Pro Tyr Lys Leu Pro Asp
1               5                   10                  15

Leu Cys Thr Glu Leu Asn Thr Ser Leu Gln Asp Val Ser Ile Ala Cys
            20                  25                  30

Val Tyr Cys Lys Ala Thr Leu Glu Arg Thr Glu Val Tyr Gln Phe Ala
        35                  40                  45

Phe Lys Asp Leu Cys Ile Val Tyr Arg Asp Cys Ile Ala Tyr Ala Ala
    50                  55                  60

Cys His Lys Cys Ile Asp Phe Tyr Ser Arg Ile Arg Glu Leu Arg Tyr
65                  70                  75                  80

Tyr Ser Asn Ser Val Tyr Gly Glu Thr Leu Glu Lys Ile Thr Asn Thr
                85                  90                  95

Glu Leu Tyr Asn Leu Leu Ile Arg Cys Leu Arg Cys Gln Lys Pro Leu
            100                 105                 110

Asn Pro Ala Glu Lys Arg Arg His Leu Lys Asp Lys Arg Arg Phe His
```

```
                    115                 120                 125
Ser Ile Ala Gly Gln Tyr Arg Gly Gln Cys Asn Thr Cys Cys Asp Gln
        130                 135                 140
Ala Arg Gln Glu Arg Leu Arg Arg Arg Glu Thr Gln Val
145                 150                 155

<210> SEQ ID NO 30
<211> LENGTH: 158
<212> TYPE: PRT
<213> ORGANISM: Human papillomavirus

<400> SEQUENCE: 30

Met Ala Arg Phe His Asn Pro Ala Glu Arg Pro Tyr Lys Leu Pro Asp
1               5                   10                  15
Leu Cys Thr Thr Leu Asp Thr Thr Leu Gln Asp Ile Thr Ile Ala Cys
                20                  25                  30
Val Tyr Cys Arg Arg Pro Leu Gln Gln Thr Glu Val Tyr Glu Phe Ala
            35                  40                  45
Phe Ser Asp Leu Tyr Val Val Tyr Arg Asp Gly Glu Pro Leu Ala Ala
        50                  55                  60
Cys Gln Ser Cys Ile Lys Phe Tyr Ala Lys Ile Arg Glu Leu Arg Tyr
65                  70                  75                  80
Tyr Ser Asp Ser Val Tyr Ala Thr Thr Leu Glu Asn Ile Thr Asn Thr
                85                  90                  95
Lys Leu Tyr Asn Leu Leu Ile Arg Cys Met Cys Cys Leu Lys Pro Leu
            100                 105                 110
Cys Pro Ala Glu Lys Leu Arg His Leu Asn Ser Lys Arg Arg Phe His
        115                 120                 125
Lys Ile Ala Gly Ser Tyr Thr Gly Gln Cys Arg Arg Cys Trp Thr Thr
    130                 135                 140
Lys Arg Glu Asp Arg Arg Leu Thr Arg Arg Glu Thr Gln Val
145                 150                 155

<210> SEQ ID NO 31
<211> LENGTH: 162
<212> TYPE: PRT
<213> ORGANISM: Human papillomavirus

<400> SEQUENCE: 31

Met Ser Ile Pro Met Ala Leu Phe His Asn Pro Glu Glu Arg Pro Tyr
1               5                   10                  15
Lys Leu Pro Asp Leu Cys Arg Thr Leu Asp Thr Thr Leu His Asp Val
                20                  25                  30
Thr Ile Asp Cys Val Tyr Cys Arg Arg Gln Leu Gln Arg Thr Glu Val
            35                  40                  45
Tyr Glu Phe Ala Phe Gly Asp Leu Asn Val Val Tyr Arg Asp Gly Val
        50                  55                  60
Pro Leu Ala Ala Cys Gln Ser Cys Ile Lys Phe Tyr Ala Lys Ile Arg
65                  70                  75                  80
Glu Leu Arg Tyr Tyr Ser Glu Ser Val Tyr Ala Thr Thr Leu Glu Thr
                85                  90                  95
Ile Thr Asn Thr Lys Leu Tyr Asp Leu Ser Ile Arg Cys Met Cys Cys
            100                 105                 110
Leu Lys Pro Leu Ser Pro Ala Glu Lys Leu Arg His Leu Asn Ser Lys
        115                 120                 125
Arg Arg Phe His Lys Ile Ala Gly Asn Phe Thr Gly Gln Cys Arg His
```

```
            130                 135                 140
Cys Trp Thr Ser Lys Arg Glu Asp Arg Arg Thr Arg Gln Glu Thr
145                 150                 155                 160

Gln Val

<210> SEQ ID NO 32
<211> LENGTH: 160
<212> TYPE: PRT
<213> ORGANISM: Human papillomavirus

<400> SEQUENCE: 32

Met Ala Arg Phe Glu Asp Pro Thr Gln Arg Pro Tyr Lys Leu Pro Asp
1               5                   10                  15

Leu Ser Thr Thr Leu Asn Ile Pro Leu His Asp Ile Arg Ile Asn Cys
            20                  25                  30

Val Phe Cys Lys Gly Glu Leu Gln Glu Arg Glu Val Phe Glu Phe Ala
        35                  40                  45

Phe Asn Asp Leu Phe Ile Val Tyr Arg Asp Cys Thr Pro Tyr Ala Ala
    50                  55                  60

Cys Leu Lys Cys Ile Ser Phe Tyr Ala Arg Val Arg Glu Leu Arg Tyr
65                  70                  75                  80

Tyr Arg Asp Ser Val Tyr Gly Glu Thr Leu Glu Ala Glu Thr Lys Thr
                85                  90                  95

Pro Leu His Glu Leu Leu Ile Arg Cys Tyr Arg Cys Leu Lys Pro Leu
            100                 105                 110

Cys Pro Thr Asp Lys Leu Lys His Ile Thr Glu Lys Arg Arg Phe His
        115                 120                 125

Asn Ile Ala Gly Ile Tyr Thr Gly Gln Cys Arg Gly Cys Arg Thr Arg
    130                 135                 140

Ala Arg His Leu Arg Gln Gln Arg Gln Ala Arg Ser Glu Thr Leu Val
145                 150                 155                 160

<210> SEQ ID NO 33
<211> LENGTH: 10
<212> TYPE: PRT
<213> ORGANISM: Human papillomavirus

<400> SEQUENCE: 33

Gly Tyr Cys Arg Asn Cys Ile Arg Lys Gln
1               5                   10

<210> SEQ ID NO 34
<211> LENGTH: 10
<212> TYPE: PRT
<213> ORGANISM: Human papillomavirus

<400> SEQUENCE: 34

Trp Thr Thr Cys Met Glu Asp Leu Leu Pro
1               5                   10

<210> SEQ ID NO 35
<211> LENGTH: 10
<212> TYPE: PRT
<213> ORGANISM: Human papillomavirus

<400> SEQUENCE: 35

Gly Ile Cys Arg Leu Cys Lys His Phe Gln
1               5                   10
```

```
<210> SEQ ID NO 36
<211> LENGTH: 10
<212> TYPE: PRT
<213> ORGANISM: Human papillomavirus

<400> SEQUENCE: 36

Lys Gly Leu Cys Arg Gln Cys Lys Gln Ile
1               5                   10

<210> SEQ ID NO 37
<211> LENGTH: 10
<212> TYPE: PRT
<213> ORGANISM: Human papillomavirus

<400> SEQUENCE: 37

Trp Leu Arg Cys Thr Val Arg Ile Pro Gln
1               5                   10

<210> SEQ ID NO 38
<211> LENGTH: 10
<212> TYPE: PRT
<213> ORGANISM: Human papillomavirus

<400> SEQUENCE: 38

Arg Gln Cys Lys His Phe Tyr Asn Asp Trp
1               5                   10

<210> SEQ ID NO 39
<211> LENGTH: 10
<212> TYPE: PRT
<213> ORGANISM: Human papillomavirus

<400> SEQUENCE: 39

Cys Arg Asn Cys Ile Ser His Glu Gly Arg
1               5                   10

<210> SEQ ID NO 40
<211> LENGTH: 10
<212> TYPE: PRT
<213> ORGANISM: Human papillomavirus

<400> SEQUENCE: 40

Cys Cys Arg Asn Cys Tyr Glu His Glu Gly
1               5                   10

<210> SEQ ID NO 41
<211> LENGTH: 10
<212> TYPE: PRT
<213> ORGANISM: Human papillomavirus

<400> SEQUENCE: 41

Ser Ser Arg Thr Arg Arg Glu Thr Gln Leu
1               5                   10

<210> SEQ ID NO 42
<211> LENGTH: 10
<212> TYPE: PRT
<213> ORGANISM: Human papillomavirus

<400> SEQUENCE: 42

Arg Leu Gln Arg Arg Arg Glu Thr Gln Val
1               5                   10

<210> SEQ ID NO 43
<211> LENGTH: 10
```

```
<212> TYPE: PRT
<213> ORGANISM: Human papillomavirus

<400> SEQUENCE: 43

Trp Arg Arg Pro Arg Thr Glu Thr Gln Val
1               5                   10

<210> SEQ ID NO 44
<211> LENGTH: 10
<212> TYPE: PRT
<213> ORGANISM: Human papillomavirus

<400> SEQUENCE: 44

Trp Lys Pro Thr Arg Arg Glu Thr Glu Val
1               5                   10

<210> SEQ ID NO 45
<211> LENGTH: 10
<212> TYPE: PRT
<213> ORGANISM: Human papillomavirus

<400> SEQUENCE: 45

Arg Arg Thr Leu Arg Arg Glu Thr Gln Val
1               5                   10

<210> SEQ ID NO 46
<211> LENGTH: 10
<212> TYPE: PRT
<213> ORGANISM: Human papillomavirus

<400> SEQUENCE: 46

Arg Arg Leu Thr Arg Arg Glu Thr Gln Val
1               5                   10

<210> SEQ ID NO 47
<211> LENGTH: 10
<212> TYPE: PRT
<213> ORGANISM: Human papillomavirus

<400> SEQUENCE: 47

Arg Leu Arg Arg Arg Arg Glu Thr Gln Val
1               5                   10

<210> SEQ ID NO 48
<211> LENGTH: 10
<212> TYPE: PRT
<213> ORGANISM: Human papillomavirus

<400> SEQUENCE: 48

Arg Leu Gln Arg Arg Asn Glu Thr Gln Val
1               5                   10

<210> SEQ ID NO 49
<211> LENGTH: 10
<212> TYPE: PRT
<213> ORGANISM: Human papillomavirus

<400> SEQUENCE: 49

Arg Leu Gln Arg Arg Arg Val Thr Gln Val
1               5                   10

<210> SEQ ID NO 50
<211> LENGTH: 10
<212> TYPE: PRT
<213> ORGANISM: Human papillomavirus
```

```
<400> SEQUENCE: 50

Thr Ser Arg Glu Pro Arg Glu Ser Thr Val
1               5                   10

<210> SEQ ID NO 51
<211> LENGTH: 10
<212> TYPE: PRT
<213> ORGANISM: Human papillomavirus

<400> SEQUENCE: 51

Gln Arg Gln Ala Arg Ser Glu Thr Leu Val
1               5                   10

<210> SEQ ID NO 52
<211> LENGTH: 10
<212> TYPE: PRT
<213> ORGANISM: Human papillomavirus

<400> SEQUENCE: 52

Arg Leu Gln Arg Arg Arg Gln Thr Gln Val
1               5                   10

<210> SEQ ID NO 53
<211> LENGTH: 10
<212> TYPE: PRT
<213> ORGANISM: Human papillomavirus

<400> SEQUENCE: 53

Arg Leu Gln Arg Arg Arg Glu Thr Ala Leu
1               5                   10

<210> SEQ ID NO 54
<211> LENGTH: 10
<212> TYPE: PRT
<213> ORGANISM: Human papillomavirus

<400> SEQUENCE: 54

Thr Ser Arg Gln Ala Thr Glu Ser Thr Val
1               5                   10

<210> SEQ ID NO 55
<211> LENGTH: 10
<212> TYPE: PRT
<213> ORGANISM: Human papillomavirus

<400> SEQUENCE: 55

Arg Arg Arg Thr Arg Gln Glu Thr Gln Val
1               5                   10

<210> SEQ ID NO 56
<211> LENGTH: 10
<212> TYPE: PRT
<213> ORGANISM: Human papillomavirus

<400> SEQUENCE: 56

Arg Arg Arg Glu Ala Thr Glu Thr Gln Val
1               5                   10

<210> SEQ ID NO 57
<211> LENGTH: 25
<212> TYPE: PRT
<213> ORGANISM: Human papillomavirus

<400> SEQUENCE: 57
```

```
Phe Asp Asp Pro Lys Gln Arg Pro Tyr Lys Leu Pro Asp Leu Cys Thr
1               5                   10                  15

Glu Leu Asn Thr Ser Leu Gln Asp Val
            20                  25

<210> SEQ ID NO 58
<211> LENGTH: 23
<212> TYPE: PRT
<213> ORGANISM: Human papillomavirus

<400> SEQUENCE: 58

Leu Leu Ile Arg Cys Leu Arg Cys Gln Lys Pro Leu Asn Pro Ala Glu
1               5                   10                  15

Lys Arg Arg His Leu Lys Asp
            20

<210> SEQ ID NO 59
<211> LENGTH: 24
<212> TYPE: PRT
<213> ORGANISM: Human papillomavirus

<400> SEQUENCE: 59

Arg His Leu Lys Asp Lys Arg Arg Phe His Ser Ile Ala Gly Gln Tyr
1               5                   10                  15

Arg Gly Gln Cys Asn Thr Cys Cys
            20

<210> SEQ ID NO 60
<211> LENGTH: 12
<212> TYPE: PRT
<213> ORGANISM: Human papillomavirus

<400> SEQUENCE: 60

Arg Pro Tyr Lys Leu Pro Asp Leu Cys Thr Glu Leu
1               5                   10

<210> SEQ ID NO 61
<211> LENGTH: 12
<212> TYPE: PRT
<213> ORGANISM: Human papillomavirus

<400> SEQUENCE: 61

Leu Leu Ile Arg Cys Leu Arg Cys Gln Lys Pro Leu
1               5                   10

<210> SEQ ID NO 62
<211> LENGTH: 12
<212> TYPE: PRT
<213> ORGANISM: Human papillomavirus

<400> SEQUENCE: 62

Arg His Leu Lys Asp Lys Arg Arg Phe His Ser Ile
1               5                   10

<210> SEQ ID NO 63
<211> LENGTH: 10
<212> TYPE: PRT
<213> ORGANISM: Human papillomavirus

<400> SEQUENCE: 63

Arg Pro Arg Arg Gln Thr Glu Thr Gln Val
1               5                   10
```

```
<210> SEQ ID NO 64
<211> LENGTH: 10
<212> TYPE: PRT
<213> ORGANISM: Human papillomavirus

<400> SEQUENCE: 64

Arg His Thr Thr Ala Thr Glu Ser Ala Val
1               5                   10

<210> SEQ ID NO 65
<211> LENGTH: 10
<212> TYPE: PRT
<213> ORGANISM: Human papillomavirus

<400> SEQUENCE: 65

Thr Ser Arg Gln Ala Thr Glu Ser Thr Val
1               5                   10

<210> SEQ ID NO 66
<211> LENGTH: 10
<212> TYPE: PRT
<213> ORGANISM: Human papillomavirus

<400> SEQUENCE: 66

Arg Cys Trp Arg Pro Ser Ala Thr Val Val
1               5                   10

<210> SEQ ID NO 67
<211> LENGTH: 10
<212> TYPE: PRT
<213> ORGANISM: Human papillomavirus

<400> SEQUENCE: 67

Pro Pro Arg Gln Arg Ser Glu Thr Gln Val
1               5                   10

<210> SEQ ID NO 68
<211> LENGTH: 72
<212> TYPE: PRT
<213> ORGANISM: Human papillomavirus

<400> SEQUENCE: 68

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 69
<211> LENGTH: 76
<212> TYPE: PRT
<213> ORGANISM: Human papillomavirus

<400> SEQUENCE: 69

Phe Ile His Thr Lys Leu Arg Lys Ser Ser Arg Gly Phe Gly Phe Thr
1               5                   10                  15

Val Val Gly Gly Asp Glu Pro Asp Glu Phe Leu Gln Ile Lys Ser Leu
```

```
              20                  25                  30

Val Leu Asp Gly Pro Ala Ala Leu Asp Gly Lys Met Glu Thr Gly Asp
            35                  40                  45

Val Ile Val Ser Val Asn Asp Thr Cys Val Leu Gly His Thr His Ala
        50                  55                  60

Gln Val Val Lys Ile Phe Gln Ser Ile Pro Ile Gly
65                  70                  75

<210> SEQ ID NO 70
<211> LENGTH: 85
<212> TYPE: PRT
<213> ORGANISM: Human papillomavirus

<400> SEQUENCE: 70

Phe Ile His Thr Lys Leu Arg Lys Ser Ser Arg Gly Phe Gly Phe Thr
1               5                   10                  15

Val Val Gly Gly Asp Glu Pro Asp Glu Phe Leu Gln Ile Lys Ser Leu
                20                  25                  30

Val Leu Asp Gly Pro Ala Ala Leu Asp Gly Lys Met Glu Thr Gly Asp
            35                  40                  45

Val Ile Val Ser Val Asn Asp Thr Cys Val Leu Gly His Thr His Ala
        50                  55                  60

Gln Val Val Lys Ile Phe Gln Ser Ile Pro Ile Gly Ala Ser Val Asp
65                  70                  75                  80

Leu Glu Leu Cys Arg
            85

<210> SEQ ID NO 71
<211> LENGTH: 78
<212> TYPE: PRT
<213> ORGANISM: Human papillomavirus

<400> SEQUENCE: 71

Lys Ser Ser Arg Gly Phe Gly Phe Thr Val Val Gly Gly Asp Glu Pro
1               5                   10                  15

Asp Glu Phe Leu Gln Ile Lys Ser Leu Val Leu Asp Gly Pro Ala Ala
                20                  25                  30

Leu Asp Gly Lys Met Glu Thr Gly Asp Val Ile Val Ser Val Asn Asp
            35                  40                  45

Thr Cys Val Leu Gly His Thr His Ala Gln Val Val Lys Ile Phe Gln
        50                  55                  60

Ser Ile Pro Ile Gly Ala Ser Val Asp Leu Glu Leu Cys Arg
65                  70                  75

<210> SEQ ID NO 72
<211> LENGTH: 88
<212> TYPE: PRT
<213> ORGANISM: Human papillomavirus

<400> SEQUENCE: 72

Phe Ile His Thr Lys Leu Arg Lys Ser Ser Arg Gly Phe Gly Phe Thr
1               5                   10                  15

Val Val Gly Gly Asp Glu Pro Asp Glu Phe Leu Gln Ile Lys Ser Leu
                20                  25                  30

Val Leu Asp Gly Pro Ala Ala Leu Asp Gly Lys Met Glu Thr Gly Asp
            35                  40                  45

Val Ile Val Ser Val Asn Asp Thr Cys Val Leu Gly His Thr His Ala
        50                  55                  60
```

Gln Val Val Lys Ile Phe Gln Ser Ile Pro Ile Gly Ala Ser Val Asp
65                  70                  75                  80

Leu Glu Leu Cys Arg Gly Tyr Pro
                85

<210> SEQ ID NO 73
<211> LENGTH: 88
<212> TYPE: PRT
<213> ORGANISM: Human papillomavirus

<400> SEQUENCE: 73

Lys Gly Lys Phe Ile His Thr Lys Leu Arg Lys Ser Ser Arg Gly Phe
1               5                   10                  15

Gly Phe Thr Val Val Gly Gly Asp Glu Pro Asp Glu Phe Leu Gln Ile
                20                  25                  30

Lys Ser Leu Val Leu Asp Gly Pro Ala Ala Leu Asp Gly Lys Met Glu
                35                  40                  45

Thr Gly Asp Val Ile Val Ser Val Asn Asp Thr Cys Val Leu Gly His
                50                  55                  60

Thr His Ala Gln Val Val Lys Ile Phe Gln Ser Ile Pro Ile Gly Ala
65                  70                  75                  80

Ser Val Asp Leu Glu Leu Cys Arg
                85

<210> SEQ ID NO 74
<211> LENGTH: 81
<212> TYPE: PRT
<213> ORGANISM: Human papillomavirus

<400> SEQUENCE: 74

Lys Gly Lys Phe Ile His Thr Lys Leu Arg Lys Ser Ser Arg Gly Phe
1               5                   10                  15

Gly Phe Thr Val Val Gly Gly Asp Glu Pro Asp Glu Phe Leu Gln Ile
                20                  25                  30

Lys Ser Leu Val Leu Asp Gly Pro Ala Ala Leu Asp Gly Lys Met Glu
                35                  40                  45

Thr Gly Asp Val Ile Val Ser Val Asn Asp Thr Cys Val Leu Gly His
                50                  55                  60

Thr His Ala Gln Val Val Lys Ile Phe Gln Ser Ile Pro Ile Gly Ala
65                  70                  75                  80

Ser

<210> SEQ ID NO 75
<211> LENGTH: 94
<212> TYPE: PRT
<213> ORGANISM: Human papillomavirus

<400> SEQUENCE: 75

Glu Leu Lys Gly Lys Phe Ile His Thr Lys Leu Arg Lys Ser Ser Arg
1               5                   10                  15

Gly Phe Gly Phe Thr Val Val Gly Gly Asp Glu Pro Asp Glu Phe Leu
                20                  25                  30

Gln Ile Lys Ser Leu Val Leu Asp Gly Pro Ala Ala Leu Asp Gly Lys
                35                  40                  45

Met Glu Thr Gly Asp Val Ile Val Ser Val Asn Asp Thr Cys Val Leu
                50                  55                  60

Gly His Thr His Ala Gln Val Val Lys Ile Phe Gln Ser Ile Pro Ile

```
                65                  70                  75                  80
Gly Ala Ser Val Asp Leu Glu Leu Cys Arg Gly Tyr Pro Leu
                    85                  90

<210> SEQ ID NO 76
<211> LENGTH: 99
<212> TYPE: PRT
<213> ORGANISM: Human papillomavirus

<400> SEQUENCE: 76

Ser Glu Leu Lys Gly Lys Phe Ile His Thr Lys Leu Arg Lys Ser Ser
1               5                   10                  15

Arg Gly Phe Gly Phe Thr Val Val Gly Gly Asp Glu Pro Asp Glu Phe
                20                  25                  30

Leu Gln Ile Lys Ser Leu Val Leu Asp Gly Pro Ala Ala Leu Asp Gly
            35                  40                  45

Lys Met Glu Thr Gly Asp Val Ile Val Ser Val Asn Asp Thr Cys Val
        50                  55                  60

Leu Gly His Thr His Ala Gln Val Val Lys Ile Phe Gln Ser Ile Pro
65                  70                  75                  80

Ile Gly Ala Ser Val Asp Leu Glu Leu Cys Arg Gly Tyr Pro Leu Pro
                85                  90                  95

Phe Asp Pro

<210> SEQ ID NO 77
<211> LENGTH: 72
<212> TYPE: PRT
<213> ORGANISM: Human papillomavirus

<400> SEQUENCE: 77

Arg Lys Ser Ala Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 78
<211> LENGTH: 72
<212> TYPE: PRT
<213> ORGANISM: Human papillomavirus

<400> SEQUENCE: 78

Arg Lys Ser Ser Arg Gly Phe Gly Phe Thr Val Val Gly Gly Glu Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70
```

<210> SEQ ID NO 79
<211> LENGTH: 72
<212> TYPE: PRT
<213> ORGANISM: Human papillomavirus

<400> SEQUENCE: 79

Arg Lys Ser Ser Arg Gly Phe Gly Phe Thr Val Val Gly Gly Asp Glu
1               5                   10                  15

Pro Asp Glu Phe Leu Gln Leu Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 80
<211> LENGTH: 72
<212> TYPE: PRT
<213> ORGANISM: Human papillomavirus

<400> SEQUENCE: 80

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ser Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 81
<211> LENGTH: 72
<212> TYPE: PRT
<213> ORGANISM: Human papillomavirus

<400> SEQUENCE: 81

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Arg Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 82
<211> LENGTH: 72
<212> TYPE: PRT
<213> ORGANISM: Human papillomavirus

<400> SEQUENCE: 82

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ala Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 83
<211> LENGTH: 72
<212> TYPE: PRT
<213> ORGANISM: Human papillomavirus

<400> SEQUENCE: 83

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Glu Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 84
<211> LENGTH: 72
<212> TYPE: PRT
<213> ORGANISM: Human papillomavirus

<400> SEQUENCE: 84

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Leu Leu Gly His Thr His Ala Gln Val Val Lys Ile Phe
    50                  55                  60

Gln Ser Ile Pro Ile Gly Ala Ser
65                  70

<210> SEQ ID NO 85
<211> LENGTH: 72
<212> TYPE: PRT
<213> ORGANISM: Human papillomavirus

<400> SEQUENCE: 85

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ser Gln Val Val Lys Ile Phe
    50                  55                  60

Gln Ser Ile Pro Ile Gly Ala Ser
65                  70

<210> SEQ ID NO 86
<211> LENGTH: 72
<212> TYPE: PRT
<213> ORGANISM: Human papillomavirus

<400> SEQUENCE: 86

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Leu Phe
    50                  55                  60

Gln Ser Ile Pro Ile Gly Ala Ser
65                  70

<210> SEQ ID NO 87
<211> LENGTH: 72
<212> TYPE: PRT
<213> ORGANISM: Human papillomavirus

<400> SEQUENCE: 87

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ser Ser
65                  70

<210> SEQ ID NO 88
<211> LENGTH: 72
<212> TYPE: PRT
<213> ORGANISM: Human papillomavirus

<400> SEQUENCE: 88

Arg Lys Ser Thr Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 89
<211> LENGTH: 72
<212> TYPE: PRT
<213> ORGANISM: Human papillomavirus

<400> SEQUENCE: 89

Arg Lys Ser Ser Arg Gly Phe Gly Phe Thr Val Val Gly Gly Asp Glu
1               5                   10                  15

Pro Gly Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65              70

<210> SEQ ID NO 90
<211> LENGTH: 72
<212> TYPE: PRT
<213> ORGANISM: Human papillomavirus

<400> SEQUENCE: 90

Arg Lys Ser Ser Arg Gly Phe Gly Phe Thr Val Val Gly Gly Asp Glu
1               5                   10                  15

Pro Asp Glu Phe Leu Gln Ile Lys Ser Leu Ala Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65              70

<210> SEQ ID NO 91
<211> LENGTH: 72
<212> TYPE: PRT
<213> ORGANISM: Human papillomavirus

<400> SEQUENCE: 91

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Ala Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65              70

<210> SEQ ID NO 92
<211> LENGTH: 72
<212> TYPE: PRT
<213> ORGANISM: Human papillomavirus

<400> SEQUENCE: 92

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Ala Asp Val Ile Val Ser Val Asn
        35                  40                  45

```
Asp Thr Cys Val Leu Gly His Thr His Ala Gln Val Val Lys Ile Phe
        50                  55                  60

Gln Ser Ile Pro Ile Gly Ala Ser
 65                  70

<210> SEQ ID NO 93
<211> LENGTH: 72
<212> TYPE: PRT
<213> ORGANISM: Human papillomavirus

<400> SEQUENCE: 93

Arg Lys Ser Ser Arg Gly Phe Gly Phe Thr Val Val Gly Gly Asp Glu
 1               5                  10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Ala Val Leu Gly His Thr His Ala Gln Val Val Lys Ile Phe
        50                  55                  60

Gln Ser Ile Pro Ile Gly Ala Ser
 65                  70

<210> SEQ ID NO 94
<211> LENGTH: 72
<212> TYPE: PRT
<213> ORGANISM: Human papillomavirus

<400> SEQUENCE: 94

Arg Lys Ser Ser Arg Gly Phe Gly Phe Thr Val Val Gly Gly Asp Glu
 1               5                  10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Ala Val Lys Ile Phe
        50                  55                  60

Gln Ser Ile Pro Ile Gly Ala Ser
 65                  70

<210> SEQ ID NO 95
<211> LENGTH: 72
<212> TYPE: PRT
<213> ORGANISM: Human papillomavirus

<400> SEQUENCE: 95

Arg Lys Ser Ser Arg Gly Phe Gly Phe Thr Val Val Gly Gly Asp Glu
 1               5                  10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
        50                  55                  60

Gln Ser Ile Ala Ile Gly Ala Ser
 65                  70

<210> SEQ ID NO 96
<211> LENGTH: 72
<212> TYPE: PRT
```

<213> ORGANISM: Human papillomavirus

<400> SEQUENCE: 96

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ala
65                  70

<210> SEQ ID NO 97
<211> LENGTH: 72
<212> TYPE: PRT
<213> ORGANISM: Human papillomavirus

<400> SEQUENCE: 97

Arg Lys Ser Ser Ser Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 98
<211> LENGTH: 72
<212> TYPE: PRT
<213> ORGANISM: Human papillomavirus

<400> SEQUENCE: 98

Arg Lys Ser Ser Arg Gly Phe Gly Phe Thr Val Val Gly Gly Leu Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 99
<211> LENGTH: 72
<212> TYPE: PRT
<213> ORGANISM: Human papillomavirus

<400> SEQUENCE: 99

Arg Lys Ser Ser Arg Gly Phe Gly Phe Thr Val Val Gly Gly Asp Glu
1               5                   10                  15

Pro Asp Glu Phe Leu Gln Ile Thr Ser Leu Val Leu Asp Gly Pro Ala
            20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 100
<211> LENGTH: 72
<212> TYPE: PRT
<213> ORGANISM: Human papillomavirus

<400> SEQUENCE: 100

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Gly Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 101
<211> LENGTH: 72
<212> TYPE: PRT
<213> ORGANISM: Human papillomavirus

<400> SEQUENCE: 101

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Ser Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 102
<211> LENGTH: 72
<212> TYPE: PRT
<213> ORGANISM: Human papillomavirus

<400> SEQUENCE: 102

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Lys
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 103
<211> LENGTH: 72
<212> TYPE: PRT
<213> ORGANISM: Human papillomavirus

<400> SEQUENCE: 103

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Phe His Thr His Ala Gln Val Val Lys Ile Phe
    50                  55                  60

Gln Ser Ile Pro Ile Gly Ala Ser
65                  70

<210> SEQ ID NO 104
<211> LENGTH: 72
<212> TYPE: PRT
<213> ORGANISM: Human papillomavirus

<400> SEQUENCE: 104

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Asn Val Lys Ile Phe
    50                  55                  60

Gln Ser Ile Pro Ile Gly Ala Ser
65                  70

<210> SEQ ID NO 105
<211> LENGTH: 72
<212> TYPE: PRT
<213> ORGANISM: Human papillomavirus

<400> SEQUENCE: 105

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Ser Ala Ser
65                  70

<210> SEQ ID NO 106
<211> LENGTH: 93
<212> TYPE: PRT
<213> ORGANISM: Human papillomavirus

<400> SEQUENCE: 106

Leu Arg Lys Glu Pro Glu Ile Ile Thr Val Thr Leu Lys Lys Gln Asn
1               5                   10                  15

```
Gly Met Gly Leu Ser Ile Val Ala Ala Lys Gly Ala Gly Gln Asp Lys
            20                  25                  30

Leu Gly Ile Tyr Val Lys Ser Val Val Lys Gly Ala Ala Asp Val
            35                  40                  45

Asp Gly Arg Leu Ala Ala Gly Asp Gln Leu Leu Ser Val Asp Gly Arg
 50                  55                  60

Ser Leu Val Gly Leu Ser Gln Glu Arg Ala Ala Glu Leu Met Thr Arg
 65                  70                  75                  80

Thr Ser Ser Val Val Thr Leu Glu Val Ala Lys Gln Gly
                85                  90

<210> SEQ ID NO 107
<211> LENGTH: 105
<212> TYPE: PRT
<213> ORGANISM: Human papillomavirus

<400> SEQUENCE: 107

Leu Ile Arg Pro Ser Val Ile Ser Ile Gly Leu Tyr Lys Glu Lys
 1               5                  10                  15

Gly Lys Gly Leu Gly Phe Ser Ile Ala Gly Gly Arg Asp Cys Ile Arg
                20                  25                  30

Gly Gln Met Gly Ile Phe Val Lys Thr Ile Phe Pro Asn Gly Ser Ala
            35                  40                  45

Ala Glu Asp Gly Arg Leu Lys Glu Gly Asp Glu Ile Leu Asp Val Asn
 50                  55                  60

Gly Ile Pro Ile Lys Gly Leu Thr Phe Gln Glu Ala Ile His Thr Phe
 65                  70                  75                  80

Lys Gln Ile Arg Ser Gly Leu Phe Val Leu Thr Val Arg Thr Lys Leu
                85                  90                  95

Val Ser Pro Ser Leu Thr Asn Ser Ser
                100                 105

<210> SEQ ID NO 108
<211> LENGTH: 105
<212> TYPE: PRT
<213> ORGANISM: Human papillomavirus

<400> SEQUENCE: 108

Gln Ser Glu Asn Glu Glu Asp Val Cys Phe Ile Val Leu Asn Arg Lys
 1               5                  10                  15

Glu Gly Ser Gly Leu Gly Phe Ser Val Ala Gly Gly Thr Asp Val Glu
                20                  25                  30

Pro Lys Ser Ile Thr Val His Arg Val Phe Ser Gln Gly Ala Ala Ser
            35                  40                  45

Gln Glu Gly Thr Met Asn Arg Gly Asp Phe Leu Leu Ser Val Asn Gly
 50                  55                  60

Ala Ser Leu Ala Gly Leu Ala His Gly Asn Val Leu Lys Val Leu His
 65                  70                  75                  80

Gln Ala Gln Leu His Lys Asp Ala Leu Val Val Ile Lys Lys Gly Met
                85                  90                  95

Asp Gln Pro Arg Pro Ser Asn Ser Ser
                100                 105

<210> SEQ ID NO 109
<211> LENGTH: 132
<212> TYPE: PRT
<213> ORGANISM: Human papillomavirus
```

```
<400> SEQUENCE: 109

Gly Ile Ser Ser Leu Gly Arg Lys Thr Pro Gly Pro Lys Asp Arg Ile
1               5                   10                  15

Val Met Glu Val Thr Leu Asn Lys Glu Pro Arg Val Gly Leu Gly Ile
                20                  25                  30

Gly Ala Cys Cys Leu Ala Leu Glu Asn Ser Pro Pro Gly Ile Tyr Ile
            35                  40                  45

His Ser Leu Ala Pro Gly Ser Val Ala Lys Met Glu Ser Asn Leu Ser
        50                  55                  60

Arg Gly Asp Gln Ile Leu Glu Val Asn Ser Val Asn Val Arg His Ala
65                  70                  75                  80

Ala Leu Ser Lys Val His Ala Ile Leu Ser Lys Cys Pro Pro Gly Pro
                85                  90                  95

Val Arg Leu Val Ile Gly Arg His Pro Asn Pro Lys Val Ser Glu Gln
                100                 105                 110

Glu Met Asp Glu Val Ile Ala Arg Ser Thr Tyr Gln Glu Ser Lys Glu
            115                 120                 125

Ala Asn Ser Ser
        130

<210> SEQ ID NO 110
<211> LENGTH: 101
<212> TYPE: PRT
<213> ORGANISM: Human papillomavirus

<400> SEQUENCE: 110

Leu Gly Arg Ser Val Ala Val His Asp Ala Leu Cys Val Glu Val Leu
1               5                   10                  15

Lys Thr Ser Ala Gly Leu Gly Leu Ser Leu Asp Gly Gly Lys Ser Ser
                20                  25                  30

Val Thr Gly Asp Gly Pro Leu Val Ile Lys Arg Val Tyr Lys Gly Gly
            35                  40                  45

Ala Ala Glu Gln Ala Gly Ile Ile Glu Ala Gly Asp Glu Ile Leu Ala
        50                  55                  60

Ile Asn Gly Lys Pro Leu Val Gly Leu Met His Phe Asp Ala Trp Asn
65                  70                  75                  80

Ile Met Lys Ser Val Pro Glu Gly Pro Val Gln Leu Leu Ile Arg Lys
                85                  90                  95

His Arg Asn Ser Ser
            100

<210> SEQ ID NO 111
<211> LENGTH: 98
<212> TYPE: PRT
<213> ORGANISM: Human papillomavirus

<400> SEQUENCE: 111

Arg Glu Glu Gly Gly Met Pro Gln Thr Val Ile Leu Pro Gly Pro Ala
1               5                   10                  15

Pro Trp Gly Phe Arg Leu Ser Gly Gly Ile Asp Phe Asn Gln Pro Leu
                20                  25                  30

Val Ile Thr Arg Ile Thr Pro Gly Ser Lys Ala Ala Ala Asn Leu
            35                  40                  45

Cys Pro Gly Asp Val Ile Leu Ala Ile Asp Gly Phe Gly Thr Glu Ser
        50                  55                  60

Met Thr His Ala Asp Ala Gln Asp Arg Ile Lys Ala Ala Ala His Gln
```

```
                65                  70                  75                  80
Leu Cys Leu Lys Ile Asp Arg Gly Glu Thr His Leu Trp Ser Pro Asn
                    85                  90                  95
Ser Ser

<210> SEQ ID NO 112
<211> LENGTH: 85
<212> TYPE: PRT
<213> ORGANISM: Human papillomavirus

<400> SEQUENCE: 112

Ile Leu Val Glu Val Gln Leu Ser Gly Gly Ala Pro Trp Gly Phe Thr
1               5                   10                  15

Leu Lys Gly Gly Arg Glu His Gly Glu Pro Leu Val Ile Thr Lys Ile
                20                  25                  30

Glu Glu Gly Ser Lys Ala Ala Ala Val Asp Lys Leu Leu Ala Gly Asp
            35                  40                  45

Glu Ile Val Gly Ile Asn Asp Ile Gly Leu Ser Gly Phe Arg Gln Glu
        50                  55                  60

Ala Ile Cys Leu Val Lys Gly Ser His Lys Thr Leu Lys Leu Val Val
65                  70                  75                  80

Lys Arg Asn Ser Ser
                85

<210> SEQ ID NO 113
<211> LENGTH: 106
<212> TYPE: PRT
<213> ORGANISM: Human papillomavirus

<400> SEQUENCE: 113

Ser Val Gly His Val Arg Gly Pro Gly Pro Ser Val Gln His Thr Thr
1               5                   10                  15

Leu Asn Gly Asp Ser Leu Thr Ser Gln Leu Thr Leu Leu Gly Gly Asn
                20                  25                  30

Ala Arg Gly Ser Phe Val His Ser Val Lys Pro Gly Ser Leu Ala Glu
            35                  40                  45

Lys Ala Gly Leu Arg Glu Gly His Gln Leu Leu Leu Glu Gly Cys
        50                  55                  60

Ile Arg Gly Glu Arg Gln Ser Val Pro Leu Asp Thr Cys Thr Lys Glu
65                  70                  75                  80

Glu Ala His Trp Thr Ile Gln Arg Cys Ser Gly Pro Val Thr Leu His
                85                  90                  95

Tyr Lys Val Asn His Glu Gly Tyr Arg Lys
            100                 105

<210> SEQ ID NO 114
<211> LENGTH: 105
<212> TYPE: PRT
<213> ORGANISM: Human papillomavirus

<400> SEQUENCE: 114

Arg Arg Pro Ala Arg Arg Ile Leu Ser Gln Val Thr Met Leu Ala Phe
1               5                   10                  15

Gln Gly Asp Ala Leu Leu Glu Gln Ile Ser Val Ile Gly Gly Asn Leu
                20                  25                  30

Thr Gly Ile Phe Ile His Arg Val Thr Pro Gly Ser Ala Ala Asp Gln
            35                  40                  45
```

```
Met Ala Leu Arg Pro Gly Thr Gln Ile Val Met Val Asp Tyr Glu Ala
    50                  55                  60

Ser Glu Pro Leu Phe Lys Ala Val Leu Glu Asp Thr Thr Leu Glu Glu
65                  70                  75                  80

Ala Val Gly Leu Leu Arg Arg Val Asp Gly Phe Cys Cys Leu Ser Val
                85                  90                  95

Lys Val Asn Thr Asp Gly Tyr Lys Arg
                100                 105

<210> SEQ ID NO 115
<211> LENGTH: 100
<212> TYPE: PRT
<213> ORGANISM: Human papillomavirus

<400> SEQUENCE: 115

Ile Leu Ser Gln Val Thr Met Leu Ala Phe Gln Gly Asp Ala Leu Leu
1               5                   10                  15

Glu Gln Ile Ser Val Ile Gly Gly Asn Leu Thr Gly Ile Phe Ile His
                20                  25                  30

Arg Val Thr Pro Gly Ser Ala Ala Asp Gln Met Ala Leu Arg Pro Gly
            35                  40                  45

Thr Gln Ile Val Met Val Asp Tyr Glu Ala Ser Glu Pro Leu Phe Lys
    50                  55                  60

Ala Val Leu Glu Asp Thr Thr Leu Glu Glu Ala Val Gly Leu Leu Arg
65                  70                  75                  80

Arg Val Asp Gly Phe Cys Cys Leu Ser Val Lys Val Asn Thr Asp Gly
                85                  90                  95

Tyr Lys Arg Leu
            100

<210> SEQ ID NO 116
<211> LENGTH: 90
<212> TYPE: PRT
<213> ORGANISM: Human papillomavirus

<400> SEQUENCE: 116

Thr Arg Val Arg Leu Val Gln Phe Gln Lys Asn Thr Asp Glu Pro Met
1               5                   10                  15

Gly Ile Thr Leu Lys Met Asn Glu Leu Asn His Cys Ile Val Ala Arg
                20                  25                  30

Ile Met His Gly Gly Met Ile His Arg Gln Gly Thr Leu His Val Gly
            35                  40                  45

Asp Glu Ile Arg Glu Ile Asn Gly Ile Ser Val Ala Asn Gln Thr Val
    50                  55                  60

Glu Gln Leu Gln Lys Met Leu Arg Glu Met Arg Gly Ser Ile Thr Phe
65                  70                  75                  80

Lys Ile Val Pro Ser Tyr Arg Thr Gln Ser
                85                  90

<210> SEQ ID NO 117
<211> LENGTH: 88
<212> TYPE: PRT
<213> ORGANISM: Human papillomavirus

<400> SEQUENCE: 117

Leu Glu Gln Lys Ala Val Leu Glu Gln Val Gln Leu Asp Ser Pro Leu
1               5                   10                  15

Gly Leu Glu Ile His Thr Thr Ser Asn Cys Gln His Phe Val Ser Gln
```

```
                20                  25                  30
Val Asp Thr Gln Val Pro Thr Asp Ser Arg Leu Gln Ile Gln Pro Gly
            35                  40                  45
Asp Glu Val Val Gln Ile Asn Glu Gln Val Val Gly Trp Pro Arg
    50                  55                  60
Lys Asn Met Val Arg Glu Leu Leu Arg Glu Pro Ala Gly Leu Ser Leu
65                  70                  75                  80
Val Leu Lys Lys Ile Pro Ile Pro
                85

<210> SEQ ID NO 118
<211> LENGTH: 92
<212> TYPE: PRT
<213> ORGANISM: Human papillomavirus

<400> SEQUENCE: 118

Gln Arg Lys Leu Val Thr Val Glu Lys Gln Asp Asn Glu Thr Phe Gly
1               5                   10                  15
Phe Glu Ile Gln Ser Tyr Arg Pro Gln Asn Gln Asn Ala Cys Ser Ser
                20                  25                  30
Glu Met Phe Thr Leu Ile Cys Lys Ile Gln Glu Asp Ser Pro Ala His
            35                  40                  45
Cys Ala Gly Leu Gln Ala Gly Asp Val Leu Ala Asn Ile Asn Gly Val
    50                  55                  60
Ser Thr Glu Gly Phe Thr Tyr Lys Gln Val Val Asp Leu Ile Arg Ser
65                  70                  75                  80
Ser Gly Asn Leu Leu Thr Ile Glu Thr Leu Asn Gly
                85                  90

<210> SEQ ID NO 119
<211> LENGTH: 109
<212> TYPE: PRT
<213> ORGANISM: Human papillomavirus

<400> SEQUENCE: 119

Arg Cys Leu Ile Gln Thr Lys Gly Gln Arg Ser Met Asp Gly Tyr Pro
1               5                   10                  15
Glu Gln Phe Cys Val Arg Ile Glu Lys Asn Pro Gly Leu Gly Phe Ser
                20                  25                  30
Ile Ser Gly Gly Ile Ser Gly Gln Gly Asn Pro Phe Lys Pro Ser Asp
            35                  40                  45
Lys Gly Ile Phe Val Thr Arg Val Gln Pro Asp Gly Pro Ala Ser Asn
    50                  55                  60
Leu Leu Gln Pro Gly Asp Lys Ile Leu Gln Ala Asn Gly His Ser Phe
65                  70                  75                  80
Val His Met Glu His Glu Lys Ala Val Leu Leu Leu Lys Ser Phe Gln
                85                  90                  95
Asn Thr Val Asp Leu Val Ile Gly Arg Glu Leu Thr Val
                100                 105

<210> SEQ ID NO 120
<211> LENGTH: 97
<212> TYPE: PRT
<213> ORGANISM: Human papillomavirus

<400> SEQUENCE: 120

Pro Thr Ser Pro Glu Ile Gln Glu Leu Arg Gln Met Leu Gln Ala Pro
1               5                   10                  15
```

His Phe Lys Gly Ala Thr Ile Lys Arg His Glu Met Thr Gly Asp Ile
            20                  25                  30

Leu Val Ala Arg Ile Ile His Gly Gly Leu Ala Glu Arg Ser Gly Leu
        35                  40                  45

Leu Tyr Ala Gly Asp Lys Leu Val Glu Val Asn Gly Val Ser Val Glu
50                  55                  60

Gly Leu Asp Pro Glu Gln Val Ile His Ile Leu Ala Met Ser Arg Gly
65                  70                  75                  80

Thr Ile Met Phe Lys Val Val Pro Val Ser Asp Pro Val Asn Ser
                85                  90                  95

Ser

<210> SEQ ID NO 121
<211> LENGTH: 141
<212> TYPE: PRT
<213> ORGANISM: Human papillomavirus

<400> SEQUENCE: 121

Pro Thr Ser Pro Glu Ile Gln Glu Leu Arg Gln Met Leu Gln Ala Pro
1               5                   10                  15

His Phe Lys Ala Leu Leu Ser Ala His Asp Thr Ile Ala Gln Lys Asp
            20                  25                  30

Phe Glu Pro Leu Leu Pro Pro Leu Pro Asp Asn Ile Pro Glu Ser Glu
        35                  40                  45

Glu Ala Met Arg Ile Val Cys Leu Val Lys Asn Gln Gln Pro Leu Gly
50                  55                  60

Ala Thr Ile Lys Arg His Glu Met Thr Gly Asp Ile Leu Val Ala Arg
65                  70                  75                  80

Ile Ile His Gly Gly Leu Ala Glu Arg Ser Gly Leu Leu Tyr Ala Gly
            85                  90                  95

Asp Lys Leu Val Glu Val Asn Gly Val Ser Val Glu Gly Leu Asp Pro
        100                 105                 110

Glu Gln Val Ile His Ile Leu Ala Met Ser Arg Gly Thr Ile Met Phe
    115                 120                 125

Lys Val Val Pro Val Ser Asp Pro Val Asn Ser Ser
        130                 135                 140

<210> SEQ ID NO 122
<211> LENGTH: 101
<212> TYPE: PRT
<213> ORGANISM: Human papillomavirus

<400> SEQUENCE: 122

Ile Gln Val Asn Gly Thr Asp Ala Asp Tyr Glu Tyr Glu Glu Ile Thr
1               5                   10                  15

Leu Glu Arg Gly Asn Ser Gly Leu Gly Phe Ser Ile Ala Gly Gly Thr
            20                  25                  30

Asp Asn Pro His Ile Gly Asp Asp Ser Ser Ile Phe Ile Thr Lys Ile
        35                  40                  45

Ile Thr Gly Gly Ala Ala Ala Gln Asp Gly Arg Leu Arg Val Asn Asp
50                  55                  60

Cys Ile Leu Gln Val Asn Glu Val Asp Val Arg Asp Val Thr His Ser
65                  70                  75                  80

Lys Ala Val Glu Ala Leu Lys Glu Ala Gly Ser Ile Val Arg Leu Tyr
            85                  90                  95

```
Val Lys Arg Arg Asn
            100
```

<210> SEQ ID NO 123
<211> LENGTH: 95
<212> TYPE: PRT
<213> ORGANISM: Human papillomavirus

<400> SEQUENCE: 123

```
Ile Gln Leu Ile Lys Gly Pro Lys Gly Leu Gly Phe Ser Ile Ala Gly
1               5                   10                  15

Gly Val Gly Asn Gln His Ile Pro Gly Asp Asn Ser Ile Tyr Val Thr
            20                  25                  30

Lys Ile Ile Glu Gly Gly Ala Ala His Lys Asp Gly Lys Leu Gln Ile
        35                  40                  45

Gly Asp Lys Leu Leu Ala Val Asn Asn Val Cys Leu Glu Glu Val Thr
50                  55                  60

His Glu Glu Ala Val Thr Ala Leu Lys Asn Thr Ser Asp Phe Val Tyr
65                  70                  75                  80

Leu Lys Val Ala Lys Pro Thr Ser Met Tyr Met Asn Asp Gly Asn
                85                  90                  95
```

<210> SEQ ID NO 124
<211> LENGTH: 203
<212> TYPE: PRT
<213> ORGANISM: Human papillomavirus

<400> SEQUENCE: 124

```
Val Asn Gly Thr Asp Ala Asp Tyr Glu Tyr Glu Glu Ile Thr Leu Glu
1               5                   10                  15

Arg Gly Asn Ser Gly Leu Gly Phe Ser Ile Ala Gly Gly Thr Asp Asn
            20                  25                  30

Pro His Ile Gly Asp Asp Ser Ser Ile Phe Ile Thr Lys Ile Ile Thr
        35                  40                  45

Gly Gly Ala Ala Ala Gln Asp Gly Arg Leu Arg Val Asn Asp Cys Ile
50                  55                  60

Leu Gln Val Asn Glu Val Asp Val Arg Asp Val Thr His Ser Lys Ala
65                  70                  75                  80

Val Glu Ala Leu Lys Glu Ala Gly Ser Ile Val Arg Leu Tyr Val Lys
                85                  90                  95

Arg Arg Lys Pro Val Ser Glu Lys Ile Met Glu Ile Lys Leu Ile Lys
            100                 105                 110

Gly Pro Lys Gly Leu Gly Phe Ser Ile Ala Gly Gly Val Gly Asn Gln
        115                 120                 125

His Ile Pro Gly Asp Asn Ser Ile Tyr Val Thr Lys Ile Ile Glu Gly
    130                 135                 140

Gly Ala Ala His Lys Asp Gly Lys Leu Gln Ile Gly Asp Lys Leu Leu
145                 150                 155                 160

Ala Val Asn Asn Val Cys Leu Glu Glu Val Thr His Glu Glu Ala Val
                165                 170                 175

Thr Ala Leu Lys Asn Thr Ser Asp Phe Val Tyr Leu Lys Val Ala Lys
            180                 185                 190

Pro Thr Ser Met Tyr Met Asn Asp Gly Tyr Ala
        195                 200
```

<210> SEQ ID NO 125
<211> LENGTH: 85

```
<212> TYPE: PRT
<213> ORGANISM: Human papillomavirus

<400> SEQUENCE: 125

Ile Leu His Arg Gly Ser Thr Gly Leu Gly Phe Asn Ile Val Gly
1               5                   10                  15

Glu Asp Gly Glu Gly Ile Phe Ile Ser Phe Ile Leu Ala Gly Pro
            20                  25                  30

Ala Asp Leu Ser Gly Glu Leu Arg Lys Gly Asp Arg Ile Ile Ser Val
        35                  40                  45

Asn Ser Val Asp Leu Arg Ala Ala Ser His Glu Gln Ala Ala Ala
    50                  55                  60

Leu Lys Asn Ala Gly Gln Ala Val Thr Ile Val Ala Gln Tyr Arg Pro
65                  70                  75                  80

Glu Glu Tyr Ser Arg
                85

<210> SEQ ID NO 126
<211> LENGTH: 110
<212> TYPE: PRT
<213> ORGANISM: Human papillomavirus

<400> SEQUENCE: 126

Ile Glu Gly Arg Gly Ile Leu Glu Gly Glu Pro Arg Lys Val Leu
1               5                   10                  15

His Lys Gly Ser Thr Gly Leu Gly Phe Asn Ile Val Gly Gly Glu Asp
            20                  25                  30

Gly Glu Gly Ile Phe Val Ser Phe Ile Leu Ala Gly Gly Pro Ala Asp
        35                  40                  45

Leu Ser Gly Glu Leu Gln Arg Gly Asp Gln Ile Leu Ser Val Asn Gly
    50                  55                  60

Ile Asp Leu Arg Gly Ala Ser His Glu Gln Ala Ala Ala Ala Leu Lys
65                  70                  75                  80

Gly Ala Gly Gln Thr Val Thr Ile Ile Ala Gln His Gln Pro Glu Asp
                85                  90                  95

Tyr Ala Arg Phe Glu Ala Lys Ile His Asp Leu Asn Ser Ser
            100                 105                 110

<210> SEQ ID NO 127
<211> LENGTH: 101
<212> TYPE: PRT
<213> ORGANISM: Human papillomavirus

<400> SEQUENCE: 127

Ile Ser Tyr Val Asn Gly Thr Glu Ile Glu Tyr Glu Phe Glu Ile
1               5                   10                  15

Thr Leu Glu Arg Gly Asn Ser Gly Leu Gly Phe Ser Ile Ala Gly Gly
            20                  25                  30

Thr Asp Asn Pro His Ile Gly Asp Asp Pro Gly Ile Phe Ile Thr Lys
        35                  40                  45

Ile Ile Pro Gly Gly Ala Ala Ala Glu Asp Gly Arg Leu Arg Val Asn
    50                  55                  60

Asp Cys Ile Leu Arg Val Asn Glu Val Asp Val Ser Glu Val Ser His
65                  70                  75                  80

Ser Lys Ala Val Glu Ala Leu Lys Glu Ala Gly Ser Ile Val Arg Leu
                85                  90                  95

Tyr Val Arg Arg Arg
```

<210> SEQ ID NO 128
<211> LENGTH: 113
<212> TYPE: PRT
<213> ORGANISM: Human papillomavirus

<400> SEQUENCE: 128

```
Ile Pro Ile Leu Glu Thr Val Val Glu Ile Lys Leu Phe Lys Gly Pro
1               5                   10                  15

Lys Gly Leu Gly Phe Ser Ile Ala Gly Gly Val Gly Asn Gln His Ile
            20                  25                  30

Pro Gly Asp Asn Ser Ile Tyr Val Thr Lys Ile Ile Asp Gly Gly Ala
        35                  40                  45

Ala Gln Lys Asp Gly Arg Leu Gln Val Gly Asp Arg Leu Leu Met Val
    50                  55                  60

Asn Asn Tyr Ser Leu Glu Glu Val Thr His Glu Glu Ala Val Ala Ile
65                  70                  75                  80

Leu Lys Asn Thr Ser Glu Val Val Tyr Leu Lys Val Gly Lys Pro Thr
                85                  90                  95

Thr Ile Tyr Met Thr Asp Pro Tyr Gly Pro Pro Asn Ser Ser Leu Thr
            100                 105                 110

Asp
```

<210> SEQ ID NO 129
<211> LENGTH: 101
<212> TYPE: PRT
<213> ORGANISM: Human papillomavirus

<400> SEQUENCE: 129

```
Gly Ile Pro Tyr Val Glu Glu Pro Arg His Val Lys Val Gln Lys Gly
1               5                   10                  15

Ser Glu Pro Leu Gly Ile Ser Ile Val Ser Gly Glu Lys Gly Gly Ile
            20                  25                  30

Tyr Val Ser Lys Val Thr Val Gly Ser Ile Ala His Gln Ala Gly Leu
        35                  40                  45

Glu Tyr Gly Asp Gln Leu Leu Glu Phe Asn Gly Ile Asn Leu Arg Ser
    50                  55                  60

Ala Thr Glu Gln Gln Ala Arg Leu Ile Ile Gly Gln Gln Cys Asp Thr
65                  70                  75                  80

Ile Thr Ile Leu Ala Gln Tyr Asn Pro His Val His Gln Leu Arg Asn
                85                  90                  95

Ser Ser Leu Thr Asp
            100
```

<210> SEQ ID NO 130
<211> LENGTH: 103
<212> TYPE: PRT
<213> ORGANISM: Human papillomavirus

<400> SEQUENCE: 130

```
Gly Ile Leu Ala Gly Asp Ala Asn Lys Lys Thr Leu Glu Pro Arg Val
1               5                   10                  15

Val Phe Ile Lys Lys Ser Gln Leu Glu Leu Gly Val His Leu Cys Gly
            20                  25                  30

Gly Asn Leu His Gly Val Phe Val Ala Glu Val Glu Asp Asp Ser Pro
        35                  40                  45
```

Ala Lys Gly Pro Asp Gly Leu Val Pro Gly Asp Leu Ile Leu Glu Tyr
 50                  55                  60

Gly Ser Leu Asp Val Arg Asn Lys Thr Val Glu Glu Val Tyr Val Glu
 65                  70                  75                  80

Met Leu Lys Pro Arg Asp Gly Val Arg Leu Lys Val Gln Tyr Arg Pro
                 85                  90                  95

Glu Glu Phe Ile Val Thr Asp
            100

<210> SEQ ID NO 131
<211> LENGTH: 93
<212> TYPE: PRT
<213> ORGANISM: Human papillomavirus

<400> SEQUENCE: 131

Leu Asn Ile Val Thr Val Thr Leu Asn Met Glu Arg His His Phe Leu
 1               5                  10                  15

Gly Ile Ser Ile Val Gly Gln Ser Asn Asp Arg Gly Asp Gly Gly Ile
                20                  25                  30

Tyr Ile Gly Ser Ile Met Lys Gly Gly Ala Val Ala Ala Asp Gly Arg
            35                  40                  45

Ile Glu Pro Gly Asp Met Leu Leu Gln Val Asn Asp Val Asn Phe Glu
 50                  55                  60

Asn Met Ser Asn Asp Asp Ala Val Arg Val Leu Arg Glu Ile Val Ser
 65                  70                  75                  80

Gln Thr Gly Pro Ile Ser Leu Thr Val Ala Lys Cys Trp
                85                  90

<210> SEQ ID NO 132
<211> LENGTH: 100
<212> TYPE: PRT
<213> ORGANISM: Human papillomavirus

<400> SEQUENCE: 132

Leu Asn Ile Ile Thr Val Thr Leu Asn Met Glu Lys Tyr Asn Phe Leu
 1               5                  10                  15

Gly Ile Ser Ile Val Gly Gln Ser Asn Glu Arg Gly Asp Gly Gly Ile
                20                  25                  30

Tyr Ile Gly Ser Ile Met Lys Gly Gly Ala Val Ala Ala Asp Gly Arg
            35                  40                  45

Ile Glu Pro Gly Asp Met Leu Leu Gln Val Asn Asp Met Asn Phe Glu
 50                  55                  60

Asn Met Ser Asn Asp Asp Ala Val Arg Val Leu Arg Asp Ile Val His
 65                  70                  75                  80

Lys Pro Gly Pro Ile Val Leu Thr Val Ala Lys Cys Trp Asp Pro Ser
                85                  90                  95

Pro Gln Asn Ser
            100

<210> SEQ ID NO 133
<211> LENGTH: 95
<212> TYPE: PRT
<213> ORGANISM: Human papillomavirus

<400> SEQUENCE: 133

Ile Ile Thr Val Thr Leu Asn Met Glu Lys Tyr Asn Phe Leu Gly Ile
 1               5                  10                  15

Ser Ile Val Gly Gln Ser Asn Glu Arg Gly Asp Gly Gly Ile Tyr Ile

```
                20                  25                  30
Gly Ser Ile Met Lys Gly Gly Ala Val Ala Ala Asp Gly Arg Ile Glu
            35                  40                  45

Pro Gly Asp Met Leu Leu Gln Val Asn Glu Ile Asn Phe Glu Asn Met
        50                  55                  60

Ser Asn Asp Asp Ala Val Arg Val Leu Arg Glu Ile Val His Lys Pro
65                  70                  75                  80

Gly Pro Ile Thr Leu Thr Val Ala Lys Cys Trp Asp Pro Ser Pro
                85                  90                  95

<210> SEQ ID NO 134
<211> LENGTH: 98
<212> TYPE: PRT
<213> ORGANISM: Human papillomavirus

<400> SEQUENCE: 134

Gln Gln Arg Glu Leu Arg Pro Arg Leu Cys Thr Met Lys Lys Gly Pro
1               5                   10                  15

Ser Gly Tyr Gly Phe Asn Leu His Ser Asp Lys Ser Lys Pro Gly Gln
            20                  25                  30

Phe Ile Arg Ser Val Asp Pro Asp Ser Pro Ala Glu Ala Ser Gly Leu
        35                  40                  45

Arg Ala Gln Asp Arg Ile Val Glu Val Asn Gly Val Cys Met Glu Gly
    50                  55                  60

Lys Gln His Gly Asp Val Val Ser Ala Ile Arg Ala Gly Gly Asp Glu
65                  70                  75                  80

Thr Lys Leu Leu Val Val Asp Arg Glu Thr Asp Glu Phe Phe Lys Asn
                85                  90                  95

Ser Ser

<210> SEQ ID NO 135
<211> LENGTH: 155
<212> TYPE: PRT
<213> ORGANISM: Human papillomavirus

<400> SEQUENCE: 135

Gly Ile Gln Met Ser Ala Asp Ala Ala Gly Ala Pro Leu Pro Arg
1               5                   10                  15

Leu Cys Cys Leu Glu Lys Gly Pro Asn Gly Tyr Gly Phe His Leu His
            20                  25                  30

Gly Glu Lys Gly Lys Leu Gly Gln Tyr Ile Arg Leu Val Glu Pro Gly
        35                  40                  45

Ser Pro Ala Glu Lys Ala Gly Leu Leu Ala Gly Asp Arg Leu Val Glu
    50                  55                  60

Val Asn Gly Glu Asn Val Glu Lys Glu Thr His Gln Gln Val Val Ser
65                  70                  75                  80

Arg Ile Arg Ala Ala Leu Asn Ala Val Arg Leu Leu Val Val Asp Pro
                85                  90                  95

Glu Thr Asp Glu Gln Leu Gln Lys Leu Gly Val Gln Val Arg Glu Glu
            100                 105                 110

Leu Leu Arg Ala Gln Glu Ala Pro Gly Gln Ala Glu Pro Pro Ala Ala
        115                 120                 125

Ala Glu Val Gln Gly Ala Gly Asn Glu Asn Glu Pro Arg Glu Ala Asp
    130                 135                 140

Lys Ser His Pro Glu Gln Arg Glu Leu Arg Asn
145                 150                 155
```

<210> SEQ ID NO 136
<211> LENGTH: 243
<212> TYPE: PRT
<213> ORGANISM: Human papillomavirus

<400> SEQUENCE: 136

Gly Ile Gln Met Ser Ala Asp Ala Ala Ala Gly Ala Pro Leu Pro Arg
1               5                   10                  15

Leu Cys Cys Leu Glu Lys Gly Pro Asn Gly Tyr Gly Phe His Leu His
            20                  25                  30

Gly Glu Lys Gly Lys Leu Gly Gln Tyr Ile Arg Leu Val Glu Pro Gly
        35                  40                  45

Ser Pro Ala Glu Lys Ala Gly Leu Leu Ala Gly Asp Arg Leu Val Glu
    50                  55                  60

Val Asn Gly Glu Asn Val Glu Lys Glu Thr His Gln Gln Val Val Ser
65                  70                  75                  80

Arg Ile Arg Ala Ala Leu Asn Ala Val Arg Leu Leu Val Val Asp Pro
                85                  90                  95

Glu Thr Asp Glu Gln Leu Gln Lys Leu Gly Val Gln Val Arg Glu Glu
            100                 105                 110

Leu Leu Arg Ala Gln Glu Ala Pro Gly Gln Ala Glu Pro Pro Ala Ala
        115                 120                 125

Ala Glu Val Gln Gly Ala Gly Asn Glu Asn Glu Pro Arg Glu Ala Asp
    130                 135                 140

Lys Ser His Pro Glu Gln Arg Glu Leu Arg Pro Arg Leu Cys Thr Met
145                 150                 155                 160

Lys Lys Gly Pro Ser Gly Tyr Gly Phe Asn Leu His Ser Asp Lys Ser
                165                 170                 175

Lys Pro Gly Gln Phe Ile Arg Ser Val Asp Pro Asp Ser Pro Ala Glu
            180                 185                 190

Ala Ser Gly Leu Arg Ala Gln Asp Arg Ile Val Glu Val Asn Gly Val
        195                 200                 205

Cys Met Glu Gly Lys Gln His Gly Asp Val Val Ser Ala Ile Arg Ala
    210                 215                 220

Gly Gly Asp Glu Thr Lys Leu Leu Val Val Asp Arg Glu Thr Asp Glu
225                 230                 235                 240

Phe Phe Lys

<210> SEQ ID NO 137
<211> LENGTH: 155
<212> TYPE: PRT
<213> ORGANISM: Human papillomavirus

<400> SEQUENCE: 137

Gln Met Ser Ala Asp Ala Ala Ala Gly Ala Pro Leu Pro Arg Leu Cys
1               5                   10                  15

Cys Leu Glu Lys Gly Pro Asn Gly Tyr Gly Phe His Leu His Gly Glu
            20                  25                  30

Lys Gly Lys Leu Gly Gln Tyr Ile Arg Leu Val Glu Pro Gly Ser Pro
        35                  40                  45

Ala Glu Lys Ala Gly Leu Leu Ala Gly Asp Arg Leu Val Glu Val Asn
    50                  55                  60

Gly Glu Asn Val Glu Lys Glu Thr His Gln Gln Val Val Ser Arg Ile
65                  70                  75                  80

```
Arg Ala Ala Leu Asn Ala Val Arg Leu Leu Val Val Asp Pro Glu Thr
                85                  90                  95

Asp Glu Gln Leu Gln Lys Leu Gly Val Gln Val Arg Glu Glu Leu Leu
            100                 105                 110

Arg Ala Gln Glu Ala Pro Gly Gln Ala Glu Pro Pro Ala Ala Ala Glu
        115                 120                 125

Val Gln Gly Ala Gly Asn Glu Asn Glu Pro Arg Glu Ala Asp Lys Ser
    130                 135                 140

His Pro Glu Gln Arg Glu Leu Arg Asn Ser Ser
145                 150                 155

<210> SEQ ID NO 138
<211> LENGTH: 98
<212> TYPE: PRT
<213> ORGANISM: Human papillomavirus

<400> SEQUENCE: 138

Leu Thr Thr Gln Gln Ile Asp Leu Gln Gly Pro Gly Pro Trp Gly Phe
1               5                   10                  15

Arg Leu Val Gly Gly Lys Asp Phe Glu Gln Pro Leu Ala Ile Ser Arg
            20                  25                  30

Val Thr Pro Gly Ser Lys Ala Ala Leu Ala Asn Leu Cys Ile Gly Asp
        35                  40                  45

Val Ile Thr Ala Ile Asp Gly Glu Asn Thr Ser Asn Met Thr His Leu
    50                  55                  60

Glu Ala Gln Asn Arg Ile Lys Gly Cys Thr Asp Asn Leu Thr Leu Thr
65                  70                  75                  80

Val Ala Arg Ser Glu His Lys Val Trp Ser Pro Leu Val Thr Asn Ser
                85                  90                  95

Ser Trp

<210> SEQ ID NO 139
<211> LENGTH: 89
<212> TYPE: PRT
<213> ORGANISM: Human papillomavirus

<400> SEQUENCE: 139

Ile Phe Met Asp Ser Phe Lys Val Val Leu Glu Gly Pro Ala Pro Trp
1               5                   10                  15

Gly Phe Arg Leu Gln Gly Gly Lys Asp Phe Asn Val Pro Leu Ser Ile
            20                  25                  30

Ser Arg Leu Thr Pro Gly Gly Lys Ala Ala Gln Ala Gly Val Ala Val
        35                  40                  45

Gly Asp Trp Val Leu Ser Ile Asp Gly Glu Asn Ala Gly Ser Leu Thr
    50                  55                  60

His Ile Glu Ala Gln Asn Lys Ile Arg Ala Cys Gly Glu Arg Leu Ser
65                  70                  75                  80

Leu Gly Leu Ser Arg Ala Gln Pro Val
                85

<210> SEQ ID NO 140
<211> LENGTH: 100
<212> TYPE: PRT
<213> ORGANISM: Human papillomavirus

<400> SEQUENCE: 140

Gln Gly His Glu Leu Ala Lys Gln Glu Ile Arg Val Arg Val Glu Lys
1               5                   10                  15
```

-continued

```
Asp Pro Glu Leu Gly Phe Ser Ile Ser Gly Val Gly Gly Arg Gly
         20                  25                  30

Asn Pro Phe Arg Pro Asp Asp Gly Ile Phe Val Thr Arg Val Gln
         35                  40                  45

Pro Glu Gly Pro Ala Ser Lys Leu Leu Gln Pro Gly Asp Lys Ile Ile
 50                  55                  60

Gln Ala Asn Gly Tyr Ser Phe Ile Asn Ile Glu His Gly Gln Ala Val
 65                  70                  75                  80

Ser Leu Leu Lys Thr Phe Gln Asn Thr Val Glu Leu Ile Ile Val Arg
                 85                  90                  95

Glu Val Ser Ser
            100

<210> SEQ ID NO 141
<211> LENGTH: 107
<212> TYPE: PRT
<213> ORGANISM: Human papillomavirus

<400> SEQUENCE: 141

Lys Asn Pro Ser Gly Glu Leu Lys Thr Val Thr Leu Ser Lys Met Lys
  1               5                  10                  15

Gln Ser Leu Gly Ile Ser Ile Ser Gly Gly Ile Glu Ser Lys Val Gln
                 20                  25                  30

Pro Met Val Lys Ile Glu Lys Ile Phe Pro Gly Gly Ala Ala Phe Leu
             35                  40                  45

Ser Gly Ala Leu Gln Ala Gly Phe Glu Leu Val Ala Val Asp Gly Glu
 50                  55                  60

Asn Leu Glu Gln Val Thr His Gln Arg Ala Val Asp Thr Ile Arg Arg
 65                  70                  75                  80

Ala Tyr Arg Asn Lys Ala Arg Glu Pro Met Glu Leu Val Val Arg Val
                 85                  90                  95

Pro Gly Pro Ser Pro Arg Pro Ser Pro Ser Asp
            100                 105

<210> SEQ ID NO 142
<211> LENGTH: 97
<212> TYPE: PRT
<213> ORGANISM: Human papillomavirus

<400> SEQUENCE: 142

Glu Gly His Ser His Pro Arg Val Val Glu Leu Pro Lys Thr Glu Glu
  1               5                  10                  15

Gly Leu Gly Phe Asn Ile Met Gly Gly Lys Glu Gln Asn Ser Pro Ile
                 20                  25                  30

Tyr Ile Ser Arg Ile Ile Pro Gly Gly Ile Ala Asp Arg His Gly Gly
             35                  40                  45

Leu Lys Arg Gly Asp Gln Leu Leu Ser Val Asn Gly Val Ser Val Glu
 50                  55                  60

Gly Glu His His Glu Lys Ala Val Glu Leu Leu Lys Ala Ala Gln Gly
 65                  70                  75                  80

Lys Val Lys Leu Val Val Arg Tyr Thr Pro Lys Val Leu Glu Glu Met
                 85                  90                  95

Glu

<210> SEQ ID NO 143
<211> LENGTH: 88
```

```
<212> TYPE: PRT
<213> ORGANISM: Human papillomavirus

<400> SEQUENCE: 143

Pro Gly Ala Pro Tyr Ala Arg Lys Thr Phe Thr Ile Val Gly Asp Ala
1               5                   10                  15

Val Gly Trp Gly Phe Val Val Arg Gly Ser Lys Pro Cys His Ile Gln
            20                  25                  30

Ala Val Asp Pro Ser Gly Pro Ala Ala Ala Gly Met Lys Val Cys
        35                  40                  45

Gln Phe Val Val Ser Val Asn Gly Leu Asn Val Leu His Val Asp Tyr
    50                  55                  60

Arg Thr Val Ser Asn Leu Ile Leu Thr Gly Pro Arg Thr Ile Val Met
65                  70                  75                  80

Glu Val Met Glu Glu Leu Glu Cys
                85

<210> SEQ ID NO 144
<211> LENGTH: 97
<212> TYPE: PRT
<213> ORGANISM: Human papillomavirus

<400> SEQUENCE: 144

Gly Gln Tyr Gly Gly Glu Thr Val Lys Ile Val Arg Ile Glu Lys Ala
1               5                   10                  15

Arg Asp Ile Pro Leu Gly Ala Thr Val Arg Asn Glu Met Asp Ser Val
            20                  25                  30

Ile Ile Ser Arg Ile Val Lys Gly Gly Ala Ala Glu Lys Ser Gly Leu
        35                  40                  45

Leu His Glu Gly Asp Glu Val Leu Glu Ile Asn Gly Ile Glu Ile Arg
    50                  55                  60

Gly Lys Asp Val Asn Glu Val Phe Asp Leu Leu Ser Asp Met His Gly
65                  70                  75                  80

Thr Leu Thr Phe Val Leu Ile Pro Ser Gln Gln Ile Lys Pro Pro Pro
                85                  90                  95

Ala

<210> SEQ ID NO 145
<211> LENGTH: 104
<212> TYPE: PRT
<213> ORGANISM: Human papillomavirus

<400> SEQUENCE: 145

Lys Pro Ser Gln Ala Ser Gly His Phe Ser Val Glu Leu Val Arg Gly
1               5                   10                  15

Tyr Ala Gly Phe Gly Leu Thr Leu Gly Gly Gly Arg Asp Val Ala Gly
            20                  25                  30

Asp Thr Pro Leu Ala Val Arg Gly Leu Leu Lys Asp Gly Pro Ala Gln
        35                  40                  45

Arg Cys Gly Arg Leu Glu Val Gly Asp Leu Val Leu His Ile Asn Gly
    50                  55                  60

Glu Ser Thr Gln Gly Leu Thr His Ala Gln Ala Val Glu Arg Ile Arg
65                  70                  75                  80

Ala Gly Gly Pro Gln Leu His Leu Val Ile Arg Arg Pro Leu Glu Thr
                85                  90                  95

His Pro Gly Lys Pro Arg Gly Val
                100
```

```
<210> SEQ ID NO 146
<211> LENGTH: 101
<212> TYPE: PRT
<213> ORGANISM: Human papillomavirus

<400> SEQUENCE: 146

Pro Val Met Ser Gln Cys Ala Cys Leu Glu Glu Val His Leu Pro Asn
1               5                   10                  15

Ile Lys Pro Gly Glu Gly Leu Gly Met Tyr Ile Lys Ser Thr Tyr Asp
            20                  25                  30

Gly Leu His Val Ile Thr Gly Thr Thr Glu Asn Ser Pro Ala Asp Arg
        35                  40                  45

Ser Gln Lys Ile His Ala Gly Asp Glu Val Thr Gln Val Asn Gln Gln
    50                  55                  60

Thr Val Val Gly Trp Gln Leu Lys Asn Leu Val Lys Lys Leu Arg Glu
65                  70                  75                  80

Asn Pro Thr Gly Val Val Leu Leu Leu Lys Lys Arg Pro Thr Gly Ser
                85                  90                  95

Phe Asn Phe Thr Pro
            100

<210> SEQ ID NO 147
<211> LENGTH: 97
<212> TYPE: PRT
<213> ORGANISM: Human papillomavirus

<400> SEQUENCE: 147

Ile Asp Asp Glu Glu Asp Ser Val Lys Ile Ile Arg Leu Val Lys Asn
1               5                   10                  15

Arg Glu Pro Leu Gly Ala Thr Ile Lys Lys Asp Glu Gln Thr Gly Ala
            20                  25                  30

Ile Ile Val Ala Arg Ile Met Arg Gly Gly Ala Ala Asp Arg Ser Gly
        35                  40                  45

Leu Ile His Val Gly Asp Glu Leu Arg Glu Val Asn Gly Ile Pro Val
    50                  55                  60

Glu Asp Lys Arg Pro Glu Glu Ile Gln Ile Leu Ala Gln Ser Gln
65                  70                  75                  80

Gly Ala Ile Thr Phe Lys Ile Ile Pro Gly Ser Lys Glu Glu Thr Pro
                85                  90                  95

Ser

<210> SEQ ID NO 148
<211> LENGTH: 452
<212> TYPE: PRT
<213> ORGANISM: Human papillomavirus

<400> SEQUENCE: 148

Met Gly Ser Ser Gln Ser Val Glu Ile Pro Gly Gly Gly Thr Glu Gly
1               5                   10                  15

Tyr His Val Leu Arg Val Gln Glu Asn Ser Pro Gly His Arg Ala Gly
            20                  25                  30

Leu Glu Pro Phe Phe Asp Phe Ile Val Ser Ile Asn Gly Ser Arg Leu
        35                  40                  45

Asn Lys Asp Asn Asp Thr Leu Lys Asp Leu Leu Lys Ala Asn Val Glu
    50                  55                  60

Lys Pro Val Lys Met Leu Ile Tyr Ser Ser Lys Thr Leu Glu Leu Arg
```

-continued

```
                65                  70                  75                  80
Glu Thr Ser Val Thr Pro Ser Asn Leu Trp Gly Gly Gln Gly Leu Leu
                    85                  90                  95
Gly Val Ser Ile Arg Phe Cys Ser Phe Asp Gly Ala Asn Glu Asn Val
                    100                 105                 110
Trp His Val Leu Glu Val Glu Ser Asn Ser Pro Ala Ala Leu Ala Gly
                    115                 120                 125
Leu Arg Pro His Ser Asp Tyr Ile Ile Gly Ala Asp Thr Val Met Asn
                    130                 135                 140
Glu Ser Glu Asp Leu Phe Ser Leu Ile Glu Thr His Glu Ala Lys Pro
145                 150                 155                 160
Leu Lys Leu Tyr Val Tyr Asn Thr Asp Thr Asp Asn Cys Arg Glu Val
                    165                 170                 175
Ile Ile Thr Pro Asn Ser Ala Trp Gly Gly Glu Gly Ser Leu Gly Cys
                    180                 185                 190
Gly Ile Gly Tyr Gly Tyr Leu His Arg Ile Pro Thr Arg Pro Phe Glu
                    195                 200                 205
Glu Gly Lys Lys Ile Ser Leu Pro Gly Gln Met Ala Gly Thr Pro Ile
                    210                 215                 220
Thr Pro Leu Lys Asp Gly Phe Thr Glu Val Gln Leu Ser Ser Val Asn
225                 230                 235                 240
Pro Pro Ser Leu Ser Pro Gly Thr Thr Gly Ile Glu Gln Ser Leu
                    245                 250                 255
Thr Gly Leu Ser Ile Ser Ser Thr Pro Pro Ala Val Ser Ser Val Leu
                    260                 265                 270
Ser Thr Gly Val Pro Thr Val Pro Leu Leu Pro Pro Gln Val Asn Gln
                    275                 280                 285
Ser Leu Thr Ser Val Pro Met Asn Pro Ala Thr Thr Leu Pro Gly
                    290                 295                 300
Leu Met Pro Leu Pro Ala Gly Leu Pro Asn Leu Pro Asn Leu Asn Leu
305                 310                 315                 320
Asn Leu Pro Ala Pro His Ile Met Pro Gly Val Gly Leu Pro Glu Leu
                    325                 330                 335
Val Asn Pro Gly Leu Pro Pro Leu Pro Ser Met Pro Pro Arg Asn Leu
                    340                 345                 350
Pro Gly Ile Ala Pro Leu Pro Leu Pro Ser Glu Phe Leu Pro Ser Phe
                    355                 360                 365
Pro Leu Val Pro Glu Ser Ser Ser Ala Ala Ser Ser Gly Glu Leu Leu
                    370                 375                 380
Ser Ser Leu Pro Pro Thr Ser Asn Ala Pro Ser Asp Pro Ala Thr Thr
385                 390                 395                 400
Thr Ala Lys Ala Asp Ala Ala Ser Ser Leu Thr Val Asp Val Thr Pro
                    405                 410                 415
Pro Thr Ala Lys Ala Pro Thr Thr Val Glu Asp Arg Val Gly Asp Ser
                    420                 425                 430
Thr Pro Val Ser Glu Lys Pro Val Ser Ala Ala Val Asp Ala Asn Ala
                    435                 440                 445
Ser Glu Ser Pro
        450

<210> SEQ ID NO 149
<211> LENGTH: 97
<212> TYPE: PRT
<213> ORGANISM: Human papillomavirus
```

<400> SEQUENCE: 149

Asn Glu Asn Val Trp His Val Leu Glu Val Glu Ser Asn Ser Pro Ala
1               5                   10                  15

Ala Leu Ala Gly Leu Arg Pro His Ser Asp Tyr Ile Ile Gly Ala Asp
            20                  25                  30

Thr Val Met Asn Glu Ser Glu Asp Leu Phe Ser Leu Ile Glu Thr His
        35                  40                  45

Glu Ala Lys Pro Leu Lys Leu Tyr Val Tyr Asn Thr Asp Thr Asp Asn
    50                  55                  60

Cys Arg Glu Val Ile Ile Thr Pro Asn Ser Ala Trp Gly Gly Glu Gly
65                  70                  75                  80

Ser Leu Gly Cys Gly Ile Gly Tyr Gly Tyr Leu His Arg Ile Pro Thr
                85                  90                  95

Arg

<210> SEQ ID NO 150
<211> LENGTH: 110
<212> TYPE: PRT
<213> ORGANISM: Human papillomavirus

<400> SEQUENCE: 150

Met Gly Ser Ser Gln Ser Val Glu Ile Pro Gly Gly Gly Thr Glu Gly
1               5                   10                  15

Tyr His Val Leu Arg Val Gln Glu Asn Ser Pro Gly His Arg Ala Gly
            20                  25                  30

Leu Glu Pro Phe Phe Asp Phe Val Ser Ile Asn Gly Ser Arg Leu
        35                  40                  45

Asn Lys Asp Asn Asp Thr Leu Lys Asp Leu Leu Lys Ala Asn Val Glu
    50                  55                  60

Lys Pro Val Lys Met Leu Ile Tyr Ser Ser Lys Thr Leu Glu Leu Arg
65                  70                  75                  80

Glu Thr Ser Val Thr Pro Ser Asn Leu Trp Gly Gln Gly Leu Leu
                85                  90                  95

Gly Val Ser Ile Arg Phe Cys Ser Phe Asp Gly Ala Asn Glu
            100                 105                 110

<210> SEQ ID NO 151
<211> LENGTH: 99
<212> TYPE: PRT
<213> ORGANISM: Human papillomavirus

<400> SEQUENCE: 151

Arg Ala Ser Glu Gln Val Trp His Val Leu Asp Val Glu Pro Ser Ser
1               5                   10                  15

Pro Ala Ala Leu Ala Gly Leu Arg Pro Tyr Thr Asp Tyr Val Val Gly
            20                  25                  30

Ser Asp Gln Ile Leu Gln Glu Ser Glu Asp Phe Phe Thr Leu Ile Glu
        35                  40                  45

Ser His Glu Gly Lys Pro Leu Lys Leu Met Val Tyr Asn Ser Lys Ser
    50                  55                  60

Asp Ser Cys Arg Glu Val Thr Val Thr Pro Asn Ala Ala Trp Gly Gly
65                  70                  75                  80

Glu Gly Ser Leu Gly Cys Gly Ile Gly Tyr Gly Tyr Leu His Arg Ile
                85                  90                  95

Pro Thr Gln

<210> SEQ ID NO 152
<211> LENGTH: 110
<212> TYPE: PRT
<213> ORGANISM: Human papillomavirus

<400> SEQUENCE: 152

Met Gly Leu Gly Val Ser Ala Glu Gln Pro Ala Gly Gly Ala Glu Gly
1               5                   10                  15

Phe His Leu His Gly Val Gln Glu Asn Ser Pro Ala Gln Gln Ala Gly
            20                  25                  30

Leu Glu Pro Tyr Phe Asp Phe Ile Ile Thr Ile Gly His Ser Arg Leu
        35                  40                  45

Asn Lys Glu Asn Asp Thr Leu Lys Ala Leu Leu Lys Ala Asn Val Glu
    50                  55                  60

Lys Pro Val Lys Leu Glu Val Phe Asn Met Lys Thr Met Arg Val Arg
65                  70                  75                  80

Glu Val Glu Val Val Pro Ser Asn Met Trp Gly Gly Gln Gly Leu Leu
                85                  90                  95

Gly Ala Ser Val Arg Phe Cys Ser Phe Arg Arg Ala Ser Glu
            100                 105                 110

<210> SEQ ID NO 153
<211> LENGTH: 440
<212> TYPE: PRT
<213> ORGANISM: Human papillomavirus

<400> SEQUENCE: 153

Met Gly Leu Gly Val Ser Ala Glu Gln Pro Ala Gly Gly Ala Glu Gly
1               5                   10                  15

Phe His Leu His Gly Val Gln Glu Asn Ser Pro Ala Gln Gln Ala Gly
            20                  25                  30

Leu Glu Pro Tyr Phe Asp Phe Ile Ile Thr Ile Gly His Ser Arg Leu
        35                  40                  45

Asn Lys Glu Asn Asp Thr Leu Lys Ala Leu Leu Lys Ala Asn Val Glu
    50                  55                  60

Lys Pro Val Lys Leu Glu Val Phe Asn Met Lys Thr Met Arg Val Arg
65                  70                  75                  80

Glu Val Glu Val Val Pro Ser Asn Met Trp Gly Gly Gln Gly Leu Leu
                85                  90                  95

Gly Ala Ser Val Arg Phe Cys Ser Phe Arg Arg Ala Ser Glu Gln Val
            100                 105                 110

Trp His Val Leu Asp Val Glu Pro Ser Ser Pro Ala Ala Leu Ala Gly
        115                 120                 125

Leu Arg Pro Tyr Thr Asp Tyr Val Val Gly Ser Asp Gln Ile Leu Gln
    130                 135                 140

Glu Ser Glu Asp Phe Phe Thr Leu Ile Glu Ser His Glu Gly Lys Pro
145                 150                 155                 160

Leu Lys Leu Met Val Tyr Asn Ser Lys Ser Asp Ser Cys Arg Glu Val
                165                 170                 175

Thr Val Thr Pro Asn Ala Ala Trp Gly Gly Glu Gly Ser Leu Gly Cys
            180                 185                 190

Gly Ile Gly Tyr Gly Tyr Leu His Arg Ile Pro Thr Gln Pro Pro Ser
        195                 200                 205

Tyr His Lys Lys Pro Pro Gly Thr Pro Pro Ser Ala Leu Pro Leu
    210                 215                 220

Gly Ala Pro Pro Pro Asp Ala Leu Pro Pro Gly Pro Thr Pro Glu Asp
225                 230                 235                 240

Ser Pro Ser Leu Glu Thr Gly Ser Arg Gln Ser Asp Tyr Met Glu Ala
            245                 250                 255

Leu Leu Gln Ala Pro Gly Ser Ser Met Glu Asp Pro Leu Pro Gly Pro
            260                 265                 270

Gly Ser Pro Ser His Ser Ala Pro Asp Pro Asp Gly Leu Pro His Phe
            275                 280                 285

Met Glu Thr Pro Leu Gln Pro Pro Pro Val Gln Arg Val Met Asp
290                 295                 300

Pro Gly Phe Leu Asp Val Ser Gly Ile Ser Leu Leu Asp Asn Ser Asn
305                 310                 315                 320

Ala Ser Val Trp Pro Ser Leu Pro Ser Ser Thr Glu Leu Thr Thr Thr
            325                 330                 335

Ala Val Ser Thr Ser Gly Pro Glu Asp Ile Cys Ser Ser Ser Ser Ser
            340                 345                 350

His Glu Arg Gly Gly Glu Ala Thr Trp Ser Gly Ser Glu Phe Glu Val
            355                 360                 365

Ser Phe Leu Asp Ser Pro Gly Ala Gln Ala Gln Ala Asp His Leu Pro
            370                 375                 380

Gln Leu Thr Leu Pro Asp Ser Leu Thr Ser Ala Ala Ser Pro Glu Asp
385                 390                 395                 400

Gly Leu Ser Ala Glu Leu Leu Glu Ala Gln Ala Glu Glu Pro Ala
            405                 410                 415

Ser Thr Glu Gly Leu Asp Thr Gly Thr Glu Ala Glu Gly Leu Asp Ser
            420                 425                 430

Gln Ala Gln Ile Ser Thr Thr Glu
            435                 440

<210> SEQ ID NO 154
<211> LENGTH: 90
<212> TYPE: PRT
<213> ORGANISM: Human papillomavirus

<400> SEQUENCE: 154

Ile Tyr Thr Val Glu Leu Lys Arg Tyr Gly Gly Pro Leu Gly Ile Thr
1               5                   10                  15

Ile Ser Gly Thr Glu Glu Pro Phe Asp Pro Ile Ile Ile Ser Ser Leu
                20                  25                  30

Thr Lys Gly Gly Leu Ala Glu Arg Thr Gly Ala Ile His Ile Gly Asp
            35                  40                  45

Arg Ile Leu Ala Ile Asn Ser Ser Ser Leu Lys Gly Lys Pro Leu Ser
50                  55                  60

Glu Ala Ile His Leu Leu Gln Met Ala Gly Glu Thr Val Thr Leu Lys
65                  70                  75                  80

Ile Lys Lys Gln Thr Asp Ala Gln Ser Ala
                85                  90

<210> SEQ ID NO 155
<211> LENGTH: 83
<212> TYPE: PRT
<213> ORGANISM: Human papillomavirus

<400> SEQUENCE: 155

Val Val Glu Leu Met Lys Lys Glu Gly Thr Thr Leu Gly Leu Thr Val
1               5                   10                  15

-continued

```
Ser Gly Gly Ile Asp Lys Asp Gly Lys Pro Arg Val Ser Asn Leu Arg
            20                  25                  30

Gln Gly Gly Ile Ala Ala Arg Ser Asp Gln Leu Asp Val Gly Asp Tyr
        35                  40                  45

Ile Lys Ala Val Asn Gly Ile Asn Leu Ala Lys Phe Arg His Asp Glu
 50                  55                  60

Ile Ile Ser Leu Leu Lys Asn Val Gly Glu Arg Val Val Leu Glu Val
65                  70                  75                  80

Glu Tyr Glu

<210> SEQ ID NO 156
<211> LENGTH: 106
<212> TYPE: PRT
<213> ORGANISM: Human papillomavirus

<400> SEQUENCE: 156

His Val Ala Thr Ala Ser Gly Pro Leu Leu Val Glu Val Ala Lys Thr
 1               5                  10                  15

Pro Gly Ala Ser Leu Gly Val Ala Leu Thr Thr Ser Met Cys Cys Asn
            20                  25                  30

Lys Gln Val Ile Val Ile Asp Lys Ile Lys Ser Ala Ser Ile Ala Asp
        35                  40                  45

Arg Cys Gly Ala Leu His Val Gly Asp His Ile Leu Ser Ile Asp Gly
 50                  55                  60

Thr Ser Met Glu Tyr Cys Thr Leu Ala Glu Ala Thr Gln Phe Leu Ala
65                  70                  75                  80

Asn Thr Thr Asp Gln Val Lys Leu Glu Ile Leu Pro His His Gln Thr
                85                  90                  95

Arg Leu Ala Leu Lys Gly Pro Asn Ser Ser
            100                 105

<210> SEQ ID NO 157
<211> LENGTH: 95
<212> TYPE: PRT
<213> ORGANISM: Human papillomavirus

<400> SEQUENCE: 157

Ile Met Ser Pro Thr Pro Val Glu Leu His Lys Val Thr Leu Tyr Lys
 1               5                  10                  15

Asp Ser Asp Met Glu Asp Phe Gly Phe Ser Val Ala Asp Gly Leu Leu
            20                  25                  30

Glu Lys Gly Val Tyr Val Lys Asn Ile Arg Pro Ala Gly Pro Gly Asp
        35                  40                  45

Leu Gly Gly Leu Lys Pro Tyr Asp Arg Leu Leu Gln Val Asn His Val
 50                  55                  60

Arg Thr Arg Asp Phe Asp Cys Cys Leu Val Val Pro Leu Ile Ala Glu
65                  70                  75                  80

Ser Gly Asn Lys Leu Asp Leu Val Ile Ser Arg Asn Pro Leu Ala
                85                  90                  95

<210> SEQ ID NO 158
<211> LENGTH: 90
<212> TYPE: PRT
<213> ORGANISM: Human papillomavirus

<400> SEQUENCE: 158

Ile Tyr Thr Val Glu Leu Lys Arg Tyr Gly Gly Pro Leu Gly Ile Thr
 1               5                  10                  15
```

```
                1               5                   10                  15
Ile Ser Gly Thr Glu Glu Pro Phe Asp Pro Ile Ile Ile Ser Ser Leu
                20                  25                  30

Thr Lys Gly Gly Leu Ala Glu Arg Thr Gly Ala Ile His Ile Gly Asp
            35                  40                  45

Arg Ile Leu Ala Ile Asn Ser Ser Leu Lys Gly Lys Pro Leu Ser
 50                  55                  60

Glu Ala Ile His Leu Leu Gln Met Ala Gly Glu Thr Val Thr Leu Lys
 65                  70                  75                  80

Ile Lys Lys Gln Thr Asp Ala Gln Ser Ala
                85                  90
```

<210> SEQ ID NO 159
<211> LENGTH: 95
<212> TYPE: PRT
<213> ORGANISM: Human papillomavirus

<400> SEQUENCE: 159

```
Ile Met Ser Pro Thr Pro Val Glu Leu His Lys Val Thr Leu Tyr Lys
 1               5                   10                  15

Asp Ser Asp Met Glu Asp Phe Gly Phe Ser Val Ala Asp Gly Leu Leu
                20                  25                  30

Glu Lys Gly Val Tyr Val Lys Asn Ile Arg Pro Ala Gly Pro Gly Asp
            35                  40                  45

Leu Gly Gly Leu Lys Pro Tyr Asp Arg Leu Leu Gln Val Asn His Val
 50                  55                  60

Arg Thr Arg Asp Phe Asp Cys Cys Leu Val Val Pro Leu Ile Ala Glu
 65                  70                  75                  80

Ser Gly Asn Lys Leu Asp Leu Val Ile Ser Arg Asn Pro Leu Ala
                85                  90                  95
```

<210> SEQ ID NO 160
<211> LENGTH: 88
<212> TYPE: PRT
<213> ORGANISM: Human papillomavirus

<400> SEQUENCE: 160

```
Ser Arg Gly Cys Glu Thr Arg Glu Leu Ala Leu Pro Arg Asp Gly Gln
 1               5                   10                  15

Gly Arg Leu Gly Phe Glu Val Asp Ala Glu Gly Phe Val Thr His Val
                20                  25                  30

Glu Arg Phe Thr Phe Ala Glu Thr Ala Gly Leu Arg Pro Gly Ala Arg
            35                  40                  45

Leu Leu Arg Val Cys Gly Gln Thr Leu Pro Ser Leu Arg Pro Glu Ala
 50                  55                  60

Ala Ala Gln Leu Leu Arg Ser Ala Pro Lys Val Cys Val Thr Val Leu
 65                  70                  75                  80

Pro Pro Asp Glu Ser Gly Arg Pro
                85
```

<210> SEQ ID NO 161
<211> LENGTH: 108
<212> TYPE: PRT
<213> ORGANISM: Human papillomavirus

<400> SEQUENCE: 161

```
Cys Ser Val Met Ile Phe Glu Val Val Glu Gln Ala Gly Ala Ile Ile
 1               5                   10                  15
```

Leu Glu Asp Gly Gln Glu Leu Asp Ser Trp Tyr Val Ile Leu Asn Gly
            20                  25                  30

Thr Val Glu Ile Ser His Pro Asp Gly Lys Val Glu Asn Leu Phe Met
        35                  40                  45

Gly Asn Ser Phe Gly Ile Thr Pro Thr Leu Asp Lys Gln Tyr Met His
 50                  55                  60

Gly Ile Val Arg Thr Lys Val Asp Asp Cys Gln Phe Val Cys Ile Ala
65                  70                  75                  80

Gln Gln Asp Tyr Trp Arg Ile Leu Asn His Val Glu Lys Asn Thr His
                85                  90                  95

Lys Val Glu Glu Glu Gly Glu Ile Val Met Val His
            100                 105

<210> SEQ ID NO 162
<211> LENGTH: 82
<212> TYPE: PRT
<213> ORGANISM: Human papillomavirus

<400> SEQUENCE: 162

Pro Arg Glu Thr Val Lys Ile Pro Asp Ser Ala Asp Gly Leu Gly Phe
1               5                   10                  15

Gln Ile Arg Gly Phe Gly Pro Ser Val Val His Ala Val Gly Arg Gly
            20                  25                  30

Thr Val Ala Ala Ala Gly Leu His Pro Gly Gln Cys Ile Ile Lys
        35                  40                  45

Val Asn Gly Ile Asn Val Ser Lys Glu Thr His Ala Ser Val Ile Ala
 50                  55                  60

His Val Thr Ala Cys Arg Lys Tyr Arg Arg Pro Thr Lys Gln Asp Ser
65                  70                  75                  80

Ile Gln

<210> SEQ ID NO 163
<211> LENGTH: 89
<212> TYPE: PRT
<213> ORGANISM: Human papillomavirus

<400> SEQUENCE: 163

Leu Glu Asn Val Ile Ala Lys Ser Leu Leu Ile Lys Ser Asn Glu Gly
1               5                   10                  15

Ser Tyr Gly Phe Gly Leu Glu Asp Lys Asn Lys Val Pro Ile Ile Lys
            20                  25                  30

Leu Val Glu Lys Gly Ser Asn Ala Glu Met Ala Gly Met Glu Val Gly
        35                  40                  45

Lys Lys Ile Phe Ala Ile Asn Gly Asp Leu Val Phe Met Arg Pro Phe
 50                  55                  60

Asn Glu Val Asp Cys Phe Leu Lys Ser Cys Leu Asn Ser Arg Lys Pro
65                  70                  75                  80

Leu Arg Val Leu Val Ser Thr Lys Pro
                85

<210> SEQ ID NO 164
<211> LENGTH: 100
<212> TYPE: PRT
<213> ORGANISM: Human papillomavirus

<400> SEQUENCE: 164

Glu Asp Phe Cys Tyr Val Phe Thr Val Glu Leu Glu Arg Gly Pro Ser

```
                1               5                   10                  15
        Gly Leu Gly Met Gly Leu Ile Asp Gly Met His Thr His Leu Gly Ala
                        20                  25                  30

Pro Gly Leu Tyr Ile Gln Thr Leu Leu Pro Gly Ser Pro Ala Ala Ala
                        35                  40                  45

Asp Gly Arg Leu Ser Leu Gly Asp Arg Ile Leu Glu Val Asn Gly Ser
                    50                  55                  60

Ser Leu Leu Gly Leu Gly Tyr Leu Arg Ala Val Asp Leu Ile Arg His
        65                  70                  75                  80

Gly Gly Lys Lys Met Arg Phe Leu Val Ala Lys Ser Asp Val Glu Thr
                        85                  90                  95

Ala Lys Lys Ile
                    100

<210> SEQ ID NO 165
<211> LENGTH: 91
<212> TYPE: PRT
<213> ORGANISM: Human papillomavirus

<400> SEQUENCE: 165

Ile Tyr Leu Glu Ala Phe Leu Glu Gly Gly Ala Pro Trp Gly Phe Thr
        1               5                   10                  15

Leu Lys Gly Gly Leu Glu His Gly Glu Pro Leu Ile Ile Ser Lys Val
                        20                  25                  30

Glu Glu Gly Gly Lys Ala Asp Thr Leu Ser Ser Lys Leu Gln Ala Gly
                        35                  40                  45

Asp Glu Val Val His Ile Asn Glu Val Thr Leu Ser Ser Ser Arg Lys
                    50                  55                  60

Glu Ala Val Ser Leu Val Lys Gly Ser Tyr Lys Thr Leu Arg Leu Val
        65                  70                  75                  80

Val Arg Arg Asp Val Cys Thr Asp Pro Gly His
                        85                  90

<210> SEQ ID NO 166
<211> LENGTH: 100
<212> TYPE: PRT
<213> ORGANISM: Human papillomavirus

<400> SEQUENCE: 166

Asn Asn Glu Leu Thr Gln Phe Leu Pro Arg Thr Ile Thr Leu Lys Lys
        1               5                   10                  15

Pro Pro Gly Ala Gln Leu Gly Phe Asn Ile Arg Gly Gly Lys Ala Ser
                        20                  25                  30

Gln Leu Gly Ile Phe Ile Ser Lys Val Ile Pro Asp Ser Asp Ala His
                        35                  40                  45

Arg Ala Gly Leu Gln Glu Gly Asp Gln Val Leu Ala Val Asn Asp Val
                    50                  55                  60

Asp Phe Gln Asp Ile Glu His Ser Lys Ala Val Glu Ile Leu Lys Thr
        65                  70                  75                  80

Ala Arg Glu Ile Ser Met Arg Val Arg Phe Phe Pro Tyr Asn Tyr His
                        85                  90                  95

Arg Gln Lys Glu
                    100

<210> SEQ ID NO 167
<211> LENGTH: 107
<212> TYPE: PRT
```

<213> ORGANISM: Human papillomavirus

<400> SEQUENCE: 167

Phe Leu Thr Glu Phe Gln Asp Lys Gln Ile Lys Asp Trp Lys Lys Arg
1               5                   10                  15

Phe Ile Gly Ile Arg Met Arg Thr Ile Thr Pro Ser Leu Val Asp Glu
                20                  25                  30

Leu Lys Ala Ser Asn Pro Asp Phe Pro Glu Val Ser Ser Gly Ile Tyr
            35                  40                  45

Val Gln Glu Val Ala Pro Asn Ser Pro Ser Gln Arg Gly Gly Ile Gln
        50                  55                  60

Asp Gly Asp Ile Ile Val Lys Val Asn Gly Arg Pro Leu Val Asp Ser
65                  70                  75                  80

Ser Glu Leu Gln Glu Ala Val Leu Thr Glu Ser Pro Leu Leu Leu Glu
                85                  90                  95

Val Arg Arg Gly Asn Asp Asp Leu Leu Phe Ser
            100                 105

<210> SEQ ID NO 168
<211> LENGTH: 94
<212> TYPE: PRT
<213> ORGANISM: Human papillomavirus

<400> SEQUENCE: 168

Asn Lys Lys Tyr Leu Gly Leu Gln Met Leu Ser Leu Thr Val Pro Leu
1               5                   10                  15

Ser Glu Glu Leu Lys Met His Tyr Pro Asp Phe Pro Asp Val Ser Ser
                20                  25                  30

Gly Val Tyr Val Cys Lys Val Val Glu Gly Thr Ala Ala Gln Ser Ser
            35                  40                  45

Gly Leu Arg Asp His Asp Val Ile Val Asn Ile Asn Gly Lys Pro Ile
        50                  55                  60

Thr Thr Thr Thr Asp Val Val Lys Ala Leu Asp Ser Asp Ser Leu Ser
65                  70                  75                  80

Met Ala Val Leu Arg Gly Lys Asp Asn Leu Leu Leu Thr Val
                85                  90

<210> SEQ ID NO 169
<211> LENGTH: 111
<212> TYPE: PRT
<213> ORGANISM: Human papillomavirus

<400> SEQUENCE: 169

Pro Gly Ser Asp Ser Ser Leu Phe Glu Thr Tyr Asn Val Glu Leu Val
1               5                   10                  15

Arg Lys Asp Gly Gln Ser Leu Gly Ile Arg Ile Val Gly Tyr Val Gly
                20                  25                  30

Thr Ser His Thr Gly Glu Ala Ser Gly Ile Tyr Val Lys Ser Ile Ile
            35                  40                  45

Pro Gly Ser Ala Ala Tyr His Asn Gly His Ile Gln Val Asn Asp Lys
        50                  55                  60

Ile Val Ala Val Asp Gly Val Asn Ile Gln Gly Phe Ala Asn His Asp
65                  70                  75                  80

Val Val Glu Val Leu Arg Asn Ala Gly Gln Val Val His Leu Thr Leu
                85                  90                  95

Val Arg Arg Lys Thr Ser Ser Thr Ser Arg Ile His Arg Asp
            100                 105                 110

<210> SEQ ID NO 170
<211> LENGTH: 93
<212> TYPE: PRT
<213> ORGANISM: Human papillomavirus

<400> SEQUENCE: 170

Pro Ala Thr Cys Pro Ile Val Pro Gly Gln Glu Met Ile Ile Glu Ile
1               5                   10                  15

Ser Lys Gly Arg Ser Gly Leu Gly Leu Ser Ile Val Gly Gly Lys Asp
            20                  25                  30

Thr Pro Leu Asn Ala Ile Val Ile His Glu Val Tyr Glu Glu Gly Ala
        35                  40                  45

Ala Ala Arg Asp Gly Arg Leu Trp Ala Gly Asp Gln Ile Leu Glu Val
    50                  55                  60

Asn Gly Val Asp Leu Arg Asn Ser Ser His Glu Ala Ile Thr Ala
65                  70                  75                  80

Leu Arg Gln Thr Pro Gln Lys Val Arg Leu Val Val Tyr
                85                  90

<210> SEQ ID NO 171
<211> LENGTH: 100
<212> TYPE: PRT
<213> ORGANISM: Human papillomavirus

<400> SEQUENCE: 171

Leu Pro Glu Thr Val Cys Trp Gly His Val Glu Glu Val Glu Leu Ile
1               5                   10                  15

Asn Asp Gly Ser Gly Leu Gly Phe Gly Ile Val Gly Gly Lys Thr Ser
            20                  25                  30

Gly Val Val Val Arg Thr Ile Val Pro Gly Gly Leu Ala Asp Arg Asp
        35                  40                  45

Gly Arg Leu Gln Thr Gly Asp His Ile Leu Lys Ile Gly Gly Thr Asn
    50                  55                  60

Val Gln Gly Met Thr Ser Glu Gln Val Ala Gln Val Leu Arg Asn Cys
65                  70                  75                  80

Gly Asn Ser Val Arg Met Leu Val Ala Arg Asp Pro Ala Gly Asp Ile
                85                  90                  95

Gln Ser Pro Ile
            100

<210> SEQ ID NO 172
<211> LENGTH: 119
<212> TYPE: PRT
<213> ORGANISM: Human papillomavirus

<400> SEQUENCE: 172

Pro Asn Phe Ser His Trp Gly Pro Arg Ile Val Glu Ile Phe Arg
1               5                   10                  15

Glu Pro Asn Val Ser Leu Gly Ile Ser Ile Val Val Gly Gln Thr Val
            20                  25                  30

Ile Lys Arg Leu Lys Asn Gly Glu Glu Leu Lys Gly Ile Phe Ile Lys
        35                  40                  45

Gln Val Leu Glu Asp Ser Pro Ala Gly Lys Thr Asn Ala Leu Lys Thr
    50                  55                  60

Gly Asp Lys Ile Leu Glu Val Ser Gly Val Asp Leu Gln Asn Ala Ser
65                  70                  75                  80

His Ser Glu Ala Val Glu Ala Ile Lys Asn Ala Gly Asn Pro Val Val
            85                  90                  95

Phe Ile Val Gln Ser Leu Ser Thr Pro Arg Val Ile Pro Asn Val
            100                 105                 110

His Asn Lys Ala Asn Ser Ser
        115

<210> SEQ ID NO 173
<211> LENGTH: 99
<212> TYPE: PRT
<213> ORGANISM: Human papillomavirus

<400> SEQUENCE: 173

Pro Gly Glu Leu His Ile Ile Glu Leu Glu Lys Asp Lys Asn Gly Leu
1               5                   10                  15

Gly Leu Ser Leu Ala Gly Asn Lys Asp Arg Ser Arg Met Ser Ile Phe
            20                  25                  30

Val Val Gly Ile Asn Pro Glu Gly Pro Ala Ala Ala Asp Gly Arg Met
        35                  40                  45

Arg Ile Gly Asp Glu Leu Leu Glu Ile Asn Asn Gln Ile Leu Tyr Gly
    50                  55                  60

Arg Ser His Gln Asn Ala Ser Ala Ile Ile Lys Thr Ala Pro Ser Lys
65                  70                  75                  80

Val Lys Leu Val Phe Ile Arg Asn Glu Asp Ala Val Asn Gln Met Ala
                85                  90                  95

Asn Ser Ser

<210> SEQ ID NO 174
<211> LENGTH: 102
<212> TYPE: PRT
<213> ORGANISM: Human papillomavirus

<400> SEQUENCE: 174

Leu Ser Ser Pro Glu Val Lys Ile Val Glu Leu Val Lys Asp Cys Lys
1               5                   10                  15

Gly Leu Gly Phe Ser Ile Leu Asp Tyr Gln Asp Pro Leu Asp Pro Thr
            20                  25                  30

Arg Ser Val Ile Val Ile Arg Ser Leu Val Ala Asp Gly Val Ala Glu
        35                  40                  45

Arg Ser Gly Gly Leu Leu Pro Gly Asp Arg Leu Val Ser Val Asn Glu
    50                  55                  60

Tyr Cys Leu Asp Asn Thr Ser Leu Ala Glu Ala Val Glu Ile Leu Lys
65                  70                  75                  80

Ala Val Pro Pro Gly Leu Val His Leu Gly Ile Cys Lys Pro Leu Val
                85                  90                  95

Glu Phe Ile Val Thr Asp
            100

<210> SEQ ID NO 175
<211> LENGTH: 104
<212> TYPE: PRT
<213> ORGANISM: Human papillomavirus

<400> SEQUENCE: 175

Ile Trp Gln Ile Glu Tyr Ile Asp Ile Glu Arg Pro Ser Thr Gly Gly
1               5                   10                  15

Leu Gly Phe Ser Val Val Ala Leu Arg Ser Gln Asn Leu Gly Lys Val
            20                  25                  30

```
Asp Ile Phe Val Lys Asp Val Gln Pro Gly Ser Val Ala Asp Arg Asp
            35                  40                  45

Gln Arg Leu Lys Glu Asn Asp Gln Ile Leu Ala Ile Asn His Thr Pro
 50                  55                  60

Leu Asp Gln Asn Ile Ser His Gln Gln Ala Ile Ala Leu Leu Gln Gln
 65                  70                  75                  80

Thr Thr Gly Ser Leu Arg Leu Ile Val Ala Arg Glu Pro Val His Thr
                85                  90                  95

Lys Ser Ser Thr Ser Ser Ser Glu
            100
```

<210> SEQ ID NO 176
<211> LENGTH: 96
<212> TYPE: PRT
<213> ORGANISM: Human papillomavirus

<400> SEQUENCE: 176

```
Asn Ser Asp Asp Ala Glu Leu Gln Lys Tyr Ser Lys Leu Leu Pro Ile
1               5                   10                  15

His Thr Leu Arg Leu Gly Val Glu Val Asp Ser Phe Asp Gly His His
            20                  25                  30

Tyr Ile Ser Ser Ile Val Ser Gly Gly Pro Val Asp Thr Leu Gly Leu
            35                  40                  45

Leu Gln Pro Glu Asp Glu Leu Leu Gly Val Asn Gly Met Gln Leu Tyr
 50                  55                  60

Gly Lys Ser Arg Arg Glu Ala Val Ser Phe Leu Lys Glu Val Pro Pro
65                  70                  75                  80

Pro Phe Thr Leu Val Cys Cys Arg Arg Leu Phe Asp Asp Glu Ala Ser
                85                  90                  95
```

<210> SEQ ID NO 177
<211> LENGTH: 118
<212> TYPE: PRT
<213> ORGANISM: Human papillomavirus

<400> SEQUENCE: 177

```
His Leu Arg Leu Leu Asn Ile Ala Cys Ala Ala Lys Ala Lys Arg Arg
1               5                   10                  15

Leu Met Thr Leu Thr Lys Pro Ser Arg Glu Ala Pro Leu Pro Phe Ile
            20                  25                  30

Leu Leu Gly Gly Ser Glu Lys Gly Phe Gly Ile Phe Val Asp Ser Val
            35                  40                  45

Asp Ser Gly Ser Lys Ala Thr Glu Ala Gly Leu Lys Arg Gly Asp Gln
 50                  55                  60

Ile Leu Glu Val Asn Gly Gln Asn Phe Glu Asn Ile Gln Leu Ser Lys
65                  70                  75                  80

Ala Met Glu Ile Leu Arg Asn Asn Thr His Leu Ser Ile Thr Val Lys
                85                  90                  95

Thr Asn Leu Phe Val Phe Lys Glu Leu Leu Thr Arg Leu Ser Glu Glu
            100                 105                 110

Lys Arg Asn Gly Ala Pro
            115
```

<210> SEQ ID NO 178
<211> LENGTH: 88
<212> TYPE: PRT
<213> ORGANISM: Human papillomavirus

<400> SEQUENCE: 178

Ile Pro Pro Ala Pro Arg Lys Val Glu Met Arg Arg Asp Pro Val Leu
1               5                   10                  15

Gly Phe Gly Phe Val Ala Gly Ser Glu Lys Pro Val Val Arg Ser
            20                  25                  30

Val Thr Pro Gly Gly Pro Ser Glu Gly Lys Leu Ile Pro Gly Asp Gln
            35                  40                  45

Ile Val Met Ile Asn Asp Glu Pro Val Ser Ala Ala Pro Arg Glu Arg
        50                  55                  60

Val Ile Asp Leu Val Arg Ser Cys Lys Glu Ser Ile Leu Leu Thr Val
65                  70                  75                  80

Ile Gln Pro Tyr Pro Ser Pro Lys
                85

<210> SEQ ID NO 179
<211> LENGTH: 101
<212> TYPE: PRT
<213> ORGANISM: Human papillomavirus

<400> SEQUENCE: 179

Leu Asn Lys Arg Thr Thr Met Pro Lys Asp Ser Gly Ala Leu Leu Gly
1               5                   10                  15

Leu Lys Val Val Gly Gly Lys Met Thr Asp Leu Gly Arg Leu Gly Ala
            20                  25                  30

Phe Ile Thr Lys Val Lys Lys Gly Ser Leu Ala Asp Val Val Gly His
            35                  40                  45

Leu Arg Ala Gly Asp Glu Val Leu Glu Trp Asn Gly Lys Pro Leu Pro
        50                  55                  60

Gly Ala Thr Asn Glu Glu Val Tyr Asn Ile Ile Leu Glu Ser Lys Ser
65                  70                  75                  80

Glu Pro Gln Val Glu Ile Ile Val Ser Arg Pro Ile Gly Asp Ile Pro
                85                  90                  95

Arg Ile His Arg Asp
            100

<210> SEQ ID NO 180
<211> LENGTH: 77
<212> TYPE: PRT
<213> ORGANISM: Human papillomavirus

<400> SEQUENCE: 180

Arg Cys Val Ile Ile Gln Lys Asp Gln His Gly Phe Gly Phe Thr Val
1               5                   10                  15

Ser Gly Asp Arg Ile Val Leu Val Gln Ser Val Arg Pro Gly Gly Ala
            20                  25                  30

Ala Met Lys Ala Gly Val Lys Glu Gly Asp Arg Ile Ile Lys Val Asn
            35                  40                  45

Gly Thr Met Val Thr Asn Ser Ser His Leu Glu Val Val Lys Leu Ile
        50                  55                  60

Lys Ser Gly Ala Tyr Val Ala Leu Thr Leu Leu Gly Ser
65                  70                  75

<210> SEQ ID NO 181
<211> LENGTH: 87
<212> TYPE: PRT
<213> ORGANISM: Human papillomavirus

```
<400> SEQUENCE: 181

Ile Leu Val Gln Arg Cys Val Ile Ile Gln Lys Asp Asp Asn Gly Phe
1               5                   10                  15

Gly Leu Thr Val Ser Gly Asp Asn Pro Val Phe Val Gln Ser Val Lys
            20                  25                  30

Glu Asp Gly Ala Ala Met Arg Ala Gly Val Gln Thr Gly Asp Arg Ile
        35                  40                  45

Ile Lys Val Asn Gly Thr Leu Val Thr His Ser Asn His Leu Glu Val
    50                  55                  60

Val Lys Leu Ile Lys Ser Gly Ser Tyr Val Ala Leu Thr Val Gln Gly
65                  70                  75                  80

Arg Pro Pro Gly Asn Ser Ser
                85

<210> SEQ ID NO 182
<211> LENGTH: 78
<212> TYPE: PRT
<213> ORGANISM: Human papillomavirus

<400> SEQUENCE: 182

Ser Val Glu Met Thr Leu Arg Arg Asn Gly Leu Gly Gln Leu Gly Phe
1               5                   10                  15

His Val Asn Tyr Glu Gly Ile Val Ala Asp Val Glu Pro Tyr Gly Tyr
            20                  25                  30

Ala Trp Gln Ala Gly Leu Arg Gln Gly Ser Arg Leu Val Glu Ile Cys
        35                  40                  45

Lys Val Ala Val Ala Thr Leu Ser His Glu Gln Met Ile Asp Leu Leu
    50                  55                  60

Arg Thr Ser Val Thr Val Lys Val Val Ile Pro Pro His
65                  70                  75

<210> SEQ ID NO 183
<211> LENGTH: 96
<212> TYPE: PRT
<213> ORGANISM: Human papillomavirus

<400> SEQUENCE: 183

Leu Lys Val Met Thr Ser Gly Trp Glu Thr Val Asp Met Thr Leu Arg
1               5                   10                  15

Arg Asn Gly Leu Gly Gln Leu Gly Phe His Val Lys Tyr Asp Gly Thr
            20                  25                  30

Val Ala Glu Val Glu Asp Tyr Gly Phe Ala Trp Gln Ala Gly Leu Arg
        35                  40                  45

Gln Gly Ser Arg Leu Val Glu Ile Cys Lys Val Ala Val Val Thr Leu
    50                  55                  60

Thr His Asp Gln Met Ile Asp Leu Leu Arg Thr Ser Val Thr Val Lys
65                  70                  75                  80

Val Val Ile Ile Pro Pro Phe Glu Asp Gly Thr Pro Arg Arg Gly Trp
                85                  90                  95

<210> SEQ ID NO 184
<211> LENGTH: 105
<212> TYPE: PRT
<213> ORGANISM: Human papillomavirus

<400> SEQUENCE: 184

His Tyr Ile Phe Pro His Ala Arg Ile Lys Ile Thr Arg Asp Ser Lys
1               5                   10                  15
```

Asp His Thr Val Ser Gly Asn Gly Leu Gly Ile Arg Ile Val Gly Gly
                20                  25                  30

Lys Glu Ile Pro Gly His Ser Gly Glu Ile Gly Ala Tyr Ile Ala Lys
            35                  40                  45

Ile Leu Pro Gly Gly Ser Ala Glu Gln Thr Gly Lys Leu Met Glu Gly
 50                  55                  60

Met Gln Val Leu Glu Trp Asn Gly Ile Pro Leu Thr Ser Lys Thr Tyr
 65                  70                  75                  80

Glu Glu Val Gln Ser Ile Ile Ser Gln Gln Ser Gly Glu Ala Glu Ile
                85                  90                  95

Cys Val Arg Leu Asp Leu Asn Met Leu
            100                 105

<210> SEQ ID NO 185
<211> LENGTH: 86
<212> TYPE: PRT
<213> ORGANISM: Human papillomavirus

<400> SEQUENCE: 185

Ser Tyr Ser Val Thr Leu Thr Gly Pro Gly Pro Trp Gly Phe Arg Leu
 1               5                  10                  15

Gln Gly Gly Lys Asp Phe Asn Met Pro Leu Thr Ile Ser Arg Ile Thr
                20                  25                  30

Pro Gly Ser Lys Ala Ala Gln Ser Gln Leu Ser Gln Gly Asp Leu Val
            35                  40                  45

Val Ala Ile Asp Gly Val Asn Thr Asp Thr Met Thr His Leu Glu Ala
 50                  55                  60

Gln Asn Lys Ile Lys Ser Ala Ser Tyr Asn Leu Ser Leu Thr Leu Gln
 65                  70                  75                  80

Lys Ser Lys Asn Ser Ser
                85

<210> SEQ ID NO 186
<211> LENGTH: 94
<212> TYPE: PRT
<213> ORGANISM: Human papillomavirus

<400> SEQUENCE: 186

Phe Ser Asp Met Arg Ile Ser Ile Asn Gln Thr Pro Gly Lys Ser Leu
 1               5                  10                  15

Asp Phe Gly Phe Thr Ile Lys Trp Asp Ile Pro Gly Ile Phe Val Ala
                20                  25                  30

Ser Val Glu Ala Gly Ser Pro Ala Glu Phe Ser Gln Leu Gln Val Asp
            35                  40                  45

Asp Glu Ile Ile Ala Ile Asn Asn Thr Lys Phe Ser Tyr Asn Asp Ser
 50                  55                  60

Lys Glu Trp Glu Glu Ala Met Ala Lys Ala Gln Glu Thr Gly His Leu
 65                  70                  75                  80

Val Met Asp Val Arg Arg Tyr Gly Lys Ala Gly Ser Pro Glu
                85                  90

<210> SEQ ID NO 187
<211> LENGTH: 98
<212> TYPE: PRT
<213> ORGANISM: Human papillomavirus

<400> SEQUENCE: 187

-continued

Gln Ser Ala His Leu Glu Val Ile Gln Leu Ala Asn Ile Lys Pro Ser
1               5                   10                  15

Glu Gly Leu Gly Met Tyr Ile Lys Ser Thr Tyr Asp Gly Leu His Val
            20                  25                  30

Ile Thr Gly Thr Thr Glu Asn Ser Pro Ala Asp Arg Cys Lys Lys Ile
            35                  40                  45

His Ala Gly Asp Glu Val Ile Gln Val Asn His Gln Thr Val Val Gly
        50                  55                  60

Trp Gln Leu Lys Asn Leu Val Asn Ala Leu Arg Glu Asp Pro Ser Gly
65                  70                  75                  80

Val Ile Leu Thr Leu Lys Lys Arg Pro Gln Ser Met Leu Thr Ser Ala
            85                  90                  95

Pro Ala

<210> SEQ ID NO 188
<211> LENGTH: 100
<212> TYPE: PRT
<213> ORGANISM: Human papillomavirus

<400> SEQUENCE: 188

Ile Leu Thr Gln Thr Leu Ile Pro Val Arg His Thr Val Lys Ile Asp
1               5                   10                  15

Lys Asp Thr Leu Leu Gln Asp Tyr Gly Phe His Ile Ser Glu Ser Leu
            20                  25                  30

Pro Leu Thr Val Ala Val Thr Ala Gly Ser Ala His Gly Lys
            35                  40                  45

Leu Phe Pro Gly Asp Gln Ile Leu Gln Met Asn Asn Glu Pro Ala Glu
        50                  55                  60

Asp Leu Ser Trp Glu Arg Ala Val Asp Ile Leu Arg Glu Ala Glu Asp
65                  70                  75                  80

Ser Leu Ser Ile Thr Val Val Arg Cys Thr Ser Gly Val Pro Lys Ser
            85                  90                  95

Ser Asn Ser Ser
        100

<210> SEQ ID NO 189
<211> LENGTH: 91
<212> TYPE: PRT
<213> ORGANISM: Human papillomavirus

<400> SEQUENCE: 189

Arg Ser Phe Gln Tyr Val Pro Val Gln Leu Gln Gly Gly Ala Pro Trp
1               5                   10                  15

Gly Phe Thr Leu Lys Gly Gly Leu Glu His Cys Glu Pro Leu Thr Val
            20                  25                  30

Ser Lys Ile Glu Asp Gly Gly Lys Ala Ala Leu Ser Gln Lys Met Arg
        35                  40                  45

Thr Gly Asp Glu Leu Val Asn Ile Asn Gly Thr Pro Leu Tyr Gly Ser
        50                  55                  60

Arg Gln Glu Ala Leu Ile Leu Ile Lys Gly Ser Phe Arg Ile Leu Lys
65                  70                  75                  80

Leu Ile Val Arg Arg Asn Ala Pro Val Ser
            85                  90

<210> SEQ ID NO 190
<211> LENGTH: 103
<212> TYPE: PRT

```
<213> ORGANISM: Human papillomavirus

<400> SEQUENCE: 190

Ile Leu Glu Lys Leu Glu Leu Phe Pro Val Glu Leu Lys Asp Glu
1               5                   10                  15

Asp Gly Leu Gly Ile Ser Ile Ile Gly Met Gly Val Gly Ala Asp Ala
            20                  25                  30

Gly Leu Glu Lys Leu Gly Ile Phe Val Lys Thr Val Thr Glu Gly Gly
                35                  40                  45

Ala Ala Gln Arg Asp Gly Arg Ile Gln Val Asn Asp Gln Ile Val Glu
    50                  55                  60

Val Asp Gly Ile Ser Leu Val Gly Val Thr Gln Asn Phe Ala Ala Thr
65                  70                  75                  80

Val Leu Arg Asn Thr Lys Gly Asn Val Arg Phe Val Ile Gly Arg Glu
                85                  90                  95

Lys Pro Gly Gln Val Ser Glu
            100

<210> SEQ ID NO 191
<211> LENGTH: 113
<212> TYPE: PRT
<213> ORGANISM: Human papillomavirus

<400> SEQUENCE: 191

Lys Asp Val Asn Val Tyr Val Asn Pro Lys Lys Leu Thr Val Ile Lys
1               5                   10                  15

Ala Lys Glu Gln Leu Lys Leu Leu Glu Val Leu Val Gly Ile Ile His
            20                  25                  30

Gln Thr Lys Trp Ser Trp Arg Arg Thr Gly Lys Gln Gly Asp Gly Glu
        35                  40                  45

Arg Leu Val Val His Gly Leu Leu Pro Gly Gly Ser Ala Met Lys Ser
    50                  55                  60

Gly Gln Val Leu Ile Gly Asp Val Leu Val Ala Val Asn Asp Val Asp
65                  70                  75                  80

Val Thr Thr Glu Asn Ile Glu Arg Val Leu Ser Cys Ile Pro Gly Pro
                85                  90                  95

Met Gln Val Lys Leu Thr Phe Glu Asn Ala Tyr Asp Val Lys Arg Glu
            100                 105                 110

Thr

<210> SEQ ID NO 192
<211> LENGTH: 90
<212> TYPE: PRT
<213> ORGANISM: Human papillomavirus

<400> SEQUENCE: 192

Thr Arg Gly Cys Glu Thr Val Glu Met Thr Leu Arg Arg Asn Gly Leu
1               5                   10                  15

Gly Gln Leu Gly Phe His Val Asn Phe Glu Gly Ile Val Ala Asp Val
            20                  25                  30

Glu Pro Phe Gly Phe Ala Trp Lys Ala Gly Leu Arg Gln Gly Ser Arg
        35                  40                  45

Leu Val Glu Ile Cys Lys Val Ala Val Ala Thr Leu Thr His Glu Gln
    50                  55                  60

Met Ile Asp Leu Leu Arg Thr Ser Val Thr Val Lys Val Val Ile Ile
65                  70                  75                  80
```

Gln Pro His Asp Asp Gly Ser Pro Arg Arg
            85                  90

<210> SEQ ID NO 193
<211> LENGTH: 96
<212> TYPE: PRT
<213> ORGANISM: Human papillomavirus

<400> SEQUENCE: 193

Val Glu Asn Ile Leu Ala Lys Arg Leu Leu Ile Leu Pro Gln Glu Glu
1               5                   10                  15

Asp Tyr Gly Phe Asp Ile Glu Glu Lys Asn Lys Ala Val Val Val Lys
            20                  25                  30

Ser Val Gln Arg Gly Ser Leu Ala Glu Val Ala Gly Leu Gln Val Gly
        35                  40                  45

Arg Lys Ile Tyr Ser Ile Asn Glu Asp Leu Val Phe Leu Arg Pro Phe
    50                  55                  60

Ser Glu Val Glu Ser Ile Leu Asn Gln Ser Phe Cys Ser Arg Arg Pro
65                  70                  75                  80

Leu Arg Leu Leu Val Ala Thr Lys Ala Lys Glu Ile Ile Lys Ile Pro
                85                  90                  95

<210> SEQ ID NO 194
<211> LENGTH: 103
<212> TYPE: PRT
<213> ORGANISM: Human papillomavirus

<400> SEQUENCE: 194

Pro Asp Ser Ala Gly Pro Gly Glu Val Arg Leu Val Ser Leu Arg Arg
1               5                   10                  15

Ala Lys Ala His Glu Gly Leu Gly Phe Ser Ile Arg Gly Gly Ser Glu
            20                  25                  30

His Gly Val Gly Ile Tyr Val Ser Leu Val Glu Pro Gly Ser Leu Ala
        35                  40                  45

Glu Lys Glu Gly Leu Arg Val Gly Asp Gln Ile Leu Arg Val Asn Asp
    50                  55                  60

Lys Ser Leu Ala Arg Val Thr His Ala Glu Ala Val Lys Ala Leu Lys
65                  70                  75                  80

Gly Ser Lys Lys Leu Val Leu Ser Val Tyr Ser Ala Gly Arg Ile Pro
                85                  90                  95

Gly Gly Tyr Val Thr Asn His
            100

<210> SEQ ID NO 195
<211> LENGTH: 100
<212> TYPE: PRT
<213> ORGANISM: Human papillomavirus

<400> SEQUENCE: 195

Leu Gln Gly Gly Asp Glu Lys Lys Val Asn Leu Val Leu Gly Asp Gly
1               5                   10                  15

Arg Ser Leu Gly Leu Thr Ile Arg Gly Gly Ala Glu Tyr Gly Leu Gly
            20                  25                  30

Ile Tyr Ile Thr Gly Val Asp Pro Gly Ser Glu Ala Gly Ser Gly
        35                  40                  45

Leu Lys Val Gly Asp Gln Ile Leu Glu Val Asn Gly Arg Ser Phe Leu
    50                  55                  60

Asn Ile Leu His Asp Glu Ala Val Arg Leu Leu Lys Ser Ser Arg His

```
                65                  70                  75                  80
Leu Ile Leu Thr Val Lys Asp Val Gly Arg Leu Pro His Ala Arg Thr
                85                  90                  95

Thr Val Asp Glu
            100

<210> SEQ ID NO 196
<211> LENGTH: 98
<212> TYPE: PRT
<213> ORGANISM: Human papillomavirus

<400> SEQUENCE: 196

Leu Arg Arg Ala Glu Leu Val Glu Ile Ile Val Glu Thr Glu Ala Gln
1               5                   10                  15

Thr Gly Val Ser Gly Ile Asn Val Ala Gly Gly Gly Lys Glu Gly Ile
            20                  25                  30

Phe Val Arg Glu Leu Arg Glu Asp Ser Pro Ala Ala Arg Ser Leu Ser
        35                  40                  45

Leu Gln Glu Gly Asp Gln Leu Leu Ser Ala Arg Val Phe Phe Glu Asn
    50                  55                  60

Phe Lys Tyr Glu Asp Ala Leu Arg Leu Leu Gln Cys Ala Glu Pro Tyr
65                  70                  75                  80

Lys Val Ser Phe Cys Leu Lys Arg Thr Val Pro Thr Gly Asp Leu Ala
                85                  90                  95

Leu Arg

<210> SEQ ID NO 197
<211> LENGTH: 94
<212> TYPE: PRT
<213> ORGANISM: Human papillomavirus

<400> SEQUENCE: 197

Ile Gln Thr Thr Gly Ala Val Ser Tyr Thr Val Glu Leu Lys Arg Tyr
1               5                   10                  15

Gly Gly Pro Leu Gly Ile Thr Ile Ser Gly Thr Glu Glu Pro Phe Asp
            20                  25                  30

Pro Ile Val Ile Ser Gly Leu Thr Lys Arg Gly Leu Ala Glu Arg Thr
        35                  40                  45

Gly Ala Ile His Val Gly Asp Arg Ile Leu Ala Ile Asn Asn Val Ser
    50                  55                  60

Leu Lys Gly Arg Pro Leu Ser Glu Ala Ile His Leu Leu Gln Val Ala
65                  70                  75                  80

Gly Glu Thr Val Thr Leu Lys Ile Lys Lys Gln Leu Asp Arg
                85                  90

<210> SEQ ID NO 198
<211> LENGTH: 105
<212> TYPE: PRT
<213> ORGANISM: Human papillomavirus

<400> SEQUENCE: 198

Ile Leu Glu Met Glu Glu Leu Leu Pro Thr Pro Leu Glu Met His
1               5                   10                  15

Lys Val Thr Leu His Lys Asp Pro Met Arg His Asp Phe Gly Phe Ser
            20                  25                  30

Val Ser Asp Gly Leu Leu Glu Lys Gly Val Tyr Val His Thr Val Arg
        35                  40                  45
```

```
Pro Asp Gly Pro Ala His Arg Gly Gly Leu Gln Pro Phe Asp Arg Val
    50                  55                  60

Leu Gln Val Asn His Val Arg Thr Arg Asp Phe Asp Cys Cys Leu Ala
65                  70                  75                  80

Val Pro Leu Leu Ala Glu Ala Gly Asp Val Leu Glu Leu Ile Ile Ser
                85                  90                  95

Arg Lys Pro His Thr Ala His Ser Ser
            100                 105

<210> SEQ ID NO 199
<211> LENGTH: 102
<212> TYPE: PRT
<213> ORGANISM: Human papillomavirus

<400> SEQUENCE: 199

Ile His Thr Val Ala Asn Ala Ser Gly Pro Leu Met Val Glu Ile Val
1               5                   10                  15

Lys Thr Pro Gly Ser Ala Leu Gly Ile Ser Leu Thr Thr Thr Ser Leu
            20                  25                  30

Arg Asn Lys Ser Val Ile Thr Ile Asp Arg Ile Lys Pro Ala Ser Val
        35                  40                  45

Val Asp Arg Ser Gly Ala Leu His Pro Gly Asp Ile Leu Ser Ile
50                  55                  60

Asp Gly Thr Ser Met Glu His Cys Ser Leu Leu Glu Ala Thr Lys Leu
65                  70                  75                  80

Leu Ala Ser Ile Ser Glu Lys Val Arg Leu Glu Ile Leu Pro Val Pro
                85                  90                  95

Gln Ser Gln Arg Pro Leu
            100

<210> SEQ ID NO 200
<211> LENGTH: 84
<212> TYPE: PRT
<213> ORGANISM: Human papillomavirus

<400> SEQUENCE: 200

Ile Thr Val Val Glu Leu Ile Lys Lys Glu Gly Ser Thr Leu Gly Leu
1               5                   10                  15

Thr Ile Ser Gly Gly Thr Asp Lys Asp Gly Lys Pro Arg Val Ser Asn
            20                  25                  30

Leu Arg Pro Gly Gly Leu Ala Ala Arg Ser Asp Leu Leu Asn Ile Gly
        35                  40                  45

Asp Tyr Ile Arg Ser Val Asn Gly Ile His Leu Thr Arg Leu Arg His
50                  55                  60

Asp Glu Ile Ile Thr Leu Leu Lys Asn Val Gly Glu Arg Val Val Leu
65                  70                  75                  80

Glu Val Glu Tyr

<210> SEQ ID NO 201
<211> LENGTH: 103
<212> TYPE: PRT
<213> ORGANISM: Human papillomavirus

<400> SEQUENCE: 201

Ile Gln Ile Val His Thr Glu Thr Thr Glu Val Val Leu Cys Gly Asp
1               5                   10                  15

Pro Leu Ser Gly Phe Gly Leu Gln Leu Gln Gly Gly Ile Phe Ala Thr
            20                  25                  30
```

```
Glu Thr Leu Ser Ser Pro Pro Leu Val Cys Phe Ile Glu Pro Asp Ser
            35                  40                  45

Pro Ala Glu Arg Cys Gly Leu Leu Gln Val Gly Asp Arg Val Leu Ser
 50                  55                  60

Ile Asn Gly Ile Ala Thr Glu Asp Gly Thr Met Glu Glu Ala Asn Gln
 65                  70                  75                  80

Leu Leu Arg Asp Ala Ala Leu Ala His Lys Val Val Leu Glu Val Glu
                 85                  90                  95

Phe Asp Val Ala Glu Ser Val
            100

<210> SEQ ID NO 202
<211> LENGTH: 92
<212> TYPE: PRT
<213> ORGANISM: Human papillomavirus

<400> SEQUENCE: 202

Ile Leu Asp Val Ser Leu Tyr Lys Glu Gly Asn Ser Phe Gly Phe Val
 1               5                  10                  15

Leu Arg Gly Gly Ala His Glu Asp Gly His Lys Ser Arg Pro Leu Val
                 20                  25                  30

Leu Thr Tyr Val Arg Pro Gly Gly Pro Ala Asp Arg Glu Gly Ser Leu
            35                  40                  45

Lys Val Gly Asp Arg Leu Leu Ser Val Asp Gly Ile Pro Leu His Gly
 50                  55                  60

Ala Ser His Ala Thr Ala Leu Ala Thr Leu Arg Gln Cys Ser His Glu
 65                  70                  75                  80

Ala Leu Phe Gln Val Glu Tyr Asp Val Ala Thr Pro
                 85                  90

<210> SEQ ID NO 203
<211> LENGTH: 102
<212> TYPE: PRT
<213> ORGANISM: Human papillomavirus

<400> SEQUENCE: 203

Gln Phe Asp Val Ala Glu Ser Val Ile Pro Ser Ser Gly Thr Phe His
 1               5                  10                  15

Val Lys Leu Pro Lys Lys Arg Ser Val Glu Leu Gly Ile Thr Ile Ser
                 20                  25                  30

Ser Ala Ser Arg Lys Arg Gly Glu Pro Leu Ile Ile Ser Asp Ile Lys
            35                  40                  45

Lys Gly Ser Val Ala His Arg Thr Gly Thr Leu Glu Pro Gly Asp Lys
 50                  55                  60

Leu Leu Ala Ile Asp Asn Ile Arg Leu Asp Asn Cys Pro Met Glu Asp
 65                  70                  75                  80

Ala Val Gln Ile Leu Arg Gln Cys Glu Asp Leu Val Lys Leu Lys Ile
                 85                  90                  95

Arg Lys Asp Glu Asp Asn
            100

<210> SEQ ID NO 204
<211> LENGTH: 91
<212> TYPE: PRT
<213> ORGANISM: Human papillomavirus

<400> SEQUENCE: 204
```

```
Met Ala Leu Thr Val Asp Val Ala Gly Pro Ala Pro Trp Gly Phe Arg
1               5                   10                  15

Ile Thr Gly Gly Arg Asp Phe His Thr Pro Ile Met Val Thr Lys Val
            20                  25                  30

Ala Glu Arg Gly Lys Ala Lys Asp Ala Asp Leu Arg Pro Gly Asp Ile
        35                  40                  45

Ile Val Ala Ile Asn Gly Glu Ser Ala Glu Gly Met Leu His Ala Glu
    50                  55                  60

Ala Gln Ser Lys Ile Arg Gln Ser Pro Ser Pro Leu Arg Leu Gln Leu
65                  70                  75                  80

Asp Arg Ser Gln Ala Thr Ser Pro Gly Gln Thr
                85                  90
```

<210> SEQ ID NO 205
<211> LENGTH: 84
<212> TYPE: PRT
<213> ORGANISM: Human papillomavirus

<400> SEQUENCE: 205

```
Ser Asn Tyr Ser Val Ser Leu Val Gly Pro Ala Pro Trp Gly Phe Arg
1               5                   10                  15

Leu Gln Gly Gly Lys Asp Phe Asn Met Pro Leu Thr Ile Ser Ser Leu
            20                  25                  30

Lys Asp Gly Gly Lys Ala Ala Gln Ala Asn Val Arg Ile Gly Asp Val
        35                  40                  45

Val Leu Ser Ile Asp Gly Ile Asn Ala Gln Gly Met Thr His Leu Glu
    50                  55                  60

Ala Gln Asn Lys Ile Lys Gly Cys Thr Gly Ser Leu Asn Met Thr Leu
65                  70                  75                  80

Gln Arg Ala Ser
```

<210> SEQ ID NO 206
<211> LENGTH: 133
<212> TYPE: PRT
<213> ORGANISM: Human papillomavirus

<400> SEQUENCE: 206

```
Thr Leu Val Glu His Ser Lys Leu Tyr Cys Gly His Cys Tyr Tyr Gln
1               5                   10                  15

Thr Val Val Thr Pro Val Ile Glu Gln Ile Leu Pro Asp Ser Pro Gly
            20                  25                  30

Ser His Leu Pro His Thr Val Thr Leu Val Ser Ile Pro Ala Ser Ser
        35                  40                  45

His Gly Lys Arg Gly Leu Ser Val Ser Ile Asp Pro Pro His Gly Pro
    50                  55                  60

Pro Gly Cys Gly Thr Glu His Ser His Thr Val Arg Val Gln Gly Val
65                  70                  75                  80

Asp Pro Gly Cys Met Ser Pro Asp Val Lys Asn Ser Ile His Val Gly
                85                  90                  95

Asp Arg Ile Leu Glu Ile Asn Gly Thr Pro Ile Arg Asn Val Pro Leu
            100                 105                 110

Asp Glu Ile Asp Leu Leu Ile Gln Glu Thr Ser Arg Leu Leu Gln Leu
        115                 120                 125

Thr Leu Glu His Asp
        130
```

-continued

```
<210> SEQ ID NO 207
<211> LENGTH: 92
<212> TYPE: PRT
<213> ORGANISM: Human papillomavirus

<400> SEQUENCE: 207

Pro Tyr Ser Val Thr Leu Ile Ser Met Pro Ala Thr Thr Glu Gly Arg
1               5                   10                  15

Arg Gly Phe Ser Val Ser Val Glu Ser Ala Cys Ser Asn Tyr Ala Thr
            20                  25                  30

Thr Val Gln Val Lys Glu Val Asn Arg Met His Ile Ser Pro Asn Asn
        35                  40                  45

Arg Asn Ala Ile His Pro Gly Asp Arg Ile Leu Glu Ile Asn Gly Thr
    50                  55                  60

Pro Val Arg Thr Leu Arg Val Glu Glu Val Glu Asp Ala Ile Ser Gln
65                  70                  75                  80

Thr Ser Gln Thr Leu Gln Leu Leu Ile Glu His Asp
                85                  90

<210> SEQ ID NO 208
<211> LENGTH: 82
<212> TYPE: PRT
<213> ORGANISM: Human papillomavirus

<400> SEQUENCE: 208

Ile His Ser Val Thr Leu Arg Gly Pro Ser Pro Trp Gly Phe Arg Leu
1               5                   10                  15

Val Gly Arg Asp Phe Ser Ala Pro Leu Thr Ile Ser Arg Val His Ala
            20                  25                  30

Gly Ser Lys Ala Ser Leu Ala Ala Leu Cys Pro Gly Asp Leu Ile Gln
        35                  40                  45

Ala Ile Asn Gly Glu Ser Thr Glu Leu Met Thr His Leu Glu Ala Gln
    50                  55                  60

Asn Arg Ile Lys Gly Cys His Asp His Leu Thr Leu Ser Val Ser Arg
65                  70                  75                  80

Pro Glu

<210> SEQ ID NO 209
<211> LENGTH: 74
<212> TYPE: PRT
<213> ORGANISM: Human papillomavirus

<400> SEQUENCE: 209

Val Cys Tyr Arg Thr Asp Asp Glu Glu Asp Leu Gly Ile Tyr Val Gly
1               5                   10                  15

Glu Val Asn Pro Asn Ser Ile Ala Ala Lys Asp Gly Arg Ile Arg Glu
            20                  25                  30

Gly Asp Arg Ile Ile Gln Ile Asn Gly Val Asp Val Gln Asn Arg Glu
        35                  40                  45

Glu Ala Val Ala Ile Leu Ser Gln Glu Glu Asn Thr Asn Ile Ser Leu
    50                  55                  60

Leu Val Ala Arg Pro Glu Ser Gln Leu Ala
65                  70

<210> SEQ ID NO 210
<211> LENGTH: 93
<212> TYPE: PRT
<213> ORGANISM: Human papillomavirus
```

```
<400> SEQUENCE: 210

Ile Pro Ala Thr Gln Pro Glu Leu Ile Thr Val His Ile Val Lys Gly
1               5                   10                  15

Pro Met Gly Phe Gly Phe Thr Ile Ala Asp Ser Pro Gly Gly Gly Gly
                20                  25                  30

Gln Arg Val Lys Gln Ile Val Asp Ser Pro Arg Cys Arg Gly Leu Lys
                35                  40                  45

Glu Gly Asp Leu Ile Val Glu Val Asn Lys Asn Val Gln Ala Leu
            50                  55                  60

Thr His Asn Gln Val Val Asp Met Leu Val Glu Cys Pro Lys Gly Ser
65                  70                  75                  80

Glu Val Thr Leu Leu Val Gln Arg Gly Gly Asn Ser Ser
                85                  90

<210> SEQ ID NO 211
<211> LENGTH: 103
<212> TYPE: PRT
<213> ORGANISM: Human papillomavirus

<400> SEQUENCE: 211

Ile Pro Asp Tyr Gln Glu Gln Asp Ile Phe Leu Trp Arg Lys Glu Thr
1               5                   10                  15

Gly Phe Gly Phe Arg Ile Leu Gly Gly Asn Glu Pro Gly Glu Pro Ile
                20                  25                  30

Tyr Ile Gly His Ile Val Pro Leu Gly Ala Ala Asp Thr Asp Gly Arg
            35                  40                  45

Leu Arg Ser Gly Asp Glu Leu Ile Cys Val Asp Gly Thr Pro Val Ile
50                  55                  60

Gly Lys Ser His Gln Leu Val Val Gln Leu Met Gln Gln Ala Ala Lys
65                  70                  75                  80

Gln Gly His Val Asn Leu Thr Val Arg Arg Lys Val Val Phe Ala Val
                85                  90                  95

Pro Lys Thr Glu Asn Ser Ser
            100

<210> SEQ ID NO 212
<211> LENGTH: 120
<212> TYPE: PRT
<213> ORGANISM: Human papillomavirus

<400> SEQUENCE: 212

Ile Pro Gly Val Val Ser Thr Val Val Gln Pro Tyr Asp Val Glu Ile
1               5                   10                  15

Arg Arg Gly Glu Asn Glu Gly Phe Gly Phe Val Ile Val Ser Ser Val
                20                  25                  30

Ser Arg Pro Glu Ala Gly Thr Thr Phe Ala Gly Asn Ala Cys Val Ala
            35                  40                  45

Met Pro His Lys Ile Gly Arg Ile Ile Glu Gly Ser Pro Ala Asp Arg
50                  55                  60

Cys Gly Lys Leu Lys Val Gly Asp Arg Ile Leu Ala Val Asn Gly Cys
65                  70                  75                  80

Ser Ile Thr Asn Lys Ser His Ser Asp Ile Val Asn Leu Ile Lys Glu
                85                  90                  95

Ala Gly Asn Thr Val Thr Leu Arg Ile Ile Pro Gly Asp Glu Ser Ser
            100                 105                 110

Asn Ala Glu Phe Ile Val Thr Asp
```

```
                115                 120
```

<210> SEQ ID NO 213
<211> LENGTH: 107
<212> TYPE: PRT
<213> ORGANISM: Human papillomavirus

<400> SEQUENCE: 213

Ile Pro Ser Glu Leu Lys Gly Lys Phe Ile His Thr Lys Leu Arg Lys
1               5                   10                  15

Ser Ser Arg Gly Phe Gly Phe Thr Val Val Gly Gly Asp Glu Pro Asp
            20                  25                  30

Glu Phe Leu Gln Ile Lys Ser Leu Val Leu Asp Gly Pro Ala Ala Leu
        35                  40                  45

Asp Gly Lys Met Glu Thr Gly Asp Val Ile Val Ser Val Asn Asp Thr
50                  55                  60

Cys Val Leu Gly His Thr His Ala Gln Val Val Lys Ile Phe Gln Ser
65                  70                  75                  80

Ile Pro Ile Gly Ala Ser Val Asp Leu Glu Leu Cys Arg Gly Tyr Pro
                85                  90                  95

Leu Pro Phe Asp Pro Asp Gly Ile His Arg Asp
            100                 105

<210> SEQ ID NO 214
<211> LENGTH: 91
<212> TYPE: PRT
<213> ORGANISM: Human papillomavirus

<400> SEQUENCE: 214

Gln Ala Thr Gln Glu Gln Asp Phe Tyr Thr Val Glu Leu Glu Arg Gly
1               5                   10                  15

Ala Lys Gly Phe Gly Phe Ser Leu Arg Gly Gly Arg Glu Tyr Asn Met
            20                  25                  30

Asp Leu Tyr Val Leu Arg Leu Ala Glu Asp Gly Pro Ala Glu Arg Cys
        35                  40                  45

Gly Lys Met Arg Ile Gly Asp Glu Ile Leu Glu Ile Asn Gly Glu Thr
50                  55                  60

Thr Lys Asn Met Lys His Ser Arg Ala Ile Glu Leu Ile Lys Asn Gly
65                  70                  75                  80

Gly Arg Arg Val Arg Leu Phe Leu Lys Arg Gly
            85                  90

<210> SEQ ID NO 215
<211> LENGTH: 104
<212> TYPE: PRT
<213> ORGANISM: Human papillomavirus

<400> SEQUENCE: 215

Arg Glu Lys Pro Leu Phe Thr Arg Asp Ala Ser Gln Leu Lys Gly Thr
1               5                   10                  15

Phe Leu Ser Thr Thr Leu Lys Lys Ser Asn Met Gly Phe Gly Phe Thr
            20                  25                  30

Ile Ile Gly Gly Asp Glu Pro Asp Glu Phe Leu Gln Val Lys Ser Val
        35                  40                  45

Ile Pro Asp Gly Pro Ala Ala Gln Asp Gly Lys Met Glu Thr Gly Asp
50                  55                  60

Val Ile Val Tyr Ile Asn Glu Val Cys Val Leu Gly His Thr His Ala
65                  70                  75                  80

```
Asp Val Val Lys Leu Phe Gln Ser Val Pro Ile Gly Gln Ser Val Asn
                85                  90                  95

Leu Val Leu Cys Arg Gly Tyr Pro
            100

<210> SEQ ID NO 216
<211> LENGTH: 93
<212> TYPE: PRT
<213> ORGANISM: Human papillomavirus

<400> SEQUENCE: 216

His Tyr Lys Glu Leu Asp Val His Leu Arg Arg Met Glu Ser Gly Phe
1               5                   10                  15

Gly Phe Arg Ile Leu Gly Gly Asp Glu Pro Gly Gln Pro Ile Leu Ile
            20                  25                  30

Gly Ala Val Ile Ala Met Gly Ser Ala Asp Arg Asp Gly Arg Leu His
        35                  40                  45

Pro Gly Asp Glu Leu Val Tyr Val Asp Gly Ile Pro Val Ala Gly Lys
    50                  55                  60

Thr His Arg Tyr Val Ile Asp Leu Met His Ala Ala Arg Asn Gly
65                  70                  75                  80

Gln Val Asn Leu Thr Val Arg Arg Lys Val Leu Cys Gly
                85                  90

<210> SEQ ID NO 217
<211> LENGTH: 106
<212> TYPE: PRT
<213> ORGANISM: Human papillomavirus

<400> SEQUENCE: 217

Glu Gly Arg Gly Ile Ser Ser His Ser Leu Gln Thr Ser Asp Ala Val
1               5                   10                  15

Ile His Arg Lys Glu Asn Glu Gly Phe Gly Phe Val Ile Ile Ser Ser
            20                  25                  30

Leu Asn Arg Pro Glu Ser Gly Ser Thr Ile Thr Val Pro His Lys Ile
        35                  40                  45

Gly Arg Ile Ile Asp Gly Ser Pro Ala Asp Arg Cys Ala Lys Leu Lys
    50                  55                  60

Val Gly Asp Arg Ile Leu Ala Val Asn Gly Gln Ser Ile Ile Asn Met
65                  70                  75                  80

Pro His Ala Asp Ile Val Lys Leu Ile Lys Asp Ala Gly Leu Ser Val
                85                  90                  95

Thr Leu Arg Ile Ile Pro Gln Glu Glu Leu
            100                 105

<210> SEQ ID NO 218
<211> LENGTH: 91
<212> TYPE: PRT
<213> ORGANISM: Human papillomavirus

<400> SEQUENCE: 218

Leu Ser Gly Ala Thr Gln Ala Glu Leu Met Thr Leu Thr Ile Val Lys
1               5                   10                  15

Gly Ala Gln Gly Phe Gly Phe Thr Ile Ala Asp Ser Pro Thr Gly Gln
            20                  25                  30

Arg Val Lys Gln Ile Leu Asp Ile Gln Gly Cys Pro Gly Leu Cys Glu
        35                  40                  45
```

```
Gly Asp Leu Ile Val Glu Ile Asn Gln Gln Asn Val Gln Asn Leu Ser
        50                  55                  60

His Thr Glu Val Val Asp Ile Leu Lys Asp Cys Pro Ile Gly Ser Glu
 65                  70                  75                  80

Thr Ser Leu Ile Ile His Arg Gly Gly Phe Phe
                85                  90

<210> SEQ ID NO 219
<211> LENGTH: 98
<212> TYPE: PRT
<213> ORGANISM: Human papillomavirus

<400> SEQUENCE: 219

Leu Ser Asp Tyr Arg Gln Pro Gln Asp Phe Asp Tyr Phe Thr Val Asp
  1               5                  10                  15

Met Glu Lys Gly Ala Lys Gly Phe Gly Phe Ser Ile Arg Gly Gly Arg
                20                  25                  30

Glu Tyr Lys Met Asp Leu Tyr Val Leu Arg Leu Ala Glu Asp Gly Pro
            35                  40                  45

Ala Ile Arg Asn Gly Arg Met Arg Val Gly Asp Gln Ile Ile Glu Ile
 50                  55                  60

Asn Gly Glu Ser Thr Arg Asp Met Thr His Ala Arg Ala Ile Glu Leu
 65                  70                  75                  80

Ile Lys Ser Gly Gly Arg Arg Val Arg Leu Leu Leu Lys Arg Gly Thr
                85                  90                  95

Gly Gln

<210> SEQ ID NO 220
<211> LENGTH: 90
<212> TYPE: PRT
<213> ORGANISM: Human papillomavirus

<400> SEQUENCE: 220

His Glu Ser Val Ile Gly Arg Asn Pro Glu Gly Gln Leu Gly Phe Glu
  1               5                  10                  15

Leu Lys Gly Gly Ala Glu Asn Gly Gln Phe Pro Tyr Leu Gly Glu Val
                20                  25                  30

Lys Pro Gly Lys Val Ala Tyr Glu Ser Gly Ser Lys Leu Val Ser Glu
            35                  40                  45

Glu Leu Leu Leu Glu Val Asn Glu Thr Pro Val Ala Gly Leu Thr Ile
 50                  55                  60

Arg Asp Val Leu Ala Val Ile Lys His Cys Lys Asp Pro Leu Arg Leu
 65                  70                  75                  80

Lys Cys Val Lys Gln Gly Gly Ile His Arg
                85                  90

<210> SEQ ID NO 221
<211> LENGTH: 100
<212> TYPE: PRT
<213> ORGANISM: Human papillomavirus

<400> SEQUENCE: 221

Ala Ser Ser Gly Ser Ser Gln Pro Glu Leu Val Thr Ile Pro Leu Ile
  1               5                  10                  15

Lys Gly Pro Lys Gly Phe Gly Phe Ala Ile Ala Asp Ser Pro Thr Gly
                20                  25                  30

Gln Lys Val Lys Met Ile Leu Asp Ser Gln Trp Cys Gln Gly Leu Gln
            35                  40                  45
```

```
Lys Gly Asp Ile Ile Lys Glu Ile Tyr His Gln Asn Val Gln Asn Leu
        50                  55                  60

Thr His Leu Gln Val Val Glu Val Leu Lys Gln Phe Pro Val Gly Ala
65                  70                  75                  80

Asp Val Pro Leu Leu Ile Leu Arg Gly Gly Pro Pro Ser Pro Thr Lys
                85                  90                  95

Thr Ala Lys Met
            100

<210> SEQ ID NO 222
<211> LENGTH: 98
<212> TYPE: PRT
<213> ORGANISM: Human papillomavirus

<400> SEQUENCE: 222

Gln Asn Leu Gly Cys Tyr Pro Val Glu Leu Glu Arg Gly Pro Arg Gly
1               5                   10                  15

Phe Gly Phe Ser Leu Arg Gly Gly Lys Glu Tyr Asn Met Gly Leu Phe
            20                  25                  30

Ile Leu Arg Leu Ala Glu Asp Gly Pro Ala Ile Lys Asp Gly Arg Ile
        35                  40                  45

His Val Gly Asp Gln Ile Val Glu Ile Asn Gly Glu Pro Thr Gln Gly
    50                  55                  60

Ile Thr His Thr Arg Ala Ile Glu Leu Ile Gln Ala Gly Gly Asn Lys
65                  70                  75                  80

Val Leu Leu Leu Leu Arg Pro Gly Thr Gly Leu Ile Pro Asp His Gly
                85                  90                  95

Leu Ala

<210> SEQ ID NO 223
<211> LENGTH: 108
<212> TYPE: PRT
<213> ORGANISM: Human papillomavirus

<400> SEQUENCE: 223

Leu Tyr Glu Asp Lys Pro Pro Asn Thr Lys Asp Leu Asp Val Phe Leu
1               5                   10                  15

Arg Lys Gln Glu Ser Gly Phe Gly Phe Arg Val Leu Gly Gly Asp Gly
            20                  25                  30

Pro Asp Gln Ser Ile Tyr Ile Gly Ala Ile Ile Pro Leu Gly Ala Ala
        35                  40                  45

Glu Lys Asp Gly Arg Leu Arg Ala Ala Asp Glu Leu Met Cys Ile Asp
    50                  55                  60

Gly Ile Pro Val Lys Gly Lys Ser His Lys Gln Val Leu Asp Leu Met
65                  70                  75                  80

Thr Thr Ala Ala Arg Asn Gly His Val Leu Leu Thr Val Arg Arg Lys
                85                  90                  95

Ile Phe Tyr Gly Glu Lys Gln Pro Glu Asp Asp Ser
            100                 105

<210> SEQ ID NO 224
<211> LENGTH: 102
<212> TYPE: PRT
<213> ORGANISM: Human papillomavirus

<400> SEQUENCE: 224

Pro Ser Gln Leu Lys Gly Val Leu Val Arg Ala Ser Leu Lys Lys Ser
```

```
            1               5                  10                 15
          Thr Met Gly Phe Gly Phe Thr Ile Ile Gly Gly Asp Arg Pro Asp Glu
                          20                 25                 30
          Phe Leu Gln Val Lys Asn Val Leu Lys Asp Gly Pro Ala Ala Gln Asp
                          35                 40                 45
          Gly Lys Ile Ala Pro Gly Asp Val Ile Val Asp Ile Asn Gly Asn Cys
                          50                 55                 60
          Val Leu Gly His Thr His Ala Asp Val Val Gln Met Phe Gln Leu Val
           65                 70                 75                 80
          Pro Val Asn Gln Tyr Val Asn Leu Thr Leu Cys Arg Gly Tyr Pro Leu
                          85                 90                 95
          Pro Asp Asp Ser Glu Asp
                         100
```

<210> SEQ ID NO 225
<211> LENGTH: 102
<212> TYPE: PRT
<213> ORGANISM: Human papillomavirus

<400> SEQUENCE: 225

```
          Pro Ala Pro Gln Glu Pro Tyr Asp Val Val Leu Gln Arg Lys Glu Asn
           1               5                  10                 15
          Glu Gly Phe Gly Phe Val Ile Leu Thr Ser Lys Asn Lys Pro Pro Pro
                          20                 25                 30
          Gly Val Ile Pro His Lys Ile Gly Arg Val Ile Glu Gly Ser Pro Ala
                          35                 40                 45
          Asp Arg Cys Gly Lys Leu Lys Val Gly Asp His Ile Ser Ala Val Asn
                          50                 55                 60
          Gly Gln Ser Ile Val Glu Leu Ser His Asp Asn Ile Val Gln Leu Ile
           65                 70                 75                 80
          Lys Asp Ala Gly Val Thr Val Thr Leu Thr Val Ile Ala Glu Glu Glu
                          85                 90                 95
          His His Gly Pro Pro Ser
                         100
```

<210> SEQ ID NO 226
<211> LENGTH: 94
<212> TYPE: PRT
<213> ORGANISM: Human papillomavirus

<400> SEQUENCE: 226

```
          Gly Leu Arg Ser Pro Ile Thr Ile Gln Arg Ser Gly Lys Lys Tyr Gly
           1               5                  10                 15
          Phe Thr Leu Arg Ala Ile Arg Val Tyr Met Gly Asp Thr Asp Val Tyr
                          20                 25                 30
          Ser Val His His Ile Val Trp His Val Glu Glu Gly Gly Pro Ala Gln
                          35                 40                 45
          Glu Ala Gly Leu Cys Ala Gly Asp Leu Ile Thr His Val Asn Gly Glu
                          50                 55                 60
          Pro Val His Gly Met Val His Pro Glu Val Val Glu Leu Ile Leu Lys
           65                 70                 75                 80
          Ser Gly Asn Lys Val Ala Val Thr Thr Thr Pro Phe Glu Asn
                          85                 90
```

<210> SEQ ID NO 227
<211> LENGTH: 101
<212> TYPE: PRT

<213> ORGANISM: Human papillomavirus

<400> SEQUENCE: 227

Ile Ser Ala Leu Gly Ser Met Arg Pro Pro Ile Ile His Arg Ala
1               5                   10                  15

Gly Lys Lys Tyr Gly Phe Thr Leu Arg Ala Ile Arg Val Tyr Met Gly
                20                  25                  30

Asp Ser Asp Val Tyr Thr Val His His Met Val Trp His Val Glu Asp
            35                  40                  45

Gly Gly Pro Ala Ser Glu Ala Gly Leu Arg Gln Gly Asp Leu Ile Thr
        50                  55                  60

His Val Asn Gly Glu Pro Val His Gly Leu Val His Thr Glu Val Val
65                  70                  75                  80

Glu Leu Ile Leu Lys Ser Gly Asn Lys Val Ala Ile Ser Thr Thr Pro
                85                  90                  95

Leu Glu Asn Ser Ser
            100

<210> SEQ ID NO 228
<211> LENGTH: 103
<212> TYPE: PRT
<213> ORGANISM: Human papillomavirus

<400> SEQUENCE: 228

Leu Cys Gly Ser Leu Arg Pro Pro Ile Val Ile His Ser Ser Gly Lys
1               5                   10                  15

Lys Tyr Gly Phe Ser Leu Arg Ala Ile Arg Val Tyr Met Gly Asp Ser
                20                  25                  30

Asp Val Tyr Thr Val His His Val Val Trp Ser Val Glu Asp Gly Ser
            35                  40                  45

Pro Ala Gln Glu Ala Gly Leu Arg Ala Gly Asp Leu Ile Thr His Ile
        50                  55                  60

Asn Gly Glu Ser Val Leu Gly Leu Val His Met Asp Val Val Glu Leu
65                  70                  75                  80

Leu Leu Lys Ser Gly Asn Lys Ile Ser Leu Arg Thr Thr Ala Leu Glu
                85                  90                  95

Asn Thr Ser Ile Lys Val Gly
            100

<210> SEQ ID NO 229
<211> LENGTH: 91
<212> TYPE: PRT
<213> ORGANISM: Human papillomavirus

<400> SEQUENCE: 229

Pro His Gln Pro Ile Val Ile His Ser Ser Gly Lys Asn Tyr Gly Phe
1               5                   10                  15

Thr Ile Arg Ala Ile Arg Val Tyr Val Gly Asp Ser Asp Ile Tyr Thr
                20                  25                  30

Val His His Ile Val Trp Asn Val Glu Glu Gly Ser Pro Ala Cys Gln
            35                  40                  45

Ala Gly Leu Lys Ala Gly Asp Leu Ile Thr His Ile Asn Gly Glu Pro
        50                  55                  60

Val His Gly Leu Val His Thr Glu Val Ile Glu Leu Leu Lys Ser
65                  70                  75                  80

Gly Asn Lys Val Ser Ile Thr Thr Thr Pro Phe
                85                  90

<210> SEQ ID NO 230
<211> LENGTH: 100
<212> TYPE: PRT
<213> ORGANISM: Human papillomavirus

<400> SEQUENCE: 230

```
Pro Ala Lys Met Glu Lys Glu Thr Thr Arg Glu Leu Leu Leu Pro
1               5                   10                  15

Asn Trp Gln Gly Ser Gly Ser His Gly Leu Thr Ile Ala Gln Arg Asp
            20                  25                  30

Asp Gly Val Phe Val Gln Glu Val Thr Gln Asn Ser Pro Ala Ala Arg
        35                  40                  45

Thr Gly Val Val Lys Glu Gly Asp Gln Ile Val Gly Ala Thr Ile Tyr
    50                  55                  60

Phe Asp Asn Leu Gln Ser Gly Glu Val Thr Gln Leu Leu Asn Thr Met
65                  70                  75                  80

Gly His His Thr Val Gly Leu Lys Leu His Arg Lys Gly Asp Arg Ser
                85                  90                  95

Pro Asn Ser Ser
            100
```

<210> SEQ ID NO 231
<211> LENGTH: 98
<212> TYPE: PRT
<213> ORGANISM: Human papillomavirus

<400> SEQUENCE: 231

```
Ser Glu Asn Cys Lys Asp Val Phe Ile Glu Lys Gln Lys Gly Glu Ile
1               5                   10                  15

Leu Gly Val Val Ile Val Glu Ser Gly Trp Gly Ser Ile Leu Pro Thr
            20                  25                  30

Val Ile Ile Ala Asn Met Met His Gly Gly Pro Ala Glu Lys Ser Gly
        35                  40                  45

Lys Leu Asn Ile Gly Asp Gln Ile Met Ser Ile Asn Gly Thr Ser Leu
    50                  55                  60

Val Gly Leu Pro Leu Ser Thr Cys Gln Ser Ile Ile Lys Gly Leu Lys
65                  70                  75                  80

Asn Gln Ser Arg Val Lys Leu Asn Ile Val Arg Cys Pro Pro Val Asn
                85                  90                  95

Ser Ser
```

<210> SEQ ID NO 232
<211> LENGTH: 178
<212> TYPE: PRT
<213> ORGANISM: Human papillomavirus

<400> SEQUENCE: 232

```
Ser Glu Asn Cys Lys Asp Val Phe Ile Glu Lys Gln Lys Gly Glu Ile
1               5                   10                  15

Leu Gly Val Val Ile Val Glu Ser Gly Trp Gly Ser Ile Leu Pro Thr
            20                  25                  30

Val Ile Ile Ala Asn Met Met His Gly Gly Pro Ala Glu Lys Ser Gly
        35                  40                  45

Lys Leu Asn Ile Gly Asp Gln Ile Met Ser Ile Asn Gly Thr Ser Leu
    50                  55                  60

Val Gly Leu Pro Leu Ser Thr Cys Gln Ser Ile Ile Lys Gly Leu Glu
```

```
                65                  70                  75                  80
Asn Gln Ser Arg Val Lys Leu Asn Ile Val Arg Cys Pro Pro Val Thr
                    85                  90                  95

Thr Val Leu Ile Arg Arg Pro Asp Leu Arg Tyr Gln Leu Gly Phe Ser
                100                 105                 110

Val Gln Asn Gly Ile Ile Cys Ser Leu Met Arg Gly Ile Ala Glu
            115                 120                 125

Arg Gly Gly Val Arg Val Gly His Arg Ile Ile Glu Ile Asn Gly Gln
130                 135                 140

Ser Val Val Ala Thr Pro His Glu Lys Ile Val His Ile Leu Ser Asn
145                 150                 155                 160

Ala Val Gly Glu Ile His Met Lys Thr Met Pro Ala Ala Met Tyr Arg
                165                 170                 175

Leu Leu

<210> SEQ ID NO 233
<211> LENGTH: 92
<212> TYPE: PRT
<213> ORGANISM: Human papillomavirus

<400> SEQUENCE: 233

Leu Arg Cys Pro Pro Val Thr Thr Val Leu Ile Arg Arg Pro Asp Leu
1               5                   10                  15

Arg Tyr Gln Leu Gly Phe Ser Val Gln Asn Gly Ile Ile Cys Ser Leu
                20                  25                  30

Met Arg Gly Gly Ile Ala Glu Arg Gly Val Arg Val Gly His Arg
            35                  40                  45

Ile Ile Glu Ile Asn Gly Gln Ser Val Val Ala Thr Pro His Glu Lys
        50                  55                  60

Ile Val His Ile Leu Ser Asn Ala Val Gly Glu Ile His Met Lys Thr
65                  70                  75                  80

Met Pro Ala Ala Met Tyr Arg Leu Leu Asn Ser Ser
                85                  90

<210> SEQ ID NO 234
<211> LENGTH: 106
<212> TYPE: PRT
<213> ORGANISM: Human papillomavirus

<400> SEQUENCE: 234

His Asn Gly Asp Leu Asp His Phe Ser Asn Ser Asp Asn Cys Arg Glu
1               5                   10                  15

Val His Leu Glu Lys Arg Arg Gly Glu Gly Leu Gly Val Ala Leu Val
                20                  25                  30

Glu Ser Gly Trp Gly Ser Leu Leu Pro Thr Ala Val Ile Ala Asn Leu
            35                  40                  45

Leu His Gly Gly Pro Ala Glu Arg Ser Gly Ala Leu Ser Ile Gly Asp
        50                  55                  60

Arg Leu Thr Ala Ile Asn Gly Thr Ser Leu Val Gly Leu Pro Leu Ala
65                  70                  75                  80

Ala Cys Gln Ala Ala Val Arg Glu Thr Lys Ser Gln Thr Ser Val Thr
                85                  90                  95

Leu Ser Ile Val His Cys Pro Pro Val Thr
            100                 105

<210> SEQ ID NO 235
```

```
<211> LENGTH: 90
<212> TYPE: PRT
<213> ORGANISM: Human papillomavirus

<400> SEQUENCE: 235

Pro Val Thr Thr Ala Ile Ile His Arg Pro His Ala Arg Glu Gln Leu
1               5                   10                  15

Gly Phe Cys Val Glu Asp Gly Ile Ile Cys Ser Leu Leu Arg Gly Gly
                20                  25                  30

Ile Ala Glu Arg Gly Gly Ile Arg Val Gly His Arg Ile Ile Glu Ile
            35                  40                  45

Asn Gly Gln Ser Val Val Ala Thr Pro His Ala Arg Ile Ile Glu Leu
50                  55                  60

Leu Thr Glu Ala Tyr Gly Glu Val His Ile Lys Thr Met Pro Ala Ala
65                  70                  75                  80

Thr Tyr Arg Leu Leu Thr Gly Asn Ser Ser
                85                  90

<210> SEQ ID NO 236
<211> LENGTH: 103
<212> TYPE: PRT
<213> ORGANISM: Human papillomavirus

<400> SEQUENCE: 236

Leu Ser Asn Ser Asp Asn Cys Arg Glu Val His Leu Glu Lys Arg Arg
1               5                   10                  15

Gly Glu Gly Leu Gly Val Ala Leu Val Glu Ser Gly Trp Gly Ser Leu
                20                  25                  30

Leu Pro Thr Ala Val Ile Ala Asn Leu Leu His Gly Gly Pro Ala Glu
            35                  40                  45

Arg Ser Gly Ala Leu Ser Ile Gly Asp Arg Leu Thr Ala Ile Asn Gly
50                  55                  60

Thr Ser Leu Val Gly Leu Pro Leu Ala Ala Cys Gln Ala Ala Val Arg
65                  70                  75                  80

Glu Thr Lys Ser Gln Thr Ser Val Thr Leu Ser Ile Val His Cys Pro
                85                  90                  95

Pro Val Thr Thr Ala Ile Met
            100

<210> SEQ ID NO 237
<211> LENGTH: 86
<212> TYPE: PRT
<213> ORGANISM: Human papillomavirus

<400> SEQUENCE: 237

Arg Lys Val Arg Leu Ile Gln Phe Glu Lys Val Thr Glu Glu Pro Met
1               5                   10                  15

Gly Ile Thr Leu Lys Leu Asn Glu Lys Gln Ser Cys Thr Val Ala Arg
                20                  25                  30

Ile Leu His Gly Gly Met Ile His Arg Gln Gly Ser Leu His Val Gly
            35                  40                  45

Asp Glu Ile Leu Glu Ile Asn Gly Thr Asn Val Thr Asn His Ser Val
50                  55                  60

Asp Gln Leu Gln Lys Ala Met Lys Glu Thr Lys Gly Met Ile Ser Leu
65                  70                  75                  80

Lys Val Ile Pro Asn Gln
                85
```

<210> SEQ ID NO 238
<211> LENGTH: 89
<212> TYPE: PRT
<213> ORGANISM: Human papillomavirus

<400> SEQUENCE: 238

Pro Val Pro Pro Asp Ala Val Arg Met Val Gly Ile Arg Lys Thr Ala
1               5                   10                  15

Gly Glu His Leu Gly Val Thr Phe Arg Val Glu Gly Gly Glu Leu Val
            20                  25                  30

Ile Ala Arg Ile Leu His Gly Gly Met Val Ala Gln Gln Gly Leu Leu
        35                  40                  45

His Val Gly Asp Ile Ile Lys Glu Val Asn Gly Gln Pro Val Gly Ser
    50                  55                  60

Asp Pro Arg Ala Leu Gln Glu Leu Leu Arg Asn Ala Ser Gly Ser Val
65                  70                  75                  80

Ile Leu Lys Ile Leu Pro Asn Tyr Gln
                85

<210> SEQ ID NO 239
<211> LENGTH: 99
<212> TYPE: PRT
<213> ORGANISM: Human papillomavirus

<400> SEQUENCE: 239

Asn Ile Asp Glu Asp Phe Asp Glu Glu Ser Val Lys Ile Val Arg Leu
1               5                   10                  15

Val Lys Asn Lys Glu Pro Leu Gly Ala Thr Ile Arg Arg Asp Glu His
            20                  25                  30

Ser Gly Ala Val Val Val Ala Arg Ile Met Arg Gly Gly Ala Ala Asp
        35                  40                  45

Arg Ser Gly Leu Val His Val Gly Asp Glu Leu Arg Glu Val Asn Gly
    50                  55                  60

Ile Ala Val Leu His Lys Arg Pro Asp Glu Ile Ser Gln Ile Leu Ala
65                  70                  75                  80

Gln Ser Gln Gly Ser Ile Thr Leu Lys Ile Ile Pro Ala Thr Gln Glu
                85                  90                  95

Glu Asp Arg

<210> SEQ ID NO 240
<211> LENGTH: 100
<212> TYPE: PRT
<213> ORGANISM: Human papillomavirus

<400> SEQUENCE: 240

Trp Glu Ala Gly Ile Gln His Ile Glu Leu Glu Lys Gly Ser Lys Gly
1               5                   10                  15

Leu Gly Phe Ser Ile Leu Asp Tyr Gln Asp Pro Ile Asp Pro Ala Ser
            20                  25                  30

Thr Val Ile Ile Ile Arg Ser Leu Val Pro Gly Gly Ile Ala Glu Lys
        35                  40                  45

Asp Gly Arg Leu Leu Pro Gly Asp Arg Leu Met Phe Val Asn Asp Val
    50                  55                  60

Asn Leu Glu Asn Ser Ser Leu Glu Glu Ala Val Glu Ala Leu Lys Gly
65                  70                  75                  80

Ala Pro Ser Gly Thr Val Arg Ile Gly Val Ala Lys Pro Leu Pro Leu
                85                  90                  95

Ser Pro Glu Glu
            100

<210> SEQ ID NO 241
<211> LENGTH: 96
<212> TYPE: PRT
<213> ORGANISM: Human papillomavirus

<400> SEQUENCE: 241

Leu Gln Gly Leu Arg Thr Val Glu Met Lys Lys Gly Pro Thr Asp Ser
1               5                   10                  15

Leu Gly Ile Ser Ile Ala Gly Gly Val Gly Ser Pro Leu Gly Asp Val
            20                  25                  30

Pro Ile Phe Ile Ala Met Met His Pro Thr Gly Val Ala Ala Gln Thr
        35                  40                  45

Gln Lys Leu Arg Val Gly Asp Arg Ile Val Thr Ile Cys Gly Thr Ser
    50                  55                  60

Thr Glu Gly Met Thr His Thr Gln Ala Val Asn Leu Leu Lys Asn Ala
65                  70                  75                  80

Ser Gly Ser Ile Glu Met Gln Val Val Ala Gly Gly Asp Val Ser Val
                85                  90                  95

<210> SEQ ID NO 242
<211> LENGTH: 97
<212> TYPE: PRT
<213> ORGANISM: Human papillomavirus

<400> SEQUENCE: 242

Pro Val His Trp Gln His Met Glu Thr Ile Glu Leu Val Asn Asp Gly
1               5                   10                  15

Ser Gly Leu Gly Phe Gly Ile Ile Gly Gly Lys Ala Thr Gly Val Ile
            20                  25                  30

Val Lys Thr Ile Leu Pro Gly Gly Val Ala Asp Gln His Gly Arg Leu
        35                  40                  45

Cys Ser Gly Asp His Ile Leu Lys Ile Gly Asp Thr Asp Leu Ala Gly
    50                  55                  60

Met Ser Ser Glu Gln Val Ala Gln Val Leu Arg Gln Cys Gly Asn Arg
65                  70                  75                  80

Val Lys Leu Met Ile Ala Arg Gly Ala Ile Glu Glu Arg Thr Ala Pro
                85                  90                  95

Thr

<210> SEQ ID NO 243
<211> LENGTH: 98
<212> TYPE: PRT
<213> ORGANISM: Human papillomavirus

<400> SEQUENCE: 243

Gln Glu Ser Glu Thr Phe Asp Val Glu Leu Thr Lys Asn Val Gln Gly
1               5                   10                  15

Leu Gly Ile Thr Ile Ala Gly Tyr Ile Gly Asp Lys Lys Leu Glu Pro
            20                  25                  30

Ser Gly Ile Phe Val Lys Ser Ile Thr Lys Ser Ser Ala Val Glu His
            35                  40                  45

Asp Gly Arg Ile Gln Ile Gly Asp Gln Ile Ile Ala Val Asp Gly Thr
    50                  55                  60

Asn Leu Gln Gly Phe Thr Asn Gln Gln Ala Val Glu Val Leu Arg His

```
                65                  70                  75                  80
Thr Gly Gln Thr Val Leu Leu Thr Leu Met Arg Arg Gly Met Lys Gln
                    85                  90                  95

Glu Ala

<210> SEQ ID NO 244
<211> LENGTH: 98
<212> TYPE: PRT
<213> ORGANISM: Human papillomavirus

<400> SEQUENCE: 244

Lys Glu Glu Val Cys Asp Thr Leu Thr Ile Glu Leu Gln Lys Lys
1               5                   10                  15

Pro Gly Lys Gly Leu Gly Leu Ser Ile Val Gly Lys Arg Asn Asp Thr
                20                  25                  30

Gly Val Phe Val Ser Asp Ile Val Lys Gly Gly Ile Ala Asp Ala Asp
            35                  40                  45

Gly Arg Leu Met Gln Gly Asp Gln Ile Leu Met Val Asn Gly Glu Asp
        50                  55                  60

Val Arg Asn Ala Thr Gln Glu Ala Val Ala Ala Leu Leu Lys Cys Ser
65                  70                  75                  80

Leu Gly Thr Val Thr Leu Glu Val Gly Arg Ile Lys Ala Gly Pro Phe
                85                  90                  95

His Ser

<210> SEQ ID NO 245
<211> LENGTH: 95
<212> TYPE: PRT
<213> ORGANISM: Human papillomavirus

<400> SEQUENCE: 245

Leu Thr Gly Glu Leu His Met Ile Glu Leu Glu Lys Gly His Ser Gly
1               5                   10                  15

Leu Gly Leu Ser Leu Ala Gly Asn Lys Asp Arg Ser Arg Met Ser Val
                20                  25                  30

Phe Ile Val Gly Ile Asp Pro Asn Gly Ala Ala Gly Lys Asp Gly Arg
            35                  40                  45

Leu Gln Ile Ala Asp Glu Leu Leu Glu Ile Asn Gly Gln Ile Leu Tyr
        50                  55                  60

Gly Arg Ser His Gln Asn Ala Ser Ser Ile Ile Lys Cys Ala Pro Ser
65                  70                  75                  80

Lys Val Lys Ile Ile Phe Ile Arg Asn Lys Asp Ala Val Asn Gln
                85                  90                  95

<210> SEQ ID NO 246
<211> LENGTH: 91
<212> TYPE: PRT
<213> ORGANISM: Human papillomavirus

<400> SEQUENCE: 246

Leu Gly Pro Pro Gln Cys Lys Ser Ile Thr Leu Glu Arg Gly Pro Asp
1               5                   10                  15

Gly Leu Gly Phe Ser Ile Val Gly Gly Tyr Gly Ser Pro His Gly Asp
                20                  25                  30

Leu Pro Ile Tyr Val Lys Thr Val Phe Ala Lys Gly Ala Ala Ser Glu
            35                  40                  45

Asp Gly Arg Leu Lys Arg Gly Asp Gln Ile Ile Ala Val Asn Gly Gln
```

```
            50                  55                  60
Ser Leu Glu Gly Val Thr His Glu Ala Val Ala Ile Leu Lys Arg
 65                  70                  75                  80
Thr Lys Gly Thr Val Thr Leu Met Val Leu Ser
                 85                  90
```

<210> SEQ ID NO 247
<211> LENGTH: 99
<212> TYPE: PRT
<213> ORGANISM: Human papillomavirus

<400> SEQUENCE: 247

```
Arg Asn Val Ser Lys Glu Ser Phe Glu Arg Thr Ile Asn Ile Ala Lys
  1               5                  10                  15
Gly Asn Ser Ser Leu Gly Met Thr Val Ser Ala Asn Lys Asp Gly Leu
                 20                  25                  30
Gly Met Ile Val Arg Ser Ile Ile His Gly Gly Ala Ile Ser Arg Asp
                 35                  40                  45
Gly Arg Ile Ala Ile Gly Asp Cys Ile Leu Ser Ile Asn Glu Glu Ser
             50                  55                  60
Thr Ile Ser Val Thr Asn Ala Gln Ala Arg Ala Met Leu Arg Arg His
 65                  70                  75                  80
Ser Leu Ile Gly Pro Asp Ile Lys Ile Thr Tyr Val Pro Ala Glu His
                 85                  90                  95
Leu Glu Glu
```

<210> SEQ ID NO 248
<211> LENGTH: 95
<212> TYPE: PRT
<213> ORGANISM: Human papillomavirus

<400> SEQUENCE: 248

```
Leu Pro Gly Cys Glu Thr Thr Ile Glu Ile Ser Lys Gly Arg Thr Gly
  1               5                  10                  15
Leu Gly Leu Ser Ile Val Gly Gly Ser Asp Thr Leu Leu Gly Ala Ile
                 20                  25                  30
Ile Ile His Glu Val Tyr Glu Glu Gly Ala Ala Cys Lys Asp Gly Arg
                 35                  40                  45
Leu Trp Ala Gly Asp Gln Ile Leu Glu Val Asn Gly Ile Asp Leu Arg
             50                  55                  60
Lys Ala Thr His Asp Glu Ala Ile Asn Val Leu Arg Gln Thr Pro Gln
 65                  70                  75                  80
Arg Val Arg Leu Thr Leu Tyr Arg Asp Glu Ala Pro Tyr Lys Glu
                 85                  90                  95
```

<210> SEQ ID NO 249
<211> LENGTH: 112
<212> TYPE: PRT
<213> ORGANISM: Human papillomavirus

<400> SEQUENCE: 249

```
Leu Asn Trp Asn Gln Pro Arg Arg Val Glu Leu Trp Arg Glu Pro Ser
  1               5                  10                  15
Lys Ser Leu Gly Ile Ser Ile Val Gly Gly Arg Gly Met Gly Ser Arg
                 20                  25                  30
Leu Ser Asn Gly Glu Val Met Arg Gly Ile Phe Ile Lys His Val Leu
                 35                  40                  45
```

```
Glu Asp Ser Pro Ala Gly Lys Asn Gly Thr Leu Lys Pro Gly Asp Arg
 50                  55                  60

Ile Val Glu Val Asp Gly Met Asp Leu Arg Asp Ala Ser His Glu Gln
 65                  70                  75                  80

Ala Val Glu Ala Ile Arg Lys Ala Gly Asn Pro Val Val Phe Met Val
                 85                  90                  95

Gln Ser Ile Ile Asn Arg Pro Arg Lys Ser Pro Leu Pro Ser Leu Leu
                100                 105                 110

<210> SEQ ID NO 250
<211> LENGTH: 94
<212> TYPE: PRT
<213> ORGANISM: Human papillomavirus

<400> SEQUENCE: 250

Leu Ser Ser Phe Lys Asn Val Gln His Leu Glu Leu Pro Lys Asp Gln
 1                5                  10                  15

Gly Gly Leu Gly Ile Ala Ile Ser Glu Glu Asp Thr Leu Ser Gly Val
                 20                  25                  30

Ile Ile Lys Ser Leu Thr Glu His Gly Val Ala Ala Thr Asp Gly Arg
                 35                  40                  45

Leu Lys Val Gly Asp Gln Ile Leu Ala Val Asp Asp Glu Ile Val Val
 50                  55                  60

Gly Tyr Pro Ile Glu Lys Phe Ile Ser Leu Leu Lys Thr Ala Lys Met
 65                  70                  75                  80

Thr Val Lys Leu Thr Ile His Ala Glu Asn Pro Asp Ser Gln
                 85                  90

<210> SEQ ID NO 251
<211> LENGTH: 99
<212> TYPE: PRT
<213> ORGANISM: Human papillomavirus

<400> SEQUENCE: 251

Gln Gly Arg His Val Glu Val Phe Glu Leu Leu Lys Pro Pro Ser Gly
 1                5                  10                  15

Gly Leu Gly Phe Ser Val Val Gly Leu Arg Ser Glu Asn Arg Gly Glu
                 20                  25                  30

Leu Gly Ile Phe Val Gln Glu Ile Gln Glu Gly Ser Val Ala His Arg
                 35                  40                  45

Asp Gly Arg Leu Lys Glu Thr Asp Gln Ile Leu Ala Ile Asn Gly Gln
 50                  55                  60

Ala Leu Asp Gln Thr Ile Thr His Gln Gln Ala Ile Ser Ile Leu Gln
 65                  70                  75                  80

Lys Ala Lys Asp Thr Val Gln Leu Val Ile Ala Arg Gly Ser Leu Pro
                 85                  90                  95

Gln Leu Val

<210> SEQ ID NO 252
<211> LENGTH: 92
<212> TYPE: PRT
<213> ORGANISM: Human papillomavirus

<400> SEQUENCE: 252

Leu Asn Tyr Glu Ile Val Val Ala His Val Ser Lys Phe Ser Glu Asn
 1                5                  10                  15

Ser Gly Leu Gly Ile Ser Leu Glu Ala Thr Val Gly His His Phe Ile
                 20                  25                  30
```

```
Arg Ser Val Leu Pro Glu Gly Pro Val Gly His Ser Gly Lys Leu Phe
        35                  40                  45

Ser Gly Asp Glu Leu Leu Glu Val Asn Gly Ile Thr Leu Leu Gly Glu
 50                  55                  60

Asn His Gln Asp Val Val Asn Ile Leu Lys Glu Leu Pro Ile Glu Val
 65                  70                  75                  80

Thr Met Val Cys Cys Arg Arg Thr Val Pro Pro Thr
                 85                  90

<210> SEQ ID NO 253
<211> LENGTH: 90
<212> TYPE: PRT
<213> ORGANISM: Human papillomavirus

<400> SEQUENCE: 253

Ile Thr Leu Leu Lys Gly Pro Lys Gly Leu Gly Phe Ser Ile Ala Gly
 1               5                  10                  15

Gly Ile Gly Asn Gln His Ile Pro Gly Asp Asn Ser Ile Tyr Ile Thr
                20                  25                  30

Lys Ile Ile Glu Gly Gly Ala Ala Gln Lys Asp Gly Arg Leu Gln Ile
        35                  40                  45

Gly Asp Arg Leu Leu Ala Val Asn Asn Thr Asn Leu Gln Asp Val Arg
 50                  55                  60

His Glu Glu Ala Val Ala Ser Leu Lys Asn Thr Ser Asp Met Val Tyr
 65                  70                  75                  80

Leu Lys Val Ala Lys Pro Gly Ser Leu Glu
                85                  90

<210> SEQ ID NO 254
<211> LENGTH: 93
<212> TYPE: PRT
<213> ORGANISM: Human papillomavirus

<400> SEQUENCE: 254

Ile Gln Tyr Glu Glu Ile Val Leu Glu Arg Gly Asn Ser Gly Leu Gly
 1               5                  10                  15

Phe Ser Ile Ala Gly Gly Ile Asp Asn Pro His Val Pro Asp Asp Pro
                20                  25                  30

Gly Ile Phe Ile Thr Lys Ile Ile Pro Gly Gly Ala Ala Ala Met Asp
        35                  40                  45

Gly Arg Leu Gly Val Asn Asp Cys Val Leu Arg Val Asn Glu Val Glu
 50                  55                  60

Val Ser Glu Val Val His Ser Arg Ala Val Glu Ala Leu Lys Glu Ala
 65                  70                  75                  80

Gly Pro Val Val Arg Leu Val Val Arg Arg Gln Asn
                85                  90

<210> SEQ ID NO 255
<211> LENGTH: 119
<212> TYPE: PRT
<213> ORGANISM: Human papillomavirus

<400> SEQUENCE: 255

Ile Leu Leu His Lys Gly Ser Thr Gly Leu Gly Phe Asn Ile Val Gly
 1               5                  10                  15

Gly Glu Asp Gly Glu Gly Ile Phe Val Ser Phe Ile Leu Ala Gly Gly
                20                  25                  30
```

```
Pro Ala Asp Leu Ser Gly Glu Leu Arg Arg Gly Asp Arg Ile Leu Ser
            35                  40                  45

Val Asn Gly Val Asn Leu Arg Asn Ala Thr His Glu Gln Ala Ala Ala
 50                  55                  60

Ala Leu Lys Arg Ala Gly Gln Ser Val Thr Ile Val Ala Gln Tyr Arg
 65                  70                  75                  80

Pro Glu Glu Tyr Ser Arg Phe Glu Ser Lys Ile His Asp Leu Arg Glu
                 85                  90                  95

Gln Met Met Asn Ser Ser Met Ser Ser Gly Ser Gly Ser Leu Arg Thr
            100                 105                 110

Ser Glu Lys Arg Ser Leu Glu
        115
```

<210> SEQ ID NO 256
<211> LENGTH: 187
<212> TYPE: PRT
<213> ORGANISM: Human papillomavirus

<400> SEQUENCE: 256

```
Tyr Glu Glu Ile Val Leu Glu Arg Gly Asn Ser Gly Leu Gly Phe Ser
 1               5                  10                  15

Ile Ala Gly Gly Ile Asp Asn Pro His Val Pro Asp Asp Pro Gly Ile
            20                  25                  30

Phe Ile Thr Lys Ile Ile Pro Gly Gly Ala Ala Ala Met Asp Gly Arg
        35                  40                  45

Leu Gly Val Asn Asp Cys Val Leu Arg Val Asn Glu Val Glu Val Ser
 50                  55                  60

Glu Val Val His Ser Arg Ala Val Glu Ala Leu Lys Glu Ala Gly Pro
 65                  70                  75                  80

Val Val Arg Leu Val Val Arg Arg Gln Pro Pro Pro Glu Thr Ile
                 85                  90                  95

Met Glu Val Asn Leu Leu Lys Gly Pro Lys Gly Leu Gly Phe Ser Ile
            100                 105                 110

Ala Gly Gly Ile Gly Asn Gln His Ile Pro Gly Asp Asn Ser Ile Tyr
        115                 120                 125

Ile Thr Lys Ile Ile Glu Gly Gly Ala Ala Gln Lys Asp Gly Arg Leu
130                 135                 140

Gln Ile Gly Asp Arg Leu Leu Ala Val Asn Asn Thr Asn Leu Gln Asp
145                 150                 155                 160

Val Arg His Glu Glu Ala Val Ala Ser Leu Lys Asn Thr Ser Asp Met
                165                 170                 175

Val Tyr Leu Lys Val Ala Lys Pro Gly Ser Leu
            180                 185
```

<210> SEQ ID NO 257
<211> LENGTH: 106
<212> TYPE: PRT
<213> ORGANISM: Human papillomavirus

<400> SEQUENCE: 257

```
Arg Val Glu Arg Leu Glu Leu Phe Pro Val Glu Leu Glu Lys Asp Ser
 1               5                  10                  15

Glu Gly Leu Gly Ile Ser Ile Ile Gly Met Gly Ala Gly Ala Asp Met
            20                  25                  30

Gly Leu Glu Lys Leu Gly Ile Phe Val Lys Thr Val Thr Glu Gly Gly
        35                  40                  45
```

```
Ala Ala His Arg Asp Gly Arg Ile Gln Val Asn Asp Leu Leu Val Glu
    50                  55                  60

Val Asp Gly Thr Ser Leu Val Gly Val Thr Gln Ser Phe Ala Ala Ser
65                  70                  75                  80

Val Leu Arg Asn Thr Lys Gly Arg Val Arg Cys Arg Phe Met Ile Gly
                85                  90                  95

Arg Glu Arg Pro Gly Glu Gln Ser Glu Val
            100                 105
```

<210> SEQ ID NO 258
<211> LENGTH: 90
<212> TYPE: PRT
<213> ORGANISM: Human papillomavirus

<400> SEQUENCE: 258

```
Gln Pro Asn Val Ile Ser Val Arg Leu Phe Lys Arg Lys Val Gly Gly
1               5                   10                  15

Leu Gly Phe Leu Val Lys Glu Arg Val Ser Lys Pro Pro Val Ile Ile
                20                  25                  30

Ser Asp Leu Ile Arg Gly Gly Ala Ala Glu Gln Ser Gly Leu Ile Gln
            35                  40                  45

Ala Gly Asp Ile Ile Leu Ala Val Asn Gly Arg Pro Leu Val Asp Leu
    50                  55                  60

Ser Tyr Asp Ser Ala Leu Glu Val Leu Arg Gly Ile Ala Ser Glu Thr
65                  70                  75                  80

His Val Val Leu Ile Leu Arg Gly Pro Glu
                85                  90
```

<210> SEQ ID NO 259
<211> LENGTH: 103
<212> TYPE: PRT
<213> ORGANISM: Human papillomavirus

<400> SEQUENCE: 259

```
Pro Ser Asp Thr Ser Ser Glu Asp Gly Val Arg Arg Ile Val His Leu
1               5                   10                  15

Tyr Thr Thr Ser Asp Asp Phe Cys Leu Gly Phe Asn Ile Arg Gly Gly
                20                  25                  30

Lys Glu Phe Gly Leu Gly Ile Tyr Val Ser Lys Val Asp His Gly Gly
            35                  40                  45

Leu Ala Glu Glu Asn Gly Ile Lys Val Gly Asp Gln Val Leu Ala Ala
    50                  55                  60

Asn Gly Val Arg Phe Asp Asp Ile Ser His Ser Gln Ala Val Glu Val
65                  70                  75                  80

Leu Lys Gly Gln Thr His Ile Met Leu Thr Ile Lys Glu Thr Gly Arg
                85                  90                  95

Tyr Pro Ala Tyr Lys Glu Met
            100
```

<210> SEQ ID NO 260
<211> LENGTH: 104
<212> TYPE: PRT
<213> ORGANISM: Human papillomavirus

<400> SEQUENCE: 260

```
Glu Ala Asn Ser Asp Glu Ser Asp Ile Ile His Ser Val Arg Val Glu
1               5                   10                  15

Lys Ser Pro Ala Gly Arg Leu Gly Phe Ser Val Arg Gly Gly Ser Glu
```

```
                20                  25                  30

His Gly Leu Gly Ile Phe Val Ser Lys Val Glu Glu Gly Ser Ser Ala
            35                  40                  45

Glu Arg Ala Gly Leu Cys Val Gly Asp Lys Ile Thr Glu Val Asn Gly
        50                  55                  60

Leu Ser Leu Glu Ser Thr Thr Met Gly Ser Ala Val Lys Val Leu Thr
65                  70                  75                  80

Ser Ser Ser Arg Leu His Met Met Val Arg Arg Met Gly Arg Val Pro
                85                  90                  95

Gly Ile Lys Phe Ser Lys Glu Lys
                100
```

<210> SEQ ID NO 261
<211> LENGTH: 116
<212> TYPE: PRT
<213> ORGANISM: Human papillomavirus

<400> SEQUENCE: 261

```
Asp Lys Ile Lys Lys Phe Leu Thr Glu Ser His Asp Arg Gln Ala Lys
1               5                   10                  15

Gly Lys Ala Ile Thr Lys Lys Tyr Ile Gly Ile Arg Met Met Ser
            20                  25                  30

Leu Thr Ser Ser Lys Ala Lys Glu Leu Lys Asp Arg His Arg Asp Phe
        35                  40                  45

Pro Asp Val Ile Ser Gly Ala Tyr Ile Ile Glu Val Ile Pro Asp Thr
    50                  55                  60

Pro Ala Glu Ala Gly Leu Lys Glu Asn Asp Val Ile Ile Ser Ile
65                  70                  75                  80

Asn Gly Gln Ser Val Val Ser Ala Asn Asp Val Ser Asp Val Ile Lys
                85                  90                  95

Arg Glu Ser Thr Leu Asn Met Val Val Arg Arg Gly Asn Glu Asp Ile
            100                 105                 110

Met Ile Thr Val
        115
```

<210> SEQ ID NO 262
<211> LENGTH: 98
<212> TYPE: PRT
<213> ORGANISM: Human papillomavirus

<400> SEQUENCE: 262

```
Tyr Arg Pro Arg Asp Asp Ser Phe His Val Ile Leu Asn Lys Ser Ser
1               5                   10                  15

Pro Glu Glu Gln Leu Gly Ile Lys Leu Val Arg Lys Val Asp Glu Pro
            20                  25                  30

Gly Val Phe Ile Phe Asn Ala Leu Asp Gly Gly Val Ala Tyr Arg His
        35                  40                  45

Gly Gln Leu Glu Glu Asn Asp Arg Val Leu Ala Ile Asn Gly His Asp
    50                  55                  60

Leu Arg Tyr Gly Ser Pro Glu Ser Ala Ala His Leu Ile Gln Ala Ser
65                  70                  75                  80

Glu Arg Arg Val His Leu Val Val Ser Arg Gln Val Gln Arg Ser
                85                  90                  95

Pro Asp
```

<210> SEQ ID NO 263

```
<211> LENGTH: 100
<212> TYPE: PRT
<213> ORGANISM: Human papillomavirus

<400> SEQUENCE: 263

Pro Thr Ile Thr Cys His Glu Lys Val Val Asn Ile Gln Lys Asp Pro
1               5                   10                  15

Gly Glu Ser Leu Gly Met Thr Val Ala Gly Ala Ser His Arg Glu
            20                  25                  30

Trp Asp Leu Pro Ile Tyr Val Ser Val Glu Pro Gly Gly Val Ile
            35                  40                  45

Ser Arg Asp Gly Arg Ile Lys Thr Gly Asp Ile Leu Leu Asn Val Asp
50                  55                  60

Gly Val Glu Leu Thr Glu Val Ser Arg Ser Glu Ala Val Ala Leu Leu
65                  70                  75                  80

Lys Arg Thr Ser Ser Ile Val Leu Lys Ala Leu Glu Val Lys Glu
            85                  90                  95

Tyr Glu Pro Gln
            100

<210> SEQ ID NO 264
<211> LENGTH: 97
<212> TYPE: PRT
<213> ORGANISM: Human papillomavirus

<400> SEQUENCE: 264

Pro Asp Gly Glu Ile Thr Ser Ile Lys Ile Asn Arg Val Asp Pro Ser
1               5                   10                  15

Glu Ser Leu Ser Ile Arg Leu Val Gly Gly Ser Glu Thr Pro Leu Val
            20                  25                  30

His Ile Ile Ile Gln His Ile Tyr Arg Asp Gly Val Ile Ala Arg Asp
            35                  40                  45

Gly Arg Leu Leu Pro Arg Asp Ile Ile Leu Lys Val Asn Gly Met Asp
50                  55                  60

Ile Ser Asn Val Pro His Asn Tyr Ala Val Arg Leu Leu Arg Gln Pro
65                  70                  75                  80

Cys Gln Val Leu Trp Leu Thr Val Met Arg Glu Gln Lys Phe Arg Ser
            85                  90                  95

Arg

<210> SEQ ID NO 265
<211> LENGTH: 99
<212> TYPE: PRT
<213> ORGANISM: Human papillomavirus

<400> SEQUENCE: 265

Pro Arg Cys Leu Tyr Asn Cys Lys Asp Ile Val Leu Arg Arg Asn Thr
1               5                   10                  15

Ala Gly Ser Leu Gly Phe Cys Ile Val Gly Gly Tyr Glu Glu Tyr Asn
            20                  25                  30

Gly Asn Lys Pro Phe Phe Ile Lys Ser Ile Val Glu Gly Thr Pro Ala
            35                  40                  45

Tyr Asn Asp Gly Arg Ile Arg Cys Gly Asp Ile Leu Leu Ala Val Asn
50                  55                  60

Gly Arg Ser Thr Ser Gly Met Ile His Ala Cys Leu Ala Arg Leu Leu
65                  70                  75                  80

Lys Glu Leu Lys Gly Arg Ile Thr Leu Thr Ile Val Ser Trp Pro Gly
```

```
                    85                  90                  95

Thr Phe Leu

<210> SEQ ID NO 266
<211> LENGTH: 101
<212> TYPE: PRT
<213> ORGANISM: Human papillomavirus

<400> SEQUENCE: 266

Leu Leu Thr Glu Glu Ile Asn Leu Thr Arg Gly Pro Ser Gly Leu
1               5                   10                  15

Gly Phe Asn Ile Val Gly Gly Thr Asp Gln Gln Tyr Val Ser Asn Asp
                20                  25                  30

Ser Gly Ile Tyr Val Ser Arg Ile Lys Glu Asn Gly Ala Ala Ala Leu
            35                  40                  45

Asp Gly Arg Leu Gln Glu Gly Asp Lys Ile Leu Ser Val Asn Gly Gln
        50                  55                  60

Asp Leu Lys Asn Leu Leu His Gln Asp Ala Val Asp Leu Phe Arg Asn
65                  70                  75                  80

Ala Gly Tyr Ala Val Ser Leu Arg Val Gln His Arg Leu Gln Val Gln
                85                  90                  95

Asn Gly Ile His Ser
            100

<210> SEQ ID NO 267
<211> LENGTH: 94
<212> TYPE: PRT
<213> ORGANISM: Human papillomavirus

<400> SEQUENCE: 267

Pro Val Asp Ala Ile Arg Ile Leu Gly Ile His Lys Arg Ala Gly Glu
1               5                   10                  15

Pro Leu Gly Val Thr Phe Arg Val Glu Asn Asn Asp Leu Val Ile Ala
                20                  25                  30

Arg Ile Leu His Gly Gly Met Ile Asp Arg Gln Gly Leu Leu His Val
            35                  40                  45

Gly Asp Ile Ile Lys Glu Val Asn Gly His Glu Val Gly Asn Asn Pro
        50                  55                  60

Lys Glu Leu Gln Glu Leu Leu Lys Asn Ile Ser Gly Ser Val Thr Leu
65                  70                  75                  80

Lys Ile Leu Pro Ser Tyr Arg Asp Thr Ile Thr Pro Gln Gln
                85                  90

<210> SEQ ID NO 268
<211> LENGTH: 94
<212> TYPE: PRT
<213> ORGANISM: Human papillomavirus

<400> SEQUENCE: 268

Gly Lys Arg Leu Asn Ile Gln Leu Lys Lys Gly Thr Glu Gly Leu Gly
1               5                   10                  15

Phe Ser Ile Thr Ser Arg Asp Val Thr Ile Gly Gly Ser Ala Pro Ile
                20                  25                  30

Tyr Val Lys Asn Ile Leu Pro Arg Gly Ala Ala Ile Gln Asp Gly Arg
            35                  40                  45

Leu Lys Ala Gly Asp Arg Leu Ile Glu Val Asn Gly Val Asp Leu Val
        50                  55                  60
```

```
Gly Lys Ser Gln Glu Glu Val Val Ser Leu Leu Arg Ser Thr Lys Met
 65                  70                  75                  80

Glu Gly Thr Val Ser Leu Leu Val Phe Arg Gln Glu Asp Ala
                 85                  90

<210> SEQ ID NO 269
<211> LENGTH: 106
<212> TYPE: PRT
<213> ORGANISM: Human papillomavirus

<400> SEQUENCE: 269

Ile Pro Asn Phe Ser Leu Asp Asp Met Val Lys Leu Val Glu Val Pro
  1               5                  10                  15

Asn Asp Gly Gly Pro Leu Gly Ile His Val Val Pro Phe Ser Ala Arg
                 20                  25                  30

Gly Gly Arg Thr Leu Gly Leu Leu Val Lys Arg Leu Glu Lys Gly Gly
                 35                  40                  45

Lys Ala Glu His Glu Asn Leu Phe Arg Glu Asn Asp Cys Ile Val Arg
 50                  55                  60

Ile Asn Asp Gly Asp Leu Arg Asn Arg Arg Phe Glu Gln Ala Gln His
 65                  70                  75                  80

Met Phe Arg Gln Ala Met Arg Thr Pro Ile Ile Trp Phe His Val Val
                 85                  90                  95

Pro Ala Ala Asn Lys Glu Gln Tyr Glu Gln
                100                 105

<210> SEQ ID NO 270
<211> LENGTH: 113
<212> TYPE: PRT
<213> ORGANISM: Human papillomavirus

<400> SEQUENCE: 270

Pro Arg Glu Phe Leu Thr Phe Glu Val Pro Leu Asn Asp Ser Gly Ser
  1               5                  10                  15

Ala Gly Leu Gly Val Ser Val Lys Gly Asn Arg Ser Lys Glu Asn His
                 20                  25                  30

Ala Asp Leu Gly Ile Phe Val Lys Ser Ile Ile Asn Gly Gly Ala Ala
                 35                  40                  45

Ser Lys Asp Gly Arg Leu Arg Val Asn Asp Gln Leu Ile Ala Val Asn
 50                  55                  60

Gly Glu Ser Leu Leu Gly Lys Thr Asn Gln Asp Ala Met Glu Thr Leu
 65                  70                  75                  80

Arg Arg Ser Met Ser Thr Glu Gly Asn Lys Arg Gly Met Ile Gln Leu
                 85                  90                  95

Ile Val Ala Ser Arg Ile Ser Lys Cys Asn Glu Leu Lys Ser Asn Ser
                100                 105                 110

Ser

<210> SEQ ID NO 271
<211> LENGTH: 99
<212> TYPE: PRT
<213> ORGANISM: Human papillomavirus

<400> SEQUENCE: 271

Ile Ser Asn Lys Asn Ala Lys Lys Ile Lys Ile Asp Leu Lys Lys Gly
  1               5                  10                  15

Pro Glu Gly Leu Gly Phe Thr Val Val Thr Arg Asp Ser Ser Ile His
                 20                  25                  30
```

```
Gly Pro Gly Pro Ile Phe Val Lys Asn Ile Leu Pro Lys Gly Ala Ala
            35                  40                  45

Ile Lys Asp Gly Arg Leu Gln Ser Gly Asp Arg Ile Leu Glu Val Asn
 50                  55                  60

Gly Arg Asp Val Thr Gly Arg Thr Gln Glu Glu Leu Val Ala Met Leu
 65                  70                  75                  80

Arg Ser Thr Lys Gln Gly Glu Thr Ala Ser Leu Val Ile Ala Arg Gln
                 85                  90                  95

Glu Gly His
```

```
<210> SEQ ID NO 272
<211> LENGTH: 106
<212> TYPE: PRT
<213> ORGANISM: Human papillomavirus

<400> SEQUENCE: 272

Ile Thr Ser Glu Gln Leu Thr Phe Glu Ile Pro Leu Asn Asp Ser Gly
 1               5                  10                  15

Ser Ala Gly Leu Gly Val Ser Leu Lys Gly Asn Lys Ser Arg Glu Thr
                20                  25                  30

Gly Thr Asp Leu Gly Ile Phe Ile Lys Ser Ile Ile His Gly Gly Ala
            35                  40                  45

Ala Phe Lys Asp Gly Arg Leu Arg Met Asn Asp Gln Leu Ile Ala Val
 50                  55                  60

Asn Gly Glu Ser Leu Leu Gly Lys Ser Asn His Glu Ala Met Glu Thr
 65                  70                  75                  80

Leu Arg Arg Ser Met Ser Met Glu Gly Asn Ile Arg Gly Met Ile Gln
                 85                  90                  95

Leu Val Ile Leu Arg Arg Pro Glu Arg Pro
            100                 105
```

```
<210> SEQ ID NO 273
<211> LENGTH: 104
<212> TYPE: PRT
<213> ORGANISM: Human papillomavirus

<400> SEQUENCE: 273

Ile Pro Arg Thr Lys Asp Thr Leu Ser Asp Met Thr Arg Thr Val Glu
 1               5                  10                  15

Ile Ser Gly Glu Gly Gly Pro Leu Gly Ile His Val Val Pro Phe Phe
                20                  25                  30

Ser Ser Leu Ser Gly Arg Ile Leu Gly Leu Phe Ile Arg Gly Ile Glu
            35                  40                  45

Asp Asn Ser Arg Ser Lys Arg Glu Gly Leu Phe His Glu Asn Glu Cys
 50                  55                  60

Ile Val Lys Ile Asn Asn Val Asp Leu Val Asp Lys Thr Phe Ala Gln
 65                  70                  75                  80

Ala Gln Asp Val Phe Arg Gln Ala Met Lys Ser Pro Ser Val Leu Leu
                 85                  90                  95

His Val Leu Pro Pro Gln Asn Arg
            100
```

```
<210> SEQ ID NO 274
<211> LENGTH: 104
<212> TYPE: PRT
<213> ORGANISM: Human papillomavirus
```

-continued

<400> SEQUENCE: 274

Pro Glu Thr His Arg Arg Val Arg Leu His Lys His Gly Ser Asp Arg
1               5                   10                  15

Pro Leu Gly Phe Tyr Ile Arg Asp Gly Met Ser Val Arg Val Ala Pro
            20                  25                  30

Gln Gly Leu Glu Arg Val Pro Gly Ile Phe Ile Ser Arg Leu Val Arg
        35                  40                  45

Gly Gly Leu Ala Glu Ser Thr Gly Leu Leu Ala Val Ser Asp Glu Ile
    50                  55                  60

Leu Glu Val Asn Gly Ile Glu Val Ala Gly Lys Thr Leu Asp Gln Val
65                  70                  75                  80

Thr Asp Met Met Val Ala Asn Ser His Asn Leu Ile Val Thr Val Lys
                85                  90                  95

Pro Ala Asn Gln Arg Asn Asn Val
            100

<210> SEQ ID NO 275
<211> LENGTH: 120
<212> TYPE: PRT
<213> ORGANISM: Human papillomavirus

<400> SEQUENCE: 275

Ile Pro Val Ser Ser Ile Ile Asp Val Asp Ile Leu Pro Glu Thr His
1               5                   10                  15

Arg Arg Val Arg Leu Tyr Lys Tyr Gly Thr Glu Lys Pro Leu Gly Phe
            20                  25                  30

Tyr Ile Arg Asp Gly Ser Ser Arg Val Thr Pro His Gly Leu Glu
        35                  40                  45

Lys Val Pro Gly Ile Phe Ile Ser Arg Leu Val Pro Gly Gly Leu Ala
    50                  55                  60

Gln Ser Thr Gly Leu Leu Ala Val Asn Asp Glu Val Leu Glu Val Asn
65                  70                  75                  80

Gly Ile Glu Val Ser Gly Lys Ser Leu Asp Gln Val Thr Asp Met Met
                85                  90                  95

Ile Ala Asn Ser Arg Asn Leu Ile Ile Thr Val Arg Pro Ala Asn Gln
            100                 105                 110

Arg Asn Asn Arg Ile His Arg Asp
        115                 120

<210> SEQ ID NO 276
<211> LENGTH: 111
<212> TYPE: PRT
<213> ORGANISM: Human papillomavirus

<400> SEQUENCE: 276

Ile Asp Val Asp Leu Val Pro Glu Thr His Arg Arg Val Arg Leu His
1               5                   10                  15

Arg His Gly Cys Glu Lys Pro Leu Gly Phe Tyr Ile Arg Asp Gly Ala
            20                  25                  30

Ser Val Arg Val Thr Pro His Gly Leu Glu Lys Val Pro Gly Ile Phe
        35                  40                  45

Ile Ser Arg Met Val Pro Gly Gly Leu Ala Glu Ser Thr Gly Leu Leu
    50                  55                  60

Ala Val Asn Asp Glu Val Leu Glu Val Asn Gly Ile Glu Val Ala Gly
65                  70                  75                  80

Lys Thr Leu Asp Gln Val Thr Asp Met Met Ile Ala Asn Ser His Asn

```
                        85                  90                  95

Leu Ile Val Thr Val Lys Pro Ala Asn Gln Arg Asn Asn Val Val
            100                 105                 110

<210> SEQ ID NO 277
<211> LENGTH: 103
<212> TYPE: PRT
<213> ORGANISM: Human papillomavirus

<400> SEQUENCE: 277

Pro Glu Gln Ile Met Gly Lys Asp Val Arg Leu Leu Arg Ile Lys Lys
1               5                   10                  15

Glu Gly Ser Leu Asp Leu Ala Leu Glu Gly Gly Val Asp Ser Pro Ile
            20                  25                  30

Gly Lys Val Val Ser Ala Val Tyr Glu Arg Gly Ala Ala Glu Arg
        35                  40                  45

His Gly Gly Ile Val Lys Gly Asp Glu Ile Met Ala Ile Asn Gly Lys
    50                  55                  60

Ile Val Thr Asp Tyr Thr Leu Ala Glu Ala Asp Ala Ala Leu Gln Lys
65                  70                  75                  80

Ala Trp Asn Gln Gly Gly Asp Trp Ile Asp Leu Val Val Ala Val Cys
                85                  90                  95

Pro Pro Lys Glu Tyr Asp Asp
            100

<210> SEQ ID NO 278
<211> LENGTH: 102
<212> TYPE: PRT
<213> ORGANISM: Human papillomavirus

<400> SEQUENCE: 278

Ile Pro Gly Asn Arg Glu Asn Lys Glu Lys Lys Val Phe Ile Ser Leu
1               5                   10                  15

Val Gly Ser Arg Gly Leu Gly Cys Ser Ile Ser Ser Gly Pro Ile Gln
            20                  25                  30

Lys Pro Gly Ile Phe Ile Ser His Val Lys Pro Gly Ser Leu Ser Ala
        35                  40                  45

Glu Val Gly Leu Glu Ile Gly Asp Gln Ile Val Glu Val Asn Gly Val
    50                  55                  60

Asp Phe Ser Asn Leu Asp His Lys Glu Ala Val Asn Val Leu Lys Ser
65                  70                  75                  80

Ser Arg Ser Leu Thr Ile Ser Ile Val Ala Ala Gly Arg Glu Leu
                85                  90                  95

Phe Met Thr Asp Glu Phe
            100

<210> SEQ ID NO 279
<211> LENGTH: 100
<212> TYPE: PRT
<213> ORGANISM: Human papillomavirus

<400> SEQUENCE: 279

Arg Ser Arg Lys Leu Lys Glu Val Arg Leu Asp Arg Leu His Pro Glu
1               5                   10                  15

Gly Leu Gly Leu Ser Val Arg Gly Gly Leu Glu Phe Gly Cys Gly Leu
            20                  25                  30

Phe Ile Ser His Leu Ile Lys Gly Gly Gln Ala Asp Ser Val Gly Leu
        35                  40                  45
```

```
Gln Val Gly Asp Glu Ile Val Arg Ile Asn Gly Tyr Ser Ile Ser
        50                  55                  60

Cys Thr His Glu Glu Val Ile Asn Leu Ile Arg Thr Lys Thr Val
 65                  70                  75                  80

Ser Ile Lys Val Arg His Ile Gly Leu Ile Pro Val Lys Ser Ser Pro
                85                  90                  95

Asp Glu Phe His
        100

<210> SEQ ID NO 280
<211> LENGTH: 92
<212> TYPE: PRT
<213> ORGANISM: Human papillomavirus

<400> SEQUENCE: 280

Arg Leu Cys Tyr Leu Val Lys Glu Gly Gly Ser Tyr Gly Phe Ser Leu
  1               5                  10                  15

Lys Thr Val Gln Gly Lys Gly Val Tyr Met Thr Asp Ile Thr Pro
             20                  25                  30

Gln Gly Val Ala Met Arg Ala Gly Val Leu Ala Asp Asp His Leu Ile
         35                  40                  45

Glu Val Asn Gly Glu Asn Val Glu Asp Ala Ser His Glu Glu Val Val
 50                  55                  60

Glu Lys Val Lys Lys Ser Gly Ser Arg Val Met Phe Leu Leu Val Asp
 65                  70                  75                  80

Lys Glu Thr Asp Lys Arg Glu Phe Ile Val Thr Asp
             85                  90

<210> SEQ ID NO 281
<211> LENGTH: 112
<212> TYPE: PRT
<213> ORGANISM: Human papillomavirus

<400> SEQUENCE: 281

Gln Phe Lys Arg Glu Thr Ala Ser Leu Lys Leu Pro His Gln Pro
  1               5                  10                  15

Arg Ile Val Glu Met Lys Lys Gly Ser Asn Gly Tyr Gly Phe Tyr Leu
             20                  25                  30

Arg Ala Gly Ser Glu Gln Lys Gly Gln Ile Ile Lys Asp Ile Asp Ser
         35                  40                  45

Gly Ser Pro Ala Glu Glu Ala Gly Leu Lys Asn Asn Asp Leu Val Val
 50                  55                  60

Ala Val Asn Gly Glu Ser Val Glu Thr Leu Asp His Asp Ser Val Val
 65                  70                  75                  80

Glu Met Ile Arg Lys Gly Gly Asp Gln Thr Ser Leu Leu Val Val Asp
             85                  90                  95

Lys Glu Thr Asp Asn Met Tyr Arg Leu Ala Glu Phe Ile Val Thr Asp
            100                 105                 110

<210> SEQ ID NO 282
<211> LENGTH: 324
<212> TYPE: PRT
<213> ORGANISM: Human papillomavirus

<400> SEQUENCE: 282

Arg Leu Cys Tyr Leu Val Lys Glu Gly Gly Ser Tyr Gly Phe Ser Leu
  1               5                  10                  15
```

```
Lys Thr Val Gln Gly Lys Gly Val Tyr Met Thr Asp Ile Thr Pro
             20                  25                  30

Gln Gly Val Ala Met Arg Ala Gly Val Leu Ala Asp Asp His Leu Ile
             35                  40                  45

Glu Val Asn Gly Glu Asn Val Glu Asp Ala Ser His Glu Lys Val Val
50                  55                  60

Glu Lys Val Lys Lys Ser Gly Ser Arg Val Met Phe Leu Leu Val Asp
65                  70                  75                  80

Lys Glu Thr Asp Lys Arg His Val Glu Gln Lys Ile Gln Phe Lys Arg
             85                  90                  95

Glu Thr Ala Ser Leu Lys Leu Leu Pro His Gln Pro Arg Ile Val Glu
            100                 105                 110

Met Lys Lys Gly Ser Asn Gly Tyr Gly Phe Tyr Leu Arg Ala Gly Ser
            115                 120                 125

Glu Gln Lys Gly Gln Ile Ile Lys Asp Ile Asp Ser Gly Ser Pro Ala
            130                 135                 140

Glu Glu Ala Gly Leu Lys Asn Asn Asp Leu Val Val Ala Val Asn Gly
145                 150                 155                 160

Glu Ser Val Glu Thr Leu Asp His Asp Ser Val Val Glu Met Ile Arg
                165                 170                 175

Lys Gly Gly Asp Gln Thr Ser Leu Leu Val Val Asp Lys Glu Thr Asp
            180                 185                 190

Asn Met Tyr Arg Leu Ala His Phe Ser Pro Phe Leu Tyr Tyr Gln Ser
                195                 200                 205

Gln Glu Leu Pro Asn Gly Ser Val Lys Glu Ala Pro Ala Pro Thr Pro
            210                 215                 220

Thr Ser Leu Glu Val Ser Ser Pro Asp Thr Thr Glu Glu Val Asp
225                 230                 235                 240

His Lys Pro Lys Leu Cys Arg Leu Ala Lys Gly Glu Asn Gly Tyr Gly
                245                 250                 255

Phe His Leu Asn Ala Ile Arg Gly Leu Pro Gly Ser Phe Ile Lys Glu
            260                 265                 270

Val Gln Lys Gly Gly Pro Ala Asp Leu Ala Gly Leu Glu Asp Glu Asp
            275                 280                 285

Val Ile Ile Glu Val Asn Gly Val Asn Val Leu Asp Glu Pro Tyr Glu
            290                 295                 300

Lys Val Val Asp Arg Ile Gln Ser Ser Gly Lys Asn Val Thr Leu Leu
305                 310                 315                 320

Val Cys Gly Lys

<210> SEQ ID NO 283
<211> LENGTH: 94
<212> TYPE: PRT
<213> ORGANISM: Human papillomavirus

<400> SEQUENCE: 283

Pro Asp Thr Thr Glu Glu Val Asp His Lys Pro Lys Leu Cys Arg Leu
1               5                   10                  15

Ala Lys Gly Glu Asn Gly Tyr Gly Phe His Leu Asn Ala Ile Arg Gly
             20                  25                  30

Leu Pro Gly Ser Phe Ile Lys Glu Val Gln Lys Gly Gly Pro Ala Asp
             35                  40                  45

Leu Ala Gly Leu Glu Asp Glu Asp Val Ile Ile Glu Val Asn Gly Val
50                  55                  60
```

```
Asn Val Leu Asp Glu Pro Tyr Glu Lys Val Val Asp Arg Ile Gln Ser
 65                  70                  75                  80

Ser Gly Lys Asn Val Thr Leu Leu Val Gly Lys Asn Ser Ser
                 85                  90
```

<210> SEQ ID NO 284
<211> LENGTH: 101
<212> TYPE: PRT
<213> ORGANISM: Human papillomavirus

<400> SEQUENCE: 284

```
Leu Thr Ser Thr Phe Asn Pro Arg Glu Cys Lys Leu Ser Lys Gln Glu
  1               5                  10                  15

Gly Gln Asn Tyr Gly Phe Phe Leu Arg Ile Glu Lys Asp Thr Glu Gly
                 20                  25                  30

His Leu Val Arg Val Val Glu Lys Cys Ser Pro Ala Glu Lys Ala Gly
             35                  40                  45

Leu Gln Asp Gly Asp Arg Val Leu Arg Ile Asn Gly Val Phe Val Asp
 50                  55                  60

Lys Glu Glu His Met Gln Val Asp Leu Val Arg Lys Ser Gly Asn
 65                  70                  75                  80

Ser Val Thr Leu Leu Val Leu Asp Gly Asp Ser Tyr Glu Lys Ala Gly
                 85                  90                  95

Ser His Glu Pro Ser
                100
```

<210> SEQ ID NO 285
<211> LENGTH: 99
<212> TYPE: PRT
<213> ORGANISM: Human papillomavirus

<400> SEQUENCE: 285

```
Leu Gly Ile Pro Thr Val Pro Gly Lys Val Thr Leu Gln Lys Asp Ala
  1               5                  10                  15

Gln Asn Leu Ile Gly Ile Ser Ile Gly Gly Ala Gln Tyr Cys Pro
                 20                  25                  30

Cys Leu Tyr Ile Val Gln Val Phe Asp Asn Thr Pro Ala Ala Leu Asp
             35                  40                  45

Gly Thr Val Ala Ala Gly Asp Glu Ile Thr Gly Val Asn Gly Arg Ser
 50                  55                  60

Ile Lys Gly Lys Thr Lys Val Glu Val Ala Lys Met Ile Gln Glu Val
 65                  70                  75                  80

Lys Gly Glu Val Thr Ile His Tyr Asn Lys Leu Gln Ala Asp Pro Lys
                 85                  90                  95

Gln Gly Met
```

<210> SEQ ID NO 286
<211> LENGTH: 98
<212> TYPE: PRT
<213> ORGANISM: Human papillomavirus

<400> SEQUENCE: 286

```
Ser Gln Gly Val Gly Pro Ile Arg Lys Val Leu Leu Lys Glu Asp
  1               5                  10                  15

His Glu Gly Leu Gly Ile Ser Ile Thr Gly Gly Lys Glu His Gly Val
                 20                  25                  30

Pro Ile Leu Ile Ser Glu Ile His Pro Gly Gln Pro Ala Asp Arg Cys
             35                  40                  45
```

```
Gly Gly Leu His Val Gly Asp Ala Ile Leu Ala Val Asn Gly Val Asn
        50                  55                  60

Leu Arg Asp Thr Lys His Lys Glu Ala Val Thr Ile Leu Ser Gln Gln
 65                  70                  75                  80

Arg Gly Glu Ile Glu Phe Glu Val Val Tyr Val Ala Pro Glu Val Asp
                85                  90                  95

Ser Asp

<210> SEQ ID NO 287
<211> LENGTH: 98
<212> TYPE: PRT
<213> ORGANISM: Human papillomavirus

<400> SEQUENCE: 287

Thr Ala Glu Ala Thr Val Cys Thr Val Thr Leu Glu Lys Met Ser Ala
 1               5                  10                  15

Gly Leu Gly Phe Ser Leu Glu Gly Gly Lys Gly Ser Leu His Gly Asp
                20                  25                  30

Lys Pro Leu Thr Ile Asn Arg Ile Phe Lys Gly Ala Ala Ser Glu Gln
            35                  40                  45

Ser Glu Thr Val Gln Pro Gly Asp Glu Ile Leu Gln Leu Gly Gly Thr
 50                  55                  60

Ala Met Gln Gly Leu Thr Arg Phe Glu Ala Trp Asn Ile Ile Lys Ala
 65                  70                  75                  80

Leu Pro Asp Gly Pro Val Thr Ile Val Ile Arg Arg Lys Ser Leu Gln
                85                  90                  95

Ser Lys

<210> SEQ ID NO 288
<211> LENGTH: 97
<212> TYPE: PRT
<213> ORGANISM: Human papillomavirus

<400> SEQUENCE: 288

Ile His Val Thr Ile Leu His Lys Glu Glu Gly Ala Gly Leu Gly Phe
 1               5                  10                  15

Ser Leu Ala Gly Gly Ala Asp Leu Glu Asn Lys Val Ile Thr Val His
                20                  25                  30

Arg Val Phe Pro Asn Gly Leu Ala Ser Gln Glu Gly Thr Ile Gln Lys
            35                  40                  45

Gly Asn Glu Val Leu Ser Ile Asn Gly Lys Ser Leu Lys Gly Thr Thr
 50                  55                  60

His His Asp Ala Leu Ala Ile Leu Arg Gln Ala Arg Glu Pro Arg Gln
 65                  70                  75                  80

Ala Val Ile Val Thr Arg Lys Leu Thr Pro Glu Glu Phe Ile Val Thr
                85                  90                  95

Asp

<210> SEQ ID NO 289
<211> LENGTH: 214
<212> TYPE: PRT
<213> ORGANISM: Human papillomavirus

<400> SEQUENCE: 289

Ile His Val Thr Ile Leu His Lys Glu Glu Gly Ala Gly Leu Gly Phe
 1               5                  10                  15
```

```
Ser Leu Ala Gly Gly Ala Asp Leu Glu Asn Lys Val Ile Thr Val His
            20                  25                  30

Arg Val Phe Pro Asn Gly Leu Ala Ser Gln Glu Gly Thr Ile Gln Lys
        35                  40                  45

Gly Asn Glu Val Leu Ser Ile Asn Gly Lys Ser Leu Lys Gly Thr Thr
    50                  55                  60

His His Asp Ala Leu Ala Ile Leu Arg Gln Ala Arg Glu Pro Arg Gln
65                  70                  75                  80

Ala Val Ile Val Thr Arg Lys Leu Thr Pro Glu Ala Met Pro Asp Leu
                85                  90                  95

Asn Ser Ser Thr Asp Ser Ala Ala Ser Ala Ser Ala Ala Ser Asp Val
            100                 105                 110

Ser Val Glu Ser Thr Ala Glu Ala Thr Val Cys Thr Val Thr Leu Glu
        115                 120                 125

Lys Met Ser Ala Gly Leu Gly Phe Ser Leu Glu Gly Gly Lys Gly Ser
    130                 135                 140

Leu His Gly Asp Lys Pro Leu Thr Ile Asn Arg Ile Phe Lys Gly Ala
145                 150                 155                 160

Ala Ser Glu Gln Ser Glu Thr Val Gln Pro Gly Asp Glu Ile Leu Gln
                165                 170                 175

Leu Gly Gly Thr Ala Met Gln Gly Leu Thr Arg Phe Glu Ala Trp Asn
            180                 185                 190

Ile Ile Lys Ala Leu Pro Asp Gly Pro Val Thr Ile Val Ile Arg Arg
        195                 200                 205

Lys Ser Leu Gln Ser Lys
    210

<210> SEQ ID NO 290
<211> LENGTH: 162
<212> TYPE: PRT
<213> ORGANISM: Human papillomavirus

<400> SEQUENCE: 290

Ile Arg Glu Ala Lys Tyr Ser Gly Val Leu Ser Ser Ile Gly Lys Ile
1               5                   10                  15

Phe Lys Glu Glu Gly Leu Leu Gly Phe Val Gly Leu Ile Pro His
            20                  25                  30

Leu Leu Gly Asp Val Val Phe Leu Trp Gly Cys Asn Leu Leu Ala His
        35                  40                  45

Phe Ile Asn Ala Tyr Leu Val Asp Asp Ser Val Ser Asp Thr Pro Gly
    50                  55                  60

Gly Leu Gly Asn Asp Gln Asn Pro Gly Ser Gln Phe Ser Gln Ala Leu
65                  70                  75                  80

Ala Ile Arg Ser Tyr Thr Lys Phe Val Met Gly Ile Ala Val Ser Met
                85                  90                  95

Leu Thr Tyr Pro Phe Leu Leu Val Gly Asp Leu Met Ala Val Asn Asn
            100                 105                 110

Cys Gly Leu Gln Ala Gly Leu Pro Pro Tyr Ser Pro Val Phe Lys Ser
        115                 120                 125

Trp Ile His Cys Trp Lys Tyr Leu Ser Val Gln Gly Gln Leu Phe Arg
    130                 135                 140

Gly Ser Ser Leu Leu Phe Arg Arg Val Ser Ser Gly Ser Cys Phe Ala
145                 150                 155                 160

Leu Glu
```

<210> SEQ ID NO 291
<211> LENGTH: 338
<212> TYPE: PRT
<213> ORGANISM: Human papillomavirus

<400> SEQUENCE: 291

```
Glu Gly Glu Met Glu Tyr Glu Glu Ile Thr Leu Glu Arg Gly Asn Ser
1               5                   10                  15

Gly Leu Gly Phe Ser Ile Ala Gly Gly Thr Asp Asn Pro His Ile Gly
            20                  25                  30

Asp Asp Pro Ser Ile Phe Ile Thr Lys Ile Ile Pro Gly Gly Ala Ala
        35                  40                  45

Ala Gln Asp Gly Arg Leu Arg Val Asn Asp Ser Ile Leu Phe Val Asn
    50                  55                  60

Glu Val Asp Val Arg Glu Val Thr His Ser Ala Ala Val Glu Ala Leu
65                  70                  75                  80

Lys Glu Ala Gly Ser Ile Val Arg Leu Tyr Val Met Arg Arg Lys Pro
                85                  90                  95

Pro Ala Glu Lys Val Met Glu Ile Lys Leu Ile Lys Gly Pro Lys Gly
            100                 105                 110

Leu Gly Phe Ser Ile Ala Gly Gly Val Gly Asn Gln His Ile Pro Gly
            115                 120                 125

Asp Asn Ser Ile Tyr Val Thr Lys Ile Ile Glu Gly Gly Ala Ala His
        130                 135                 140

Lys Asp Gly Arg Leu Gln Ile Gly Asp Lys Ile Leu Ala Val Asn Ser
145                 150                 155                 160

Val Gly Leu Glu Asp Val Met His Glu Asp Ala Val Ala Ala Leu Lys
                165                 170                 175

Asn Thr Tyr Asp Val Val Tyr Leu Lys Val Ala Lys Pro Ser Asn Ala
            180                 185                 190

Tyr Leu Ser Asp Ser Tyr Ala Pro Pro Asp Ile Thr Thr Ser Tyr Ser
        195                 200                 205

Gln His Leu Asp Asn Glu Ile Ser His Ser Ser Tyr Leu Gly Thr Asp
    210                 215                 220

Tyr Pro Thr Ala Met Thr Pro Thr Ser Pro Arg Arg Tyr Ser Pro Val
225                 230                 235                 240

Ala Lys Asp Leu Leu Gly Glu Glu Asp Ile Pro Arg Glu Pro Arg Arg
                245                 250                 255

Ile Val Ile His Arg Gly Ser Thr Gly Leu Gly Phe Asn Ile Val Gly
            260                 265                 270

Gly Glu Asp Gly Glu Gly Ile Phe Ile Ser Phe Ile Leu Ala Gly Gly
        275                 280                 285

Pro Ala Asp Leu Ser Gly Glu Leu Arg Lys Gly Asp Gln Ile Leu Ser
    290                 295                 300

Val Asn Gly Val Asp Leu Arg Asn Ala Ser His Glu Gln Ala Ala Ile
305                 310                 315                 320

Ala Leu Lys Asn Ala Gly Gln Thr Val Thr Ile Ile Ala Gln Tyr Lys
                325                 330                 335

Pro Glu
```

<210> SEQ ID NO 292
<211> LENGTH: 105
<212> TYPE: PRT
<213> ORGANISM: Human papillomavirus

```
<400> SEQUENCE: 292

His Val Met Arg Arg Lys Pro Pro Ala Glu Lys Val Met Glu Ile Lys
1               5                   10                  15

Leu Ile Lys Gly Pro Lys Gly Leu Gly Phe Ser Ile Ala Gly Gly Val
                20                  25                  30

Gly Asn Gln His Ile Pro Gly Asp Asn Ser Ile Tyr Val Thr Lys Ile
            35                  40                  45

Ile Glu Gly Gly Ala Ala His Lys Asp Gly Arg Leu Gln Ile Gly Asp
50                  55                  60

Lys Ile Leu Ala Val Asn Ser Val Gly Leu Glu Asp Val Met His Glu
65                  70                  75                  80

Asp Ala Val Ala Ala Leu Lys Asn Thr Tyr Asp Val Val Tyr Leu Lys
                85                  90                  95

Val Ala Lys Pro Ser Asn Ala Tyr Leu
                100                 105

<210> SEQ ID NO 293
<211> LENGTH: 97
<212> TYPE: PRT
<213> ORGANISM: Human papillomavirus

<400> SEQUENCE: 293

Arg Glu Asp Ile Pro Arg Glu Pro Arg Ile Val Ile His Arg Gly
1               5                   10                  15

Ser Thr Gly Leu Gly Phe Asn Ile Val Gly Gly Glu Asp Gly Glu Gly
                20                  25                  30

Ile Phe Ile Ser Phe Ile Leu Ala Gly Gly Pro Ala Asp Leu Ser Gly
            35                  40                  45

Glu Leu Arg Lys Gly Asp Gln Ile Leu Ser Val Asn Gly Val Asp Leu
50                  55                  60

Arg Asn Ala Ser His Glu Gln Ala Ala Ile Ala Leu Lys Asn Ala Gly
65                  70                  75                  80

Gln Thr Val Thr Ile Ile Ala Gln Tyr Lys Pro Glu Phe Ile Val Thr
                85                  90                  95

Asp

<210> SEQ ID NO 294
<211> LENGTH: 99
<212> TYPE: PRT
<213> ORGANISM: Human papillomavirus

<400> SEQUENCE: 294

Leu Glu Tyr Glu Glu Ile Thr Leu Glu Arg Gly Asn Ser Gly Leu Gly
1               5                   10                  15

Phe Ser Ile Ala Gly Gly Thr Asp Asn Pro His Ile Gly Asp Asp Pro
                20                  25                  30

Ser Ile Phe Ile Thr Lys Ile Ile Pro Gly Gly Ala Ala Ala Gln Asp
            35                  40                  45

Gly Arg Leu Arg Val Asn Asp Ser Ile Leu Phe Val Asn Glu Val Asp
50                  55                  60

Val Arg Glu Val Thr His Ser Ala Ala Val Glu Ala Leu Lys Glu Ala
65                  70                  75                  80

Gly Ser Ile Val Arg Leu Tyr Val Met Arg Arg Lys Pro Pro Ala Glu
                85                  90                  95

Asn Ser Ser
```

<210> SEQ ID NO 295
<211> LENGTH: 88
<212> TYPE: PRT
<213> ORGANISM: Human papillomavirus

<400> SEQUENCE: 295

Arg Asp Met Ala Glu Ala His Lys Glu Ala Met Ser Arg Lys Leu Gly
1               5                   10                  15

Gln Ser Glu Ser Gln Gly Pro Pro Arg Ala Phe Ala Lys Val Asn Ser
            20                  25                  30

Ile Ser Pro Gly Ser Pro Ala Ser Ile Ala Gly Leu Gln Val Asp Asp
        35                  40                  45

Glu Ile Val Glu Phe Gly Ser Val Asn Thr Gln Asn Phe Gln Ser Leu
    50                  55                  60

His Asn Ile Gly Ser Val Val Gln His Ser Gly Ala Leu Ala Pro
65                  70                  75                  80

Thr Ile Leu Leu Ser Val Ser Met
                85

<210> SEQ ID NO 296
<211> LENGTH: 102
<212> TYPE: PRT
<213> ORGANISM: Human papillomavirus

<400> SEQUENCE: 296

Gln Asn Asp Asn Gly Asp Ser Tyr Leu Val Leu Ile Arg Ile Thr Pro
1               5                   10                  15

Asp Glu Asp Gly Lys Phe Gly Phe Asn Leu Lys Gly Gly Val Asp Gln
            20                  25                  30

Lys Met Pro Leu Val Val Ser Arg Ile Asn Pro Glu Ser Pro Ala Asp
        35                  40                  45

Thr Cys Ile Pro Lys Leu Asn Glu Gly Asp Gln Ile Val Leu Ile Asn
    50                  55                  60

Gly Arg Asp Ile Ser Glu His Thr His Asp Gln Val Val Met Phe Ile
65                  70                  75                  80

Lys Ala Ser Arg Glu Ser His Ser Arg Glu Leu Ala Leu Val Ile Arg
                85                  90                  95

Arg Arg Ala Val Arg Ser
            100

<210> SEQ ID NO 297
<211> LENGTH: 88
<212> TYPE: PRT
<213> ORGANISM: Human papillomavirus

<400> SEQUENCE: 297

Ile Arg Met Lys Pro Asp Glu Asn Gly Arg Phe Gly Phe Asn Val Lys
1               5                   10                  15

Gly Gly Tyr Asp Gln Lys Met Pro Val Ile Val Ser Arg Val Ala Pro
            20                  25                  30

Gly Thr Pro Ala Asp Leu Cys Val Pro Arg Leu Asn Glu Gly Asp Gln
        35                  40                  45

Val Val Leu Ile Asn Gly Arg Asp Ile Ala Glu His Thr His Asp Gln
    50                  55                  60

Val Val Leu Phe Ile Lys Ala Ser Cys Glu Arg His Ser Gly Glu Leu
65                  70                  75                  80

Met Leu Leu Val Arg Pro Asn Ala

```
                    85

<210> SEQ ID NO 298
<211> LENGTH: 95
<212> TYPE: PRT
<213> ORGANISM: Human papillomavirus

<400> SEQUENCE: 298

Gly Asp Ile Phe Glu Val Glu Leu Ala Lys Asn Asp Asn Ser Leu Gly
1               5                   10                  15

Ile Ser Val Thr Gly Gly Val Asn Thr Ser Val Arg His Gly Gly Ile
            20                  25                  30

Tyr Val Lys Ala Val Ile Pro Gln Gly Ala Ala Glu Ser Asp Gly Arg
        35                  40                  45

Ile His Lys Gly Asp Arg Val Leu Ala Val Asn Gly Val Ser Leu Glu
    50                  55                  60

Gly Ala Thr His Lys Gln Ala Val Glu Thr Leu Arg Asn Thr Gly Gln
65                  70                  75                  80

Val Val His Leu Leu Leu Glu Lys Gly Gln Ser Pro Thr Ser Lys
                85                  90                  95

<210> SEQ ID NO 299
<211> LENGTH: 106
<212> TYPE: PRT
<213> ORGANISM: Human papillomavirus

<400> SEQUENCE: 299

Pro Glu Arg Glu Ile Thr Leu Val Asn Leu Lys Lys Asp Ala Lys Tyr
1               5                   10                  15

Gly Leu Gly Phe Gln Ile Ile Gly Gly Glu Lys Met Gly Arg Leu Asp
            20                  25                  30

Leu Gly Ile Phe Ile Ser Ser Val Ala Pro Gly Gly Pro Ala Asp Phe
        35                  40                  45

His Gly Cys Leu Lys Pro Gly Asp Arg Leu Ile Ser Val Asn Ser Val
    50                  55                  60

Ser Leu Glu Gly Val Ser His His Ala Ala Ile Glu Ile Leu Gln Asn
65                  70                  75                  80

Ala Pro Glu Asp Val Thr Leu Val Ile Ser Gln Pro Lys Glu Lys Ile
                85                  90                  95

Ser Lys Val Pro Ser Thr Pro Val His Leu
            100                 105

<210> SEQ ID NO 300
<211> LENGTH: 98
<212> TYPE: PRT
<213> ORGANISM: Human papillomavirus

<400> SEQUENCE: 300

Glu Leu Glu Val Glu Leu Leu Ile Thr Leu Ile Lys Ser Glu Lys Ala
1               5                   10                  15

Ser Leu Gly Phe Thr Val Thr Lys Gly Asn Gln Arg Ile Gly Cys Tyr
            20                  25                  30

Val His Asp Val Ile Gln Asp Pro Ala Lys Ser Asp Gly Arg Leu Lys
        35                  40                  45

Pro Gly Asp Arg Leu Ile Lys Val Asn Asp Thr Asp Val Thr Asn Met
    50                  55                  60

Thr His Thr Asp Ala Val Asn Leu Leu Arg Ala Ala Ser Lys Thr Val
65                  70                  75                  80
```

```
Arg Leu Val Ile Gly Arg Val Leu Glu Leu Pro Arg Ile Pro Met Leu
                85                  90                  95
Pro His

<210> SEQ ID NO 301
<211> LENGTH: 104
<212> TYPE: PRT
<213> ORGANISM: Human papillomavirus

<400> SEQUENCE: 301

Thr Glu Glu Asn Thr Phe Glu Val Lys Leu Phe Lys Asn Ser Ser Gly
1               5                   10                  15

Leu Gly Phe Ser Phe Ser Arg Glu Asp Asn Leu Ile Pro Glu Gln Ile
                20                  25                  30

Asn Ala Ser Ile Val Arg Val Lys Lys Leu Phe Ala Gly Gln Pro Ala
            35                  40                  45

Ala Glu Ser Gly Lys Ile Asp Val Gly Asp Val Ile Leu Lys Val Asn
        50                  55                  60

Gly Ala Ser Leu Lys Gly Leu Ser Gln Gln Glu Val Ile Ser Ala Leu
65                  70                  75                  80

Arg Gly Thr Ala Pro Glu Val Phe Leu Leu Leu Cys Arg Pro Pro Pro
                85                  90                  95

Gly Val Leu Pro Glu Ile Asp Thr
                100

<210> SEQ ID NO 302
<211> LENGTH: 94
<212> TYPE: PRT
<213> ORGANISM: Human papillomavirus

<400> SEQUENCE: 302

Met Leu Pro His Leu Pro Asp Ile Thr Leu Thr Cys Asn Lys Glu
1               5                   10                  15

Glu Leu Gly Phe Ser Leu Cys Gly Gly His Asp Ser Leu Tyr Gln Val
                20                  25                  30

Val Tyr Ile Ser Asp Ile Asn Pro Arg Ser Val Ala Ala Ile Glu Gly
            35                  40                  45

Asn Leu Gln Leu Leu Asp Val Ile His Tyr Val Asn Gly Val Ser Thr
        50                  55                  60

Gln Gly Met Thr Leu Glu Glu Val Asn Arg Ala Leu Asp Met Ser Leu
65                  70                  75                  80

Pro Ser Leu Val Leu Lys Ala Thr Arg Asn Asp Leu Pro Val
                85                  90

<210> SEQ ID NO 303
<211> LENGTH: 92
<212> TYPE: PRT
<213> ORGANISM: Human papillomavirus

<400> SEQUENCE: 303

Val Cys Ser Glu Arg Arg Tyr Arg Gln Ile Thr Ile Pro Arg Gly Lys
1               5                   10                  15

Asp Gly Phe Gly Phe Thr Ile Cys Cys Asp Ser Pro Val Arg Val Gln
                20                  25                  30

Ala Val Asp Ser Gly Gly Pro Ala Glu Arg Ala Gly Leu Gln Gln Leu
            35                  40                  45

Asp Thr Val Leu Gln Leu Asn Glu Arg Pro Val Glu His Trp Lys Cys
```

```
                    50                  55                  60

Val Glu Leu Ala His Glu Ile Arg Ser Cys Pro Ser Glu Ile Ile Leu
 65                  70                  75                  80

Leu Val Trp Arg Met Val Pro Gln Val Lys Pro Gly
                 85                  90
```

<210> SEQ ID NO 304
<211> LENGTH: 93
<212> TYPE: PRT
<213> ORGANISM: Human papillomavirus

<400> SEQUENCE: 304

```
Arg Pro Ser Pro Pro Arg Val Arg Ser Val Glu Val Ala Arg Gly Arg
 1               5                  10                  15

Ala Gly Tyr Gly Phe Thr Leu Ser Gly Gln Ala Pro Cys Val Leu Ser
                20                  25                  30

Cys Val Met Arg Gly Ser Pro Ala Asp Phe Val Gly Leu Arg Ala Gly
                35                  40                  45

Asp Gln Ile Leu Ala Val Asn Glu Ile Asn Val Lys Lys Ala Ser His
            50                  55                  60

Glu Asp Val Val Lys Leu Ile Gly Lys Cys Ser Gly Val Leu His Met
 65                  70                  75                  80

Val Ile Ala Glu Gly Val Gly Arg Phe Glu Ser Cys Ser
                85                  90
```

<210> SEQ ID NO 305
<211> LENGTH: 124
<212> TYPE: PRT
<213> ORGANISM: Human papillomavirus

<400> SEQUENCE: 305

```
Ser Glu Asp Glu Thr Phe Ser Trp Pro Gly Pro Lys Thr Val Thr Leu
 1               5                  10                  15

Lys Arg Thr Ser Gln Gly Phe Gly Phe Thr Leu Arg His Phe Ile Val
                20                  25                  30

Tyr Pro Pro Glu Ser Ala Ile Gln Phe Ser Tyr Lys Asp Glu Glu Asn
                35                  40                  45

Gly Asn Arg Gly Gly Lys Gln Arg Asn Arg Leu Glu Pro Met Asp Thr
            50                  55                  60

Ile Phe Val Lys Gln Val Lys Glu Gly Gly Pro Ala Phe Glu Ala Gly
 65                  70                  75                  80

Leu Cys Thr Gly Asp Arg Ile Ile Lys Val Asn Gly Glu Ser Val Ile
                85                  90                  95

Gly Lys Thr Tyr Ser Gln Val Ile Ala Leu Ile Gln Asn Ser Asp Thr
                100                 105                 110

Thr Leu Glu Leu Ser Val Met Pro Lys Asp Glu Asp
            115                 120
```

<210> SEQ ID NO 306
<211> LENGTH: 96
<212> TYPE: PRT
<213> ORGANISM: Human papillomavirus

<400> SEQUENCE: 306

```
Ser Ala Lys Asn Arg Trp Arg Leu Val Gly Pro Val His Leu Thr Arg
 1               5                  10                  15

Gly Glu Gly Gly Phe Gly Leu Thr Leu Arg Gly Asp Ser Pro Val Leu
                20                  25                  30
```

```
Ile Ala Ala Val Ile Pro Gly Ser Gln Ala Ala Ala Gly Leu Lys
        35                  40                  45

Glu Gly Asp Tyr Ile Val Ser Val Asn Gly Gln Pro Cys Arg Trp Trp
 50                  55                  60

Arg His Ala Glu Val Val Thr Glu Leu Lys Ala Ala Gly Glu Ala Gly
 65                  70                  75                  80

Ala Ser Leu Gln Val Val Ser Leu Leu Pro Ser Ser Arg Leu Pro Ser
                85                  90                  95
```

<210> SEQ ID NO 307
<211> LENGTH: 104
<212> TYPE: PRT
<213> ORGANISM: Human papillomavirus

<400> SEQUENCE: 307

```
Ile Ser Phe Ser Ala Asn Lys Arg Trp Thr Pro Pro Arg Ser Ile Arg
 1               5                  10                  15

Phe Thr Ala Glu Glu Gly Asp Leu Gly Phe Thr Leu Arg Gly Asn Ala
                20                  25                  30

Pro Val Gln Val His Phe Leu Asp Pro Tyr Cys Ser Ala Ser Val Ala
            35                  40                  45

Gly Ala Arg Glu Gly Asp Tyr Ile Val Ser Ile Gln Leu Val Asp Cys
 50                  55                  60

Lys Trp Leu Thr Leu Ser Glu Val Met Lys Leu Leu Lys Ser Phe Gly
 65                  70                  75                  80

Glu Asp Glu Ile Glu Met Lys Val Ser Leu Leu Asp Ser Thr Ser
                85                  90                  95

Ser Met His Asn Lys Ser Ala Thr
                100
```

<210> SEQ ID NO 308
<211> LENGTH: 126
<212> TYPE: PRT
<213> ORGANISM: Human papillomavirus

<400> SEQUENCE: 308

```
Thr Leu Asn Glu Glu His Ser His Ser Asp Lys His Pro Val Thr Trp
 1               5                  10                  15

Gln Pro Ser Lys Asp Gly Asp Arg Leu Ile Gly Arg Ile Leu Leu Asn
                20                  25                  30

Lys Arg Leu Lys Asp Gly Ser Val Pro Arg Asp Ser Gly Ala Met Leu
            35                  40                  45

Gly Leu Lys Val Val Gly Gly Lys Met Thr Glu Ser Gly Arg Leu Cys
 50                  55                  60

Ala Phe Ile Thr Lys Val Lys Lys Gly Ser Leu Ala Asp Thr Val Gly
 65                  70                  75                  80

His Leu Arg Pro Gly Asp Glu Val Leu Glu Trp Asn Gly Arg Leu Leu
                85                  90                  95

Gln Gly Ala Thr Phe Glu Glu Val Tyr Asn Ile Ile Leu Glu Ser Lys
            100                 105                 110

Pro Glu Pro Gln Val Glu Leu Val Val Ser Arg Pro Ile Gly
        115                 120                 125
```

<210> SEQ ID NO 309
<211> LENGTH: 101
<212> TYPE: PRT
<213> ORGANISM: Human papillomavirus

<400> SEQUENCE: 309

| Gln | Glu | Met | Asp | Arg | Glu | Glu | Leu | Glu | Leu | Glu | Val | Asp | Leu | Tyr |
|---|---|---|---|---|---|---|---|---|---|---|---|---|---|---|
| 1 | | | | 5 | | | | | 10 | | | | | 15 |

Arg Met Asn Ser Gln Asp Lys Leu Gly Leu Thr Val Cys Tyr Arg Thr
              20                  25                  30

Asp Asp Glu Asp Ile Gly Ile Tyr Ile Ser Glu Ile Asp Pro Asn
          35                  40                  45

Ser Ile Ala Ala Lys Asp Gly Arg Ile Arg Glu Gly Asp Arg Ile Ile
        50                  55                  60

Gln Ile Asn Gly Ile Glu Val Gln Asn Arg Glu Glu Ala Val Ala Leu
65                  70                  75                  80

Leu Thr Ser Glu Glu Asn Lys Asn Phe Ser Leu Leu Ile Ala Arg Pro
                85                  90                  95

Glu Leu Gln Leu Asp
            100

<210> SEQ ID NO 310
<211> LENGTH: 107
<212> TYPE: PRT
<213> ORGANISM: Human papillomavirus

<400> SEQUENCE: 310

Gln Gly Glu Glu Thr Lys Ser Leu Thr Leu Val Leu His Arg Asp Ser
1               5                   10                  15

Gly Ser Leu Gly Phe Asn Ile Ile Gly Gly Arg Pro Ser Val Asp Asn
                20                  25                  30

His Asp Gly Ser Ser Glu Gly Ile Phe Val Ser Lys Ile Val Asp
            35                  40                  45

Ser Gly Pro Ala Ala Lys Glu Gly Leu Gln Ile His Asp Arg Ile
        50                  55                  60

Ile Glu Val Asn Gly Arg Asp Leu Ser Arg Ala Thr His Asp Gln Ala
65                  70                  75                  80

Val Glu Ala Phe Lys Thr Ala Lys Glu Pro Ile Val Val Gln Val Leu
                85                  90                  95

Arg Arg Thr Pro Arg Thr Lys Met Phe Thr Pro
            100                 105

<210> SEQ ID NO 311
<211> LENGTH: 98
<212> TYPE: PRT
<213> ORGANISM: Human papillomavirus

<400> SEQUENCE: 311

Ile Leu Ala His Val Lys Gly Ile Glu Lys Glu Val Asn Val Tyr Lys
1               5                   10                  15

Ser Glu Asp Ser Leu Gly Leu Thr Ile Thr Asp Asn Gly Val Gly Tyr
                20                  25                  30

Ala Phe Ile Lys Arg Ile Lys Asp Gly Gly Val Ile Asp Ser Val Lys
            35                  40                  45

Thr Ile Cys Val Gly Asp His Ile Glu Ser Ile Asn Gly Glu Asn Ile
        50                  55                  60

Val Gly Trp Arg His Tyr Asp Val Ala Lys Lys Leu Lys Glu Leu Lys
65                  70                  75                  80

Lys Glu Glu Leu Phe Thr Met Lys Leu Ile Glu Pro Lys Lys Ala Phe
                85                  90                  95

Glu Ile

<210> SEQ ID NO 312
<211> LENGTH: 109
<212> TYPE: PRT
<213> ORGANISM: Human papillomavirus

<400> SEQUENCE: 312

Arg Gly Glu Lys Lys Asn Ser Ser Gly Ile Ser Gly Ser Gln Arg
1               5                   10                  15

Arg Tyr Ile Gly Val Met Met Leu Thr Leu Ser Pro Ser Ile Leu Ala
                20                  25                  30

Glu Leu Gln Leu Arg Glu Pro Ser Phe Pro Asp Val Gln His Gly Val
            35                  40                  45

Leu Ile His Lys Val Ile Leu Gly Ser Pro Ala His Arg Ala Gly Leu
        50                  55                  60

Arg Pro Gly Asp Val Ile Leu Ala Ile Gly Glu Gln Met Val Gln Asn
65                  70                  75                  80

Ala Glu Asp Val Tyr Glu Ala Val Arg Thr Gln Ser Gln Leu Ala Val
                85                  90                  95

Gln Ile Arg Arg Gly Arg Glu Thr Leu Thr Leu Tyr Val
            100                 105

<210> SEQ ID NO 313
<211> LENGTH: 110
<212> TYPE: PRT
<213> ORGANISM: Human papillomavirus

<400> SEQUENCE: 313

Ile Leu Glu Glu Lys Thr Val Val Leu Gln Lys Lys Asp Asn Glu Gly
1               5                   10                  15

Phe Gly Phe Val Leu Arg Gly Ala Lys Ala Asp Thr Pro Ile Glu Glu
                20                  25                  30

Phe Thr Pro Thr Pro Ala Phe Pro Ala Leu Gln Tyr Leu Glu Ser Val
            35                  40                  45

Asp Glu Gly Gly Val Ala Trp Gln Ala Gly Leu Arg Thr Gly Asp Phe
        50                  55                  60

Leu Ile Glu Val Asn Asn Glu Asn Val Val Lys Val Gly His Arg Gln
65                  70                  75                  80

Val Val Asn Met Ile Arg Gln Gly Gly Asn His Leu Val Leu Lys Val
                85                  90                  95

Val Thr Val Thr Arg Asn Leu Asp Pro Asp Asp Asn Ser Ser
            100                 105                 110

<210> SEQ ID NO 314
<211> LENGTH: 113
<212> TYPE: PRT
<213> ORGANISM: Human papillomavirus

<400> SEQUENCE: 314

Ile Leu Lys Glu Lys Thr Val Leu Leu Gln Lys Lys Asp Ser Glu Gly
1               5                   10                  15

Phe Gly Phe Val Leu Arg Gly Ala Lys Ala Gln Thr Pro Ile Glu Glu
                20                  25                  30

Phe Thr Pro Thr Pro Ala Phe Pro Ala Leu Gln Tyr Leu Glu Ser Val
            35                  40                  45

Asp Glu Gly Gly Val Ala Trp Arg Ala Gly Leu Arg Met Gly Asp Phe
        50                  55                  60

Leu Ile Glu Val Asn Gly Gln Asn Val Lys Val Gly His Arg Gln
65                  70                  75                  80

Val Val Asn Met Ile Arg Gln Gly Gly Asn Thr Leu Met Lys Val
                85                  90                  95

Val Met Val Thr Arg His Pro Asp Met Asp Glu Ala Val Gln Asn Ser
                100                 105                 110

Ser

<210> SEQ ID NO 315
<211> LENGTH: 110
<212> TYPE: PRT
<213> ORGANISM: Human papillomavirus

<400> SEQUENCE: 315

Ser Asp Tyr Val Ile Asp Asp Lys Val Ala Val Leu Gln Lys Arg Asp
1               5                   10                  15

His Glu Gly Phe Gly Phe Val Leu Arg Gly Ala Lys Ala Glu Thr Pro
                20                  25                  30

Ile Glu Glu Phe Thr Pro Thr Pro Ala Phe Pro Ala Leu Gln Tyr Leu
            35                  40                  45

Glu Ser Val Asp Val Glu Gly Val Ala Trp Arg Ala Gly Leu Arg Thr
50                  55                  60

Gly Asp Phe Leu Ile Glu Val Asn Gly Val Asn Val Val Lys Val Gly
65                  70                  75                  80

His Lys Gln Val Val Ala Leu Ile Arg Gln Gly Gly Asn Arg Leu Val
                85                  90                  95

Met Lys Val Val Ser Val Thr Arg Lys Pro Glu Glu Asp Gly
                100                 105                 110

<210> SEQ ID NO 316
<211> LENGTH: 98
<212> TYPE: PRT
<213> ORGANISM: Human papillomavirus

<400> SEQUENCE: 316

Ser Asn Ser Pro Arg Glu Glu Ile Phe Gln Val Ala Leu His Lys Arg
1               5                   10                  15

Asp Ser Gly Glu Gln Leu Gly Ile Lys Leu Val Arg Arg Thr Asp Glu
                20                  25                  30

Pro Gly Val Phe Ile Leu Asp Leu Leu Glu Gly Gly Leu Ala Ala Gln
            35                  40                  45

Asp Gly Arg Leu Ser Ser Asn Asp Arg Val Leu Ala Ile Asn Gly His
50                  55                  60

Asp Leu Lys Tyr Gly Thr Pro Glu Leu Ala Ala Gln Ile Ile Gln Ala
65                  70                  75                  80

Ser Gly Glu Arg Val Asn Leu Thr Ile Ala Arg Pro Gly Lys Pro Gln
                85                  90                  95

Pro Gly

<210> SEQ ID NO 317
<211> LENGTH: 104
<212> TYPE: PRT
<213> ORGANISM: Human papillomavirus

<400> SEQUENCE: 317

Ile Gln Cys Val Thr Cys Gln Glu Lys His Ile Thr Val Lys Lys Glu
1               5                   10                  15

```
Pro His Glu Ser Leu Gly Met Thr Val Ala Gly Gly Arg Gly Ser Lys
            20                  25                  30

Ser Gly Glu Leu Pro Ile Phe Val Thr Ser Val Pro Pro His Gly Cys
        35                  40                  45

Leu Ala Arg Asp Gly Arg Ile Lys Arg Gly Asp Val Leu Leu Asn Ile
 50                  55                  60

Asn Gly Ile Asp Leu Thr Asn Leu Ser His Ser Glu Ala Val Ala Met
 65                  70                  75                  80

Leu Lys Ala Ser Ala Ala Ser Pro Ala Val Ala Leu Lys Ala Leu Glu
                85                  90                  95

Val Gln Ile Val Glu Glu Ala Thr
            100

<210> SEQ ID NO 318
<211> LENGTH: 110
<212> TYPE: PRT
<213> ORGANISM: Human papillomavirus

<400> SEQUENCE: 318

Met Gly Leu Gly Val Ser Ala Glu Gln Pro Ala Gly Gly Ala Glu Gly
1               5                   10                  15

Phe His Leu His Gly Val Gln Glu Asn Ser Pro Ala Gln Gln Ala Gly
            20                  25                  30

Leu Glu Pro Tyr Phe Asp Phe Ile Thr Ile Gly His Ser Arg Leu
        35                  40                  45

Asn Lys Glu Asn Asp Thr Leu Lys Ala Leu Leu Lys Ala Asn Val Glu
 50                  55                  60

Lys Pro Val Lys Leu Glu Val Phe Asn Met Lys Thr Met Arg Val Arg
 65                  70                  75                  80

Glu Val Glu Val Val Pro Ser Asn Met Trp Gly Gln Gly Leu Leu
                85                  90                  95

Gly Ala Ser Val Arg Phe Cys Ser Phe Arg Arg Ala Ser Glu
            100                 105                 110

<210> SEQ ID NO 319
<211> LENGTH: 109
<212> TYPE: PRT
<213> ORGANISM: Human papillomavirus

<400> SEQUENCE: 319

Arg Ala Ser Glu Gln Val Trp His Val Leu Asp Val Glu Pro Ser Ser
1               5                   10                  15

Pro Ala Ala Leu Ala Gly Leu Arg Pro Tyr Thr Asp Tyr Val Val Gly
            20                  25                  30

Ser Asp Gln Ile Leu Gln Glu Ser Glu Asp Phe Phe Thr Leu Ile Glu
        35                  40                  45

Ser His Glu Gly Lys Pro Leu Lys Leu Met Val Tyr Asn Ser Lys Ser
 50                  55                  60

Asp Ser Cys Arg Glu Ser Gly Met Trp His Trp Leu Trp Val Ser Thr
 65                  70                  75                  80

Pro Asp Pro Asn Ser Ala Pro Gln Leu Pro Gln Glu Ala Thr Trp His
                85                  90                  95

Pro Thr Thr Phe Cys Ser Thr Thr Trp Cys Pro Thr Thr
            100                 105

<210> SEQ ID NO 320
```

```
<211> LENGTH: 101
<212> TYPE: PRT
<213> ORGANISM: Human papillomavirus

<400> SEQUENCE: 320

Ile Ser Val Thr Asp Gly Pro Lys Phe Glu Val Lys Leu Lys Lys Asn
1               5                   10                  15

Ala Asn Gly Leu Gly Phe Ser Phe Val Gln Met Glu Lys Glu Ser Cys
            20                  25                  30

Ser His Leu Lys Ser Asp Leu Val Arg Ile Lys Arg Leu Phe Pro Gly
        35                  40                  45

Gln Pro Ala Glu Glu Asn Gly Ala Ile Ala Ala Gly Asp Ile Ile Leu
50                  55                  60

Ala Val Asn Gly Arg Ser Thr Glu Gly Leu Ile Phe Gln Glu Val Leu
65                  70                  75                  80

His Leu Leu Arg Gly Ala Pro Gln Glu Val Thr Leu Leu Leu Cys Arg
                85                  90                  95

Pro Pro Pro Gly Ala
            100

<210> SEQ ID NO 321
<211> LENGTH: 100
<212> TYPE: PRT
<213> ORGANISM: Human papillomavirus

<400> SEQUENCE: 321

Gln Pro Glu Pro Leu Arg Pro Arg Leu Cys Arg Leu Val Arg Gly Glu
1               5                   10                  15

Gln Gly Tyr Gly Phe His Leu His Gly Glu Lys Gly Arg Arg Gly Gln
            20                  25                  30

Phe Ile Arg Arg Val Glu Pro Gly Ser Pro Ala Glu Ala Ala Ala Leu
        35                  40                  45

Arg Ala Gly Asp Arg Leu Val Glu Val Asn Gly Val Asn Val Glu Gly
50                  55                  60

Glu Thr His His Gln Val Val Gln Arg Ile Lys Ala Val Glu Gly Gln
65                  70                  75                  80

Thr Arg Leu Leu Val Val Asp Gln Glu Thr Asp Glu Glu Leu Arg Arg
                85                  90                  95

Arg Asn Ser Ser
            100

<210> SEQ ID NO 322
<211> LENGTH: 99
<212> TYPE: PRT
<213> ORGANISM: Human papillomavirus

<400> SEQUENCE: 322

Pro Leu Arg Glu Leu Arg Pro Arg Leu Cys His Leu Arg Lys Gly Pro
1               5                   10                  15

Gln Gly Tyr Gly Phe Asn Leu His Ser Asp Lys Ser Arg Pro Gly Gln
            20                  25                  30

Tyr Ile Arg Ser Val Asp Pro Gly Ser Pro Ala Ala Arg Ser Gly Leu
        35                  40                  45

Arg Ala Gln Asp Arg Leu Ile Glu Val Asn Gly Gln Asn Val Glu Gly
50                  55                  60

Leu Arg His Ala Glu Val Val Ala Ser Ile Lys Ala Arg Glu Asp Glu
65                  70                  75                  80
```

Ala Arg Leu Leu Val Asp Pro Glu Thr Asp Glu His Phe Lys Arg
                85                  90                  95

Asn Ser Ser

<210> SEQ ID NO 323
<211> LENGTH: 92
<212> TYPE: PRT
<213> ORGANISM: Human papillomavirus

<400> SEQUENCE: 323

Pro Gly Val Arg Glu Ile His Leu Cys Lys Asp Glu Arg Gly Lys Thr
1               5                   10                  15

Gly Leu Arg Leu Arg Lys Val Asp Gln Gly Leu Phe Val Gln Leu Val
                20                  25                  30

Gln Ala Asn Thr Pro Ala Ser Leu Val Gly Leu Arg Phe Gly Asp Gln
            35                  40                  45

Leu Leu Gln Ile Asp Gly Arg Asp Cys Ala Gly Trp Ser Ser His Lys
        50                  55                  60

Ala His Gln Val Val Lys Lys Ala Ser Gly Asp Lys Ile Val Val Val
65                  70                  75                  80

Val Arg Asp Arg Pro Phe Gln Arg Thr Val Thr Met
                85                  90

<210> SEQ ID NO 324
<211> LENGTH: 90
<212> TYPE: PRT
<213> ORGANISM: Human papillomavirus

<400> SEQUENCE: 324

Pro Phe Gln Arg Thr Val Thr Met His Lys Asp Ser Met Gly His Val
1               5                   10                  15

Gly Phe Val Ile Lys Lys Gly Lys Ile Val Ser Leu Val Lys Gly Ser
                20                  25                  30

Ser Ala Ala Arg Asn Gly Leu Leu Thr Asn His Tyr Val Cys Glu Val
            35                  40                  45

Asp Gly Gln Asn Val Ile Gly Leu Lys Asp Lys Lys Ile Met Glu Ile
        50                  55                  60

Leu Ala Thr Ala Gly Asn Val Val Thr Leu Thr Ile Ile Pro Ser Val
65                  70                  75                  80

Ile Tyr Glu His Ile Val Glu Phe Ile Val
                85                  90

<210> SEQ ID NO 325
<211> LENGTH: 96
<212> TYPE: PRT
<213> ORGANISM: Human papillomavirus

<400> SEQUENCE: 325

Ser Leu Glu Arg Pro Arg Phe Cys Leu Leu Ser Lys Glu Gly Lys
1               5                   10                  15

Ser Phe Gly Phe His Leu Gln Gln Glu Leu Gly Arg Ala Gly His Val
                20                  25                  30

Val Cys Arg Val Asp Pro Gly Thr Ser Ala Gln Arg Gln Gly Leu Gln
            35                  40                  45

Glu Gly Asp Arg Ile Leu Ala Val Asn Asn Asp Val Val Glu His Glu
        50                  55                  60

Asp Tyr Ala Val Val Val Arg Arg Ile Arg Ala Ser Ser Pro Arg Val
65                  70                  75                  80

```
Leu Leu Thr Val Leu Ala Arg His Ala His Asp Val Ala Arg Ala Gln
                85                  90                  95

<210> SEQ ID NO 326
<211> LENGTH: 92
<212> TYPE: PRT
<213> ORGANISM: Human papillomavirus

<400> SEQUENCE: 326

Leu Arg Asp Arg Pro Phe Glu Arg Thr Ile Thr Met His Lys Asp Ser
1               5                   10                  15

Thr Gly His Val Gly Phe Ile Phe Lys Asn Gly Lys Ile Thr Ser Ile
            20                  25                  30

Val Lys Asp Ser Ser Ala Ala Arg Asn Gly Leu Leu Thr Glu His Asn
        35                  40                  45

Ile Cys Glu Ile Asn Gly Gln Asn Val Ile Gly Leu Lys Asp Ser Gln
    50                  55                  60

Ile Ala Asp Ile Leu Ser Thr Ser Gly Thr Val Val Thr Ile Thr Ile
65                  70                  75                  80

Met Pro Ala Phe Ile Phe Glu His Met Asn Ser Ser
                85                  90

<210> SEQ ID NO 327
<211> LENGTH: 88
<212> TYPE: PRT
<213> ORGANISM: Human papillomavirus

<400> SEQUENCE: 327

Leu Glu Ile Lys Gln Gly Ile Arg Glu Val Ile Leu Cys Lys Asp Gln
1               5                   10                  15

Asp Gly Lys Ile Gly Leu Arg Leu Lys Ser Ile Asp Asn Gly Ile Phe
            20                  25                  30

Val Gln Leu Val Gln Ala Asn Ser Pro Ala Ser Leu Val Gly Leu Arg
        35                  40                  45

Phe Gly Asp Gln Val Leu Gln Ile Asn Gly Glu Asn Cys Ala Gly Trp
    50                  55                  60

Ser Ser Asp Lys Ala His Lys Val Leu Lys Gln Ala Phe Gly Glu Lys
65                  70                  75                  80

Ile Thr Met Arg Ile His Arg Asp
                85

<210> SEQ ID NO 328
<211> LENGTH: 94
<212> TYPE: PRT
<213> ORGANISM: Human papillomavirus

<400> SEQUENCE: 328

Gln Arg Arg Arg Val Thr Val Arg Lys Ala Asp Ala Gly Gly Leu Gly
1               5                   10                  15

Ile Ser Ile Lys Gly Gly Arg Glu Asn Lys Met Pro Ile Leu Ile Ser
            20                  25                  30

Lys Ile Phe Lys Gly Leu Ala Ala Asp Gln Thr Glu Ala Leu Phe Val
        35                  40                  45

Gly Asp Ala Ile Leu Ser Val Asn Gly Glu Asp Leu Ser Ser Ala Thr
    50                  55                  60

His Asp Glu Ala Val Gln Val Leu Lys Lys Thr Gly Lys Glu Val Val
65                  70                  75                  80
```

```
Leu Glu Val Lys Tyr Met Lys Asp Val Ser Pro Tyr Phe Lys
                85                  90

<210> SEQ ID NO 329
<211> LENGTH: 88
<212> TYPE: PRT
<213> ORGANISM: Human papillomavirus

<400> SEQUENCE: 329

Pro Val Arg Arg Val Arg Val Lys Gln Glu Ala Gly Gly Leu Gly
1               5                   10                  15

Ile Ser Ile Lys Gly Gly Arg Glu Asn Arg Met Pro Ile Leu Ile Ser
                20                  25                  30

Lys Ile Phe Pro Gly Leu Ala Ala Asp Gln Ser Arg Ala Leu Arg Leu
            35                  40                  45

Gly Asp Ala Ile Leu Ser Val Asn Gly Thr Asp Leu Arg Gln Ala Thr
50                  55                  60

His Asp Gln Ala Val Gln Ala Leu Lys Arg Ala Gly Lys Glu Val Leu
65                  70                  75                  80

Leu Glu Val Lys Phe Ile Arg Glu
                85

<210> SEQ ID NO 330
<211> LENGTH: 100
<212> TYPE: PRT
<213> ORGANISM: Human papillomavirus

<400> SEQUENCE: 330

Glu Pro Phe Tyr Ser Gly Glu Arg Thr Val Thr Ile Arg Gln Thr
1               5                   10                  15

Val Gly Gly Phe Gly Leu Ser Ile Lys Gly Gly Ala Glu His Asn Ile
                20                  25                  30

Pro Val Val Val Ser Lys Ile Ser Lys Glu Gln Arg Ala Glu Leu Ser
            35                  40                  45

Gly Leu Leu Phe Ile Gly Asp Ala Ile Leu Gln Ile Asn Gly Ile Asn
50                  55                  60

Val Arg Lys Cys Arg His Glu Glu Val Val Gln Val Leu Arg Asn Ala
65                  70                  75                  80

Gly Glu Glu Val Thr Leu Thr Val Ser Phe Leu Lys Arg Ala Pro Ala
                85                  90                  95

Phe Leu Lys Leu
            100

<210> SEQ ID NO 331
<211> LENGTH: 99
<212> TYPE: PRT
<213> ORGANISM: Human papillomavirus

<400> SEQUENCE: 331

Ser His Gln Gly Arg Asn Arg Arg Thr Val Thr Leu Arg Arg Gln Pro
1               5                   10                  15

Val Gly Gly Leu Gly Leu Ser Ile Lys Gly Gly Ser Glu His Asn Val
                20                  25                  30

Pro Val Val Ile Ser Lys Ile Phe Glu Asp Gln Ala Ala Asp Gln Thr
            35                  40                  45

Gly Met Leu Phe Val Gly Asp Ala Val Leu Gln Val Asn Gly Ile His
50                  55                  60

Val Glu Asn Ala Thr His Glu Glu Val Val His Leu Leu Arg Asn Ala
```

```
                65                  70                  75                  80
Gly Asp Glu Val Thr Ile Thr Val Glu Tyr Leu Arg Glu Ala Pro Ala
                    85                  90                  95

Phe Leu Lys

<210> SEQ ID NO 332
<211> LENGTH: 91
<212> TYPE: PRT
<213> ORGANISM: Human papillomavirus

<400> SEQUENCE: 332

Arg Gly Glu Thr Lys Glu Val Glu Val Thr Lys Thr Glu Asp Ala Leu
1               5                   10                  15

Gly Leu Thr Ile Thr Asp Asn Gly Ala Gly Tyr Ala Phe Ile Lys Arg
                20                  25                  30

Ile Lys Glu Gly Ser Ile Ile Asn Arg Ile Glu Ala Val Cys Val Gly
            35                  40                  45

Asp Ser Ile Glu Ala Ile Asn Asp His Ser Ile Val Gly Cys Arg His
        50                  55                  60

Tyr Glu Val Ala Lys Met Leu Arg Glu Leu Pro Lys Ser Gln Pro Phe
65                  70                  75                  80

Thr Leu Arg Leu Val Gln Pro Lys Arg Ala Phe
                85                  90

<210> SEQ ID NO 333
<211> LENGTH: 88
<212> TYPE: PRT
<213> ORGANISM: Human papillomavirus

<400> SEQUENCE: 333

His Ser Ile His Ile Glu Lys Ser Asp Thr Ala Ala Asp Thr Tyr Gly
1               5                   10                  15

Phe Ser Leu Ser Ser Val Glu Glu Asp Gly Ile Arg Arg Leu Tyr Val
                20                  25                  30

Asn Ser Val Lys Glu Thr Gly Leu Ala Ser Lys Lys Gly Leu Lys Ala
            35                  40                  45

Gly Asp Glu Ile Leu Glu Ile Asn Asn Arg Ala Ala Asp Ala Leu Asn
        50                  55                  60

Ser Ser Met Leu Lys Asp Phe Leu Ser Gln Pro Ser Leu Gly Leu Leu
65                  70                  75                  80

Val Arg Thr Tyr Pro Glu Leu Glu
                85

<210> SEQ ID NO 334
<211> LENGTH: 97
<212> TYPE: PRT
<213> ORGANISM: Human papillomavirus

<400> SEQUENCE: 334

Pro Leu Asn Val Tyr Asp Val Gln Leu Thr Lys Thr Gly Ser Val Cys
1               5                   10                  15

Asp Phe Gly Phe Ala Val Thr Ala Gln Val Asp Glu Arg Gln His Leu
                20                  25                  30

Ser Arg Ile Phe Ile Ser Asp Val Leu Pro Asp Gly Leu Ala Tyr Gly
            35                  40                  45

Glu Gly Leu Arg Lys Gly Asn Glu Ile Met Thr Leu Asn Gly Glu Ala
        50                  55                  60
```

```
Val Ser Asp Leu Asp Leu Lys Gln Met Glu Ala Leu Phe Ser Glu Lys
 65                  70                  75                  80

Ser Val Gly Leu Thr Leu Ile Ala Arg Pro Pro Asp Thr Lys Ala Thr
                 85                  90                  95

Leu

<210> SEQ ID NO 335
<211> LENGTH: 103
<212> TYPE: PRT
<213> ORGANISM: Human papillomavirus

<400> SEQUENCE: 335

Gln Arg Val Glu Ile His Lys Leu Arg Gln Gly Glu Asn Leu Ile Leu
 1               5                  10                  15

Gly Phe Ser Ile Gly Gly Gly Ile Asp Gln Asp Pro Ser Gln Asn Pro
                20                  25                  30

Phe Ser Glu Asp Lys Thr Asp Lys Gly Ile Tyr Val Thr Arg Val Ser
             35                  40                  45

Glu Gly Gly Pro Ala Glu Ile Ala Gly Leu Gln Ile Gly Asp Lys Ile
 50                  55                  60

Met Gln Val Asn Gly Trp Asp Met Thr Met Val Thr His Asp Gln Ala
 65                  70                  75                  80

Arg Lys Arg Leu Thr Lys Arg Ser Glu Glu Val Val Arg Leu Leu Val
                 85                  90                  95

Thr Arg Gln Ser Leu Gln Lys
            100

<210> SEQ ID NO 336
<211> LENGTH: 86
<212> TYPE: PRT
<213> ORGANISM: Human papillomavirus

<400> SEQUENCE: 336

Arg Lys Glu Val Glu Val Phe Lys Ser Glu Asp Ala Leu Gly Leu Thr
 1               5                  10                  15

Ile Thr Asp Asn Gly Ala Gly Tyr Ala Phe Ile Lys Arg Ile Lys Glu
                20                  25                  30

Gly Ser Val Ile Asp His Ile His Leu Ile Ser Val Gly Asp Met Ile
             35                  40                  45

Glu Ala Ile Asn Gly Gln Ser Leu Leu Gly Cys Arg His Tyr Glu Val
 50                  55                  60

Ala Arg Leu Leu Lys Glu Leu Pro Arg Gly Arg Thr Phe Thr Leu Lys
 65                  70                  75                  80

Leu Thr Glu Pro Arg Lys
                 85

<210> SEQ ID NO 337
<211> LENGTH: 91
<212> TYPE: PRT
<213> ORGANISM: Human papillomavirus

<400> SEQUENCE: 337

His Ser His Pro Arg Val Val Glu Leu Pro Lys Thr Asp Glu Gly Leu
 1               5                  10                  15

Gly Phe Asn Val Met Gly Gly Lys Glu Gln Asn Ser Pro Ile Tyr Ile
                20                  25                  30

Ser Arg Ile Ile Pro Gly Gly Val Ala Glu Arg His Gly Gly Leu Lys
             35                  40                  45
```

-continued

```
Arg Gly Asp Gln Leu Leu Ser Val Asn Gly Val Ser Val Glu Gly Glu
            50                  55                  60

His His Glu Lys Ala Val Glu Leu Leu Lys Ala Ala Lys Asp Ser Val
 65                  70                  75                  80

Lys Leu Val Val Arg Tyr Thr Pro Lys Val Leu
                85                  90

<210> SEQ ID NO 338
<211> LENGTH: 97
<212> TYPE: PRT
<213> ORGANISM: Human papillomavirus

<400> SEQUENCE: 338

Leu Ser Asn Gln Lys Arg Gly Val Lys Val Leu Lys Gln Glu Leu Gly
 1               5                  10                  15

Gly Leu Gly Ile Ser Ile Lys Gly Gly Lys Glu Asn Lys Met Pro Ile
                20                  25                  30

Leu Ile Ser Lys Ile Phe Lys Gly Leu Ala Ala Asp Gln Thr Gln Ala
            35                  40                  45

Leu Tyr Val Gly Asp Ala Ile Leu Ser Val Asn Gly Ala Asp Leu Arg
50                  55                  60

Asp Ala Thr His Asp Glu Ala Val Gln Ala Leu Lys Arg Ala Gly Lys
65                  70                  75                  80

Glu Val Leu Leu Glu Val Lys Tyr Met Arg Glu Ala Thr Pro Tyr Val
                85                  90                  95

Lys

<210> SEQ ID NO 339
<211> LENGTH: 98
<212> TYPE: PRT
<213> ORGANISM: Human papillomavirus

<400> SEQUENCE: 339

Ile Gln Arg Ser Ser Ile Lys Thr Val Glu Leu Ile Lys Gly Asn Leu
 1               5                  10                  15

Gln Ser Val Gly Leu Thr Leu Arg Leu Val Gln Ser Thr Asp Gly Tyr
                20                  25                  30

Ala Gly His Val Ile Ile Glu Thr Val Ala Pro Asn Ser Pro Ala Ala
            35                  40                  45

Ile Ala Asp Leu Gln Arg Gly Asp Arg Leu Ile Ala Ile Gly Gly Val
50                  55                  60

Lys Ile Thr Ser Thr Leu Gln Val Leu Lys Leu Ile Lys Gln Ala Gly
65                  70                  75                  80

Asp Arg Val Leu Val Tyr Tyr Glu Arg Pro Val Gly Gln Ser Asn Gln
                85                  90                  95

Gly Ala

<210> SEQ ID NO 340
<211> LENGTH: 103
<212> TYPE: PRT
<213> ORGANISM: Human papillomavirus

<400> SEQUENCE: 340

Ile Leu Thr Leu Thr Ile Leu Arg Gln Thr Gly Gly Leu Gly Ile Ser
 1               5                  10                  15

Ile Ala Gly Gly Lys Gly Ser Thr Pro Tyr Lys Gly Asp Asp Glu Gly
                20                  25                  30
```

```
Ile Phe Ile Ser Arg Val Ser Glu Glu Gly Pro Ala Ala Arg Ala Gly
            35                  40                  45

Val Arg Val Gly Asp Lys Leu Leu Glu Val Asn Gly Val Ala Leu Gln
 50                  55                  60

Gly Ala Glu His His Glu Ala Val Glu Ala Leu Arg Gly Ala Gly Thr
 65                  70                  75                  80

Ala Val Gln Met Arg Val Trp Arg Glu Arg Met Val Glu Pro Glu Asn
                 85                  90                  95

Ala Glu Phe Ile Val Thr Asp
            100
```

<210> SEQ ID NO 341
<211> LENGTH: 105
<212> TYPE: PRT
<213> ORGANISM: Human papillomavirus

<400> SEQUENCE: 341

```
Arg Glu Leu Cys Ile Gln Lys Ala Pro Gly Arg Leu Gly Ile Ser
 1               5                  10                  15

Ile Arg Gly Gly Ala Arg Gly His Ala Gly Asn Pro Arg Asp Pro Thr
                 20                  25                  30

Asp Glu Gly Ile Phe Ile Ser Lys Val Ser Pro Thr Gly Ala Ala Gly
            35                  40                  45

Arg Asp Gly Arg Leu Arg Val Gly Leu Arg Leu Leu Glu Val Asn Gln
 50                  55                  60

Gln Ser Leu Leu Gly Leu Thr His Gly Glu Ala Val Gln Leu Leu Arg
 65                  70                  75                  80

Ser Val Gly Asp Thr Leu Thr Val Leu Val Cys Asp Gly Phe Glu Ala
                 85                  90                  95

Ser Thr Asp Ala Ala Leu Glu Val Ser
            100                 105
```

<210> SEQ ID NO 342
<211> LENGTH: 105
<212> TYPE: PRT
<213> ORGANISM: Human papillomavirus

<400> SEQUENCE: 342

```
Leu Glu Gly Pro Tyr Pro Val Glu Glu Ile Arg Leu Pro Arg Ala Gly
 1               5                  10                  15

Gly Pro Leu Gly Leu Ser Ile Val Gly Gly Ser Asp His Ser Ser His
                 20                  25                  30

Pro Phe Gly Val Gln Glu Pro Gly Val Phe Ile Ser Lys Val Leu Pro
            35                  40                  45

Arg Gly Leu Ala Ala Arg Ser Gly Leu Arg Val Gly Asp Arg Ile Leu
 50                  55                  60

Ala Val Asn Gly Gln Asp Val Arg Asp Ala Thr His Gln Glu Ala Val
 65                  70                  75                  80

Ser Ala Leu Leu Arg Pro Cys Leu Glu Leu Ser Leu Leu Val Arg Arg
                 85                  90                  95

Asp Pro Ala Glu Phe Ile Val Thr Asp
            100                 105
```

<210> SEQ ID NO 343
<211> LENGTH: 97
<212> TYPE: PRT
<213> ORGANISM: Human papillomavirus

<400> SEQUENCE: 343

```
Pro Leu Arg Gln Arg His Val Ala Cys Leu Ala Arg Ser Glu Arg Gly
1               5                   10                  15

Leu Gly Phe Ser Ile Ala Gly Gly Lys Gly Ser Thr Pro Tyr Arg Ala
            20                  25                  30

Gly Asp Ala Gly Ile Phe Val Ser Arg Ile Ala Glu Gly Gly Ala Ala
        35                  40                  45

His Arg Ala Gly Thr Leu Gln Val Gly Asp Arg Val Leu Ser Ile Asn
    50                  55                  60

Gly Val Asp Val Thr Glu Ala Arg His Asp His Ala Val Ser Leu Leu
65                  70                  75                  80

Thr Ala Ala Ser Pro Thr Ile Ala Leu Leu Leu Glu Arg Glu Ala Gly
                85                  90                  95

Gly
```

<210> SEQ ID NO 344
<211> LENGTH: 114
<212> TYPE: PRT
<213> ORGANISM: Human papillomavirus

<400> SEQUENCE: 344

```
Thr Leu Thr Ile Leu Arg Gln Thr Gly Gly Leu Gly Ile Ser Ile Ala
1               5                   10                  15

Gly Gly Lys Gly Ser Thr Pro Tyr Lys Gly Asp Asp Glu Gly Ile Phe
            20                  25                  30

Ile Ser Arg Val Ser Glu Gly Pro Ala Ala Arg Ala Gly Val Arg
        35                  40                  45

Val Gly Asp Lys Leu Leu Glu Gly Ile Phe Val Ser Arg Ile Ala Glu
    50                  55                  60

Gly Gly Ala Ala His Arg Ala Gly Thr Leu Gln Val Gly Asp Arg Val
65                  70                  75                  80

Leu Ser Ile Asn Gly Val Asp Val Thr Glu Ala Arg His Asp His Ala
                85                  90                  95

Val Ser Leu Leu Thr Ala Ala Ser Pro Thr Ile Ala Leu Leu Leu Glu
                100                 105                 110

Arg Glu
```

<210> SEQ ID NO 345
<211> LENGTH: 95
<212> TYPE: PRT
<213> ORGANISM: Human papillomavirus

<400> SEQUENCE: 345

```
Ile Pro Pro Val Thr Thr Val Leu Ile Lys Arg Pro Asp Leu Lys Tyr
1               5                   10                  15

Gln Leu Gly Phe Ser Val Gln Asn Gly Ile Ile Cys Ser Leu Met Arg
            20                  25                  30

Gly Gly Ile Ala Glu Arg Gly Gly Val Arg Val Gly His Arg Ile Ile
        35                  40                  45

Glu Ile Asn Gly Gln Ser Val Val Ala Thr Ala His Glu Lys Ile Val
    50                  55                  60

Gln Ala Leu Ser Asn Ser Val Gly Glu Ile His Met Lys Thr Met Pro
65                  70                  75                  80

Ala Ala Met Phe Arg Leu Leu Thr Gly Gln Glu Asn Ser Ser Leu
                85                  90                  95
```

<210> SEQ ID NO 346
<211> LENGTH: 110
<212> TYPE: PRT
<213> ORGANISM: Human papillomavirus

<400> SEQUENCE: 346

Ile His Phe Ser Asn Ser Glu Asn Cys Lys Glu Leu Gln Leu Glu Lys
1               5                   10                  15

His Lys Gly Glu Ile Leu Gly Val Val Val Glu Ser Gly Trp Gly
            20                  25                  30

Ser Ile Leu Pro Thr Val Ile Leu Ala Asn Met Met Asn Gly Gly Pro
        35                  40                  45

Ala Ala Arg Ser Gly Lys Leu Ser Ile Gly Asp Gln Ile Met Ser Ile
50                  55                  60

Asn Gly Thr Ser Leu Val Gly Leu Pro Leu Ala Thr Cys Gln Gly Ile
65                  70                  75                  80

Ile Lys Gly Leu Lys Asn Gln Thr Gln Val Leu Asn Ile Val Ser
                85                  90                  95

Cys Pro Pro Val Thr Thr Val Leu Ile Lys Arg Asn Ser Ser
            100                 105                 110

<210> SEQ ID NO 347
<211> LENGTH: 101
<212> TYPE: PRT
<213> ORGANISM: Human papillomavirus

<400> SEQUENCE: 347

Ile Trp Glu Gln His Thr Val Thr Leu His Arg Ala Pro Gly Phe Gly
1               5                   10                  15

Phe Gly Ile Ala Ile Ser Gly Gly Arg Asp Asn Pro His Phe Gln Ser
            20                  25                  30

Gly Glu Thr Ser Ile Val Ile Ser Asp Val Leu Lys Gly Gly Pro Ala
        35                  40                  45

Glu Gly Gln Leu Gln Glu Asn Asp Arg Val Ala Met Val Asn Gly Val
    50                  55                  60

Ser Met Asp Asn Val Glu His Ala Phe Ala Val Gln Gln Leu Arg Lys
65                  70                  75                  80

Ser Gly Lys Asn Ala Lys Ile Thr Ile Arg Arg Lys Lys Lys Val Gln
                85                  90                  95

Ile Pro Asn Ser Ser
            100

<210> SEQ ID NO 348
<211> LENGTH: 95
<212> TYPE: PRT
<213> ORGANISM: Human papillomavirus

<400> SEQUENCE: 348

Ile Ser Ser Gln Pro Ala Lys Pro Thr Lys Val Thr Leu Val Lys Ser
1               5                   10                  15

Arg Lys Asn Glu Glu Tyr Gly Leu Arg Leu Ala Ser His Ile Phe Val
            20                  25                  30

Lys Glu Ile Ser Gln Asp Ser Leu Ala Ala Arg Asp Gly Asn Ile Gln
        35                  40                  45

Glu Gly Asp Val Val Leu Lys Ile Asn Gly Thr Val Thr Glu Asn Met
    50                  55                  60

```
Ser Leu Thr Asp Ala Lys Thr Leu Ile Glu Arg Ser Lys Gly Lys Leu
 65                  70                  75                  80

Lys Met Val Val Gln Arg Asp Arg Ala Thr Leu Leu Asn Ser Ser
                 85                  90                  95

<210> SEQ ID NO 349
<211> LENGTH: 90
<212> TYPE: PRT
<213> ORGANISM: Human papillomavirus

<400> SEQUENCE: 349

Ile Arg Met Lys Leu Val Lys Phe Arg Lys Gly Asp Ser Val Gly Leu
  1               5                  10                  15

Arg Leu Ala Gly Gly Asn Asp Val Gly Ile Phe Val Ala Gly Val Leu
                 20                  25                  30

Glu Asp Ser Pro Ala Ala Lys Glu Gly Leu Glu Gly Asp Gln Ile
             35                  40                  45

Leu Arg Val Asn Asn Val Asp Phe Thr Asn Ile Ile Arg Glu Glu Ala
 50                  55                  60

Val Leu Phe Leu Leu Asp Leu Pro Lys Gly Glu Val Thr Ile Leu
 65                  70                  75                  80

Ala Gln Lys Lys Lys Asp Val Phe Ser Asn
                 85                  90

<210> SEQ ID NO 350
<211> LENGTH: 99
<212> TYPE: PRT
<213> ORGANISM: Human papillomavirus

<400> SEQUENCE: 350

Ile Gln His Thr Val Thr Leu His Arg Ala Pro Gly Phe Gly Phe Gly
  1               5                  10                  15

Ile Ala Ile Ser Gly Gly Arg Asp Asn Pro His Phe Gln Ser Gly Glu
                 20                  25                  30

Thr Ser Ile Val Ile Ser Asp Val Leu Lys Gly Gly Pro Ala Glu Gly
             35                  40                  45

Gln Leu Gln Glu Asn Asp Arg Val Ala Met Val Asn Gly Val Ser Met
 50                  55                  60

Asp Asn Val Glu His Ala Phe Ala Val Gln Gln Leu Arg Lys Ser Gly
 65                  70                  75                  80

Lys Asn Ala Lys Ile Thr Ile Arg Arg Lys Lys Lys Val Gln Ile Pro
                 85                  90                  95

Asn Ser Ser

<210> SEQ ID NO 351
<211> LENGTH: 90
<212> TYPE: PRT
<213> ORGANISM: Human papillomavirus

<400> SEQUENCE: 351

His Ala Pro Asn Thr Lys Met Val Arg Phe Lys Lys Gly Asp Ser Val
  1               5                  10                  15

Gly Leu Arg Leu Ala Gly Gly Asn Asp Val Gly Ile Phe Val Ala Gly
                 20                  25                  30

Ile Gln Glu Gly Thr Ser Ala Glu Gln Glu Gly Leu Gln Gly Asp
             35                  40                  45

Gln Ile Leu Lys Val Asn Thr Gln Asp Phe Arg Gly Leu Val Arg Glu
 50                  55                  60
```

```
Asp Ala Val Leu Tyr Leu Leu Glu Ile Pro Lys Gly Glu Met Val Thr
 65                  70                  75                  80

Ile Leu Ala Gln Ser Arg Ala Asp Val Tyr
                 85                  90

<210> SEQ ID NO 352
<211> LENGTH: 79
<212> TYPE: PRT
<213> ORGANISM: Human papillomavirus

<400> SEQUENCE: 352

Arg Val Leu Leu Met Lys Ser Arg Ala Asn Glu Glu Tyr Gly Leu Arg
 1               5                  10                  15

Leu Gly Ser Gln Ile Phe Val Lys Glu Met Thr Arg Thr Gly Leu Ala
                20                  25                  30

Thr Lys Asp Gly Asn Leu His Glu Gly Asp Ile Ile Leu Lys Ile Asn
             35                  40                  45

Gly Thr Val Thr Glu Asn Met Ser Leu Thr Asp Ala Arg Lys Leu Ile
 50                  55                  60

Glu Lys Ser Arg Gly Lys Leu Gln Leu Val Leu Arg Asp Ser
 65                  70                  75

<210> SEQ ID NO 353
<211> LENGTH: 104
<212> TYPE: PRT
<213> ORGANISM: Human papillomavirus

<400> SEQUENCE: 353

Arg Gly Tyr Ser Pro Asp Thr Arg Val Val Arg Phe Leu Lys Gly Lys
 1               5                  10                  15

Ser Ile Gly Leu Arg Leu Ala Gly Gly Asn Asp Val Gly Ile Phe Val
                20                  25                  30

Ser Gly Val Gln Ala Gly Ser Pro Ala Asp Gly Gln Gly Ile Gln Glu
             35                  40                  45

Gly Asp Gln Ile Leu Gln Val Asn Asp Val Pro Phe Gln Asn Leu Thr
 50                  55                  60

Arg Glu Glu Ala Val Gln Phe Leu Leu Gly Leu Pro Pro Gly Glu Glu
 65                  70                  75                  80

Met Glu Leu Val Thr Gln Arg Lys Gln Asp Ile Phe Trp Lys Met Val
                 85                  90                  95

Gln Ser Glu Phe Ile Val Thr Asp
            100

<210> SEQ ID NO 354
<211> LENGTH: 106
<212> TYPE: PRT
<213> ORGANISM: Human papillomavirus

<400> SEQUENCE: 354

Ile Pro Gly Asn Ser Thr Ile Trp Glu Gln His Thr Ala Thr Leu Ser
 1               5                  10                  15

Lys Asp Pro Arg Arg Gly Phe Gly Ile Ala Ile Ser Gly Gly Arg Asp
                20                  25                  30

Arg Pro Gly Gly Ser Met Val Val Ser Asp Val Val Pro Gly Gly Pro
             35                  40                  45

Ala Glu Gly Arg Leu Gln Thr Gly Asp His Ile Val Met Val Asn Gly
 50                  55                  60
```

```
Val Ser Met Glu Asn Ala Thr Ser Ala Phe Ala Ile Gln Ile Leu Lys
 65                  70                  75                  80

Thr Cys Thr Lys Met Ala Asn Ile Thr Val Lys Arg Pro Arg Arg Ile
                 85                  90                  95

His Leu Pro Ala Glu Phe Ile Val Thr Asp
            100                 105

<210> SEQ ID NO 355
<211> LENGTH: 98
<212> TYPE: PRT
<213> ORGANISM: Human papillomavirus

<400> SEQUENCE: 355

Gln Asp Val Gln Met Lys Pro Val Lys Ser Val Leu Val Lys Arg Arg
  1               5                  10                  15

Asp Ser Glu Glu Phe Gly Val Lys Leu Gly Ser Gln Ile Phe Ile Lys
                 20                  25                  30

His Ile Thr Asp Ser Gly Leu Ala Ala Arg His Arg Gly Leu Gln Glu
             35                  40                  45

Gly Asp Leu Ile Leu Gln Ile Asn Gly Val Ser Ser Gln Asn Leu Ser
 50                  55                  60

Leu Asn Asp Thr Arg Arg Leu Ile Glu Lys Ser Glu Gly Lys Leu Ser
 65                  70                  75                  80

Leu Leu Val Leu Arg Asp Arg Gly Gln Phe Leu Val Asn Ile Pro Asn
                 85                  90                  95

Ser Ser

<210> SEQ ID NO 356
<211> LENGTH: 10
<212> TYPE: PRT
<213> ORGANISM: Human papillomavirus

<400> SEQUENCE: 356

Gln Cys Trp Arg Pro Ser Ala Thr Val Val
  1               5                  10

<210> SEQ ID NO 357
<211> LENGTH: 10
<212> TYPE: PRT
<213> ORGANISM: Human papillomavirus

<400> SEQUENCE: 357

Trp Arg Pro Gln Arg Thr Gln Thr Gln Val
  1               5                  10

<210> SEQ ID NO 358
<211> LENGTH: 10
<212> TYPE: PRT
<213> ORGANISM: Human papillomavirus

<400> SEQUENCE: 358

Arg Arg Arg Ile Arg Arg Glu Thr Gln Val
  1               5                  10

<210> SEQ ID NO 359
<211> LENGTH: 148
<212> TYPE: PRT
<213> ORGANISM: Human papillomavirus

<400> SEQUENCE: 359

Met Phe Phe Pro Asn Pro Glu Glu Arg Pro Tyr Lys Leu Pro Ala Leu
```

```
1               5                  10                 15
Cys Glu Glu Val Asn Ile Ser Ile His Glu Ile Glu Leu Asp Cys Val
                20                 25                 30

Tyr Cys Glu Arg Gln Leu Tyr Arg Cys Glu Val Tyr Asp Phe Ile Phe
                35                 40                 45

Arg Asp Leu Cys Val Val Tyr Arg Lys Gly Lys Pro Leu Gly Val Cys
                50                 55                 60

Gln Pro Cys Leu Leu Phe Tyr Ser Lys Val Arg Gln Tyr Arg Arg Tyr
65                 70                 75                 80

Asn Gln Ser Val Tyr Gly Arg Thr Leu Glu Asn Leu Thr Asn Lys Gln
                85                 90                 95

Leu Cys Asn Ile Leu Ile Arg Cys Gly Lys Cys Gln Lys Pro Leu Cys
                100                105                110

Pro Leu Glu Lys Gln Arg His Val Asp Glu Asn Lys Arg Phe His Gln
                115                120                125

Ile Ala Asp Gln Trp Thr Gly Arg Cys Thr Gln Cys Trp Arg Pro Ser
                130                135                140

Ala Thr Val Val
145

<210> SEQ ID NO 360
<211> LENGTH: 149
<212> TYPE: PRT
<213> ORGANISM: Human papillomavirus

<400> SEQUENCE: 360

Met Phe Gln Asp Thr Asp Glu Lys Pro Arg Asn Leu His Glu Leu Cys
1               5                  10                 15

Glu Ala Leu Glu Thr Thr Val His Glu Ile Ser Leu Pro Cys Val Gln
                20                 25                 30

Cys Lys Lys Thr Leu Asp Arg Asn Glu Val Tyr Asp Phe Leu Phe Thr
                35                 40                 45

Asp Leu Lys Ile Val Tyr Arg Cys Gly Asn Pro Tyr Gly Val Cys Lys
                50                 55                 60

Gln Cys Leu Arg Leu Leu Ser Lys Val Ser Glu Tyr Arg Tyr Phe Asn
65                 70                 75                 80

Tyr Ser Val Tyr Gly Asn Thr Leu Glu Glu Ile Val His Lys Pro Leu
                85                 90                 95

Asn Glu Ile Thr Ile Arg Cys Ile Thr Cys Gln Arg Pro Leu Cys Pro
                100                105                110

Gln Glu Lys Gln Arg His Val Asp Arg Lys Lys Arg Phe His Asn Ile
                115                120                125

Ser Asn Arg Trp Thr Gly Arg Cys Ser Val Cys Trp Arg Pro Gln Arg
130                135                140

Thr Gln Thr Gln Val
145

<210> SEQ ID NO 361
<211> LENGTH: 158
<212> TYPE: PRT
<213> ORGANISM: Human papillomavirus

<400> SEQUENCE: 361

Met Ala Arg Phe Pro Asn Pro Ala Glu Arg Pro Tyr Lys Leu Pro Asp
1               5                  10                 15

Leu Cys Thr Ala Leu Asp Thr Thr Leu His Asp Ile Thr Ile Asp Cys
```

```
                20                  25                  30

Val Tyr Cys Lys Thr Gln Leu Gln Gln Thr Glu Val Tyr Glu Phe Ala
            35                  40                  45

Phe Ser Asp Leu Phe Ile Val Tyr Arg Asn Gly Glu Pro Tyr Ala Ala
        50                  55                  60

Cys Gln Lys Cys Ile Lys Phe His Ala Lys Val Arg Glu Leu Arg His
 65                  70                  75                  80

Tyr Ser Asn Ser Val Tyr Ala Thr Thr Leu Glu Ser Ile Thr Asn Thr
                85                  90                  95

Lys Leu Tyr Asn Leu Ser Ile Arg Cys Met Ser Cys Leu Lys Pro Leu
            100                 105                 110

Cys Pro Ala Glu Lys Leu Arg His Val Asn Thr Lys Arg Arg Phe His
        115                 120                 125

Gln Ile Ala Gly Ser Tyr Thr Gly Gln Cys Arg His Cys Trp Thr Ser
    130                 135                 140

Asn Arg Glu Asp Arg Arg Ile Arg Arg Glu Thr Gln Val
145                 150                 155

<210> SEQ ID NO 362
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Gly Leu Gly Phe
1

<210> SEQ ID NO 363
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys or Arg
<220> FEATURE:
<221> NAME/KEY: MOD_RES
<222> LOCATION: (6)..(6)
<223> OTHER INFORMATION: Asn, Lys, Ser, Glu or Arg
<220> FEATURE:
<221> NAME/KEY: MOD_RES
<222> LOCATION: (8)..(8)
<223> OTHER INFORMATION: Ala or Ser

<400> SEQUENCE: 363

Xaa Xaa Arg Phe His Xaa Ile Xaa
1               5

<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu or Ser
<220> FEATURE:
```

```
<221> NAME/KEY: MOD_RES
<222> LOCATION: (6)..(6)
<223> OTHER INFORMATION: Ile, Tyr, His, Leu or Met
<220> FEATURE:
<221> NAME/KEY: MOD_RES
<222> LOCATION: (7)..(7)
<223> OTHER INFORMATION: Arg, Ile or Cys

<400> SEQUENCE: 364

Leu Xaa Ile Arg Cys Xaa Xaa Cys
1               5

<210> SEQ ID NO 365
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, Ile or Cys
<220> FEATURE:
<221> NAME/KEY: MOD_RES
<222> LOCATION: (3)..(3)
<223> OTHER INFORMATION: Gln or Leu
<220> FEATURE:
<221> NAME/KEY: MOD_RES
<222> LOCATION: (4)..(4)
<223> OTHER INFORMATION: Lys or Arg
<220> FEATURE:
<221> NAME/KEY: MOD_RES
<222> LOCATION: (7)..(7)
<223> OTHER INFORMATION: Cys, Thr, Gly or Asn

<400> SEQUENCE: 365

Xaa Cys Xaa Xaa Pro Leu Xaa Pro
1               5

<210> SEQ ID NO 366
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (4)..(4)
<223> OTHER INFORMATION: Cys, Thr, Gly or Asn
<220> FEATURE:
<221> NAME/KEY: MOD_RES
<222> LOCATION: (6)..(6)
<223> OTHER INFORMATION: Glu, Ala or Gln

<400> SEQUENCE: 366

Xaa Pro Leu Xaa Pro Xaa Glu Lys
1               5
```

ANTIBODIES FOR ONCOGENIC STRAINS OF HPV AND METHODS OF THEIR USE

CROSS-REFERENCE

This application is a continuation application of Ser. No. 13/364,954, filed Feb. 2, 2012, which is a continuation of Ser. No. 12/660,613, filed Mar. 1, 2010, which is a continuation application of Ser. No. 12/156,013, filed May 28, 2008 which is a continuation application Ser. No. 11/021,949, filed Dec. 23, 2004 which claims the benefit of U.S. provisional patent application Ser. No. 60/532,373, filed Dec. 23, 2003, which applications are incorporated herein by reference in their entirety.

SEQUENCE LISTING

The instant application contains a Sequence Lisiting which has been submitted via EFS-Web and is hereby incorporated by reference in its entirety. Said ASCll copy, created on Dec. 17, 2014 is named 34170-702.304_SL.txt and is 316,184 bytes in size.

FIELD OF INVENTION

The present invention relates to detection of oncogenic strains of human papillomavirus (HPV).

BACKGROUND OF THE INVENTION

Cervical cancer is the second most common cancer diagnosis in women and is linked to high-risk human papillomavirus infection 99.7 % of the time. Currently, 12,000 new cases of invasive cervical cancer are diagnosed in US women annually, resulting in 5,000 deaths each year. Furthermore, there are approximately 400,000 cases of cervical cancer and close to 200,000 deaths annually worldwide. Human papillomaviruses (HPVs) are one of the most common causes of sexually transmitted disease in the world. Overall, 50-75 % of sexually active men and women acquire genital HPV infections at some point in their lives. An estimated 5.5 million people become infected with HPV each year in the US alone, and at least 20 million are currently infected. The more than 100 different isolates of HPV have been broadly subdivided into high-risk and low-risk subtypes based on their association with cervical carcinomas or with benign cervical lesions or dysplasias.

A number of lines of evidence point to HPV infections as the etiological agents of cervical cancers. Multiple studies in the 1980's reported the presence of HPV variants in cervical dysplasias, cancer, and in cell lines derived from cervical cancer. Further research demonstrated that the E6-E7 region of the genome from oncogenic HPV 18 is selectively retained in cervical cancer cells, suggesting that HPV infection could be causative and that continued expression of the E6-E7 region is required for maintenance of the immortalized or cancerous state. Further research demonstrated that the E6-E7 genes from HPV 16 were sufficient to immortalize human keratinocytes in culture. It was also demonstrated that although E6-E7 genes from high risk HPVs could transform cell lines, the E6-E7 regions from low risk, or non-oncogenic variants such as HPV 6 and HPV 11 were unable to transform human keratinocytes. HPV 16 and 18 infection was examined by in situ hybridization and E6 protein expression by immunocytochemistry in 623 cervical tissue samples at various stages of tumor progression and found a significant correlation between histological abnormality and HPV infection.

A significant unmet need exists for early and accurate diagnosis of oncogenic HPV infection as well as for treatments directed at the causative HPV infection, preventing the development of cervical cancer by intervening earlier in disease progression. Human papillomaviruses characterized to date are associated with lesions confined to the epithelial layers of skin, or oral, pharyngeal, respiratory, and, most importantly, anogenital mucosae. Specific human papillomavirus types, including HPV 6 and 11, frequently cause benign mucosal lesions, whereas other types such as HPV 16, 18, and a host of other strains, are predominantly found in high-grade lesions and cancer. Individual types of human papillomaviruses (HPV) which infect mucosal surfaces have been implicated as the causative agents for carcinomas of the cervix, breast (Yu et al. (1999) Anticancer Res. 19:55555057-5061; Liu et al. (2001) J. Hum. Virol. 44:329-334), anus, penis, prostate (Dc Villiers et al. (1989) Virology 171:248:253), larynx and the buccal cavity, tonsils (Snijders et al. (1994) J. Gen. Virol. 75 (Pt 10):2769-2775), nasal passage (Trujillo et al. (1996) Virus Genes 12:165-178; Wu et al. (1993) Lancet 341:522-524), skin (Trenfield et al. (1993) Australas. J. Dermatol. 34:71-78), bladder (Baithun et al. (1998) Cancer Surv. 31:17-27), head and neck squamous-cell carcinomas (Braakhuis et al. (2004) J. Natl. Cancer Inst. 96:978-980), occasional periungal carcinomas, as well as benign anogenital warts. The identification of particular HPV types is used for identifying patients with premalignant lesions who are at risk of progression to malignancy. Although visible anogenital lesions are present in some persons infected with human papillomavirus, the majority of individuals with HPV genital tract infection do not have clinically apparent disease, but analysis of cytomorphological traits present in cervical smears can be used to detect HPV infection. Papanicolaou tests are a valuable screening tool, but they miss a large proportion of HPV-infected persons due to the unfortunate false positive and false negative test results. In addition, they are not amenable to worldwide testing because interpretation of results requires trained pathologists.

HPV infection is also associated with Netherton's syndrome (Weber et al. (2001) Br. J. Dermatol. 144:1044-1049) and epidermolysis verruciformis (Rubaie et al. (1998) Int. J. Dermatol. 37:766-771). HPV can also be transmitted to a fetus by the mother (Smith et al. (2004) Sex. Transm. Dis. 31:57-62; Xu et al. (1998) Chin. Med. Sci. J. 13:29-31; Cason et al. (1998) Intervirology 41:213-218).

The detection and diagnosis of disease is a prerequisite for the treatment of disease. Numerous markers and characteristics of diseases have been identified and many are used for the diagnosis of disease. Many diseases are preceded by, and are characterized by, changes in the state of the affected cells. Changes can include the expression of pathogengenes or proteins in infected cells, changes in the expression patterns of genes or proteins in affected cells, and changes in cell morphology. The detection, diagnosis, and monitoring of diseases can be aided by the accurate assessment of these changes. Inexpensive, rapid, early and accurate detection of pathogens can allow treatment and prevention of diseases that range in effect from discomfort to death.

LITERATURE

Literature of interest includes the following references: Zozulya et al., (Genome Biology 2:0018.1-0018.12, 2001;

Mombairts (Annu. Rev. Neurosci 22:487-509, 1999); Raming et al., (Nature 361: 353-356, 1993); Belluscio et al., (Neuron 20:69-81, 1988); Ronnet et al., (Annu. Rev. Physiol. 64:189-222, 2002); Lu et al., (Traffic 4:416-533, 2003); Buck (Cell 100:611-618, 2000); Malnic et al., (Cell 96:713-723, 1999); Firestein (Nature 413:211-218, 2001); Zhao et al., (Science 279:237-242, 1998); Touhara et al., (Proc. Natl. Acad. Sci. 96: 4040-4045, 1999); Sklar et al., (J. Biol. Chem 261:15538-15543, 1986); Dryer et al., (TiPS 20:413-417, 1999); Ivic et al., (J Neurobiol. 50:56-68, 2002); Munger (2002) Front. Biosci. 7:d641-9; Glaunsinger (2000) Oncogene 19:5270-80; Gardiol (1999) Oncogene 18:5487-96; Pim (1999) Oncogene 18:7403-8; Meschede (1998) J. Clin. Microbiol. 36:475-80; Kiyono (1997) Proc. Natl. Acad. Sci. 94:11612-6; and Lee (1997) Proc. Natl. Acad. Sci. 94:6670-5; Banks (1987) J. Gen. Virol. 68:1351-1359; Fuchs et al., (Hum. Genet. 108:1-13, 2001); and Giovane et al. (1999) Journal of Molecular Recognition 12:141-152 and published US patent applications 20030143679 and 20030105285; and U.S. Pat. Nos. 6,610,511, 6,492,143 6,410,249, 6,322,794, 6,344,314, 5,415,995, 5753233, 5,876,723, 5,648,459, 6,391,539, 5,665,535 and 4,777,239.

SUMMARY OF THE INVENTION

The subject invention provides antibodies, including polyclonal and monoclonal antibodies, that bind to the E6 proteins from at least three different oncogenic strains of HPV. In general, the antibodies bind to amino acids motifs that are conserved between the E6 proteins of different HPV strains, particularly HPV strains 16 and 18. The subject antibodies may be used to detect HPV E6 protein in a sample, and, accordingly, the antibodies find use in a variety of diagnostic applications, including methods of diagnosing cancer. Kits for performing the subject methods and containing the subject antibodies are also provided.

In certain embodiments, the invention provides an antibody composition comprising a monoclonal antibody that specifically binds to the E6 proteins of at least three (e.g., 4, 5, 6, 7 or 8 or more, usually up to 10 or 12) different oncogenic HPV strains. The antibody composition may comprise a mixture of monoclonal antibodies that specifically bind to the E6 proteins of HPV strains 16, 18, 31, 33 and 45 (e.g., HPV strains 16, 18, 31, 33, 45, 52 and 58, HPV strains 16, 18, 31, 33, 45, 52, 58, 35 and 59 or HPV strains 16, 18, 26, 30, 31, 33, 34, 45, 51, 52, 53, 58, 59, 66, 68 b, 69, 70, 73 and 82, wherein at least one of said monoclonal antibodies specifically binds to the E6 proteins of at least three different oncogenic HPV strains. In certain embodiments, the monoclonal antibody may bind to the E6 proteins of HPV strains 16 and 18, wherein said antibody binds SEQ ID NOS: 1, 3 or 5 of HPV strain 16 E6 and SEQ ID NOS: 2, 4 or 6 of HPV strain 18 E6. In certain embodiments, the monoclonal antibody binds to E6 proteins of HPV strains 16 and 45 or HPV strains 16, 18, 31, 33 and 45.

The invention also provides a method of detecting an HPV E6 protein in a sample. This methods generally involves contacting the subject antibody composition with the sample, and detecting any binding of the antibodies in the composition to the sample, wherein binding of an antibody to the sample indicates the presence of an HPV E6 protein. The sample may be suspected of containing an oncogenic strain of HPV.

The invention also provides a system for detecting the presence of an oncogenic HPV E6 polypeptide in a sample. This system generally comprises a first and a second binding partner for an oncogenic HPV E6 polypeptide, wherein the first binding partner is a PDZ domain protein and said second binding partner is an subject antibody. At least one of said binding partners is attached to a solid support.

The invention also provides a method of detecting the presence of an oncogenic HPV E6 protein in a sample. This method generally comprises: contacting a sample containing an oncogenic HPV E6 protein with a PDZ domain polypeptide; and detecting any binding of the oncogenic HPV E6 protein in said sample to said PDZ domain polypeptide using an subject antibody, wherein binding of the oncogenic HPV E6 protein to said PDZ domain polypeptide indicates the presence of an oncogenic HPV E6 protein in said sample.

The invention also provides a kit containing a subject antibody; and instructions for using the antibody to detect a HPV E6 protein. The kit may also contain a PDZ domain polypeptide.

The invention also provides a peptide of less than 15 amino acids comprising any one of the sequences set forth in Table 1.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is an alignment of E6 amino acid sequences from various oncogenic strains of HPV. From top to bottom, the various HPV E6 amino acid sequences are set forth in the sequence listing as SEQ ID NOS: 13-32, respectively. Amino acid sequence from three other oncogenic strains of HPV (strains 34, 67 and 70) are found in the sequence listing as SEQ Ill NOS: 359-361.

FIG. 2 is an alignment of E6 amino acid sequences from a subset of oncogenic strains of HPV shown in FIG. 1. FIG. 2 discloses SEQ ID NOS 15-18, 13 and 28-29, respectively, in order of appearance.

DEFINITIONS

Figure 3:
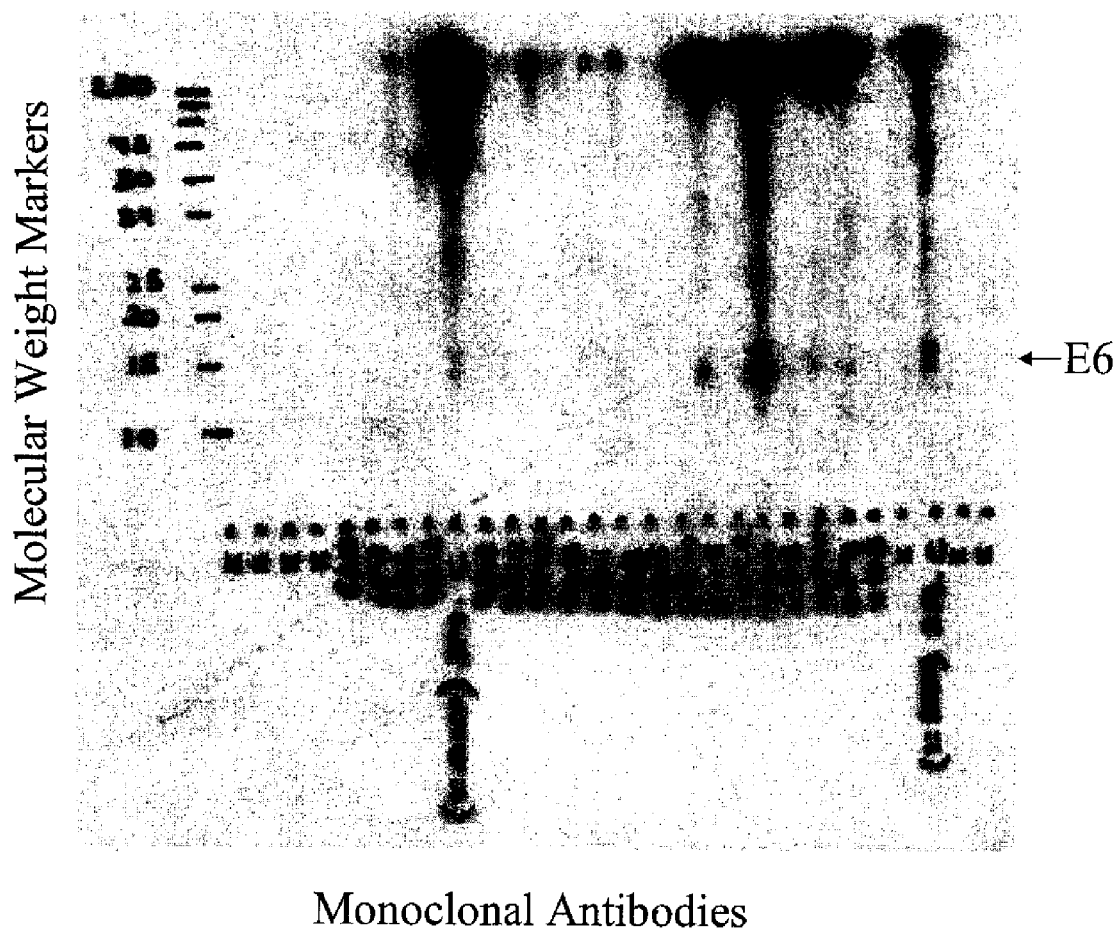
FIG. 3 is a slot western blot showing antibody reactivity with E6 protein.
Figure 4:
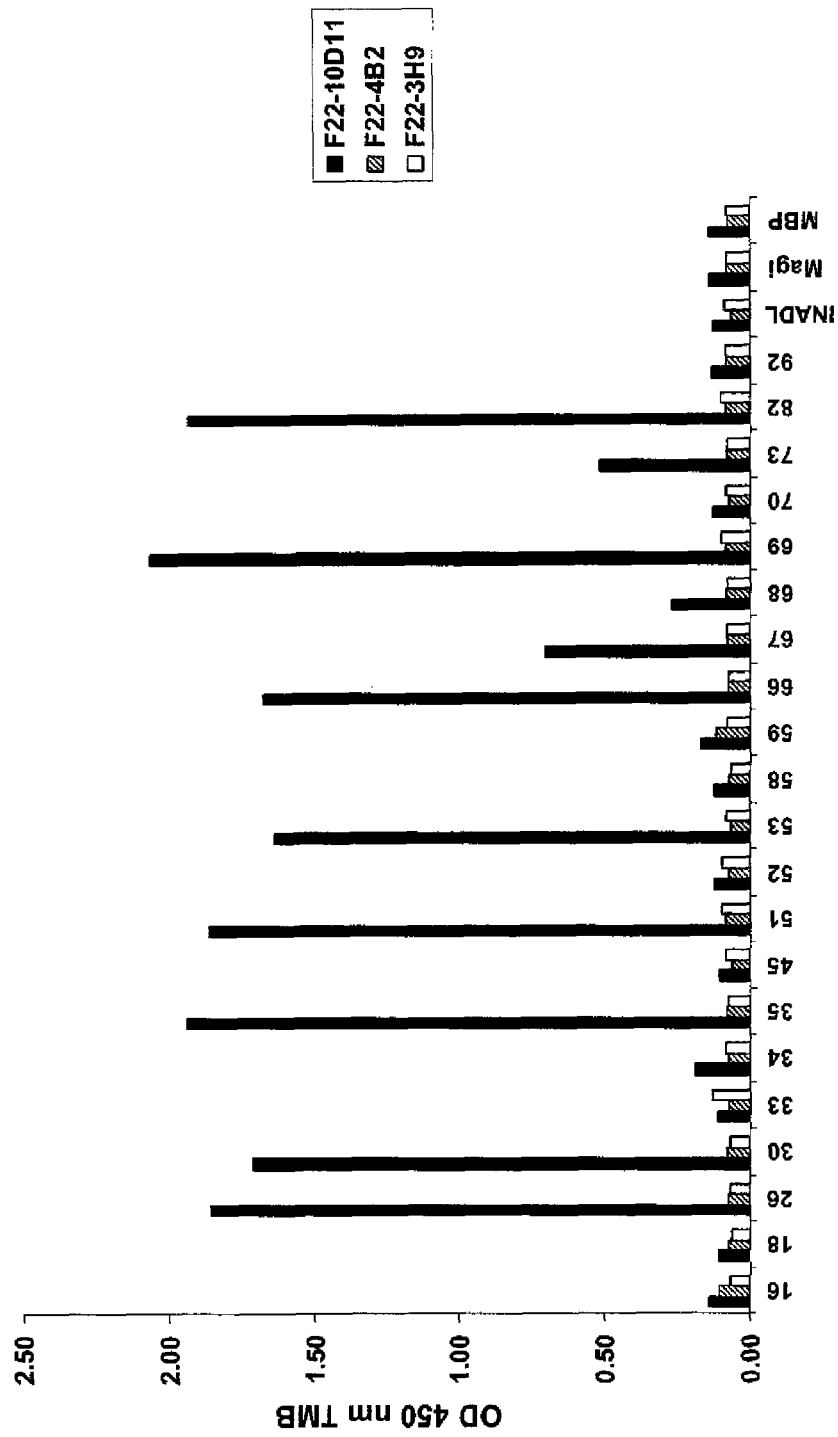
FIG. 4 is graph showing cross-reactivity of F22-10 D11 monoclonal antibody.

Before the present invention is further described, it is to be understood that this invention is not limited to particular embodiments described, as such may of course vary. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this invention belongs.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Throughout this application, various publications, patents and published patent applications are cited. The disclosures of these publications, patents and published patent applications referenced in this application are hereby incorporated by reference in their entirety into the present disclosure. Citation herein by Applicant of a publication, patent, or published patent application is not an admission by Applicant of said publication, patent, or published patent application as prior art.

It must be noted that as used herein and in the appended claims, the singular forms "a", "and", and "the" include plural referents unless the context clearly dictates otherwise. Thus, for example, reference to "a sample" includes a plurality of such sample, and reference to "the antibody" includes reference to one or more antibodies and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

A "biopolymer" is a polymer of one or more types of repeating units, regardless of the source. Biopolymers may be found in biological systems and particularly include polypeptides and polynucleotides, as well as such compounds containing amino acids, nucleotides, or analogs thereof. The term "polynucleotide" refers to a polymer of nucleotides, or analogs thereof, of any length, including oligonucleotides that range from 10-100 nucleotides in length and polynucleotides of greater than 100 nucleotides in length. The term "polypeptide" refers to a polymer of amino acids of any length, including peptides that range from 6-50 amino acids in length and polypeptides that are greater than about 50 amino acids in length.

In most embodiments, the terms "polypeptide" and "protein" are used interchangeably. The term "polypeptide" includes polypeptides in which the conventional backbone has been replaced with non-naturally occurring or synthetic backbones, and peptides in which one or more of the conventional amino acids have been replaced with a non-naturally occurring or synthetic amino acid capable of participating in peptide bonding interactions. The term "fusion protein" or grammatical equivalents thereof is meant a protein composed of a plurality of polypeptide components, that while typically not attached in their native state, typically are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc., and the like.

In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 50 amino acids. In some embodiments, peptides are between 5 and 30 or between 8 and 15 amino acids in length.

The term "capture agent" refers to an agent that binds an analyte through an interaction that is sufficient to permit the agent to bind and concentrate the analyte from a homogeneous mixture of different analytes. The binding interaction is typically mediated by an affinity region of the capture agent. Typical capture agents include any polypeptide, e.g., a PDZ protein, however antibodies may be employed. Capture agents usually "specifically bind" one or more analytes, e.g., an oncogenic E6 protein. Accordingly, the term "capture agent" refers to a molecule or a multi-molecular complex which can specifically bind an analyte, e.g., specifically bind an analyte for the capture agent, with a dissociation constant ($K_D$) of less than about $10^{-6}$ M without binding to other targets.

The term "specific binding" refers to the ability of a capture agent to preferentially bind to a particular analyte that is present in a homogeneous mixture of different analytes. Typically, a specific binding interaction will discriminate between desirable and undesirable analytes in a sample, typically more than about 10 to 100-fold or more (e.g., more than about 1000- or 10,000-fold). Typically, the affinity between a capture agent and analyte when they are specifically bound in a capture agent/analyte complex is at least $10^{-7}$, at least $10^{-8}$ M, at least $10^{-9}$ M, usually up to about $10^{-10}$ M.

The term "capture agent/analyte complex" is a complex that results from the specific binding of a capture agent with an analyte, i.e., a "binding partner pair". A capture agent and an analyte for the capture agent will typically specifically bind to each other under "conditions suitable to for specific binding", where such conditions are those conditions (in terms of salt concentration, pH, detergent, protein concentration, temperature, etc.) which allow for binding to occur between capture agents and analytes to bind in solution. Such conditions, particularly with respect to antibodies and their antigens, are well known in the art (see, e.g., Harlow and Lane (*Antibodies: A Laboratory Manual Cold Spring Harbor Laboratory*, Cold Spring Harbor, N.Y. (1989)). Conditions suitable for specific binding typically permit capture agents and target pairs that have a dissociation constant ($K_D$) of less than about $10^{-6}$ M to bind to each other, but not with other capture agents or targets.

As used herein, "binding partners" and equivalents refer to pairs of molecules that can be found in a capture agent/analyte complex, i.e., exhibit specific binding with each other.

The phrase "surface-bound capture agent" refers to a capture agent that is immobilized on a surface of a solid substrate, where the substrate can have a variety of configurations, e.g., a sheet, bead, strip, or other structure, such as a plate with wells.

The term "pre-determined" refers to an element whose identity is known prior to its use. For example, a "pre-determined analyte" is an analyte whose identity is known prior to any binding to a capture agent. An element may be known by name, sequence, molecular weight, its function, or any other attribute or identifier. In some embodiments, the term "analyte of interest", i.e., an known analyte that is of interest, is used synonymously with the term "pre-determined analyte".

The terms "antibody" and "immunoglobulin" are used interchangeably herein to refer to a type capture agent that has at least an epitope binding domain of an antibody. These terms are well understood by those in the field, and refer to a protein containing one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, F(ab')$_2$, and or other antibody fragments that retain specific binding to antigen.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al, *Immunology*, Benjamin, N.Y., 2 nd ed. (1984), and Hunkapiller and Hood, Nature, 323, 15-16 (1986). Monoclonal antibodies, polyclonal antibodies, and "phage display" antibodies are well known in the art and encompassed by the term "antibodies".

The term "mixture", as used herein, refers to a combination of elements, e.g., capture agents or analytes, that are interspersed and not in any particular order. A mixture is homogeneous and not spatially separable into its different constituents. Examples of mixtures of elements include a number of different elements that are dissolved in the same aqueous solution, or a number of different elements attached to a solid support at random or in no particular order in which the different elements are not specially distinct. In other words, a mixture is not addressable. To be specific, an array of capture agents, as is commonly known in the art, is not a mixture of capture agents because the species of capture agents are spatially distinct and the array is addressable.

"Isolated" or "purified" general refers to isolation of a substance (compound, polynucleotide, protein, polypeptide, polypeptide composition) such that the substance comprises the majority percent of the sample in which it resides. Typically in a sample a substantially purified component comprises 50 %, preferably 80 %-85 %, more preferably 90-95 % of the sample. Techniques for purifying polynucleotides and polypeptides, e.g., antibodies, of interest are well-known in the art and include, for example, ion-exchange chromatography, affinity chromatography and sedimentation according to density.

The term "assessing" refers to any form of measurement, and includes determining if an element is present or not. The terms "determining", "measuring", "evaluating", "assessing" and "assaying" are used interchangeably and include both quantitative and qualitative determinations. Assessing may be relative or absolute. "Assessing the presence of" includes determining the amount of something present, as well as determining whether it is present or absent.

The term 'marker' or "biological marker", as used herein, refers to a measurable or detectable entity in a biological sample. Examples or markers include nucleic acids, proteins, or chemicals that are present in biological samples. One example of a marker is the presence of viral or pathogen proteins or nucleic acids in a biological sample from a human source.

The term "sample" as used herein relates to a material or mixture of materials, typically, although not necessarily, in fluid form, i.e., aqueous, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). The term "biological sample" is meant to distinguish between a sample in a clinical setting from a sample that may be a recombinant sample or derived from a recombinant sample.

Components in a sample are termed "analytes" herein. In many embodiments, the sample is a complex sample containing at least about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $10^9$, $10^{10}$, $10^{11}$, $10^{12}$ or more species of analyte.

The term "analyte" is used herein interchangeably and refers to a known or unknown component of a sample, which will specifically bind to a capture agent if the analyte and the capture agent are members of a specific binding pair. In general, analytes are biopolymers, i.e., an oligomer or polymer such as an oligonucleotide, a peptide, a polypeptide, an antibody, or the like. In this case, an "analyte" is referenced as a moiety in a mobile phase (typically fluid), to be detected by a "capture agent" which, in some embodiments, is bound to a substrate, or in other embodiments, is in solution. However, either of the "analyte" or "capture agent" may be the one which is to be evaluated by the other (thus, either one could be an unknown mixture of analytes, e.g., polypeptides, to be evaluated by binding with the other).

A "fusion protein" or "fusion polypeptide" as used herein refers to a composite protein, i.e., a single contiguous amino acid sequence, made up of two (or more) distinct, heterologous polypeptides that are not normally fused together in a single amino acid sequence. Thus, a fusion protein can include a single amino acid sequence that contains two entirely distinct amino acid sequences or two similar or identical polypeptide sequences, provided that these sequences are not normally found together in the same configuration in a single amino acid sequence found in nature. Fusion proteins can generally be prepared using either recombinant nucleic acid methods, i.e., as a result of transcription and translation of a recombinant gene fusion product, which fusion comprises a segment encoding a polypeptide of the invention and a segment encoding a heterologous protein, or by chemical synthesis methods well known in the art.

Figure 1:
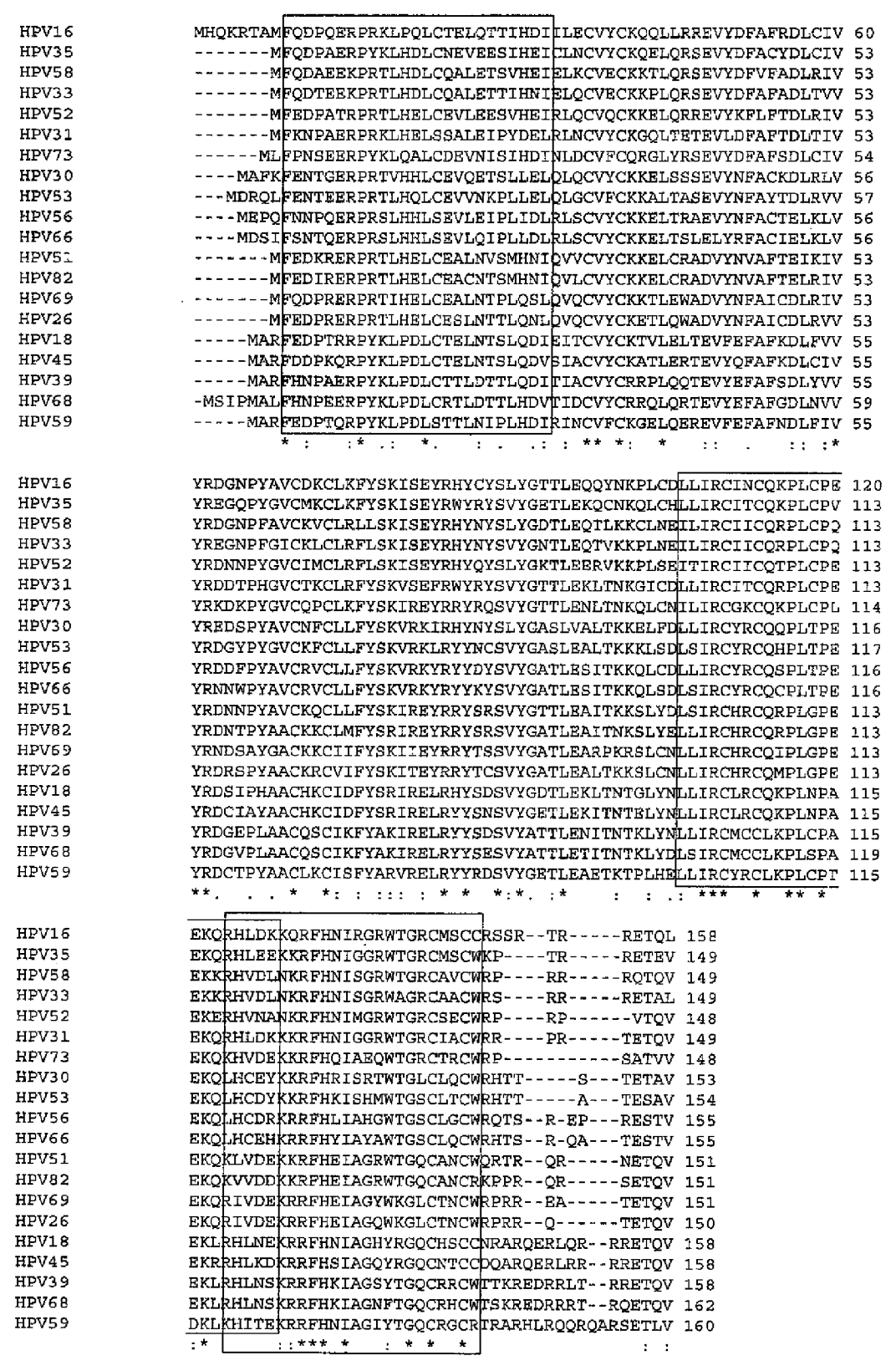

An "oncogenic HPV strain" is an HPV strain that is known to cause cervical cancer as determined by the National Cancer Institute (NCI, 2001). "Oncogenic E6 proteins" are E6 proteins encoded by the above oncogenic HPV strains. The sequences of exemplary oncogenic E6 proteins of interest are shown in FIG. 1. The sequences of various HPV proteins are also found as database entries at NCBI's Genbank database, as follows: HPV16-E6: GI:9627100; HPV18-E6: GI:9626069; HPV31-E6: GI:9627109; HPV35-E6: GI:9627127; HPV30-E6: GI:9627320; HPV39-E6: GI:9627165; HPV45-E6: GI:9627356; HPV51-E6: GI:9627155; HPV52-E6: 01:9627370; HPV56-E6: GI:9627383; HPV59-E6: GI:9627962; HPV58-E6: GI:9626489; HPV33-E6: GI:9627118; HPV66-E6: GI:9628582; HPV68b-E6: GI:184383; HPV69-E6: GI:9634605; HPV26-E6: GI:396956; HPV53-E6: GI:9627377; HPV73: GI:1491692; HPV82: GI:9634614, HPV34 GI:396989; HPV67 GI:3228267; and HPV70 GI:1173493.

An "oncogenic E6 protein binding partner" can be any molecule that specifically hinds to an oncogenic E6 protein. Suitable oncogenic E6 protein binding partners include a PDZ domain (as described below), antibodies against oncogenic E6 proteins (such as those described below); other proteins that recognize oncogenic E6 protein (e.g., p53, E6-AP or E6-BP); DNA (i.e., cruciform DNA); and other partners such as aptamers. In some embodiments, detection of more than 1 oncogenic E6 protein (e.g., all oncogenic E6 proteins, E6 proteins from HPV strains 16 and 18, or E6 proteins from HPV strains 16 and 45 etc.) is desirable, and, as such, an oncogenic E6 protein binding partner may be antibody that binds to these proteins, as described below, or a mixture of antibodies that each bind to a different proteins. As is known in the art, such binding partners may be labeled to facilitate their detection. In general, binding partner bind E6 with an binding affinity of less then $10^{-5}$ M, e.g., less than $10^{-6}$, less than $10^{-7}$, less than $10^{-8}$ M (e.g., less than $10^{-9}$ M, $10^{-10}$, $10^{-11}$, etc.).

As used herein, the term "PDZ domain" refers to protein sequence of less than approximately 90 amino acids, (i.e., about 80-90, about 70-80, about 60-70 or about 50-60 amino acids), characterized by homology to the brain synaptic protein PSD-95, the Drosophila septate junction protein Discs-Large (DLG), and the epithelial tight junction protein ZO1 (ZO1). PDZ domains are also known as Discs-Large homology repeats ("DHRs") and GLGF(SEQ ID NO: 362) repeats. PDZ domains generally appear to maintain a core consensus sequence (Doyle, D. A., 1996, Cell 85: 1067-76).

PDZ domains are found in diverse membrane-associated proteins including members of the MAGUK family of guanylate kinase homologs, several protein phosphatases and kinases, neuronal nitric oxide synthase, tumor suppressor proteins, and several dystrophin-associated proteins, collectively known as syntrophins.

Exemplary PDZ domain-containing proteins and PDZ domain sequences are shown in TABLE 2 The term "PDZ domain" also encompasses variants (e.g., naturally occurring variants) of the sequences (e.g., polymorphic variants, variants with conservative substitutions, and the like) and domains from alternative species (e.g. mouse, rat). Typically, PDZ domains are substantially identical to those shown in U.S. patent application Ser. Nos. 09/724,553 and 10/938,249), e.g., at least about 70 %, at least about 80 %, or at least about 90 % amino acid residue identity when compared and aligned for maximum correspondence. It is appreciated in the art that PDZ domains can be mutated to give amino acid changes that can strengthen or weaken binding and to alter specificity, yet they remain PDZ domains (Schneider et al., 1998, Nat. Biotech. 17:170-5). Unless otherwise indicated, a reference to a particular PDZ domain (e.g. a MAGI-1 domain 2) is intended to encompass the particular PDZ domain and HPV E6-binding variants thereof. In other words, if a reference is made to a particular PDZ domain, a reference is also made to variants of that PDZ domain that bind oncogenic E6 protein of HPV, as described below. In this respect it is noted that the numbering of PDZ domains in a protein may change. For example, the MAGI-1 domain 2, as referenced herein, may be referenced as MAGI-1 domain 1 in other literature. As such, when a particular PDZ domain of a protein is referenced in this application, this reference should be understood in view of the sequence of that domain, as described herein, particularly in the sequence listing. Table 2 shows the relationship between the sequences of the sequence listing and the names and Genbank accession numbers for various domains, where appropriate. Further description of PDZ proteins, particularly a description of MAGI-1 domain 2 protein, is found in Ser. No. 10/630,590, filed Jul. 29, 2003 and published as US20040018487. This publication is incorporated by reference herein in its entirety for all purposes.

As used herein, the term "PDZ protein" refers to a naturally occurring protein containing a PDZ domain. Exemplary PDZ proteins include CASK, MPP1, DLG1, DLG2, PSD95, NeDLG, TIP-33, SYN1a, LDP, LIM, LIMK1, LIMK2, MPP2, NOS1, AF6, PTN-4, prIL16, 41.8 kD, KIAA0559, RGS12, KIAA0316, DVL1, TIP-40, TIAM1, MINT1, MAGI-1, MAGI-2, MAGI-3, KIAA0303, CBP, MINT3, TIP-2, KIAA0561, and TIP-1.

As used herein, the term "PL protein" or "PDZ Ligand protein" refers to a protein that forms a molecular complex with a PDZ-domain, or to a protein whose carboxy-terminus, when expressed separately from the full length protein (e.g., as a peptide fragment of 4-25 residues, e.g., 8, 10, 12, 14 or 16 residues), forms such a molecular complex. The molecular complex can be observed in vitro using a variety of assays described infra.

As used herein, a "PL sequence" refers to the amino acid sequence of the C-terminus of a PL protein (e.g., the C-terminal 2, 3, 4, 5, 6, 7, 8, 9, 10, 12, 14, 16, 20 or 25 residues) ("C-terminal PL sequence") or to an internal sequence known to bind a PDZ domain ("internal PL sequence").

As used herein, a "PL fusion protein" is a fusion protein that has a PL sequence as one domain, typically as the C-terminal domain of the fusion protein. An exemplary PL fusion protein is a tat-PL sequence fusion.

In the case of the PDZ domains described herein, a "HPV E6-binding variant" of a particular PDZ domain is a PDZ domain variant that retains HPV E6 PDZ ligand binding activity. Assays for determining whether a PDZ domain variant binds HPV E6 are described in great detail below, and guidance for identifying which amino acids to change in a specific PDZ domain to make it into a variant may be found in a variety of sources. In one example, a PDZ domain may be compared to other PDZ domains described herein and amino acids at corresponding positions may be substituted, for example. In another example, the sequence a PDZ domain of a particular PDZ protein may be compared to the sequence of an equivalent PDZ domain in an equivalent PDZ protein from another species. For example, the sequence of a PDZ domain from a human PDZ protein may be compared to the sequence of other known and equivalent PDZ domains from other species (e.g., mouse, rat, etc.) and any amino acids that are variant between the two sequences may be substituted into the human PDZ domain to make a variant of the PDZ domain. For example, the sequence of the human MAGI-1 PDZ domain 2 may be compared to equivalent MAGI-1 PDZ domains from other species (e.g. mouse Genbank gi numbers 7513782 and 28526157 or other homologous sequences) to identify amino acids that may be substituted into the human MAGI-1-PDZ domain to make a variant thereof. Such method may be applied to any of the MAGI-1 PDZ domains described herein. Minimal MAGI-PDZ domain 2 sequence is provided as SEQ ID NOS:68-76. Particular variants may have 1, up to 5, up to about 10, up to about 15, up to about 20 or up to about 30 or more, usually up to about 50 amino acid changes as compared to a sequence set forth in the sequence listing. Exemplary MAGI-1 PDZ variants include the sequences set forth in SEQ ID NOS: 76-105. In making a variant, if a GFG motif is present in a PDZ domain, in general, it should not be altered in sequence.

In general, variant PDZ domain polypeptides have a PDZ domain that has at least about 70 or 80 %, usually at least about 90 %, and more usually at least about 98 % sequence identity with a variant PDZ domain polypeptide described herein, as measured by BLAST 2.0 using default parameters, over a region extending over the entire PDZ domain.

As used herein, a "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical or chemical means. Labels useful in the present invention include biotin for staining with labeled streptavidin conjugate, magnetic beads (e.g., Dynabeads™), fluorescent dyes (e.g., fluorescein, Texas red, rhodamine, green fluorescent protein, enhanced green fluorescent protein, and the like), radiolabels (e.g., $^3$H, $^{125}$I, $^{35}$S, $^{14}$C, or $^{32}$P), enzymes (e.g., hydrolases, particularly phosphatases such as alkaline phosphatase, esterases and glycosidases, or oxidoreductases, particularly peroxidases such as horse radish peroxidase, and others commonly used in ELISAs), substrates, cofactors, inhibitors, chemiluminescent groups, chromogenic agents, and colorimetric labels such as colloidal gold or colored glass or plastic (e.g., polystyrene, polypropylene, latex, etc.) beads. Patents disclosing such labels include U.S. Pat. Nos. 3,817,837; 3,850,752; 3,939,350; 3,996,345; 4,277,437; 4,275,149; and 4,366,241. Means of detecting such labels are well known to those of skill in the art.

As used herein, the terms "sandwich", "sandwich ELISA", "Sandwich diagnostic" and "capture ELISA" all refer to the concept of detecting a biological polypeptide with two different test agents. For example, a PDZ protein could be directly or indirectly attached to a solid support. Test sample could be passed over the surface and the PDZ protein could bind its cognate PL protein(s). A labeled antibody or alternative detection reagent could then be used to determine whether a specific PL protein had bound the PDZ protein.

By "solid phase support" or "carrier" is intended any support capable of binding polypeptide, antigen or antibody. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to a PDZ domain polypeptide or an E6 antibody. Thus, the support configuration can be spherical, as in a bead, or cylindrical, as in the inside surface of a test tube, or the external surface of a rod. Alternatively, the surface can be flat, such as a sheet, culture dish, test strip, etc. Those skilled in the art will know many other suitable carriers for binding antibody, peptide or antigen, or can ascertain the same by routine experimentation.

In some embodiments "proteasome inhibitors", i.e., inhibitors of the proteasome, may be used. These inhibitors, including carbobenzoxyl-leucinyl-leuciny-I norvalinal II (MG 115) or CBZ-LLL, can be purchased from chemical supply companies (e.g., Sigma). As a skilled person would understand, proteasome inhibitors are not protease inhibitors.

As used herein, a "plurality" of components has its usual meaning. In some embodiments, the plurality is at least 5, and often at least 25, at least 40, or at least 60 or more, usually up to about 100 or 1000.

Reference to an "amount" of a E6 protein in these contexts is not intended to require quantitative assessment, and may be either qualitative or quantitative, unless specifically indicated otherwise.

The term "non-naturally occurring" or "recombinant" means artificial or otherwise not found in nature. Recombinant cells usually contain nucleic acid that is not usually found in that cell, recombinant nucleic acid usually contain a fusion of two or more nucleic acids that is not found in nature, and a recombinant polypeptide is usually produced by a recombinant nucleic acid.

"Subject", "individual," "host" and "patient" are used interchangeably herein, to refer to any animal, e.g., mammal, human or non-human. Generally, the subject is a mammalian subject. Exemplary subjects include, but are not necessarily limited to, humans, non-human primates, mice, rats, cattle, sheep, goats, pigs, dogs, cats, birds, deer, elk, rabbit, reindeer, deer, and horses, with humans being of particular interest.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The subject invention provides antibodies, including polyclonal and monoclonal antibodies, that bind to E6 proteins from at least three oncogenic strains of HPV. In general, the antibodies bind to amino acid motifs that are conserved between the E6 proteins of different HPV strains, particularly HPV strains 16 and 18. The subject antibodies may be used to detect HPV E6 protein in a sample, and, accordingly, the antibodies find use in a variety of diagnostic applications, including methods of diagnosing cancer. Kits for performing the subject methods and containing the subject antibodies are also provided.

In further describing the invention in greater detail than provided in the Summary and as informed by the Background and Definitions provided above, the subject antibodies are described first, followed by a description of methods in which the subject antibodies find use. Finally, kits for performing the subject methods are described.

Antibody Compositions

The invention provides antibodies, particularly monoclonal antibodies, that bind to E6 proteins of multiple strains of HPV. In other words, the invention provides antibodies that "recognize", i.e., specifically bind to with $K_D$ of $10^{-6}$ M or less, multiple E6 proteins. In other words, the subject antibodies each bind to (i.e., cross-react with) a plurality of different E6 proteins (i.e., at least 2, at least 3, at least 4, at least 5, at least 6 or at least 10, usually up to about 12, 15 or 20 or more different E6 proteins) from oncogenic, and, in certain embodiments, non-oncogenic strains of HPV. In general, the subject antibodies bind to amino acid motifs that are conserved between the E6 proteins of different HPV strains, and, accordingly, bind to E6 proteins that have this motif. In many embodiments the antibodies bind at least the E6 proteins of HPV strains 16 and 18 (e.g. the E6 proteins of HPV strains 16, 18, 31, 33 and 45; 16, 18 and 45; or, in other embodiments, the E6 proteins of all of the HPV strains listed in FIG. 1 or 2). In other embodiments, the antibodies bind to at least the E6 proteins from HPV strains 16 and 45. The subject antibodies may bind E6 protein from non-oncogenic strains of HPV (e.g., HPV strains 6 and/or 11) and, accordingly, the subject antibodies may bind to E6 proteins from oncogenic, as well as non-oncogenic, strains of HPV.

The subject antibodies may specifically bind to one of three sequence motifs found in HPV E6 proteins. These motifs are boxed in FIG. 1, and generally correspond to regions of sequence similarity between E6 proteins from different strains of HPV. In general, therefore, a subject antibody binds to peptides having the following sequence: FQDPQERPRKLPQLCTELQTTIHDI (SEQ ID NO:1) and FEDPTRRPYKLPDLCTELNTSLQDI (SEQ ID NO:2), corresponding to a first common sequence motif in the E6 proteins of HPV strains 16 and 18, respectively, LLIRCINC-QKPLCPEEKQRHLDK (SEQ ID NO:3) and LLIRCLRC-QKPLNPAEKLRHLNE (SEQ ID NO:4), corresponding to a second common sequence motif in the E6 proteins of HPV strains 16 and 18, respectively, or RHLDKKQRFHNIRGR-WTGRCMSCC (SEQ ID NO:5) and RHLNEKRRFHNI-AGHYRGQCHSCC (SEQ ID NO:6) corresponding to a third common sequence motif in the E6 proteins of HPV strains 16 and 18, respectively. If a subject antibody binds to other E6 proteins, then it usually binds to the other E6 proteins at positions equivalent to those discussed above, or boxed in FIG. 1, where "positions equivalent to" generally means a stretch of contiguous amino acids that correspond to, i.e., are aligned with, the boxed amino acids when the sequence of the other E6 proteins are with those in FIG. 1.

Accordingly, since antibodies generally recognize motifs smaller than those listed above, a subject antibody may recognize peptides that are smaller than and contained within the motifs described above. For example, a subject antibody may bind to a peptide having any 9 contiguous amino acids set forth in any one of SEQ NOS:1-6. In particular, a subject antibody may recognize the sequences RPRKLPQLCTEL (SEQ ID NO:7) and RPYKLPDLCTEL (SEQ ID NO:8), corresponding to sub-sequences of the first common sequences of E6 proteins of HPV strains 16 and 18, described above, LLIRCINCQKPL (SEQ ID NO:9) and LLIRCLRCQKPL (SEQ ID NO:10) corresponding to sub-sequences of the second common sequences of E6 proteins of HPV strains 16 and 18, as described above, or RHLDK-KQRFHNI (SEQ ID NO:11) and RHLNEKRRFHNI (SEQ ID NO:12) corresponding to sub-sequences of the third common sequences of E6 proteins of HPV strains 16 and 18, as described above. Since these sub-sequences are generally conserved between different E6 proteins, as discussed above, antibodies that bind to the above-recited sequences generally bind to E6 proteins from other HPV strains.

In certain alternative embodiments, the subject antibodies will bind to E6 proteins from HPV strains 16 and 45. In general, therefore, a subject antibody binds to peptides having the following sequence: FQDPQER-PRKLPQLCTELQTTIHDI (SEQ ID NO:1) and FDDP-KQRPYKLPDLCTELNTSLQDV (SEQ ID NO:57), corresponding to a first common sequence motif in the E6 proteins of HPV strains 16 and 45, respectively, LLIRCINC-QKPLCPEEKQRHLDK (SEQ ID NO:3) and LLIRCLRC-QKPLNPAEKRRHLKD (SEQ ID NO: 58), corresponding to a second common sequence motif in the E6 proteins of HPV strains 16 and 45, respectively, or RHLDKKQRFH-NIRGRWTGRCMSCC (SEQ ID NO:5) and RHLKD-KRRFHSIAGQYRGQCNTCC (SEQ ID NO:59) corresponding to a third common sequence motif in the E6 proteins of HPV strains 16 and 45, respectively. If a subject antibody binds to other E6 proteins, then it usually binds to the other E6 proteins at positions equivalent to those discussed above, or boxed in FIG. 1. For example, the E6 proteins from HPV58, HPV33, HPV52, HPV31, HPV16, HPV18 and HPV45 are shown in FIG. 2, and the above-referenced motifs are boxed therein.

Accordingly, since antibodies generally recognize motifs smaller than those listed above, a subject antibody may recognize peptides that are smaller than and contained within the motifs described above. For example, a subject antibody may bind to a peptide having any 9 contiguous amino acids set forth in any one of SEQ NOS: 1, 3, 5, 57, 58 and 59. In particular, a subject antibody may recognize the sequences RPRKLPQLCTEL (SEQ ID NO:7) and RPYKLPDLCTEL (SEQ ID NO:60), corresponding to sub-sequences of the first common sequences of E6 proteins of HPV strains 16 and 45, described above, LLIRCINCQKPL (SEQ ID NO:9) and LLIRCLRCQKPL (SEQ ID NO: 61) corresponding to sub-sequences of the second common sequences of E6 proteins of HPV strains 16 and 45, as described above, or RHLDKKQRFHNI (SEQ ID NO:11)

and RHLKDKRRFHSI (SEQ ID NO: 62) corresponding to sub-sequences of the third common sequences of E6 proteins of HPV strains 16 and 45, as described above. Since these sub-sequences are generally conserved between different E6 proteins, as discussed above, antibodies that bind to the above-recited sequences generally bind to E6 proteins from other HPV strains. In certain embodiments, cysteine residues can be replaced by serine residues to avoid disulfide bridge formation.

Methods for making antibodies, particular monoclonal antibodies, are well known in the art and described in various well known laboratory manuals (e.g., Harlow et al., *Antibodies: A Laboratory Manual*, First Edition (1988) Cold spring Harbor, N.Y.; Harlow and Lane, *Using Antibodies: A Laboratory Manual*, CSHL Press (1999) and Ausubel, et al., *Short Protocols in Molecular Biology*, 3 rd ed., Wiley & Sons, (1995)). Accordingly, given the peptide sequences set forth above and in the accompanying tables, methods for making the subject antibodies do not need to be described herein in any great detail. Any fragment of a longer full-length E6 protein that contains a subject common motif (e.g., the full length protein), a full length E6 protein, or a fusion protein thereof may be used to make the subject antibodies. In certain embodiments, a full length E6 protein, a peptide containing a recited sequence, or a chemically modified (e.g., conjugated) derivative or fusion thereof (e.g., a MBP or GST fusion), may be used as an antigen. In certain embodiments, a nucleic acid encoding the polypeptide may be employed, or a mixture of different polypeptides (e.g., a mixture of E6 polypeptides, each polypeptide from a different HPV strain) may be used as an antigen (Michel (2002) Vaccine 20:A83-A88). Accordingly an antigen is mixed with an adjuvant, and a suitable non-human animal (e.g., a mouse, chicken, goat, rabbit, hamster, horse, rat or guinea pig, etc.) is immunized using standard immunization techniques (e.g., intramuscular injection) and once a specific immune response of the has been established, blood from the animal may be collected and polyclonal antisera that specifically binds to described peptides may be isolated. In many cases, cells from the spleen of the immunized animal are fused with a myeloma cell line, and, after fusion, the cells are grown in selective medium containing e.g., hypoxanthine, aminopterin, and thymidine (HAT), to select for hybridoma growth, and after 2-3 weeks, hybridoma colonies appear. Supernatants from these cultured hybridoma cells are screened for antibody secretion, usually by enzyme-linked immunosorbent assay (ELISA) or the like, and positive clones secreting monoclonal antibodies specific for the antigen can be selected and expanded according to standard procedures.

Exemplary peptides suitable for immunizations are described in Table 1. The peptides are shown as a "consensus" sequence (i.e. peptides in which one of several amino acids may exist at one or more positions) in order to indicate that any one or a mixture of different peptides that are described by the consensus could be used to make the subject antibodies. Accordingly, when a consensus sequence is described, every individual peptide that falls within the consensus should be considered explicitly described. In particular embodiments, exemplary species of peptide encompassed by the consensus sequences have a sequence found in a naturally-occurring HPV E6 protein, such as those described in FIG. 1. Such exemplary sequences can be identified as sequences starting at the amino acid positions defined by the third column of Table 1, "Starting AA" of particular HPV types "HPV type", and corresponding positions of other HPV E6 proteins (i.e., those positions that are aligned with the positions indicated in Table 1).

Accordingly, peptides having 9, 10, 11, 12, 13, 14, 15 or more, usually up to about 20 or more contiguous amino acids of any of the peptides described above may be used for immunizations. In some embodiments, a recited peptide sequence may be contained within a larger peptide that may be 1, 2, 3, 4, 5, 6, 7, 8, 9 or 10 or more, sometimes up to about 15 or 20 or more amino acids greater in size than a recited polypeptide. Accordingly, a subject peptide may be from about 8 to about 30 amino acids in length. In certain embodiments, a subject peptide is about 9-20 amino acids in length, and usually contains an amino acid sequence described above.

Accordingly, depending on the antibodies desired, a suitable animal is immunized with a subject peptide or a mixture of subject peptides (e.g., a mixture of 2, 3, 4, 5 about 6 or more, about 10 or more or about 15 or more, usually up to about 20 or 30 or more peptides described above). Antibodies are usually isolated from the animal and tested for binding to different HPV E6 proteins using standard methods (e.g., ELISA, western blot, etc.). In many embodiments, therefore, antibodies will be screened for binding to E6 proteins from HPV strains 16 and 18, HPV strains 16, 18, 31, 33 and 45, or, in certain embodiments, all of the HPV strains shown in FIG. 1 or 2, and maybe others. Accordingly, antibodies that bind to, i.e., cross-react with, E6 proteins from more than one strain of HPV may be identified, and permanent cell lines producing those antibodies may be established using known methods. In other words, antibodies are usually tested for binding to more than one antigen, and those antigens are usually E6 proteins from various HPV strains, or fragments thereof. In most embodiments, the antibodies will be tested for binding to antigens in native and denatured states. Antibodies that bind to a plurality of E6 proteins have desirable binding properties, and, accordingly, find use in the subject methods.

As is well known in the art, the subject antibodies may be conjugated to a detectable label, or may be part of a signal generating system, as described above.

Accordingly, using the methods set forth above, an antibody composition for detecting a plurality of HPV E6 proteins is provided. In certain embodiments, a mixture of different antibodies that recognize at least 5, 7, 9, 12, 15, 20 or 24 different strains of HPV may be employed. The composition may contain at least one antibody that recognizes at least 3 different oncogenic E6 proteins. The composition may contain 1, 2, 3, 4, or 5 or more different antibodies, each antibody of the composition recognizing at least one (e.g., 2, 3, about 5, about 10, etc.) E6 protein. Collectively, the antibodies bind to all or a portion of the E6 proteins shown in FIG. 1, and, in certain embodiments, may also bind to non-oncogenic E6 proteins. The antibodies may be mixed, or separate from each other, i.e., in different vessels.

Any of the above-described antibodies may bind to an epitope set forth in Table 1.

TABLE 1

Epitopes

| Sequence | HPV type | Starting AA |
| --- | --- | --- |
| (K/R)-(K/R)-R-F-H-(N/K/S/E/R)-I-(A/S) (SEQ ID NO: 363) | 59 | 124 |
| F-H-(N/K/S/E/R)-I-(A/S)-(G/H)-X-(W/Y) | 59 | 127 |
| H-(N/K/S/E/R)-I-(A/S)-(G/H)-(R/Q)-(W/Y)-(T/K/R) | 59 | 128 |
| P-(E/A/Q)-E-K-(Q/L/K/R)-(R/K/L)-(H/V/I/L)-(V/L/C) | 26 | 112 |
| (G/H)-(R/Q/T/M/G/A/Y/H/S/N/I)-(W/Y/F)-(T/R/K/A)-G-(R/Q/S/L)-C-(R/L/M/A/T) | 59 | 132 |
| (W/Y/F)-(T/R/K/A)-G-(R/Q/S/L)-C-(R/L/M/A/T)-(L/R/A/T)-(N/R/S/A/Q/G) | 59 | 134 |
| G-(R/Q/S/L)-C-(R/L/M/A/T)-(L/R/A/T)-(N/R/S/A/Q/G)-C-(W/C/R) | 59 | 136 |
| (R/K)-P-(R/Y)-(K/T/S)-(L/V)-(H/P)-(D/E/H/Q)-L | 59 | 10 |
| (M/R/L)-F-(E/Q/D/H)-(D/N)-(P/T)-(Q/R/A/E/T)-(E/Q)-(R/K) | 59 | 3 |
| (D/N)-(P/T)-(Q/R/A/E/T)-(E/Q)-(R/K)-(R/K)-P-(R/Y) | 59 | 6 |
| (L/V)-(H/P)-(D/E/Q)-L-(C/S)-(E/T/Q)-(E/V/A/T)-(L/V)-(N/E/D) | 59 | 14 |
| (D/E/N)-(L/V/I)-(Q/E/R/T)-(L/V/I)-(Q/N/D/S/A/N)-C-V-(F/Y/E)- | 59 | 26 |
| L-(L/S)-I-R-C-(I/Y/H/L/M)-(R/I/C)-C (SEQ ID NO: 364) | 59 | 101 |
| (R/I/C)-C-(Q/L)-(K/R)-P-L-(C/T/G/N)-P (SEQ ID NO: 365) | 59 | 107 |
| (K/R)-P-L-(C/T/G/N)-P-(E/A/Q)-E-K (SEQ ID NO: 366) | 59 | 110 |
| P-(E/A/Q)-E-K-(Q/L/K)-(R/L/K)-(H/I)-(L/V/C) | 26 | 112 |
| K-(Q/L/K)-(R/L/K)-(H/I)-(L/V/C)-(D/E/N)-(E/D/Y/L/K/S)-(K/N) | 26 | 115 |
| (L/V/C)-(D/E/N)-(E/D/Y/L/K/S)-(K/N)-(K/R)-R-F-H | 26 | 119 |
| I-(A/S)-(G/H)-(R/Q)-(W/Y)-(T/K/R)-G-(R/Q/L/S) | 26 | 128 |
| (W/Y)-(T/K/R)-G-(R/Q/L/S)-C-(M/A/L/R/T)-(N/S/A/R)-C | 26 | 132 |

Certain hybridomas that produce the monoclonal antibodies described above and below may be deposited at the ATCC. Any of the deposited hybridomas, the antibodies produced by those hybridomas, as well as other antibodies that bind the same epitopes as the antibodies produced by those hybridomas, are also embodiments of this invention and may be claimed herein. Such antibodies may be employed in any of the methods described herein.

Methods for Detecting an HPV E6 Protein in a Sample

The invention provides a method of detecting an HPV E6 protein in a sample. In general, the methods involve contacting a subject antibody composition with a sample, and assessing any binding of the antibody to the sample. In most embodiments, binding of the antibody to the sample indicates the presence of an HPV E6 protein.

The antibodies of the invention may be screened for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and cellular immunostaining (fixed or native) assays to name but a few. Such assays are routine and well known in the art (see, e.g., Ausubel et al., eds, 1994, *Current Protocols in Molecular Biology*, Vol. 1, John Wiley & Sons, Inc., New York, which is incorporated by reference herein in its entirety). Exemplary immunoassays are described briefly below (but are not intended by way of limitation).

Immunoprecipitation protocols generally involve lysing a population of cells in a lysis buffer such as RIPA buffer (1 % NP-40 or Triton X-100, 1 % sodium deoxycholate, 0.1 % SDS, 0.15 M NaCl, 0.01 M sodium phosphate at pH 7.2, 1 % Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4 ° C., adding protein A and/or protein G sepharose beads to the cell lysate, incubating for about an hour or more at 4 ° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads).

Western blot analysis generally involves preparation of protein samples followed by electrophoresis of the protein samples in a polyacrylamide gel (e.g., 8 %-20 % SDS-PAGE depending on the molecular weight of the antigen), and transfer of the separated protein samples from the polyacrylamide gel to a membrane such as nitrocellulose, PVDF or nylon. Following transfer, the membrane is blocked in blocking solution (e.g., PBS with 3 % BSA or non-fat milk), washed in washing buffer (e.g., PBS-Tween 20), and incubated with primary antibody (the antibody of interest) diluted in blocking buffer. After this incubation, the membrane is washed in washing buffer, incubated with a secondary antibody (which recognizes the primary antibody, e.g., an anti-human antibody) conjugated to an enzymatic substrate (e.g., horseradish peroxidase or alkaline phosphatase) or radioactive molecule (e.g., 32 P or 125I), and after a further wash, the presence of the antigen may be detected. One of skill in the art would be knowledgeable as to the parameters that can be modified to increase the signal detected and to reduce the background noise.

ELISAs involve preparing antigen, coating the well of a 96 well multiwell plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

Antibodies of the invention may be screened using immunocytochemistry methods on cells (e.g., mammalian cells, such as CHO cells) transfected with a vector enabling the expression of an antigen or with vector alone using techniques commonly known in the art. Antibodies that bind antigen transfected cells, but not vector-only transfected cells, are antigen specific.

In certain embodiments, however, the assay is an antigen capture assay, and an array or microarray of antibodies may be employed for this purpose. Methods for making and using microarrays of polypeptides are known in the art (see e.g. U.S. Pat. Nos. 6,372,483, 6,352,842, 6,346,416 and 6,242,266).

Systems for Detecting an Oncogenic HPV E6 Protein

The invention provides a system for detecting the presence of an oncogenic HPV E6 polypeptide in a sample. In general, the system comprises a first and a second binding partner for an oncogenic HPV E6 polypeptide. In most embodiments, the first binding partner is a PDZ, domain protein and the second binding partner is a subject antibody.

The subject antibodies may be used along with certain PDZ domain proteins as part of a system for detecting E6 protein from oncogenic strains of HPV. As mentioned above, oncogenic HPV E6 proteins contain a "PDZ-ligand" ("PL") that is bound by certain PDZ domain polypeptides. Non-oncogenic HPV E6 proteins do not contain such a PDZ-ligand, and, accordingly, are not bound by PDZ-domain polypeptides. Many PDZ domains suitable for use in the subject system are generally described in Table 2, and include MAGI-1 PDZ domain 2, the PDZ domain of TIP-1, and the PDZ domains 1 and 2 of DLG1, and many others. As would be recognized by one of skill in the art, a PDZ domain may be employed as part of a fusion protein, particularly in embodiments in which the PDZ domain polypeptide is anchored to a substrate. Accordingly, the subject system generally contains a suitable PDZ domain polypeptide, which is usually a fusion protein, and a subject antibody.

In certain embodiments, one of the binding partners is attached to a solid support, and the other binding partner may be labeled or part of a signal producing system. Proteins may be covalently bound or noncovalently attached through nonspecific bonding. If covalent bonding between the fusion protein and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

TABLE 2

| SEQ ID NO. | name | GI or Acc. # | Sequence |
|---|---|---|---|
| 106 | AF6 domain 1 | 430993 | LRKEPEIITVTLKKQNGMGLSIVAAKGAGQDKLGIYVK SVVKGGAADVDGRLAAGDQLLSVDGRSLVGLSQERAAE LMTRTSSVVTLEVAKQG |
| 107 | AIPC domain 1 | 12751451 | LIRPSVISIIGLYKEKGKGLGESIAGGRDCIRGQMGIF VKTIFPNGSAAEDGRLKEGDEILDVNGIPIKGLTFQEA IHTFKQIRSGLEVLTVRTKLVSPSLTNSS |
| 108 | AIPC domain 3 | 12751451 | QSENEEDVCFIVLNRKEGSGLGESVAGGTDVEPKSITV HRVFSQGAASQEGTMNRGDFLLSVNGASLAGLAHGNVL KVLHQAQLHKDALVVIKKGMDQPRPSNSS |
| 109 | AIPC domain 2 | 12751451 | GISSLGRKTPGPKDRIVMEVTLNKEPRVGLGIGACCLA LENSPPGIYIHSLAPGSVAKMESNLSRGDQILEVNSVN VRHAALSKVHAILSKCPPGPVRLVIGRHPNPKVSEQEM DEVIARSTYQESKEANSS |
| 110 | AIPC domain 4 | 12751451 | LGRSVAVHDALCVEVLKESAGLGLSLDGGKSSVTGDGP LVIKRVYKGGAAEQAGIIEAGDEILAINGKPLVGLMHF DAWNIMKSVPEGPVQLLIRKHRNSS |
| 111 | ALP domain 1 | 2773059 | REEGGMPQTVILPGPAPWGFRLSGGIDFNQPLVITRIT PGSKAAAANLCPGDVILAIDGFGTESMTHADAQDRIKA AAHQLCLKIDRGETHLWSPNSS |
| 112 | APXL1 domain 1 | 13651263 | ILVEVQLSGGAPWGFTLKGGREHGEPLVITKIEEGSKA AAVDKLLAGDEIVGINDIGLSGFRQEAICLVKGSHKTL KLVVKRNSS |

TABLE 2-continued

| SEQ ID NO. | name | GI or Acc. # | Sequence |
|---|---|---|---|
| 113 | CARD11 domain 1 | 12382772 | SVGHVRGPGPSVQHTTLNGDSLTSQLTLLGGNARGSFV HSVKPGSLAEKAGLREGHQLLLLEGCIRGERQSVPLDT CTKEEAHWTIQRCSGPVTLHYKVNHEGYRK |
| 114 | CARD14 domain 1 | 13129123 | RRPARRILSQVTMLAFQGDALLEQISVIGGNLTGIFIH RVTPGSAADQMALRPGTQIVMVDYEASEPLFKAVLEDT TLEEAVGLLRRVDGFCCLSVKVNTDGYKR |
| 115 | CARD14 domain 1 | 13129123 | ILSQVTMLAFQGDALLEQISVIGGNLTGIFIHRVTPGS AADQMALRPGTQIVMVDYEASEPLFKAVLEDTTLEEAV GLLRRVDGFCCLSVKVNTDGYKRL |
| 116 | CASK domain 1 | 3087815 | TRVRLVQFQKNTDEPMGITLKMNELNHCIVARIMHGGM IHRQGTLHVGDEIREINGISVANQTVEQLQKMLREMRG SITFKIVPSYRTQS |
| 117 | CNK1 domain 1 | 3930780 | LEQKAVLEQVQLDSPLGLEIHTTSNCQHFVSQVDTQVP TDSRLQIQPGDEVVQINEQVVVGWPRKNMVRELLREPA GLSLVLKKIPIP |
| 118 | Cytohesin binding Protein domain 1 | 3192908 | QRKLVTVEKQDNETFGFEIQSYRPQNQNACSSEMFTLI CKIQEDSPAHCAGLQAGDVLANINGVSTEGFTYKQVVD LIRSSGNLLTIETLNG |
| 119 | Densin domain 1 | 16755892 | RCLIQTKGQRSMDGYPEQFCVRIEKNPGLGFSISGGIS GQGNPFKPSDKGIFVTRVQPDGPASNLLQPGDKILQAN GHSFVHMEHEKAVLLLKSFQNTVDLVIQRELTV |
| 120 | DLG 6 splice variant 2 domain 1 | AB053303 | PTSPEIQELRQMLQAPHFKGATIKRHEMTGDILVARII HGGLAERSGLLYAGDKLVEVNGVSVEGLDPEQVIHILA MSRGTIMFKVVPVSDPPVNSS |
| 121 | DLG 6 splice variant 1 domain 1 | 14647140 | PTSPEIQELRQMLQAPHFKALLSAHDTIAQKDFEPLLP PLPDNIPESEEAMRIVCLVKNQQPLGATIKRHEMTGDI LVARIIHGGLAERSGLLYAGDKLVEVNGVSVEGLDPEQ VIHILAMSRGTIMFKVVPVSDPPVNSS |
| 122 | DLG1 domain 1 | 475816 | IQVNGTDADYEYEEITLERGNSGLGFSIAGGTDNPHIG DDSSIFITKIITGGAAAQDGRLRVNDCILQVNEVDVRD VTHSKAVEALKEAGSIVRLYVKRRN |
| 123 | DLG1 domain 2 | 475816 | IQLIKGPKGLGESIAGGVGNQHIPGDNSIYVTKIIEGG AAHKDGKLQIGDKLLAVNNVCLEEVTHEEAVTALKNTS DFVYLKVAKPTSMYMNDGN |
| 124 | DLG1 domains 1 and 2 | 475816 | VNGTDADYEYEEITLERGNSGLGFSIAGGTDNPHIGDD SSIFITKIITGGAAAQDGRLRVNDCILQVNEVDVRDVT HSKAVEALKEAGSIVRLYVKRRKPVSEKIMEIKLIKGP KGLGFSIAGGVGNQHIPGDNSIYVTKIIEGGAAHKDGK LQIGDKLLAVNNVCLEEVTHEEAVTALKNTSDFVYLKV AKPTSMYMNDGYA |
| 125 | DLG1 domain 3 | 475816 | ILHRGSTGLGFNIVGGEDGEGIFISFILAGGPADLSGE LRKGDRIISVNSVDLRAASHEQAAAALKNAGQAVTIVA QYRPEEYSR |
| 126 | DLG2 domain 3 | 12736552 | IEGRGILEGEPRKVVLHKGSTGLGFNIVGGEDGEGIFV SFILAGGPADLSGELQRGDQILSVNGIDLRGASHEQAA AALKGAGQTVTIIAQHQPEDYARFEAKIHDLNSS |
| 127 | DLG2 domain 1 | 12736552 | ISYVNGTEIEYEFEEITLERGNSGLGFSIAGGTDNPHI GIDDPGIFITKIIPGGAAAEDGRLRVNDCILRVNEVDV SEVSHSKAVEALKEAGSIVRLYVRRR |
| 128 | DLG2 domain 2 | 12736552 | IPILETVVEIKLFKGPKGLGFSIAGGVGNQHIPGDNSI YVTKIIDGGAAQKDGRLQVGDRLLMVNNYSLEEVTHEE AVAILKNTSEVVYLKVGKPTTIYMTDPYGPPNSSLTD |
| 129 | DLG5 domain 1 | 3650451 | GIPYVEEPRHVKVQKGSEPLGISIVSGEKGGIYVSKVT VGSIAHQAGLEYGDQLLEFNGINLRSATEQQARLIIGQ QCDTITILAQYNPHVHQLRNSSLTD |
| 130 | DLG5 domain 2 | 3650451 | GILAGDANKKTLEPRVVFIKKSQLELGVHLCGGNLHGV FVAEVEDDSPAKGPDGLVPGDLILEYGSLDVRNKTVEE VYVEMLKPRDGVRLKVQYRPEEFIVTD |

TABLE 2-continued

| SEQ ID NO. | name | GI or Acc. # | Sequence |
|---|---|---|---|
| 131 | DVL1 domain 1 | 2291005 | LNIVTVTLNMERHHFLGISIVGQSNDRGDGGIYIGSIM KGGAVAADGRIEPGDMLLQVNDVNFENMSNDDAVRVLR EIVSQTGPISLTVAKCW |
| 132 | DVL2 domain 1 | 2291007 | LNIITVTLNMEKYNFLGISIVGQSNERGDGGIYIGSIM KGGAVAADGRIEPGDMLLQVNDMNFENMSNDDAVRVLR DIVHKPGPIVLTVAKCWDPSPQNS |
| 133 | DVL3 domain 1 | 6806886 | IITVTLNMEKYNFLGISIVGQSNERGDGGIYIGSIMKG GAVAADGRIEPGDMLLQVNEINFENMSNDDAVRVLREI VHKPGPITLTVAKCWDPSP |
| 134 | EBP50 domain 2 | 3220018 | QQRELRPRLCTMKKGPSGYGFNLHSDKSKPGQFIRSVD PDSPAEASGLRAQDRIVEVNGVCMEGKQHGDVVSAIRA GGDETKLLVVDRETDEFFKNSS |
| 135 | EBP50 domain 1 | 3220018 | GIQMSADAAAGAPLPRLCCLEKGPNGYGFHLHGEKGKL GQYIRLVEPGSPAEKAGLLAGDRLVEVNGENVEKETHQ QVVSRIRAALNAVRLLVVDPETDEQLQKLGVQVREELL RAQEAPGQAEPPAAAEVQGAGNENEPREADKSHPEQRE LRN |
| 136 | EBP50 domains 1 and 2 | 3220018 | GIQMSADAAAGAPLPRLCCLEKGPNGYGFHLHGEKGKL GQYIRLVEPGSPAEKAGLLAGDRLVEVNGENVEKETHQ QVVSRIRAALNAVRLLVVDPETDEQLQKLGVQVREELL RAQEAPGQAEPPAAAEVQGAGNENEFREADKSHPEQRE LRPRLCTMKKGPSGYGENILHSDKSKPGQFIRSVDPDS PAEASGLRAQDRIVEVNGVCMEGKQHGDVVSAIRAGGD ETKLLVVDRETDEFFK |
| 137 | EBP50 domain 1 | 3220018 | QMSADAAAGAPLPRLCCLEKGPNGYGEFILHGEKGKLG QYIRLVEPGSPAEKAGLLAGDRLVEVNGENVEKETHQQ VVSRIRAALNAVRLLVVDPETDEQLQKLGVQVREELLR AQEAPGQAEPPAAAEVQGAGNENEPREADKSHPEQREL RNSS |
| 138 | ELFIN 1 domain 1 | 2957144 | LTTQQIDLQGPGPWGFRLVGGKDFEQPLAISRVTPGSK AALANLCIGDVITAIDGENTSNMTHLEAQNRIKGCTDN LTLTVARSEHKVWSPLVTNSSW |
| 139 | ENIGMA domain 1 | 561636 | IFMDSFKVVLEGPAPWGFRLQGGKDFNVPLSISRLTPG GKAAQAGVAVGDWVLSIDGENAGSLTHIEAQNKIRACG ERLSLGLSRAQPV |
| 140 | ERBIN domain 1 | 8923908 | QGHELAKQEIRRVREKDPELGFSISGGVGGRGNPFRPD DDGIFVTRVQPEGPASKLLQPGDKIIQANGYSFINIEH GQAVSLLKTFQNTVELIIVREVSS |
| 141 | FLJ00011 domain 1 | 10440352 | KNPSGELKTVTLSKMKQSLGISISGGIESKVQPMVKIE KIFPGGAAFLSGALQAGFELVAVDGENLEQVTHQRAVD TIRRAYRNKAREPMELVVRVPGSPRPSPSD |
| 142 | FLJ11215 domain 1 | 11436365 | EGHSHPRVVELPKTEEGLGFNIMGGKEQNSPIYISRII PGGIADRHGGLKRGDQLLSVNGVSVEGEHHEKAVELLK AAQGKVKLVVRYTPKVLEEME |
| 143 | FLJ12428 domain 1 | BC012040 | PGAPYARKTFTIVGDAVGWGFVVRGSKPCHIQAVDPSG PAAAAGMKVCQFVVSNGLNVLHVDYRTVSNLILTGPR TIVMEVMEELEC |
| 144 | FLJ12615 domain 1 | 10434209 | GQYGGETVKIVRIEKARDIPLGATVRNEMDSVIISRIV KGGAAEKSGLLHEGDEVLEINGIEIRGKDVNEVFDLLS DMHGTLTFVLIPSQQIKPPPA |
| 145 | FLJ21687 domain 1 | 10437836 | KPSQASGHFSVELVRGYAGFGLTLGGGRDVAGDTPLAV RGLLKDGPAQRCGRLEVGDLVLHINGESTQGLTHAQAV ERIRAGGPQLHLVIRRPLETHPGKPRGV |
| 146 | FLJ31349 domain 1 | AK055911 | PVMSQCACLEEVHLPNIKPGEGLGMYIKSTYDGLHVIT GTTENSPADRSQKIHAGDEVTQVNQQTVVGWQLKNLVK KLRENPTGVVLLLKKRPTGSFNFTP |
| 147 | FLJ32798 domain 1 | AK057360 | IDDEEDSVKIIRLVKNREPLGATIKKDEQTGAIIVARI MRGGAADRSGLIHVGDELREVNGIPVEDKRPEEIIQIL AQSQGAITFKIIPGSKEETPS |

TABLE 2-continued

| SEQ ID NO. | name | GI or Acc. # | Sequence |
|---|---|---|---|
| 148 | GORASP 2 domains 1 and 2 | 13994253 | MGSSQSVEIPGGGTEGYHVLRVQENSPGHRAGLEPFFD FIVSINGSRLNKDNDTLKDLLKANVEKPVKMLIYSSKT LELRETSVTPSNLWGGQGLLGVSIRFCSFDGANENVWH VLEVESNSPAALAGLRPHSDYIIGADTVMNESEDLFSL IETHEAKPLKLYVYNTDTDNCREVIITPNSAWGGEGSL GCGIGYGYLHRIPTRPFEEGKKISLPGQMAGTPITPLK DGFTEVQLSSVNPPSLSPPGTTGIEQSLTGLSISSTPP AVSSVLSTGVPTVPLLPPQVNQSLTSVPPMNPATTLPG LMPLPAGLPNLPNLNLNLPAPHIMPGVGLPELVNPGLP PLPSMPPRNLPGIAPLPLPSEFLPSFPLVPESSSAASS GELLSSLPPTSNAPSDPATTTAKADAASSLTVDVTPPT AKAPTTVEDRVGDSTPVSEKPVSAAVDANASESP |
| 149 | GORASP 2 domain 2 | 13994253 | NENVWHVLEVESNSPAALAGLRPHSDYHGADTVMNESE DLFSLIETHEAKPLKLYVYNTDTDNCREVIITPNSAWG GEGSLGCGIGYGYLHRIPTR |
| 150 | GORASP 2 domain 1 | 13994253 | MGSSQSVEIPGGGTEGYHVLRVQENSPGHRAGLEPFED FIVSINGSRLNKDNDTLKDLLKANVEKPVKMLIYSSKT LELRETSVTPSNLWGGQGLLGVSIRFCSFDGANE |
| 151 | GORASP 1 domain 2 | 29826292 | RASEQVWHVLDVEPSSPAALAGLRPYTDYVVGSDQILQ ESEDFFTLIESHEGKPLKLMVYNSKSDSCREVTVTPNA AWGGEGSLGCGIGYGYLHRIPTQ |
| 152 | GORASP 1 domain 1 | 29826292 | MGLGVSAEQPAGGAEGFHLHGVQENSPAQQAGLEPYFD FIITIGHSRLNKENDTLKALLKANVEKPVKLEVFNMKT MRVREVEVVPSNMWGGQGLLGASVRFCSFRRASE |
| 153 | GORASP 1 domains 1 and 2 | 29826292 | MGLGVSAEQPAGGAEGFHLHGVQENSPAQQAGLEPYFD FIITIGHSRLNKENDTLKALLKANVEKPVKLEVFNMKT MRVREVEVVPSNMWGGQGLLGASVRFCSFRRASEQVWH VLDVEPSSPAALAGLRPYTDYVVGSDQILQESEDFFTL IESHEGKPLKLMVYNSKSDSCREVTVTPNAAWGGEGSL GCGIGYGYLHRIPTQPPSYHKKPPGTPPPSALPLGAPP PDALPPGPTPEDSPSLETGSRQSDYMEALLQAPGSSME DPLPGPGSPSHSAPDPDGLPHFMETPLQPPPPVQRVMD PGFLDVSGISLLDNSNASVWPSLPSSTELTTTAVSTSG PEDICSSSSSHERGGEATWSGSEFEVSFLDSPGAQAQA DHLPQLTLPDSLTSAASPEDGLSAELLEAQAEEEPAST EGLDTGTEAEGLDSQAQISTTE |
| 154 | GRIP 1 domain 6 | 4539083 | IYTVELKRYGGPLGITISGTEEPFDPIIISSLTKGGLA ERTGAIHIGDRILAINSSSLKGKPLSEAIHLLQMAGET VTLKIKKQTDAQSA |
| 155 | GRIP 1 domain 1 | 4539083 | VVELMKKEGTTLGLTVSGGIDKDGKPRVSNLRQGGIAA RSDQLDVGDYIKAVNGINLAKFRHDEIISLLKNVGERV VLEVEYE |
| 156 | GRIP 1 domain 3 | 4539083 | HVATASGPLLVEVAKTPGASLGVALTTSMCCNKQVIVI DKIKSASIADRCGALHVGDHILSIDGTSMEYCTLAEAT QFLANTTDQVKLEILPHHQTRLALKGPNSS |
| 157 | GRIP 1 domain 7 | 4539083 | IMSPTPVELHKVTLYKDSDMEDFGFSVADGLLEKGVYV KNIRPAGPGDLGGLKPYDRLLQVNHVRTRDFDCCLVVP LIAESGNKLDLVISRNPLA |
| 158 | GRIP 1 domain 4 | 4539083 | IYTVELKRYGGPLGITISGTEEPFDPIIISSLTKGGLA ERTGAIHIGDRILAINSSSLKGKPLSEAIHLLQMAGET VTLKIKKQTDAQSA |
| 159 | GRIP 1 domain 5 | 4539083 | IMSPTPVELHKVTLYKDSDMEDFGFSVADGLLEKGVYV KNIRPAGPGDLGGLKPYDRLLQVNHVRTRIDFDCCLVV PLIAESGNKLDLVISRNPLA |
| 160 | GTPase activating enzyme domain 1 | 2389008 | SRGCETRELALPRDGQGRLGFEVDAEGFVTHVERFTFA ETAGLRPGARLLRVCGQTLPSLRPEAAAQLLRSAPKVC VTVLPPDESGRP |
| 161 | Guanine exchange factor domain 1 | 6650765 | CSVMIFEVVEQAGAIILEDGQELDSWYVILNGTVEISH PDGKVENLFMGNSFGITPTLDKQYMHGIVRTKVDDCQF VCIAQQDYWRILNIIVEKNTHKVEEEGEIVMVH |

TABLE 2-continued

| SEQ ID NO. | name | GI or Acc. # | Sequence |
|---|---|---|---|
| 162 | HEMBA 1000505 domain 2 | 10436367 | PRETVKIPDSADGLGFQIRGFGPSVVHAVGRGTVAAAA GLHPGQCIIKVNGINVSKETHASVIAHVTACRKYRRPT KQDSIQ |
| 163 | HEMBA 1000505 domain 1 | 10436367 | LENVIAKSLLIKSNEGSYGFGLEDKNKVPIIKLVEKGS NAEMAGMEVGKKIFAINGDLVFMRPFNEVDCFLKSCLN SRKPLRVLVSTKP |
| 164 | HEMBA 1003117 domain 1 | 7022001 | EDFCYVFTVELERGPSGLGMGLIDGMHTHLGAPGLYIQ TLLPGSPAAADGRLSLGDRILEVNGSSLLGLGYLRAVD LIRHGGKKMRFLVAKSDVETAKKI |
| 165 | hShroom domain 1 | 18652858 | IYLEAFLEGGAPWGFTLKGGLEHGEPLIISKVEEGGKA DTLSSKLQAGDEVVHINEVTLSSSRKEAVSLVKGSYKT LRLVVRRDVCTDPGH |
| 166 | HSPC227 domain 1 | 7106843 | NNELTQFLPRTITLKKPPGAQLGFNIRGGKASQLGIFI SKVIPDSDAHRAGLQEGDQVLAVNDVDFQDIEHSKAVE ILKTAREISMRVRFFPYNYHRQKE |
| 167 | HTRA 3 domain 1 | AY040094 | FLTEFQDKQIKDWKKRFIGIRMRTITPSLVDELKASNP DFPEVSSGIYVQEVAPNSPSQRGGIQDGDIIVKVNGRP LVDSSELQEAVLTESPLLLEVRRGNDDLLFS |
| 168 | HTRA 4 domain 1 | AL576444 | NKKYLGLQMLSLTVPLSEELKMHYPDFPDVSSGVYVCK VVEGTAAQSSGLRDHDVIVNINGKPITTTTDVVKALDS DSLSMAVLRGKDNLLLTV |
| 169 | INADL domain 3 | 2370148 | PGSDSSLFETYNVELVRKDGQSLGIRIVGYVGTSHTGE ASGIYVKSIIPGSAAYHNGHIQVNDKIVAVDGVNIQGF ANHDVVEVLRNAGQVVHLTLVRRKTSSSTSRIHRD |
| 170 | INADL domain 8 | 2370148 | PATCPIVPGQEMIIEISKGRSGLGLSIVGGKDTPLNAI VIHEVYEEGAAARDGRLWAGDQILEVNGVDLRNSSHEE AITALRQTPQKVRLVVY |
| 171 | INADL domain 2 | 2370148 | LPETVCWGHVEEVELINDGSGLGFGIVGGKTSGVVVRT IVPGGLADRDGRLQTGDHILKIGGTNVQGMTSEQVAQV LRNCGNSVRMLVARDPAGDIQSPI |
| 172 | INADL domain 6 | 2370148 | PNFSHWGPPRIVEIFREPNVSLGISIVVGQTVIKRLKN GEELKGIFIKQVLEDSPAGKTNALKTGDKILEVSGVDL QNASHSEAVEAIKNAGNPVVFIVQSLSSTPRVIPNVHN KANSS |
| 173 | INADL domain 7 | 2370148 | PGELHIIELEKDKNGLGLSLAGNKDRSRMSIFVVGINP EGPAAADGRMRIGDELLEINNQILYGRSHQNASAIIKT APSKVKLVFIRNEDAVNQMANSS |
| 174 | INADL domain 5 | 2370148 | LSSPEVKIVELVKDCKGLGFSILDYQDPLDPTRSVIVI RSLVADGVAERSGGLLPGDRLVSVNEYCLDNTSLAEAV EILKAVPPGLVHLGICKPLVEFIVTD |
| 175 | INADL domain 1 | 2370148 | IWQIEYIDIERPSTGGLGFSVVALRSQNLGKVDIFVKD VQPGSVADRDQRLKENDQILAINHTPLDQNISHQQAIA LLQQTTGSLRLIVAREPVHTKSSTSSSE |
| 176 | INADL domain 4 | 2370148 | NSDDAELQKYSKLLPIHTLRLGVEVDSFIDGHHYISSI VSGGPVDTLGLLQPEDELLEVNGMQLYGKSRREAVSFL KEVPPPFTLVCCRRLFDDEAS |
| 177 | KIAA0313 domain 1 | 7657260 | HLRLLNIACAAKAKRRLMTLTKPSREAPLPFILLGGSE KGFGIFVDSVDSGSKATEAGLKRGDQILEVNGQNFENI QLSKAMEILRNNTHLSITVKTNLFVFKELLTRLSEEKR NGAP |
| 178 | KIAA0316 domain 1 | 6683123 | IPPAPRKVEMRRDPVLGFGFVAGSEKPVVVRSVTPGGP SEGKLIPGDQIVMINDEPVSAAPRERVIDLVRSCKESI LLTVIQPYPSPK |
| 179 | KIAA0340 domain 1 | 2224620 | LNKRTTMPKDSGALLGLKVVGGKMTDLGRLGAFITKVK KGSLADVVGHLRAGDEVLEWNGKPLPGATNEEVYNIIL ESKSEPQVEIIVSRPIGDIPRIHRD |

TABLE 2-continued

| SEQ ID NO. | name | GI or Acc. # | Sequence |
|---|---|---|---|
| 180 | KIAA0380 domain 1 | 2224700 | RCVIIQKDQHGFGFTVSGDRIVLVQSVRPGGAAMKAGV KEGDRIIKVNGTMVTNSSHLEVVKLIKSGAYVALTLLG S |
| 181 | KIAA0382 domain 1 | 7662087 | ILVQRCVIIQKDDNGFGLTVSGDNPVFVQSVKEDGAAM RAGVQTGDRIIKVNGTLVTHSNHLEVVKLIKSGSYVAL TVQGRPPGNSS |
| 182 | KIAA0440 domain 1 | 2662160 | SVEMTLRRNGLGQLGFHVNYEGIVADVEPYGYAWQAGL RQGSRLVEICKVAVATLSHEQMIDLLRTSVTVKVVIIP PH |
| 183 | KIAA0545 domain 1 | 14762850 | LKVMTSGWETVDMTLRRNGLGQLGFHVKYDGTVAEVED YGFAWQAGLRQGSRLVEICKVAVVTLTHDQMIDLLRTS VTVKVVIIPPFEDGTPRRGW |
| 184 | KIAA0559 domain 1 | 3043641 | HYIFPHARIKITRDSKDHTVSGNGLGIRIVGGKEIPGH SGEIGAYIAKILPGGSAEQTGKLMEGMQVLEWNGIPLT SKTYEEVQSIISQQSGEAEICVRLDLNML |
| 185 | KIAA0613 domain 1 | 3327039 | SYSVTLTGPGPWGFRLQGGKDFNMPLTISRITPGSKAA QSQLSQGDLVVAIDGVNTDTMTHLEAQNKIKSASYNLS LTLQKSKNSS |
| 186 | KIAA0858 domain 1 | 4240204 | FSDMRISINQTPGKSLDFGFTIKWDIPGIFVASVEAGS PAEFSQLQVDDEIIAINNTKFSYNDSKEWEEAMAKAQE TGHLVMDVRRYGKAGSPE |
| 187 | KIAA0902 domain 1 | 4240292 | QSAHLEVIQLANIKPSEGLGMYIKSTYDGLHVITGTTE NSPADRCKKIHAGDEVIQVNHQTVVGWQLKNLVNALRE DPSGVILTLKKRPQSMLTSAPA |
| 188 | KIAA0967 domain 1 | 4589577 | ILTQTLIPVRHTVKIDKDTLLQDYGFHISESLPLTVVA VTAGGSAHGKLFPGDQILQMNNEPAEDLSWERAVDILR EAEDSLSITVVRCTSGVPKSSNSS |
| 189 | KIAA1202 domain 1 | 6330421 | RSFQYVPVQLQGGAPWGFTLKGGLEHCEPLTVSKIEDG GKAALSQKMRTGDELVNINGTPLYGSRQEALILIKGSF RILKLIVRRRNAPVS |
| 190 | KIAA1222 domain 1 | 6330610 | ILEKLELFPVELEKDEDGLGISIIGMGVGADAGLEKLG IFVKTVTEGGAAQRDGRIQVNDQIVEVDGISLVGVTQN FAATVLRNTKGNVREVIGREKPGQVSE |
| 191 | KIAA1284 domain 1 | 6331369 | KDVNVYVNPKKLTVIKAKEQLKLLEVLVGIIHQTKWSW RRTGKQGDGERLVVHGLLPGGSAMKSGQVLIGDVLVAV NDVDVTTENIERVLSCIPGPMQVKLTFENAYDVKRET |
| 192 | KIAA1389 domain 1 | 7243158 | TRGCETVEMTLRRNGLGQLGFHVNFEGIVADVEPFGFA WKAGLRQGSRLVEICKVAVATLTHEQMIDLLRTSVTVK VVIIQPHDDGSPRR |
| 193 | KIAA1415 domain 1 | 7243210 | VENILAKRLLILPQEEDYGEDIEEKNKAVVVKSVQRGS LAEVAGLQVGRKIYSINEDLVFLRPFSEVESILNQSFC SRRPLRLLVATKAKEIIKIP |
| 194 | KIAA1526 domain 1 | 5817166 | PDSAGPGEVRLVSLRRAKAHEGLGFSIRGGSEHGVGIY VSLVEPGSLAEKEGLRVGDQILRVNDKSLARVTHAEAV KALKGSKKLVLSVYSAGRIPGGYVTNH |
| 195 | KIAA1526 domain 2 | 5817166 | LQGGDEKKVNLVLGDGRSLGLTIRGGAEYGLGIYITGV DPGSEAEGSGLKVGDQILEVNGRSFLNILHDEAVRLLK SSRHLILTVKDVGRLPHARTTVDE |
| 196 | KIAA1620 domain 1 | 10047316 | LRRAELVEIIVETEAQTGVSGINVAGGGKEGIFVRELR EDSPAARSLSLQEGDQLLSARVFFENFKYEDALRLLQC AEPYKVSFCLKRTVPTGDLALR |
| 197 | KIAA1719 domain 5 | 1267982 | IQTTGAVSYTVELKRYGGPLGITISGTEEPFDPIVISG LTKRGLAERTGAIHVGDRILAINNVSLKGRPLSEAIHL LQVAGETVTLKIKKQLDR |
| 198 | KIAA1719 domain 6 | 1267982 | ILEMEELLLPTPLEMHKVTLHKDPMRHDFGFSVSDGLL EKGVYVHTVRPDGPAHRGGLQPFDRVLQVNHVRTRDFD CCLAVPLLAEAGDVLELIISRKPHTAHSS |

TABLE 2-continued

| SEQ ID NO. | name | GI or Acc. # | Sequence |
|---|---|---|---|
| 199 | KIAA1719 domain 2 | 1267982 | IHTVANASGPLMVEIVKTPGSALGISLTTTSLRNKSVI TIDRIKPASVVDRSGALHPGDHILSIDGTSMEHCSLLE ATKLLASISEKVRLEILPVPQSQRPL |
| 200 | KIAA1719 domain 1 | 1267982 | ITVVELIKKEGSTLGLTISGGTDKDGKPRVSNLRPGGL AARSDLLNIGDYIRSVNGIHLTRLRHDEIITLLKNVGE RVVLEVEY |
| 201 | KIAA1719 domain 3 | 1267982 | IQIVIITETTEVVLCGDPLSGFGLQLQGGIFATETLSS PPLVCFIEPDSPAERCGLLQVGDRVLSINGIATEDGTM EEANQLLRDAALAHKVVLEVEFDVAESV |
| 202 | KIAA1719 domain 1 | 1267982 | ILDVSLYKEGNSFGFVLRGGAHEDGHKSRPLVLTYVRP GGPADREGSLKVGDRLLSVDGIPLHGASHATALATLRQ CSHEALFQVEYDVATP |
| 203 | KIAA1719 domain 4 | 1267982 | QFDVAESVIPSSGTFHVKLPKKRSVELGITISSASRKR GEPLIISDIKKGSVAHRTGTLEPGDKLLAIDNIRLDNC PMEDAVQILRQCEDLVKLKIRKDEDN |
| 204 | LIM mystique domain 1 | 12734250 | MALTVDVAGPAPWGFRITGGRDFHTPIMVTKVAERGKA KDADLRPGDIIVAINGESAEGMLHAEAQSKIRQSPSPL RLQLDRSQATSPGQT |
| 205 | LIM protein domain 1 | 3108092 | SNYSVSLVGPAPWGFRLQGGKDFNMPLTISSLKDGGKA AQANVRIGDVVLSIDGINAQGMTHLEAQNKIKGCTGSL NMTLQRAS |
| 206 | LIMK1 domain 1 | 4587498 | TLVEHSKLYCGHCYYQTVVTPVIEQILPDSPGSHLPHT VTLVSIPASSHGKRGLSVSIDPPHGPPGCGTEHSHTVR VQGVDPGCMSPDVKNSIHVGDRILEINGTPIRNVPLDE IDLLIQETSRLLQLTLEHD |
| 207 | LIMK2 domain 1 | 1805593 | PYSVTLISMPATTEGRRGFSVSVESACSNYATTVQVKE VNRMHISPNNRNAIHPGDRILEINGTPVRTLRVEEVED AISQTSQTLQLLIEHD |
| 208 | LIM-RIL domain 1 | 1085021 | IHSVTLRGPSPWGFRLVGRDFSAPLTISRVHAGSKASL AALCPGDLIQAINGESTELMTHLEAQNRIKGCHDHLTL SVSRPE |
| 209 | LU-1 domain 1 | U52111 | VCYRTDDEEDLGIYVGEVNPNSIAAKDGRIREGDRIIQ INGVDVQNREEAVAILSQEENTNISLLVARPESQLA |
| 210 | MAGI 1 domain 2 | 3370997 | IPATQPELITVHIVKGPMGFGFTIADSPGGGGQRVKQI VDSPRCRGLKEGDLIVEVNKKNVQALTHNQVVDMLVEC PKGSEVTLLVQRGGNSS |
| 211 | MAGI 1 domain 5 | 3370997 | IPDYQEQDIFLWRKETGFGFRILGGNEPGEPIYIGHIV PLGAADTDGRLRSGDELICVDGTPVIGKSHQLVVQLMQ QAAKQGHVNLTVRRKVVFAVPKTENSS |
| 212 | MAGI 1 domain 4 | 3370997 | IPGVVSTVVQPYDVEIRRGENEGFGEVIVSSVSRPEAG TTFAGNACVAMPHKIGRIIEGSPADRCGKLKVGDRILA VNGCSITNKSHSDIVNLIKEAGNTVTLRIIPGDESSNA EFIVTD |
| 213 | MAGI 1 domain 1 | 3370997 | IPSELKGKFIHTKLRKSSRGFGFTVVGGDEPDEFLQIK SLVLDGPAALDGKMETGDVIVSVNDTCVLGHTHAQVVK IFQSIPIGASVDLELCRGYPLPFDPDGIHRD |
| 214 | MAGI 1 domain 3 | 3370997 | QATQEQDFYTVELERGAKGFGFSLRGGREYNMDLYVLR LAEDGPAERCGKMRIGDEILEINGETTKNMKHSRAIEL IKNGGRRVRLFLKRG |
| 215 | Magi 2 domain 1 | 2947231 | REKPLFTRDASQLKGTFLSTTLKKSNMGFGFTIIGGDE PDEFLQVKSVIPDGPAAQDGKMETGDVIVYINEVCVLG HTHADVVKLFQSVPIGQSVNLVLCRGYP |
| 216 | Magi 2 domain 3 | 2947231 | HYKELDVHLRRMESGFGFRILGGDEPGQPILIGAVIAM GSADRDGRLHPGDELVYVDGIPVAGKTHRYVIDLMHHA ARNGQVNLTVRRKVLCG |

TABLE 2-continued

| SEQ ID NO. | name | GI or Acc. # | Sequence |
|---|---|---|---|
| 217 | Magi 2 domain 4 | 2947231 | EGRGISSHSLQTSDAVIHRKENEGFGFVIISSLNRPES GSTITVPHKIGRIIDGSPADRCAKLKVGDRILAVNGQS IINMPHADIVKLIKDAGLSVTLRIIPQEEL |
| 218 | Magi 2 domain 2 | 2947231 | LSGATQAELMTLTIVKGAQGFGFTIADSPTGQRVKQIL DIQGCPGLCEGDLIVEINQQNVQNLSHTEVVDILKDCP IGSETSLIIHRGGFF |
| 219 | Magi 2 domain 5 | 2947231 | LSDYRQPQDFDYFTVDMEKGAKGFGFSIRGGREYKMDL YVLRLAEDGPAIRNGRMRVGDQIIEINGESTRDMTHAR AIELIKSGGRRVRLLLKRGTGQ |
| 220 | Magi 2 domain 6 | 2947231 | HESVIGRNPEGQLGFELKGGAENGQFPYLGEVKPGKVA YESGSKLVSEELLLEVNETPVAGLTIRDVLAVIKHCKD PLRLKCVKQGGIHR |
| 221 | MAGI 3 domain 2 | 10047344 | ASSGSSQPELVTIPLIKGPKGFGFAIADSPTGQKVKMI LDSQWCQGLQKGDIIKEIYHQNVQNLTHLQVVEVLKQF PVGADVPLLILRGGPPSPTKTAKM |
| 222 | MAGI 3 domain 5 | 10047344 | QNLGCYPVELERGPRGFGFSLRGGKEYNMGLFILRLAE DGPAIKDGRIHVGDQIVEINGEPTQGITHTRAIELIQA GGNKVLLLLRPGTGLIPDHGLA |
| 223 | MAGI 3 domain 3 | 10047344 | LYEDKPPNTKDLDVFLRKQESGFGFRVLGGDGPDQSIY IGAIIPLGAAEKDGRLRAADELMCIDGIPVKGKSHKQV LDLMTTAARNGHVLLTVRRKIFYGEKQPEDDS |
| 224 | MAGI 3 domain 1 | 10047344 | PSQLKGVLVRASLKKSTMGFGFTIIGGDRPDEFLQVKN VLKDGPAAQDGKIAPGDVIVDINGNCVLGHTHADVVQM FQLVPVNQYVNLTLCRGYPLPDDSED |
| 225 | MAGI 3 domain 4 | 10047344 | PAPQEPYDVVLQRKENEGFGFVILTSKNKPPPGVIPHK IGRVTEGSPADRCGKLKVGDHISAVNGQSIVELSHDNI VQLIKDAGVTVTLTVIAEEEHHGPPS |
| 226 | MAST1 domain 1 | 4589589 | GLRSPITIQRSGKKYGFTLRAIRVYMGDTDVYSVHHIV WHVEEGGPAQEAGLCAGDLITHVNGEPVHGMVHPEVVE LILKSGNKVAVTTTPFEN |
| 227 | MAST2 domain 1 | 3882334 | ISALGSMRPPIIIHRAGKKYGFTLRAIRVYMGDSDVYT VHHMVWHVEDGGPASEAGLRQGDLITHVNGEPVHGLVH TEVVELILKSGNKVAISTTPLENSS |
| 228 | MAST3 domain 1 | 3043645 | LCGSLRPPIVIHSSGKKYGFSLRAIRVYMGDSDVYTVH HVVWSVEDGSPAQEAGLRAGDLITHINGESVLGLVHMD VVELLLKSGNKISLRTTALENTSIKVG |
| 229 | MAST4 domain 1 | 2224546 | PHQPIVIHSSGKNYGFTIRAIRVYVGDSDIYTVHHIVW NVEEGSPACQAGLKAGDLITHINGEPVHGLVHTEVIEL LLKSGNKVSITTTPF |
| 230 | MGC5395 domain 1 | BC012477 | PAKMEKEETTRELLLPNWQGSGSHGLTIAQRDDGVFVQ EVTQNSPAARTGVVKEGDQIVGATIYFDNLQSGEVTQL LNTMGHHTVGLKLHRKGDRSPNSS |
| 231 | MINT1 domain 1 | 2625024 | SENCKdVFIEKQKGEILGVVIVESGWGSILPTVIIANM MHGGPAEKSGKLNIGDQIMSINGTSLVGLPLSTCQSII KGLKNQSRVKLNIVRCPPVNSS |
| 232 | MINT1 domains 1 and 2 | 2625024 | SENCKDVFIEKQKGEILGVVIVESGWGSILPTVIIANM MHGGPAEKSGKLNIGDQIMSINGTSLVGLPLSTCQSII KGLENQSRVKLNIVRCPPVTTVLIRRPDLRYQLGFSVQ NGIICSLMRGGIAERGGVRVGHRIIEINGQSVVATPHE KIVHILSNAVGEIHMKTMPAAMYRLL |
| 233 | MINT1 domain 2 | 2625024 | LRCPPVTTVLIRRPDLRYQLGESVQNGIICSLMRGGIA ERGGVRVGHRIIEINGQSVVATPHEKIVHILSNAVGEI HMKTMPAAMYRLLNSS |
| 234 | MINT3 domain 1 | 3169808 | HNGDLDHFSNSDNCREVHLEKRRGEGLGVALVESGWGS LLPTAVIANLLHGGPAERSGALSIGDRLTAINGTSLVG LPLAACQAAVRETKSQTSVTLSIVHCPPVT |

TABLE 2-continued

| SEQ ID NO. | name | GI or Acc. # | Sequence |
|---|---|---|---|
| 235 | MINT3 domain 2 | 3169808 | PVTTAIIHRPHAREQLGFCVEDGIICSLLRGGIAERGG IRVGHRIIEINGQSVVATPHARIIELLTEAYGEVHIKT MPAATYRLLTGNSS |
| 236 | MINT3 domain 1 | 3169808 | LSNSDNCREVHLEKRRGEGLGVALVESGWGSLLPTAVI ANLLHGGPAERSGALSIGDRLTAINGTSLVGLPLAACQ AAVRETKSQTSVTLSIVHCPPVTTAIM |
| 237 | MPP1 domain 1 | 189785 | RKVRLIQFEKVTEEPMGITLKLNEKQSCTVARILHGGM IHRQGSLHVGDEILEINGTNVTNHSVDQLQKAMKETKG MISLKVIPNQ |
| 238 | MPP2 domain 1 | 939884 | PVPPDAVRMVGIRKTAGEHLGVTFRVEGGELVIARILH GGMVAQQGLLHVGDIIKEVNGQPVGSDPRALQELLRNA SGSVILKILPNYQ |
| 239 | MPP3 domain 1 | 21536463 | NIDEDFDEESVKIVRLVKNKEPLGATIRRDEHSGAVVV ARIMRGGAADRSGLVHVGDELREVNGIAVLHKRPDEIS QILAQSQGSITLKIIPATQEEDR |
| 240 | MUPP1 domain 5 | 2104784 | WEAGIQHIELEKGSKGLGFSILDYQDPIDPASTVIIIR SLVPGGIAEKDGRLLPGDRLMFVNDVNLENSSLEEAVE ALKGAPSGTVRIGVAKPLPLSPEE |
| 241 | MUPP1 domain 12 | 2104784 | LQGLRTVEMKKGPTDSLGISIAGGVGSPLGDVPIFIAM MHPTGVAAQTQKLRVGDRIVTICGTSTEGMTHTQAVNL LKNASGSIEMQVVAGGDVSV |
| 242 | MUPP1 domain 2 | 2104784 | PVHWQHMETIELYNDGSGLGEGIIGGKATGVIVKTILP GGVADQHGRLCSGDHILKIGDTDLAGMSSEQVAQVLRQ CGNRVKLMIARGAIEERTAPT |
| 243 | MUPP1 domain 3 | 2104784 | QESETEDVELTKNVQGLGITIAGYIGDKKLEPSGIFVK SITKSSAVEHDGRIQIGDQIIAVDGTNLQGFTNQQAVE VLRHTGQTVLLTLMRRGMKQEA |
| 244 | MUPP1 domain 11 | 2104784 | KEEEVCDTLTIELQKKPGKGLGLSIVGKRNDTGVFVSD IVKGGIADADGRLMQGDQILMVNGEDVRNATQEAVAAL LKCSLGTVTLEVGRIKAGPFHS |
| 245 | MUPP1 domain 8 | 2104784 | LTGELHMIELEKGHSGLGLSLAGNKDRSRMSVFIVGID PNGAAGKDGRLQIADELLEINGQILYGRSHQNASSIIK CAPSKVKIIFIRNKDAVNQ |
| 246 | MUPP1 domain 13 | 2104784 | LGPPQCKSITLERGPDGLGFSIVGGYGSPHGDLPIYVK TVFAKGAASEDGRLKRGDQIIAVNGQSLEGVTHEEAVA ILKRTKGTVTLMVLS |
| 247 | MUPP1 domain 6 | 2104784 | RNVSKESFERTINIAKGNSSLGMTVSANKDGLGMIVRS IIHGGAISRDGRIAIGDCILSINEESTISVTNAQARAM LRRHSLIGPDIKITYVPAEHLEE |
| 248 | MUPP1 domain 1 | 02104784 | LPGCETTIEISKGRTGLGLSIVGGSDTLLGAIIIHEVY EEGAACKDGRLWAGDQILEVNGIDLRKATHDEAINVLR QTPQRVRLTLYRDEAPYKE |
| 249 | MUPP1 domain 7 | 2104784 | LNWNQPRRVELWREPSKSLGISIVGGRGMGSRLSNGEV MRGIFIKHVLEDSPAGKNGTLKPGDRIVEVDGMDLRDA SHEQAVEAIRKAGNPVVFMVQSIINRPRKSPLPSLL |
| 250 | MUPP1 domain 9 | 2104784 | LSSFKNVQHLELPKDQGGLGIATSEEDTLSGVIIKSLT EHGVAATDGRLKVGDQILAVDDEIVVGYPIEKFISLLK TAKMTVKLTIHAENPDSQ |
| 251 | MUPP1 domain 1 | 2104784 | QGRHVEVFELLKPPSGGLGFSVVGLRSENRGELGIFVQ EIQEGSVAHRDGRLKETDQILAINGQALDQTITHQQAI SILQKAKDTVQLVIARGSLPQLV |
| 252 | MUPP1 domain 4 | 2104784 | LNYEIVVAHVSKFSENSGLGISLEATVGHHFIRSVLPE GPVGHSGKLFSGDELLEVNGITLLGENHQDVVNILKEL PIEVTMVCCRRTVPPT |
| 253 | NeDLG domain 2 | 10863920 | ITLLKGPKGLGESIAGGIGNQHIPGDNSIYITKIIEGG AAQKDGRLQIGDRLLAVNNTNLQDVRHEEAVASLKNTS DMVYLKVAKPGSLE |

TABLE 2-continued

| SEQ ID NO. | name | GI or Acc. # | Sequence |
|---|---|---|---|
| 254 | NeDLG domain 1 | 10863920 | IQYEEIVLERGNSGLGFSIAGGIDNPHVPDDPGIFITK IIPGGAAAMDGRLGVNDCVLRVNEVEVSEVVHSRAVEA LKEAGPVVRLVVRRQN |
| 255 | NeDLG domain 3 | 10863920 | ILLHKGSTGLGFNIVGGEDGEGIFVSFILAGGPADLSG ELRRGDRILSVNGVNLRNATHEQAAAALKRAGQSVTIV AQYRPEEYSRFESKIHDLREQMMNSSMSSGSGSLRTSE KRSLE |
| 256 | NeDLG domains 1 and 2 | 10863920 | YEEIVLERGNSGLGFSIAGGIDNPHVPDDPGIFITKII PGGAAAMDGRLGVNDCVLRVNEVEVSEVVHSRAVEALK EAGPVVRLVVRRQPPPETIMEVNLLKGPKGLGFSIAG GIGNQHIPGDNSIYITKIIEGGAAQKDGRLQIGDRLLA VNNTNLQDVRHEEAVASLKNTSDMVYLKVAKPGSL |
| 257 | Neurabin II domain 1 | AJ401189 | RVERLELFPVELEKDSEGLGISIIGMGAGADMGLEKLG IFVKTVTEGGAAHRDGRIQVNDLLVEVDGTSLVGVTQS FAASVLRNTKGRVRCRFMIGRERPGEQSEV |
| 258 | NOS1 domain 1 | 642525 | QPNVISVRLFKRKVGGLGELVKERVSKPPVIISDLIRG GAAEQSGLIQAGDIILAVNGRPLVDLSYDSALEVLRGI ASETHVVLILRGPE |
| 259 | novel PDZ gene domain 2 | 7228177 | PSDTSSEDGVRRIVHLYTTSDDFCLGFNIRGGKEFGLG IYVSKVDHGGLAEENGIKVGDQVLAANGVRFDDISHSQ AVEVLKGQTHIMLTIKETGRYPAYKEM |
| 260 | novel PDZ gene domain 1 | 7228177 | EANSDESDIIHSVRVEKSPAGRLGFSVRGGSEHGLGIF VSKVEEGSSAERAGLCVGDKITEVNGLSLESTTMGSAV KVLTSSSRLHMMVRRMGRVPGIKFSKEK |
| 261 | novel serine protease domain 1 | 1621243 | DKIKKFLTESHDRQAKGKAITKKKYIGIRMMSLTSSKA KELKDRHRDEPDVISGAYIIEVIPDTPAEAGGLKENDV IISINGQSVVSANDVSDVIKRESTLNMVVRRGNEDIMI TV |
| 262 | Numb BP domain 2 | AK056823 | YRPRDDSFHVILNKSSPEEQLGIKLVRKVDEPGVFIFN ALDGGVAYRHGQLEENDRVLAINGHDLRYGSPESAAHL IQASERRVHLVVSRQVRQRSPD |
| 263 | Numb BP domain 3 | AK056823 | PTITCHEKVVNIQKDPGESLGMTVAGGASHREWDLPIY VISVEPGGVISRDGRIKTGDILLNVDGVELTEVSRSEA VALLKRTSSSIVLKALEVKEYEPQ |
| 264 | Numb BP domain 1 | AK056823 | PDGEITSIKINRVDPSESLSIRLVGGSETPLVHIIIQH IYRDGVIARDGRLLPRDIILKVNGMDISNVPHNYAVRL LRQPCQVLWLTVMREQKFRSR |
| 265 | Numb BP domain 4 | AK056823 | PRCLYNCKDIVLRRNTAGSLGFCIVGGYEEYNGNKPFF IKSIVEGTPAYNDGRIRCGDILLAVNGRSTSGMIHACL ARLLKELKGRITLTIVSWPGTFL |
| 266 | outer membrane domain 1 | 7023825 | LLTEEEINLTRGPSGLGFNIVGGTDQQYVSNDSGIYVS RIKENGAAALDGRLQEGDKILSVNGQDLKNLLHQDAVD LFRNAGYAVSLRVQHRLQVQNGIHS |
| 267 | p55T domain 1 | 12733367 | PVDAIRILGIHKRAGEPLGVTFRVENNDLVIARILHGG MIDRQGLLHVGDIIKEVNGHEVGNNPKELQELLKNISG SVTLKILPSYRDTITPQQ |
| 268 | PAR3 domain 2 | 8037914 | GKRLNIQLKKGTEGLGFSITSRDVTIGGSAPIYVKNIL PRGAAIQDGRLKAGDRLIEVNGVDLVGKSQEEVVSLLR STKMEGTVSLLVFRQEDA |
| 269 | PAR3 domain 1 | 8037914 | IPNFSLDDMVKLVEVPNDGGPLGIHVVPFSARGGRTLG LLVKRLEKGGKAEHENLFRENDCIVRINDGDLRNRRFE QAQHMFRQAMRTPIIWFHVVPAANKEQYEQ |
| 270 | PAR3 domain 3 | 8037914 | PREFLTFEVPLNDSGSAGLGVSVKGNRSKENHADLGIF VKSIINGGAASKDGRLRVNDQLIAVNGESLLGKTNQDA METLRRSMSTEGNKRGMIQLIVASRISKCNELKSNSS |
| 271 | PAR3L domain 2 | 18874467 | ISNKNAKKIKIDLKKGPEGLGFTVVTRDSSIHGPGPIF VKNILPKGAAIKDGRLQSGDRILEVNGRDVTGRTQEEL VAMLRSTKQGETASLVIARQEGH |

TABLE 2-continued

| SEQ ID NO. | name | GI or Acc. # | Sequence |
|---|---|---|---|
| 272 | PAR3L domain 3 | 18874467 | ITSEQLTFEIPLNDSGSAGLGVSLKGNKSRETGTDLGI FIKSIIHGGAAFKDGRLRMNDQLIAVNGESLLGKSNHE AMETLRRSMSMEGNIRGMIQLVILRRPERP |
| 273 | PAR3L domain 1 | 18874467 | IPRTKDTLSDMTRTVEISGEGGPLGIHVVPFFSSLSGR ILGLFIRGIEDNSRSKREGLEHENECIVKINNVDLVDK TFAQAQDVFRQAMKSPSVLLHVLPPQNR |
| 274 | PAR6 domain 1 | 2613011 | PETHRRVRLHKHGSDRPLGFYIRDGMSVRVAPQGLERV PGIFISRLVRGGLAESTGLLAVSDEILEVNGIEVAGKT LDQVTDMMVANSHNLIVTVKPANQRNNV |
| 275 | PAR6 beta domain 1 | 1353716 | IPVSSIIDVDILPETHRRVRLYKYGTEKPLGFYIRDGS SVRVTPHGLEKVPGIFISRLVPGGLAQSTGLLAVNDEV LEVNGIEVSGKSLDQVTDMMIANSRNLIITVRPANQRN NRIHRD |
| 276 | PAR6 GAMMA domain 1 | 13537118 | IDVDLVPETHRRVRLHRHGCEKPLGFYIRDGASVRVTP HGLEKVPGIFISRMVPGGLAESTGLLAVNDEVLEVNGI EVAGKTLDQVTDMMIANSHNLIVTVKPANQRNNVV |
| 277 | PDZ-73 domain 3 | 5031978 | PEQIMGKDVRLLRIKKEGSLDLALEGGVDSPIGKVVVS AVYERGAAERHGGIVKGDEIMAINGKIVTDYTLAEADA ALQKAWNQGGDWIDLVVAVCPPKEYDD |
| 278 | PDZ-73 domain 2 | 5031978 | IPGNRENKEKKVFISLVGSRGLGCSISSGPIQKPGIFI SHVKPGSLSAEVGLEIGDQIVEVNGVDFSNLDHKEAVN VLKSSRSLTISIVAAAGRELFMTDEF |
| 279 | PDZ-73 domain 1 | 5031978 | RSRKLKEVRLDRLHPEGLGLSVRGGLEFGCGLFISHLI KGGQADSVGLQVGDEIVRINGYSISSCTHEEVINLIRT KKTVSIKVRHIGLIPVKSSPDEFH |
| 280 | PDZK1 domain 2 | 2944188 | RLCYLVKEGGSYGFSLKTVQGKKGVYMTDITPQGVAMR AGVLADDHLIEVNGENVEDASHEEVVEKVKKSGSRVMF LLVDKETDKREFIVTD |
| 281 | PDZK1 domain 3 | 2944188 | QFKRETASLKLLPHQPRIVEMKKGSNGYGEYLRAGSEQ KGQIIKDIDSGSPAEEAGLKNNDLVVAVNGESVETLDH DSVVEMIRKGGDQTSLLVVDKETDNMYRLAEFIVTD |
| 282 | PDZK1 domains 2 and 3 and 4 | 2944188 | RLCYLVKEGGSYGFSLKTVQGKKGVYMTDITPQGVAMR AGVLADDHLIEVNGENVEDASHEKVVEKVKKSGSRVMF LLVDKETDKRHVEQKIQFKRETASLKLLPHQPRIVEMK KGSNGYGFYLRAGSEQKGQIIKDIDSGSPAEEAGLKNN DLVVAVNGESVETLDHDSVVEMIRKGGDQTSLLVVDKE TDNMYRLAHFSPFLYYQSQELPNGSVKEAPAPTPTSLE VSSPPDTTEEVDHKPKLCRLAKGENGYGFHLNAIRGLP GSFIKEVQKGGPADLAGLEDEDVIIEVNGVNVLDEPYE KVVDRIQSSGKNVTLLVCGK |
| 283 | PDZK1 domain 4 | 2944188 | PDTTEEVDHKPKLCRLAKGENGYGFHLNAIRGLPGSFI KEVQKGGPADLAGLEDEDVIIEVNGVNVLDEPYEKVVD RIQSSGKNVTLLVGKNSS |
| 284 | PDZK1 domain 1 | 2944188 | LTSTFNPRECKLSKQEGQNYGFFLRIEKDTEGHLVRVV EKCSPAEKAGLQDGDRVLRINGVFVDKEEHMQVVDLVR KSGNSVTLLVLDGDSYEKAGSHEPS |
| 285 | PICK1 domain 1 | 4678411 | LGIPTVPGKVTLQKDAQNLIGISIGGGAQYCPCLYIVQ VFDNTPAALDGTVAAGDEITGVNGRSIKGKTKVEVAKM IQEVKGEVTIHYNKLQADPKQGM |
| 286 | PIST domain 1 | 98374330 | SQGVGPIRKVLLLKEDHEGLGISITGGKEHGVPILISE IHPGQPADRCGGLHVGDAILAVNGVNLRDTKHKEAVTI LSQQRGEIEFEVVYVAPEVDSD |
| 287 | prIL16 domain 2 | 1478492 | TAEATVCTVTLEKMSAGLGFSLEGGKGSLHGDKPLTIN RIFKGAASEQSETVQPGDEILQLGGTAMQGLTRFEAWN IIKALPDGPVTIVIRRKSLQSK |
| 288 | prIL16 domain 1 | 1478492 | IHVTILHKEEGAGLGFSLAGGADLENKVITVHRVFPNG LASQEGTIQKGNEVLSINGKSLKGTTHHDALAILRQAR EPRQAVIVTRKLTPEEFIVTD |

TABLE 2-continued

| SEQ ID NO. | name | GI or Acc. # | Sequence |
|---|---|---|---|
| 289 | prIL16 domains 1 and 2 | 1478492 | IHVTILHKEEGAGLGFSLAGGADLENKVITVHRVFPNG LASQEGTIQKGNEVLSINGKSLKGTTHHDALAILRQAR EPRQAVIVTRKLTPEAMPDLNSSTDSAASASAASDVSV ESTAEATVCTVTLEKMSAGLGFSLEGGKGSLHGDKPLT INRIFKGAASEQSETVQPGDEILQLGGTAMQGLTRFEA WNIIKALPDGPVTIVIRRKSLQSK |
| 290 | PSAP domain 1 | 6409315 | IREAKYSGVLSSIGKIFKEEGLLGFFVGLIPHLLGDVV FLWGCNLLAHFINAYLVDDSVSDTPGGLGNDQNPGSQF SQALAIRSYTKEVMGIAVSMLTYPFLLVGDLMAVNNCG LQAGLPPYSPVFKSWIHCWKYLSVQGQLFRGSSLLFRR VSSGSCFALE |
| 291 | PSD95 domains 1 and 2 and 3 | 3318652 | EGEMEYEEITLERGNSGLGFSIAGGTDNPHIGDDPSIF ITKIIPGGAAAQDGRLRVNDSILFVNEVDVREVTHSAA VEALKEAGSIVRLYVMRRKPPAEKVMEIKLIKGPKGLG FSIAGGVGNQHIPGDNSIYVTKIIEGGAAHKDGRLQIG DKILAVNSVGLEDVMHEDAVAALKNTYDVVYLKVAKPS NAYLSDSYAPPDITTSYSQHLDNEISHSSYLGTDYPTA MTPTSPRRYSPVAKDLLGEEDIPREPRRIVIHRGSTGL GFNIVGGEDGEGIFISFILAGGPADLSGELRKGDQILS VNGVDLRNASHEQAAIALKNAGQTVTIIAQYKPE |
| 292 | PSD95 domain 2 | 3318652 | HVMRRKPPAEKVMEIKLIKGPKGLGFSIAGGVGNQHIP GDNSIYVTKIIEGGAAHKDGRLQIGDKILAVNSVGLED VMHEDAVAALKNTYDVVYLKVAKPSNAYL |
| 293 | PSD95 domain 3 | 3318652 | REDIPREPRRIVIHRGSTGLGFNIVGGEDGEGIFISFI LAGGPADLSGELRKGDQILSVNGVDLRNASHEQAAIAL KNAGQTVTIIAQYKPEFIVTD |
| 294 | PSD95 domain 1 | 3318652 | LEYEeITLERGNSGLGESIAGGTDNPHIGDDPSIFITK IIPGGAAAQDGRLRVNDSILFVNEVDVREVTHSAAVEA LKEAGSIVRLYVMRRKPPAENSS |
| 295 | PSMD9 domain 1 | 9184389 | RDMAEAHKEAMSRKLGQSESQGPPRAFAKVNSISPGSP ASIAGLQVDDEIVEFGSVNTQNFQSLHNIGSVVQHSEG ALAPTILLSVSM |
| 296 | PTN-3 domain 1 | 179912 | QNDNGDSYLVLIRITPDEDGKFGFNLKGGVDQKMPLVV SRINPESPADTCIPKLNEGDQIVLINGRDISEHTHDQV VMFIKASRESHSRELAVIRRRAVRS |
| 297 | PTN-4 domain 1 | 190747 | IRMKPDENGRFGFNVKGGYDQKMPVIVSRVAPGTPADL CVPRLNEGDQVVLINGRDIAEHTHDQVVLFIKASCERH SGELMLLVRPNA |
| 298 | PTPL1 domain 2 | 515030 | GDIFEVELAKNDNSLGISVTGGVNTSVRHGGIYVKAVI PQGAAESDGRIHKGDRVLAVNGVSLEGATHKQAVETLR NTGQVVHLLLEKGQSPTSK |
| 299 | PTPL1 domain 1 | 515030 | PEREITLVNLKKDAKYGLGFQIIGGEKMGRLDLGIFIS SVAPGGPADFHGCLKPGDRLISVNSVSLEGVSHHAAIE ILQNAPEDVTLVISQPKEKISKVPSTPVHL |
| 300 | PTPL1 domain 4 | 515030 | ELEVELLITLIKSEKASLGFTVTKGNQRIGCYVHDVIQ DPAKSDGRLKPGDRLIKVNDTDVTNMTHTDAVNLLRAA SKTVRLVIGRVLELPRIPMLPH |
| 301 | PTPL1 domain 3 | 515030 | TEENTFEVKLFKNSSGLGFSFSREDNLIPEQINASIVR VKKLFAGQPAAESGKIDVGDVILKVNGASLKGLSQQEV ISALRGTAPEVFLLLCRPPPGVLPEIDT |
| 302 | PTPL1 domain 5 | 515030 | MLPHLLPDITLTCNKEELGFSLCGGHDSLYQVVYISDI NPRSVAAIEGNLQLLDVIHYVNGVSTQGMTLEEVNRAL DMSLPSLVLKATRNDLPV |
| 303 | RGS 3 domain 1 | 18644735 | VCSERRYRQITIPRGKDGFGFTICCDSPVRVQAVDSGG PAERAGLQQLDTVLQLNERPVEHWKCVELAHEIRSCPS EIILLVWRMVPQVKPG |
| 304 | RGS12 domain 1 | 3290015 | RPSPPRVRSVEVARGRAGYGFTLSGQAPCVLSCVMRGS PADFVGLRAGDQILAVNEINVKKASHEDVVKLIGKCSG VLHMVIAEGVGRFESCS |

TABLE 2-continued

| SEQ ID NO. | name | GI or Acc. # | Sequence |
|---|---|---|---|
| 305 | Rho-GAP 10 domain 1 | 50345878 | SEDETFSWPGPKTVTLKRTSQGFGFTLRHFIVYPPESA IQFSYKDEENGNRGGKQRNRLEPMDTIFVKQVKEGGPA FEAGLCTGDRIIKVNGESVIGKTYSQVIALIQNSDTTL ELSVMPKDED |
| 306 | Rhophilin domain 1 | AY082588 | SAKNRWRLVGPVHLTRGEGGFGLTLRGDSPVLIAAVIP GSQAAAAGLKEGDYIVSVNGQPCRWWRHAEVVTELKAA GEAGASLQVVSLLPSSRLPS |
| 307 | Rhophilin-like domain 1 | AF268032 | ISFSANKRWTPPRSIRFTAEEGDLGFTLRGNAPVQVHF LDPYCSASVAGAREGDYIVSIQLVDCKWLTLSEVMKLL KSFGEDEIEMKVVSLLDSTSSMHNKSAT |
| 308 | RIM2 domain 1 | 12734165 | TLNEEHSHSDKHPVTWQPSKDGDRLIGRILLNKRLKDG SVPRDSGAMLGLKVVGGKMTESGRLCAFITKVKKGSLA DTVGHLRPGDEVLEWNGRLLQGATFEEVYNIILESKPE PQVELVVSRPIG |
| 309 | SEMCAP 3 domain 2 | 5889526 | QEMDREELELEEVDLYRMNSQDKLGLTVCYRTDDEDDI GIYISEIDPNSIAAKDGRIREGDRIIQINGIEVQNREE AVALLTSEENKNFSLLIARPELQLD |
| 310 | SEMCAP 3 domain 1 | 5889526 | QGEETKSLTLVLHRDSGSLGFNIIGGRPSVDNHDGSSS EGIFVSKIVDSGPAAKEGGLQIHDRIIEVNGRDLSRAT HDQAVEAFKTAKEPIVVQVLRRTPRTKMFTP |
| 311 | semcap2 domain 1 | 7019938 | ILAHVKGIEKEVNVYKSEDSLGLTITDNGVGYAFIKRI KDGGVIDSVKTICVGDHIESINGENIVGWRHYDVAKKL KELKKEELFTMKLIEPKKAFEI |
| 312 | serine protease domain 1 | 2738914 | RGEKKNSSSGISGSQRRYIGVMMLTLSPSILAELQLRE PSFPDVQHGVLIHKVILGSPAHRAGLRPGDVILAIGEQ MVQNAEDVYEAVRTQSQLAVQIRRGRETLTLYV |
| 313 | Shank 1 domain 1 | 6049185 | ILEEKTVVLQKKDNEGFGFVLRGAKADTPIEEFTPTPA FPALQYLESVDEGGVAWQAGLRTGDFLIEVNNENVVKV GHRQVVNMIRQGGNHLVLKVVTVTRNLDPDDNSS |
| 314 | Shank 2 domain 1 | 7025450 | ILKEKTVLLQKKDSEGFGFVLRGAKAQTPIEEFTPTPA FPALQYLESVDEGGVAWRAGLRMGDFLIEVNGQNVVKV GHRQVVNMIRQGGNTLMVKVVMVTRHPDMDEAVQNSS |
| 315 | Shank 3 domain 1 | * | SDYVIDDKVAVLQKRDHEGFGFVLRGAKAETPIEEFTP TPAFPALQYLESVDEGVAWRAGLRTGDFLIEVNGVNV VKVGHKQVVALIRQGGNRLVMKVVSVTRKPEEDG |
| 316 | sim to lig of numb px2 domain 2 | 22477649 | SNSPREEIFQVALHKRDSGEQLGIKLVRRTDEPGVFIL DLLEGGLAAQDGRLSSNDRVLAINGHDLKYGTPELAAQ IIQASGERVNLTIARPGKPQPG |
| 317 | sim to lig of numb px2 domain 3 | 22477649 | IQCVTCQEKHITVKKEPHESLGMTVAGGRGSKSGELPI FVTSVPPHGCLARDGRIKRGDVLLNINGIDLTNLSHSE AVAMLKASAASPAVALKALEVQIVEEAT |
| 318 | Similar to GRASP65 domain 1 | 14286261 | MGLGVSAEQPAGGAEGFHLHGVQENSPAQQAGLEPYFD FIITIGHSRLNKENDTLKALLKANVEKPVKLEVFNMKT MRVREVEVVPSNMWGGQGLLGASVRFCSFRRASE |
| 319 | Similar to GRASP65 domain 2 | 14286261 | RASEQVWHVLDVEPSSPAALAGLRPYTDYVVGSDQILQ ESEDFFTLIESHEGKPLKLMVYNSKSDSCRESGMWHWL WVSTPDPNSAPQLPQEATWHPTTFCSTTWCPTT |
| 320 | Similar to Protein-Tyrosine-Phosphatase Homolog domain 1 | 21595065 | ISVTDGPKFEVKLKKNANGLGFSFVQMEKESCSHLKSD LVRIKRLFPGQPAEENGAIAAGDIILAVNGRSTEGLIF QEVLHLLRGAPQEVTLLLCRPPPGA |
| 321 | SIP1 domain 1 | 2047327 | QPEPLRPRLCRLVRGEQGYGFHLHGEKGRRGQFIRRVE PGSPAEAAALRAGDRLVEVNGVNVEGETHHQVVQRIKA VEGQTRLLVVDQETDEELRRRNSS |
| 322 | SIP1 domain 2 | 2047327 | PLRELRPRLCHLRKGPQGYGENLHSDKSRPGQYIRSVD PGSPAARSGLRAQDRLIEVNGQNVEGLRHAEVVASIKA REDEARLLVVDPETDEHFKRNSS |

TABLE 2-continued

| SEQ ID NO. | name | GI or Acc. # | Sequence |
|---|---|---|---|
| 323 | SITAC 18 domain 1 | 8886071 | PGVREIHLCKDERGKFGLRLRKVDQGLFVQLVQANTPA SLVGLRFGDQLLQIDGRDCAGWSSHKAHQVVKKASGDK IVVVVRDRPFQRTVTM |
| 324 | SITAC 18 domain 2 | 8886071 | PFQRTVTMHKDSMGHVGFVIKKGKIVSLVKGSSAARNG LLTNHYVCEVDGQNVIGLKDKKIMEILATAGNVVTLTI IPSVIYEHIVEFIV |
| 325 | SNPC IIa domain 1 | 20809633 | SLERPRFCLLSKEEGKSFGFHLQQELGRAGHVVCRVDP GTSAQRQGLQEGDRILAVNNDVVEHEDYAVVVRRIRAS SPRVLLTVLARHAHDVARAQ |
| 326 | SYNTENIN domain 2 | 2795862 | LRDRPFERTITMHKDSTGHVGFIFKNGKITSIVKDSSA ARNGLLTEHNICEINGQNVIGLKDSQIADILSTSGTVV TITIMPAFIFEHMNSS |
| 327 | SYNTENIN domain 1 | 2795862 | LEIKQGIREVILCKDQDGKIGLRLKSIDNGIFVQLVQA NSPASLVGLRFGDQVLQINGENCAGWSSDKAHKVLKQA FGEKITMRIHRD |
| 328 | Syntrophin 1 alpha domain 1 | 1145727 | QRRRVTVRKADAGGLGISIKGGRENKMPILISKIFKGL AADQTEALFVGDAILSVNGEDLSSATHDEAVQVLKKTG KEVVLEVKYMKDVSPYFK |
| 329 | Syntrophin beta 2 domain 1 | 476700 | PVRRVRVVKQEAGGLGISIKGGRENRMPILISKIFPGL AADQSRALRLGDAILSVNGTDLRQATHDQAVQALKRAG KEVLLEVKFIRE |
| 330 | Syntrophin gamma 1 domain 1 | 9507162 | EPFYSGERTVTIRRQTVGGFGLSIKGGAEHNIPVVVSK ISKEQRAELSGLLFIGDAILQINGINVRKCRHEEVVQV LRNAGEEVTLTVSFLKRAPAFLKL |
| 331 | Syntrophin gamma 2 domain 1 | 9507164 | SHQGRNRRTVTLRRQPVGGLGLSIKGGSEHNVPVVISK IFEDQAADQTGMLFVGDAVLQVNGIHVENATHEEVVHL LRNAGDEVTITVEYLREAPAFLK |
| 332 | TAX2-like protein domain 1 | 3253116 | RGETKEVEVTKTEDALGLTITDNGAGYAFIKRIKEGSI INRIEAVCVGDSIEAINDHSIVGCRHYEVAKMLRELPK SQPFTLRLVQPKRAF |
| 333 | TIAM1 domain 1 | 4507500 | HSIHIEKSDTAADTYGFSLSSVEEDGIRRLYVNSVKET GLASKKGLKAGDEILEINNRAADALNSSMLKDFLSQPS LGLLVRTYPELE |
| 334 | TIAM2 domain 1 | 6912703 | PLNVYDVQLTKTGSVCDFGFAVTAQVDERQHLSRIFIS DVLPDGLAYGEGLRKGNEIMTLNGEAVSDLDLKQMEAL FSEKSVGLTLIARPPDTKATL |
| 335 | TIP1 domain 1 | 2613001 | QRVEIHKLRQGENLILGFSIGGGIDQDPSQNPFSEDKT DKGIYVTRVSEGGPAEIAGLQIGDKIMQVNGWDMTMVT HDQARKRLTKRSEEVVRLLVTRQSLQK |
| 336 | TIP2 domain 1 | 2613003 | RKEVEVFKSEDALGLTITDNGAGYAFIKRIKEGSVIDH IHLISVGDMIEAINGQSLLGCRHYEVARLLKELPRGRT FTLKLTEPRK |
| 337 | TIP33 domain 1 | 2613007 | HSHPRVVELPKTDEGLGFNVMGGKEQNSPIYISRIIPG GVAERHGGLKRGDQLLSVNGVSVEGEHHEKAVELLKAA KDSVKLVVRYTPKVL |
| 338 | TIP43 domain 1 | 2613011 | LSNQKRGVKVLKQELGGLGISIKGGKENKMPILISKIF KGLAADQTQALYVGDAILSVNGADLRDATHDEAVQALK RAGKEVLLEVKYMREATPYVK |
| 339 | Unknown PDZ domain 1 | 22382223 | IQRSSIKTVELIKGNLQSVGLTLRLVQSTDGYAGHVII ETVAPNSPAAIADLQRGDRLIAIGGVKITSTLQVLKLI KQAGDRVLVYYERPVGQSNQGA |
| 340 | Vartul domain 1 | 1469875 | ILTLTILRQTGGLGISIAGGKGSTPYKGDDEGIFISRV SEEGPAARAGVRVGDKLLEVNGVALQGAEHHEAVEALR GAGTAVQMRVWRERMVEPENAEFIVTD |
| 341 | Vartul domain 4 | 1469875 | RELCIQKAPGERLGISIRGGARGHAGNPRDPTDEGIFI SKVSPTGAAGRDGRLRVGLRLLEVNQQSLLGLTHGEAV QLLRSVGDTLTVLVCDGFEASTDAALEVS |

TABLE 2-continued

| SEQ ID NO. | name | GI or Acc. # | Sequence |
|---|---|---|---|
| 342 | Vartul domain 3 | 1469875 | LEGPYPVEEIRLPRAGGPLGLSIVGGSDHSSHPFGVQE PGVFISKVLPRGLAARSGLRVGDRILAVNGQDVRDATH QEAVSALLRPCLELSLLVRRDPAEFIVTD |
| 343 | Vartul domain 2 | 1469875 | PLRQRHVACLARSERGLGFSIAGGKGSFPYRAGDAGIF VSRIAEGGAAHRAGTLQVGDRVLSINGVDVTEARHDHA VSLLTAASPTIALLLEREAGG |
| 344 | Vartul domains 1 and 2 | 1469875 | TLTILRQTGGLGISIAGGKGSTPYKGDDEGIFISRVSE EGPAARAGVRVGDKLLEGIFVSRIAEGGAAHRAGTLQV GDRVLSINGVDVTEARHDHAVSLLTAASPTIALLLERE |
| 345 | X-11 beta domain 2 | 3005559 | IPPVTTVLIKRPDLKYQLGESVQNGIICSLMRGGIAER GGVRVGHRIIEINGQSVVATAHEKIVQALSNSVGEIHM KTMPAAMFRLLTGQENSSL |
| 346 | X-11 beta domain 1 | 3005559 | IHFSNSENCKELQLEKHKGEILGVVVVESGWGSILPTV ILANMMNGGPAARSGKLSIGDQIMSINGTSLVGLPLAT CQGIIKGLKNQTQVKLNIVSCPPVTTVLIKRNSS |
| 347 | ZO-1 domain 1 | 292937 | IWEQHTVTLHRAPGEGFGIAISGGRDNPHFQSGETSIV ISDVLKGGPAEGQLQENDRVAMVNGVSMDNVEHAFAVQ QLRKSGKNAKITIRRKKKVQIPNSS |
| 348 | ZO-1 domain 2 | 292937 | ISSQPAKPTKVTLVKSRKNEEYGLRLASHIFVKEISQD SLAARDGNIQEGDVVLKINGTVTENMSLTDAKTLIERS KGKLKMVVQRDRATLLNSS |
| 349 | ZO-1 domain 3 | 292937 | IRMKLVKFRKGDSVGLRLAGGNDVGIFVAGVLEDSPAA KEGLEEGDQILRVNNVDFTNIIREEAVLFLLDLPKGEE VTILAQKKKDVFSN |
| 350 | ZO-2 domain 1 | 12734763 | IQHTVTLHRAPGFGFGIAISGGRDNPHFQSGETSIVIS DVLKGGPAEGQLQENDRVAMVNGVSMDNVEHAFAVQQL RKSGKNAKITIRRKKKVQIPNSS |
| 351 | ZO-2 domain 3 | 12734763 | HAPNTKMVRFKKGDSVGLRLAGGNDVGIFVAGIQEGTS AEQEGLQEGDQILKVNTQDFRGLVREDAVLYLLEIPKG EMVTILAQSRADVY |
| 352 | ZO-2 domain 2 | 12734763 | RVLLMKSRANEEYGLRLGSQIFVKEMTRTGLATKDGNL HEGDIILKINGTVTENMSLTDARKLIEKSRGKLQLVVL RDS |
| 353 | ZO-3 domain 3 | 10092690 | RGYSPDTRVVRFLKGKSIGLRLAGGNDVGIFVSGVQAG SPADGQGIQEGDQILQVNDVPFQNLTREEAVQFLLGLP PGEEMELVTQRKQDIFWKMVQSEFIVTD |
| 354 | ZO-3 domain 1 | 10092690 | IPGNSTIWEQHTATLSKDPRRGFGIAISGGRDRPGGSM VVSDVVPGGPAEGRLQTGDHIVMVNGVSMENATSAFAI QILKTCTKMANITVKRPRRIHLPAEFIVTD |
| 355 | ZO-3 domain 2 | 10092690 | QDVQMKPVKSVLVKRRDSEEFGVKLGSQIFIKHITDSG LAARHRGLQEGDLILQINGVSSQNLSLNDTRRLIEKSE GKLSLLVLRDRGQFLVNIPNSS |

*: No GI number for this PDZ domain containing protein as it was computer cloned using rat Shank3 sequence against human genomic clone AC000036 and in silico spliced together nucleotides 6400-6496, 6985-7109, 7211-7400 to create hypothetical human Shank3.

Methods for Detecting the Presence of an Oncogenic HPV E6 Protein in a Sample

The invention provides a method of detecting the presence of an oncogenic HPV E6 protein in a sample. In general, the method involves contacting a biological sample containing or potentially containing an oncogenic HPV E6 protein with a PDZ domain polypeptide and detecting any binding of the oncogenic HPV E6 protein in said sample to the PDZ domain polypeptide using a subject antibody. In alternative embodiments, a sample may be contacted with a subject antibody, and the presence of the E6 protein may be detected using the PDZ domain polypeptide. In most embodiments, binding of an oncogenic HPV E6 protein to the PDZ domain polypeptide and a subject antibody indicates the presence of an oncogenic HPV E6 protein in the sample.

Biological samples to be analyzed using the methods of the invention may be obtained from any mammal, e.g., a human or a non-human animal model of HPV. In many embodiments, the biological sample is obtained from a living subject.

In some embodiments, the subject from whom the sample is obtained is apparently healthy, where the analysis is performed as a part of routine screening. In other embodiments, the subject is one who is susceptible to HPV, (e.g., as determined by family history; exposure to certain environmental factors; etc.). In other embodiments, the subject has symptoms of HPV (e.g., cervical warts, or the like). In other embodiments, the subject has been provisionally diagnosed as having HPV (e.g. as determined by other tests based on e.g., PCR).

The biological sample may be derived from any tissue, organ or group of cells of the subject. In some embodiments a cervical scrape, biopsy, or lavage is obtained from a subject. In other embodiments, the sample is a blood or urine sample.

In some embodiments, the biological sample is processed, e.g., to remove certain components that may interfere with an assay method of the invention, using methods that are standard in the art. In some embodiments, the biological sample is processed to enrich for proteins, e.g., by salt precipitation, and the like. In certain embodiments, the sample is processed in the presence proteasome inhibitor to inhibit degradation of the E6 protein.

In the assay methods of the invention, in some embodiments, the level of E6 protein in a sample may be quantified and/or compared to controls. Suitable control samples are from individuals known to be healthy, e.g., individuals known not to have HPV. Control samples can be from individuals genetically related to the subject being tested, but can also be from genetically unrelated individuals. A suitable control sample also includes a sample from an individual taken at a time point earlier than the time point at which the test sample is taken, e.g., a biological sample taken from the individual prior to exhibiting possible symptoms of HPV.

In certain embodiments, a sample is contacted to a solid support-bound PDZ domain polypeptide under conditions suitable for binding of the PDZ domain polypeptide to any PL proteins in the sample, and, after separation of unbound sample proteins from the bound proteins, the bound proteins are detected using the subject antibody using known methods.

Kits

The present invention also includes kits for carrying out the methods of the invention. A subject kit usually contains a subject antibody. In many embodiments, the kits contain a first and second binding partner, where the first binding partner is a PDZ domain polypeptide and the second binding partner is a subject antibody. In some embodiments, the second binding partner is labeled with a detectable label. In other embodiments, a secondary labeling component, such as a detectably labeled secondary antibody, is included. In some embodiments, a subject kit further comprises a means, such as a device or a system, for isolating oncogenic HPV E6 from the sample. The kit may optionally contain proteasome inhibitor.

A subject kit can further include, if desired, one or more of various conventional components, such as, for example, containers with one or more buffers, detection reagents or antibodies. Printed instructions, either as inserts or as labels, indicating quantities of the components to be used and guidelines for their use, can also be included in the kit. In the present disclosure it should be understood that the specified materials and conditions are important in practicing the invention but that unspecified materials and conditions are not excluded so long as they do not prevent the benefits of the invention from being realized. Exemplary embodiments of the diagnostic methods of the invention are described above in detail.

In a subject kit, the oncogenic E6 detection reaction may be performed using an aqueous or solid substrate, where the kit may comprise reagents for use with several separation and detection platforms such as test strips, sandwich assays, etc. In many embodiments of the test strip kit, the test strip has bound thereto a PDZ domain polypeptide that specifically binds the PL domain of an oncogenic E6 protein and captures oncogenic E6 protein on the solid support. The kit usually comprises a subject antibody for detection, which is either directly or indirectly detectable, and which binds to the oncogenic E6 protein to allow its detection. Kits may also include components for conducting western blots (e.g., pre-made gels, membranes, transfer systems, etc.); components for carrying out ELISAs (e.g., 96-well plates); components for carrying out immunoprecipitation (e.g. protein A); columns, especially spin columns, for affinity or size separation of oncogenic E6 protein from a sample (e.g. gel filtration columns, PDZ domain polypeptide columns, size exclusion columns, membrane cut-off spin columns etc.).

Subject kits may also contain control samples containing oncogenic or non-oncogenic E6, and/or a dilution series of oncogenic E6, where the dilution series represents a range of appropriate standards with which a user of the kit can compare their results and estimate the level of oncogenic E6 in their sample. Such a dilution series may provide an estimation of the progression of any cancer in a patient. Fluorescence, color, or autoradiological film development results may also be compared to a standard curves of fluorescence, color or film density provided by the kit.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also provided by the subject invention are kits including at least a computer readable medium including programming as discussed above and instructions. The instructions may include installation or setup directions. The instructions may include directions for use of the invention with options or combinations of options as described above. In certain embodiments, the instructions include both types of information.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

Utility

The antibodies and methods of the instant invention are useful for a variety of diagnostic analyses. The instant antibodies and methods are useful for diagnosing infection by an oncogenic strain of HPV in an individual; for determining the likelihood of having cancer; for determining a patient's response to treatment for HPV; for determining the severity of HPV infection in an individual; and for monitoring the progression of HPV in an individual. The antibodies and the methods of the instant invention are useful in the diagnosis of infection with an oncogenic or a non-oncogenic strain of HPV associated with cancer, including cervical, ovarian, breast, anus, penis, prostate, larynx and the buccal cavity, tonsils, nasal passage, skin, bladder, head and neck squamous-cell, occasional periungal carcinomas, as well as benign anogenital warts. The antibodies and the methods of the instant invention are useful in the diagnosis of infection with an oncogenic or a non-oncogenic strain of HPV associated with Netherton's syndrome, epidermolysis verruciformis, endometriosis, and other disorders. The antibodies and the methods of the instant invention are useful in the diagnosis of infection with an oncogenic or a non-oncogenic strain of HPV in adult women, adult men, fetuses, infants, children, and immunocompromised individuals.

The subject methods may generally be performed on biological samples from living subjects. A particularly advantageous feature of the invention is that the methods can simultaneously detect, in one reaction, several known oncogenic strains of HPV.

In particular embodiments, the antibodies of the invention may be employed in immunohistological examination of a sample.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Sequence Analysis of HPV E6 Proteins to Determine Oncogenic Potential

PDZ proteins are known to bind certain carboxyl-terminal sequences of proteins (PLs). PL sequences that bind PDZ domains are predictable, and have been described in greater detail in U.S. patent application Ser. Nos. 09/710,059, 09/724,553 and 09/688,017. One of the major classes of PL motifs is the set of proteins terminating in the sequences -X-(S/T)-X-(V/I/L). We have examined the C-terminal sequences of E6 proteins from a number of HPV strains. All of the strains determined to be oncogenic by the National Cancer Institute exhibit a consensus PDZ binding sequence. Those E6 proteins from papillomavirus strains that are not cancerous lack a sequence that would be predicted to bind to PDZ domains, thus suggesting that interaction with PDZ proteins is a prerequisite for causing cancer in humans. This correlation between presence of a PL and ability to cause cancer is 100 % in the sequences examined (Table 3 A). In theory, with the disclosed PL consensus sequences from the patents listed supra, new variants of HPVs can be assessed for their ability to bind PDZ proteins and oncogenicity can be predicted on the basis of whether a PL is present. Earlier this year, five new oncogenic strains of Human papillomavirus were identified and their E6 proteins sequenced. As predicted, these proteins all contain a PL consensus sequence (Table 3 B).

TABLE 3A

Correlation of E6 PDZ-ligands and oncogenicity

| HPV strain | E6 C-terminal sequence | PL yes/no | Onco-genic | Seq ID No |
|---|---|---|---|---|
| HPV 4 | GYCRNCIRKQ | No | No | 33 |
| HPV 11 | WTTCMEDLLP | No | No | 34 |
| HPV 20 | GICRLCKHFQ | No | No | 35 |
| HPV 24 | KGLCRQCKQI | No | No | 36 |
| HPV 28 | WLRCTVRIPQ | No | No | 37 |
| HPV 36 | RQCKHFYNDW | No | No | 38 |
| HPV 48 | CRNCISHEGR | No | No | 39 |
| HPV 50 | CCRNCYEHEG | No | No | 40 |
| HPV 16 | SSRTRRETQL | Yes | Yes | 41 |
| HPV 18 | RLQRRRETQV | Yes | Yes | 42 |
| HPV 31 | WRRPRTETQV | Yes | Yes | 43 |
| HPV 35 | WKPTRRETEV | Yes | Yes | 44 |
| HPV 30 | RRTLRRETQV | Yes | Yes | 45 |
| HPV 39 | RRLTRRETQV | Yes | Yes | 46 |
| HPV 45 | RLRRRRETQV | Yes | Yes | 47 |
| HPV 51 | RLQRRNETQV | Yes | Yes | 48 |
| HPV 52 | RLQRRRVTQV | Yes | Yes | 49 |
| HPV 56 | TSREPRESTV | Yes | Yes | 50 |
| HPV 59 | QRQARSETLV | Yes | Yes | 51 |
| HPV 58 | RLQRRRQTQV | Yes | Yes | 52 |
| HPV 33 | RLQRRRETAL | Yes | Yes | 53 |
| HPV 66 | TSRQATESTV | Yes | Yes* | 54 |
| HPV 68 | RRRTRQETQV | Yes | Yes | 55 |
| HPV 69 | RRREATETQV | Yes | Yes | 56 |
| HPV 34 | QCWRPSATVV | Yes | Yes | 356 |
| HPV 67 | WRPQRTQTQV | Yes | Yes | 357 |
| HPV 70 | RRRIRRETQV | Yes | Yes | 358 |

Table 3A: E6 C-terminal sequences and oncogenicity.
HPV variants are listed at the left.
Sequences were identified from Genbank sequence records.
PL Yes/No was defined by a match or non-match to the consenses determined by the inventors and by Songyang et al. -X-(S/T)-X-(V/I/L).
Oncogenicity data collected from National Cancer Institute; Kawashima et al. (1986) J. Virol. 57:688-692; Kirii et al. (1998) Virus Genes 17:117-121; Forslund et al. (1996) J. Clin. Microbiol. 34:802-809.
*Only found in oncogenic strains co-transfected with other oncogenic proteins.

TABLE 3B

Correlation of recently identified oncogenic E6 proteins

| HPV strain | E6 C-terminal sequence | PL yes/no | onco-genic | Seq ID No |
|---|---|---|---|---|
| HPV 26 | RPRRQTETQV | Yes | Yes | 63 |
| HPV 53 | RHTTATESAV | Yes | Yes | 64 |
| HPV 66 | TSRQATESTV | Yes | Yes | 65 |
| HPV 73 | RCWRPSATVV | Yes | Yes | 66 |
| HPV 82 | PPRQRSETQV | Yes | Yes | 67 |

Table 3B: E6 C-terminal sequences and oncogenicity.
HPV variants are listed at the left.
Sequences were identified from Genbank sequence records.
PL Yes/No was defined by a match or non-match to the consensus sequence: -X-(S/T)-X-(V/I/L).
Oncogenicity data on new strains collected from N Engl J Med 2003; 348:518-527.

These tables provide a classification of the HPV strains based on the sequence of the C-terminal four amino acids of the E6 protein encoded by the HPV genome. The 21 oncogenic strains of HPV fall into one of 11 classes (based on the C-terminal four amino acids), and HPV strains not specifically listed above may also fall into these classes. As such, it is desirable to detect HPV strains from all 11 classes: the instant methods provide such detection.

A cross-reactive antibody of the invention may recognize E6 proteins from HPV strains of multiple (e.g., 2, 3, 4, 5, 6, or 7 or more different) classes.

Example 2

Identification of PDZ Domains that Interact with the C-Termini of Oncogenic E6 Proteins In order to determine the PDZ domains that can be used to detect oncogenic E6 proteins in a diagnostic assay, the assay was used to identify interactions between E6 PLs and PDZ domains. Peptides were synthesized corresponding to the C-terminal amino acid sequences of E6 proteins from oncogenic strains of human papillomavirus. These peptides were assessed for the ability to bind PDZ domains using an assay and PDZ proteins synthesized from the expression constructs described in greater detail in U.S. patent application Ser. Nos. 09/710,059, 09/724,553 and 09/688,017. Results of these assays that show a high binding affinity are listed in Table 4 below.

As we can see below, there a large number of PDZ domains that bind some of the oncogenic E6 proteins and the second PDZ domain from MAGI-1 binds all of the oncogenic E6 PLs tested. The PDZ domain of TIP-1 binds all but one of the oncogenic E6 PLs tested, and may be useful in conjunction with MAGI-1 domain 2 for detecting the presence of oncogenic E6 proteins.

In a similar manner, peptides corresponding to the C-terminal ends of several non-oncogenic E6 proteins were tested with assay. None of the peptides showed any affinity for binding PDZ domains.

TABLE 4 higher affinity interactions between HPV E6 PLs and PDZ domains

| HPV strain | PDZ binding partner (signal 4 and 5 of 0-5) | HPV strain | PDZ binding partner (signal 4 and 5 of 0-5) |
|---|---|---|---|
| HPV 35 (T E V) | Atrophin-1 interact. prot. (PDZ # 1, 3, 5)<br>Magi1 (PDZ # 2, 3, 4, 5)<br>Lim-Ril<br>FLJ 11215<br>MUPP-1 (PDZ #10)<br>KIAA 1095 (PDZ #1)<br>PTN-4<br>INADL (PDZ #8)<br>Vartul (PDZ # 1, 2, 3)<br>Syntrophin-1 alpha<br>Syntrophin gamma-1<br>TAX IP2<br>KIAA 0807<br>KIAA 1634 (PDZ #1)<br>DLG1 (PDZ1, 2)<br>NeDLG (1, 2, 3,)<br>Sim. Rat outer membrane (PDZ #1)<br>MUPP-1 (PDZ #13)<br>PSD 95 (1, 2, 3) | HPV 33 (T A L) | Magi1 (PDZ #2)<br>TIP1<br>DLG1<br>Vartul (PDZ #1)<br>KIAA 0807<br>KIAA 1095 (Semcap3) (PDZ #1)<br>KIAA 1934 (PDZ #1)<br>NeDLG (PDZ #1, 2)<br>Rat outer membrane (PDZ #1)<br>PSD 95 (PDZ #3 and 1-3) |
| HPV 58 (T Q V) | Atrophin-1 interact. prot. (PDZ # 1)<br>Magi1 (PDZ #2)<br>DLG1 (PDZ1, 2)<br>DLG2 (PDZ #2)<br>KIAA 0807<br>KIAA 1634 (PDZ #1)<br>NeDLG (1, 2)<br>Sim. Rat outer membrane (PDZ #1)<br>PSD 95 (1, 2, 3)<br>INADL (PDZ #8)<br>TIP-1 | HPV 66 (S T V) | DLG1 (PDZ #1, 2)<br>NeDLG (PDZ #2)<br>PSD 95 (PDZ #1, 2, 3)<br>Magi1 (PDZ #2)<br>KIAA 0807<br>KIAA 1634 (PDZ #1)<br>DLG2 (PDZ #2)<br>Rat outer membrane (PDZ #1)<br>NeDLG (1, 2)<br>TIP-1 |
| HPV 16* (T Q L)<br>HPV 18* (T Q V) | TIP-1<br>Magi1 (PDZ #2)<br>TIP1<br>Magi1 (PDZ #2) | HPV 52 (T Q V) | Magi1 (PDZ #2) |

Table 4: Interactions between the E6 C-termini of several HPV variants and human PDZ domains. HPV strain denotes the strain from which the E6 C-terminal peptide sequence information was taken. Peptides used in the assay varied from 18 to 20 amino acids in length, and the terminal four residues are listed in parenthesis. Names to the right of each HPV E6 variant denote the human PDZ domain(s) (with domain number in parenthesis for proteins with multiple PDZ domains) that saturated binding with the E6 peptide in assay *denotes that the PDZ domains of hDlg1 were not tested against these proteins yet due to limited material, although both have been shown to bind hDlg1 in the literature.

The subject antibodies may be used with these oncogenic HPV E6-binding PDZ proteins in methods of detecting oncogenic strains of HPV.

Materials and Methods for Examples 3-7

Immunization protocol: Five 8 week-old female BALB/c mice are immunized intraperitoneally, in the footpad, or subcutaneously on day zero with 20 μg of MBP-E6 fusion protein or 100 μg of E6 conjugated-peptide and 20 μg of polyI/polyC polymer or complete Freund's adjuvant. Animals are boosted with 20 μg of E6 protein and polyI/polyC or incomplete Freund's adjuvant. Test bleeds are performed 3 days after the last boost and screened by ELISA against the corresponding E6 protein. Immunoreactive mice have a final boost three days prior to fusion.

ELISA screening of serum antibody titer and B cell hybridoma supernatants: ELISA plates are coated with appropriate fusion protein, washed, and blocked with PBS containing 2% BSA (Sigma). Then the test sample (immune sera or hybridoma supernatant) is added, along with a pre-immune or irrelevant supernatant negative control. After incubation the plate is washed and anti-mouse IgG-HRP conjugate (Jackson Laboratories) in PBS/2 % BSA is added.

After thorough washing, TMB substrate is added for 30 minutes, followed by termination of the reaction with 0.18 M $H_2SO_4$. The plate is then read at 450 nm using a Molecular Devices' THERMO Max microplate reader.

Fusion: On the day of fusion, the animals are sacrificed, blood collected, and the spleens excised and minced with scissors. The cells are then gently teased up and down with a pipette, filtered through a sterile 70 μm nylon filter and washed by centrifugation. Splenocytes and the FOX-NY myeloma partner (maintained prior to fusion in log growth) are resuspended in serum-free-RPMI medium, combined at a ratio of 4:1 and spun down together. The fusion is then performed by adding 1 ml of 50 % PEG (Sigma) drop-wise over one minute, followed by stirring the cells for one minute. Then 2 ml of RPMI/15 % FCS media is added drop-wise over two minutes, followed by 8 ml of RPMI/15 % FCS over 2 minutes with constant stirring. This mixture is centrifuged, and the cells are gently resuspended at $10^8$ cells/ml in RPMI/15 % FCS+1 × HAT media (Sigma) and plated out in 96-well flat bottom plates at 200 μl/well. After 5 days ~100 μl old medium is replaced by aspirating out of wells, and adding 100 μl fresh RPMI/HAT medium. Hybridomas are kept in RPMI/HAT for ~7 days. Then are grown in RPMI/15 % FCS containing 1 × HT for ~1 week. Wells are assayed for antibody activity by ELISA when they are 10-30 % confluent.

Hybridoma cloning, antibody purification and isotyping: Wells whose supernatants give the desired activity were selected for cloning. Cells are cloned by limiting dilution in a 96-well flat bottom plate. Purification of antibodies from tissue culture supernatants is performed by protein G and A affinity chromatography (Amersham). The isotype of the antibodies is determined using Cytometric bead array.

Cell lines: Cervical cancer cell lines expressing listed strains of HPV E6 were purchased from ATCC, and are shown in the following table:

| ATCC Name | Common Name | Organism | Tissue | E6 type | GenBank Accession # |
|---|---|---|---|---|---|
| HTB-31 | C-33A | human | cervix | None | |
| HTB-32 | HT-3 | human | cervix | 30 | |
| HTB-33 | ME-180 | human | cervix | 68b | M73258 |
| HTB-34 | MS751 | human | cervix | 45 | X74479 |
| HTB-35 | SiHa | human | cervix | 16 | |
| CRL-1550 | CaSki | human | cervix | 16 | |
| CRL-1594 | C-41 | human | cervix | 18 | |
| CRL-1595 | C-4-II | human | cervix | 18 | |

Stably or transiently transfected cells were produced using the following methods:

The following stable cell lines were made: 3 A-HA-E6-26 (expresses HPV 26 E6); C33A-HA-E6-53 (expresses HPV 53 E6); C33 A-HA-E6-58 (expresses HPV 58 E6); C33 A-HA-E6-59 (expresses HPV 59 E6); C33 A-HA-E6-66 (expresses HPV 66 E6); C33 A-HA-E6-69 (expresses HPV 69 E6) and C33 A-HA-E6-73 (expresses HPV 73 E6).

Calcium Phosphate Transfection of Mammalian Cell Lines

Materials: Deionized water, 2 M $CaCl_2$, 2 × HBS pH 7.1, 25 mM Chloroquine (1000 ×), DNA.

Day 0: Plate 0.8 million cells in each well of a 6-well plate the night before transfection. (2 wells for each construct, therefore, 3 constructs in a 6-well plate)

Day 1: a) Aliquot appropriate cell media and add Chloroquine (Add 12.5 μl for every 10 ml of media. The extra 2.5 μl is to account for the 500 ul of the calcium phosphate+ DNA solution that will be added to the cells later). b) Aspirate media off the cells and add 2 mL of the media+ Chloroquine solution. Return cells to incubator. c) In a 5 mL polypropylene tube, add the following in the order listed: i) deionized water, ii) DNA and iii) 2 M $CaCl_2$ as follows:

| DNA | Deionized water | 2M CaCl2 | 2X HBS |
|---|---|---|---|
| 10 μg | (DNA + 64 + dH20 = 500 μl | 64 μl | 500 μl | d) Add 500 μl of the DNA mix drop wise to the 2 × HBS while bubbling with automatic pipetman and Pasteur pipette; e) Add 500 μl DNA/calcium/phosphate solution to each well; and f) Incubate in incubator for 8 hours, then replace media with normal growth media.

Day 3: Start selection with G-418 (Gibco) at 1 mg/ml

Cells for transient expression of HPV 51 E6 were produced by standard methods.

Example 3

HPV-E6 Recombinant Protein Expression and Purification

Polynucleotides encoding E6 proteins of high-risk HPV types listed above were chemically synthesized (DNA 2.0, Menlo Park, Calif.) or cloned via RT-PCR from cervical cancer cell lines. Both maltose-binding-protein-E6 (MBP-E6) and glutathione-S-transferase-E6 (GST-E6) fusion protein types were used. Production of GST-E6 and MBP-E6 proteins were by standard protocols recommended by the suppliers (Amersham and New England Biolabs, respectively). Proteins were expressed in DH5α *E. coli* using IPTG driven induction. A 2 h induction at 37° C. yielded GST-E6 or MBP-E6 recombinant proteins at ~1 mg/L, whereas induction overnight at 20 ° C. and purification including rebinding of protein to the gel matrix resulted in final yield of 2-10 mg/L. Purity of MBP-E6 proteins was estimated to be >90 % based on PAGE analysis. Recombinant E6 fusion proteins were used as immunogens.

Example 4

Immunization, Fusion, Screening and Cloning of Hybridomas Secreting Monoclonal Antibodies Against E6 Protein Mice were immunized with each of the HPV E6 proteins. A variety of immunization protocols including varying antigen doses (100 μg-10 μg), adjuvants (CFA/IFA, poly(I)-poly (C), CpG+Alum) and routes (subcutaneous, intraperitoneal) were tested. A service facility for animal care, handling of immunizations and sera collection was contracted (Josman, Napa, Calif.). Immunization projects were set up with 5-15 mice each. Sera of immunized mice were tested in ELISA against the recombinant E6 protein. Mice showing sufficiently high titers (OD above 1 at 1:1000 dilution) against E6 in their sera were selected for fusions.

To increase the frequency of hybridomas secreting of anti-E6 antibodies, the recombinant E6 protein used in the final boost contained a different tag from that used during the immunization (GST-E6 was used in the boost when immunizations occurred with MBP-E6, and vice versa)

Example 5

Spleen Cells of Selected Mice were Fused

Hybridoma supernatants were tested via direct antigen ELISA against the MBP-E6 used in the immunization and MBP protein as negative control. Supernatants that showed reactivity for MBP-E6 (immunogen) but not for MBP were selected for further analysis. Selected supernatants were tested further by slot western blot for reactivity against recombinant MBP-E6 and GST-E6, to reconfirm presence of anti-E6 mAb. At this stage, hybridomas were cloned by limiting dilution to isolate hybridoma clones secreting anti-E6 mAb.

To further characterize the reactivity of the hybridomas, selected supernatants were tested in an ELISA against the recombinant E6 proteins, as well as GST-INADL (PDZ) and GST-MAGI1-PDZ1 that served as negative controls. GST-INADL represents a class of proteins that, when purified in prokaryotic expression systems, tend to be associated with a bacterial contaminating that are also present in the MBP-/GST-E6 protein preparations used for immunizations. This control ensured that reactivity found in supernatants reflected a mAb binding to HPV-E6, and not against the associated contaminants.

Example 6

Cross-Reactivity Pattern of Anti-E6 Monoclonal Antibodies

The cross-reactivity pattern of anti-E6 mAbs against E6 proteins other than the one used as immunogen was tested. For this E6 panel test, a direct ELISA approach is used (recombinant E6 protein is coated on the plate).

Monoclonal antibodies against the E6 protein of high-risk HPV types that cause cervical cancer (e.g., HPV 16, 18, 26, 30, 31, 34, 45, 51, 52, 53, 58, 59, 66, 68b, 69, 70, 73, 82) were produced.

A summary of results showing cross-reactivity of the antibodies produced is shown In Table 5 below.

TABLE 5

| mAb designation | HPV-E6 type binding profile - direct ELISA | HPV-E6 binding profile S2 ELISA | Endogenous E6 detection S2 ELISA | Immunogen and boosts/last boost | Immunization route and adjuvant |
| --- | --- | --- | --- | --- | --- |
| F12-1B9 | 18, 45, 66 | N.D. | N.D. | HPV18-[MBP]-E6/ | subcutaneous/Adjuvant: |
| F12-1C9 | 18 | N.D. | N.D. | HPV18-[GST]-E6 | complete/incomplete |
| F12-1H12 | 18 | N.D. | N.D. | | Freund's (initial/follow up |
| F12-2D2 | 18, 45, 66 | N.D. | N.D. | | injections) |
| F12-3B2 | 18 | N.D. | N.D. | | |
| F12-3D5 | 18, 45, 66, 82 | 18, 45 | 18, 45 | | |
| F12-4A11 | 18 | 18 | 18 | | |
| F12-4 E2 | 18 | 18, 45 | N.D. | | |
| F12-5C2 | 18 | N.D. | N.D. | | |
| F12-6D9 | 18, 45 | N.D. | N.D. | | |
| F12-6F5 | 18 | N.D. | N.D. | | |
| F12-6F6 | 18, 45 | N.D. | N.D. | | |
| F12-6H2 | 18, 45, 66, 82 | N.D. | N.D. | | |
| F12-7A10 | 18, 45 | N.D. | N.D. | | |
| F12-7F10 | 18 | N.D. | N.D. | | |
| F12-8A3 | 18, 45 | N.D. | N.D. | | |
| F12-8B8 | 18 | N.D. | N.D. | | |
| F16-4H12 | 16, 35 | 16 | N.D. | HPV16-[MBP]-E6/ | subcutaneous/Adjuvant: |
| F16-5D5 | 16, 35 | 16 | does not recognize 16 | HPV16-[GST]-E6 | complete/incomplete Freund's (initial/follow up injections) |
| F17-1 E11 | 26, 51, 52, 53, 58 | N.D. | N.D. | HPV58-[MBP]-E6/ | subctaneous/Adjuvant: |
| F17-6G9 | 33, 58 | 58 | does not recognize 58 | HPV58-[GST]-E6 | complete/incomplete Freund's (initial/follow up injections) |
| F18-3G11 | 16 | 16 | does not recognize 16 | HPV16-[GST]-E6/ HPV16-[MBP]-E6 | subcutaneous/Adjuvant: complete/incomplete |
| F18-4C9 | 16 | N.D. | N.D. | | Freund's (initial/follow up |
| F18-5H3 | 16 | N.D. | N.D. | | injections) |
| F18-7H8 | 16 | N.D. | N.D. | | |
| F18-8G11 | 16 | N.D. | N.D. | | |
| F18-9B10 | 16, 73 | N.D. | N.D. | | |
| F18-10 E6 | 16 | 16 | 16 | | |
| F18-10 E10 | 16 | N.D. | N.D. | | |
| F19-6D10 | 18, 68b | 18, 68b | does not recognize 18 or 68b | DNA plasmid immunization; boost with HPV18-E6 (MBP-E6/GST-E6) | |
| F19-6F9 | 18, 68b | 18, 68b | N.D. | | |
| F19-7B12 | 18, 35, 68b | N.D. | N.D. | | |
| F19-7C7 | 18, 68b | N.D. | N.D. | | |
| F19-8E2 | 18, 35, 68b | N.D. | N.D. | | |
| F20-2H5 | 16, 18, 35, 45 | 18, 35, 45 | does not recognize 18 or 45; 35 N.D. | HPV45-[MBP]-E6/ HPV45-[GST]-E6 | subcutaneous/Adjuvant: complete/incomplete Freund's (initial/follow up injections) |
| F21-1D12 | 18, 30, 52, 58 | 30, 58 | does not recognize 30 or 58 | HPV58-[MBP]-E6/ HPV58-[GST]-E6 | footpad injection/Adjuvant: CpG-ALUM |

TABLE 5-continued

| mAb designation | HPV-E6 type binding profile - direct ELISA | HPV-E6 binding profile S2 ELISA | Endogenous E6 detection S2 ELISA | Immunogen and boosts/last boost | Immunization route and adjuvant |
|---|---|---|---|---|---|
| F21-3A3 | 18, 58 | N.D. | N.D. | | |
| F21-3H2 | 18, 30, 52, 58 | 58 | N.D. | | |
| F21-4 E10 | 18, 30, 52, 58 | 58 | N.D. | | |
| F21-4F9 | 18, 33, 58 | N.D. | N.D. | | |
| F21-4H1 | 18, 30, 33, 52, 58 | 33, 58 | 33, 58 | | |
| F21-5B2 | 16, 18, 30, 52, 58, 59, 68b | N.D. | N.D. | | |
| F22-1C12 | 26, 51, 69 | 51 | 51 | HPV51-[MBP]-E6/ | subctaneous/Adjuvant: |
| F22-10D11 | 26, 30, 31, 35, 51, 53, 66, 69, 82 | N.D. | N.D. | HPV51-[GST]-E6 | complete/incomplete Freund's (initial/follow up injections) |
| F22-10F10 | 26, 51, 69 | 51 | N.D. | | |
| F24-2D6 | 26, 51, 69, 82 | 26, 69 | 26, 69 | HPV69-[MBP]-E6/ | subcutaneous/Adjuvant: |
| F24-4B12 | 26, 51, 53, 69, 73, 82 | N.D. | N.D. | HPV69-[GST]-E6 | complete/incomplete Freund's (initial/follow up injections) |
| F24-4F2 | 26, 51, 69, 82 | 26, 69, 82 | 26, 69; 82 N.D. | | |
| F24-4G1 | 26, 51, 69, 82 | N.D. | N.D. | | |
| F24-8H12 | 26, 51, 69, 82 | 26, 69, 82 | N.D. | | |
| F24-9H12 | 26, 51, 69, 82 | 26, 69 | N.D. | | |
| F25-2D11 | 73 | N.D. | N.D. | HPV73-[MBP]-E6/ | subcutaneous/Adjuvant: |
| F25-3D10 | 53, 73, 82 | N.D. | N.D. | HPV73-[GST]-E6 | complete/incomplete |
| F25-3 E5 | 16, 34, 59, 70, 73 | N.D. | N.D. | | Freund's (initial/follow up injections) |
| F25-4C11 | 16, 34, 59, 70, 73 | 34 | does not recognize 73, 34 N.D. | | |
| F26-1B10 | 51, 53 | N.D. | N.D. | HPV53-[MBP]-E6/ | subcutaneous/Adjuvant: |
| F26-1B11 | 53 | N.D. | N.D. | HPV53-[GST]-E6 | complete/incomplete |
| F26-1D9 | 53 | N.D. | N.D. | | Freund's (initial/follow up injections) |
| F26-1D11 | 53 | N.D. | N.D. | | |
| F26-2B12 | 53 | N.D. | N.D. | | |
| F26-2G5 | 53 | N.D. | N.D. | | |
| F26-3A8 | 30, 53, 66 | N.D. | N.D. | | |
| F26-5H5 | 53 | N.D. | N.D. | | |
| F26-6D10 | 53 | N.D. | N.D. | | |
| F26-8B7 | 53 | N.D. | N.D. | | |
| F26-8H9 | 53 | N.D. | N.D. | | |
| F26-9C2 | 53 | N.D. | N.D. | | |
| F26-9C7 | 53 | N.D. | N.D. | | |
| F26-9D8 | 53 | N.D. | N.D. | | |
| F26-9G5 | 53, 73, 82 | N.D. | N.D. | | |
| F27-3A4 | 59 | N.D. | N.D. | HPV59-[MBP]-E6/ HPV59-[GST]-E6 | subcutaneous/Adjuvant: complete/incomplete Freund's (initial/follow up injections) |
| 6F4 | 16 | 16, 35, 69 | recognizes 16 and 69, 35 N.D. | HPV16-[GST]E6/HPV16-[GST]E6 | poly-I/poly-C adjuvant/three immunizations |
| 4C6 | 16 | 16 | N.D. | HPV16-[GST]E6/HPV16-[GST]E6 | poly-I/poly-C adjuvant/three immunizations |
| 3F8 | 16 | 16, 35, 51, 82, 31, 33 and 58 | N.D. | HPV16-[MBP]E6-C-terminal portion/HPV16-[MBP]E6-C-terminal portion | poly-I/poly-C adjuvant/three immunizations |

FIG. 3 shows results obtained from a slot western blot of recombinant E6 protein, probed with hybridoma supernatants.

Example 7

Selection of Antibodies for HPV Diagnostic Test

Supernatants from hybridomas reacting with E6 proteins are tested together with the oncogenic PL detector in a sandwich ELISA with recombinant E6 fusion protein.

Monoclonal antibodies are tested in HPV diagnostic ELISA for their ability to detect E6 from cervical cancer cell lines or cells transfected with E6 (if cell lines are unavailable).

It is evident from the above results and discussion that the subject invention provides an important new means for detecting HPV E6 proteins. In particular, the subject invention provides a system for detecting oncogenic strains of HPV. It is superior to current methods because the PDZ protein isolates the oncogenic E6 protein from other analytes of a complex biological sample, and the protein is detected using an antibody that cross-reacts with more than one E6 protein. The specificity of detection lies in the PDZ protein and the antibody does not need to bind only oncogenic E6 proteins, as currently required in conventional methods. Accordingly, the subject methods and systems find use in a variety of different diagnostic applications. Accordingly, the present invention represents a significant contribution to the art.

What is claimed is:

1. A monoclonal antibody that is non-human and that binds to a sub-sequence of a common sequence of an early gene protein from at least two oncogenic human papillomavirus (HPV) strains selected from the group consisting of HPV strains 16, 18, 31, 33, 52, and 58, wherein the common sequence is an amino acid sequence motif that is conserved within a same gene protein from the at least two oncogenic HPV strains, wherein the common sequence comprises at least 9 contiguous amino acids within a region of sequence similarity between the same early gene protein of the at least two oncogenic HPV strains, wherein the region of sequence similarity is located within amino acids 1-43 of the N-terminus of the same early gene protein or within 41 amino acids of the C-terminus of the same early gene protein, and wherein:

a) the early gene protein from the at least two oncogenic HPV strains is encoded by a nucleic acid sequence within the HPV early gene protein 6-HPV early gene protein 7 (E6-E7) region of an HPV genome; and b) a dissociation constant of the monoclonal antibody for the early gene protein from the at least two oncogenic HPV strains is less than $10^{-5}$ M.

2. The monoclonal antibody of claim 1, wherein the antibody binds to SEQ ID NO: 7 or 8 with a dissociation constant of less than $10^{-5}$ M.

3. The monoclonal antibody of claim 1, wherein the antibody binds to an E6 peptide having SEQ ID NO: 11 or 12 with a dissociation constant of less than $10^{-5}$ M.

4. The monoclonal antibody of claim 1, wherein the antibody binds to an HPV E6 peptide having SEQ ID NO: 1, 2, 3, 4, 5, 6, 57, 58, or 59 with a dissociation constant of less than $10^{-5}$ M.

5. The monoclonal antibody of claim 1, wherein the antibody has a dissociation constant of less than $10^{-7}$ M for each of the at least two oncogenic strains.

6. The monoclonal antibody of claim 1, wherein the antibody has a dissociation constant of less than $10^{-8}$ M for each of the at least two oncogenic strains.

7. The monoclonal antibody of claim 1, wherein the antibody has a dissociation constant of less than $10^{-9}$ M for each of the at least two oncogenic strains.

8. An antibody composition comprising a mixture of monoclonal antibodies that bind to HPV early protein 6 (E6) proteins of oncogenic human papillomavirus (HPV) strains, wherein at least one of said monoclonal antibodies is the monoclonal antibody according to claim 1.

9. The antibody composition of claim 8, wherein at least said monoclonal antibody according to claim 1 binds to an E6 peptide having SEQ ID NO: 1, 2, 3, 4, 5, 6, 57, 58, or 59.

10. The antibody composition of claim 8, wherein said mixture of monoclonal antibodies binds to E6 proteins of HPV strains 16, 18, and 45.

11. The antibody composition of claim 8, wherein said mixture of monoclonal antibodies binds to E6 proteins of HPV strains 16, 18, 31, 33, 45, 52, 58, 35 and 59.

12. A diagnostic kit for the detection of a human papillomavirus (HPV) E6 polypeptide in a sample, comprising: the antibody composition of claim 8.

13. The diagnostic kit of claim 12, wherein said monoclonal antibodies are labeled.

14. The diagnostic kit of claim 12, further comprising a PDZ domain polypeptide that binds to an oncogenic HPV E6 polypeptide in a sample.

15. A method of detecting a human papillomavirus (HPV) E6 protein in a sample, comprising: contacting the antibody composition of claim 8 with said sample; and detecting any binding of said antibodies within said composition to said sample, wherein binding of said antibodies within said composition to said sample indicates the presence of an HPV E6 protein.

16. The method of claim 15, wherein said sample is suspected of containing an oncogenic strain of HPV.

17. A method of detecting the presence of an oncogenic human papillomavirus (HPV) early protein 6 (E6) protein in a sample, said method comprising: contacting a sample with a PDZ domain polypeptide; and detecting any binding of said oncogenic HPV E6 protein to said sample to said PDZ domain polypeptide using the antibody composition of claim 8; wherein binding of said oncogenic HPV E6 protein to said PDZ domain polypeptide indicates the presence of an oncogenic HPV E6 protein in said sample.

18. A system for detecting the presence of an oncogenic human papillomavirus (HPV) early protein 6 (E6) polypeptide in a sample, said system comprising: a first and a second binding partner for an oncogenic HPV E6 polypeptide, wherein said first binding partner is a PDZ domain protein and said second binding partner is the antibody of claim 1.

19. The system of claim 18, wherein at least one of said binding partners is attached to a solid support.

20. The monoclonal antibody of claim 1, wherein the at least two oncogenic HPV strains are selected from the group consisting of HPV strains: 16, 31, and 33.

21. The monoclonal antibody of claim 1, wherein the at least two oncogenic HPV strains are selected from the group consisting of HPV strains: 52, and 58.

22. The monoclonal antibody of claim 1, wherein the at least two oncogenic HPV strains are selected from the group consisting of HPV strains: 16 and 18.

23. The monoclonal antibody of claim 1, wherein the early gene protein is E6.

24. The monoclonal antibody of claim 1, wherein the antibody binds the oncogenic protein encoded by a nucleic acid sequence that encodes for a protein selected from the group consisting of SEQ ID NOs: 13, 14, 15, 16, 17, and 18 with a dissociation constant of less than $10^{-5}$ M.

25. The monoclonal antibody of claim 1, wherein the common sequence has a sequence corresponding to SEQ ID NO: 1.

26. The monoclonal antibody of claim 1, wherein the sub-sequence has a sequence corresponding to SEQ ID NO: 7.

27. The monoclonal antibody of claim 1, wherein the monoclonal antibody is a humanized antibody.

28. The monoclonal antibody of claim 1, wherein the monoclonal antibody is a chimeric antibody.

29. The monoclonal antibody of claim 1, wherein the dissociation constant of the monoclonal antibody for the early gene protein from the at least two oncogenic HPV strains is less than $10^{-5}$ M when measured by direct enzyme-linked immunosorbent assay (ELISA).

30. The monoclonal antibody of claim 1, wherein the dissociation constant of the monoclonal antibody for the early gene protein from the at least two oncogenic HPV strains is less than $10^{-8}$ M when measured by direct enzyme-linked immunosorbent assay (ELISA).

31. The monoclonal antibody of claim 1, wherein the monoclonal antibody is a mouse antibody.

* * * * *